United States Patent
Bender et al.

(10) Patent No.: US 10,221,129 B2
(45) Date of Patent: Mar. 5, 2019

(54) INHIBITORS OF HUMAN IMMUNODEFICIENCY VIRUS REPLICATION

(71) Applicant: ViiV HEALTHCARE UK (NO.5) LIMITED, Brentford, Middlesex (GB)

(72) Inventors: John A. Bender, Wallingford, CT (US); Robert G. Gentles, Wallingford, CT (US); Annapurna Pendri, Wallingford, CT (US); Alan Xiangdong Wang, Wallingford, CT (US); Nicholas A. Meanwell, Wallingford, CT (US); Brett R. Beno, Wallingford, CT (US); Robert A. Fridell, Wallingford, CT (US); Makonen Belema, Wallingford, CT (US); Van N. Nguyen, Auburn, MI (US); Zhong Yang, Southington, CT (US); Gan Wang, Cheshire, CT (US); Selvakumar Kumaravel, Bangalore (IN); Srinivasan Thangathirupathy, Bangalore (IN); Rajesh Onkardas Bora, Bangalore (IN); Shilpa Maheshwarappa Holehatti, Bangalore (IN); Mallikarjuna Rao Mettu, Bangalore (IN); Manoranjan Panda, Bangalore (IN)

(73) Assignee: VIIV HEALTHCARE UK (NO.5) LIMITED, Brentford, Middlesex (GB)

(*) Notice: Subject to any disclaimer, the term of this patent is extended or adjusted under 35 U.S.C. 154(b) by 0 days.

(21) Appl. No.: 15/565,690

(22) PCT Filed: Apr. 22, 2016

(86) PCT No.: PCT/US2016/028762
§ 371 (c)(1),
(2) Date: Oct. 11, 2017

(87) PCT Pub. No.: WO2016/172424
PCT Pub. Date: Oct. 27, 2016

(65) Prior Publication Data
US 2018/0086697 A1    Mar. 29, 2018

Related U.S. Application Data

(60) Provisional application No. 62/151,780, filed on Apr. 23, 2015.

(51) Int. Cl.
*C07C 307/06* (2006.01)
*C07C 307/10* (2006.01)
(Continued)

(52) U.S. Cl.
CPC ............ *C07C 307/06* (2013.01); *A61P 31/18* (2018.01); *C07C 307/10* (2013.01); *C07C 311/08* (2013.01); *C07D 205/04* (2013.01); *C07D 207/325* (2013.01); *C07D 209/08* (2013.01); *C07D 209/30* (2013.01); *C07D 209/32* (2013.01); *C07D 209/86* (2013.01); *C07D 211/96* (2013.01); *C07D 213/42* (2013.01); *C07D 215/12* (2013.01); *C07D 215/38* (2013.01); *C07D 217/08* (2013.01); *C07D 217/22* (2013.01); *C07D 231/12* (2013.01); *C07D 231/56* (2013.01); *C07D 233/64* (2013.01); *C07D 235/08* (2013.01); *C07D 241/04* (2013.01); *C07D 249/12* (2013.01); *C07D 261/08* (2013.01); *C07D 263/32* (2013.01); *C07D 277/28* (2013.01); *C07D 277/62* (2013.01); *C07D 295/185* (2013.01); *C07D 295/26* (2013.01); *C07D 333/72* (2013.01); *C07D 417/12* (2013.01);
(Continued)

(58) Field of Classification Search
CPC ..... C07C 307/06; C07C 307/10; C07C 311/08; A61K 31/65
USPC .............................. 564/78; 514/600
See application file for complete search history.

(56) References Cited

U.S. PATENT DOCUMENTS 9,220,710 B2 * 12/2015 Bondy ................ C07D 403/12
9,951,043 B2 *  4/2018 Brizgys ............... C07D 401/12
(Continued)

FOREIGN PATENT DOCUMENTS

EP    0 810 208 A2    12/1997
EP    0810208 A2 * 12/1997  .......... C07C 307/06
(Continued)

*Primary Examiner* — Venkataraman Balasubramanian
(74) *Attorney, Agent, or Firm* — Robert H. Brink; Kathryn A. Lutomski; Edward R. Gimmi

(57) ABSTRACT

Compounds of Formula I, including pharmaceutically acceptable salts thereof, and compositions and methods for treating human immunodeficiency virus (HIV) infection are set forth:

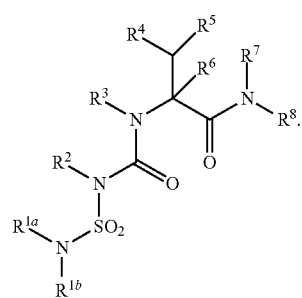

20 Claims, No Drawings

(51) Int. Cl.

| | | |
|---|---|---|
| *C07C 311/08* | (2006.01) | |
| *A61P 31/18* | (2006.01) | |
| *A61K 31/65* | (2006.01) | |
| *C07D 215/12* | (2006.01) | |
| *C07D 215/38* | (2006.01) | |
| *C07D 217/08* | (2006.01) | |
| *C07D 217/22* | (2006.01) | |
| *C07D 231/12* | (2006.01) | |
| *C07D 231/56* | (2006.01) | |
| *C07D 233/64* | (2006.01) | |
| *C07D 333/72* | (2006.01) | |
| *C07D 235/08* | (2006.01) | |
| *C07D 241/04* | (2006.01) | |
| *C07D 417/12* | (2006.01) | |
| *C07D 417/14* | (2006.01) | |
| *C07D 249/12* | (2006.01) | |
| *C07D 471/04* | (2006.01) | |
| *C07D 261/08* | (2006.01) | |
| *C07D 263/32* | (2006.01) | |
| *C07D 205/04* | (2006.01) | |
| *C07D 207/325* | (2006.01) | |
| *C07D 277/28* | (2006.01) | |
| *C07D 498/04* | (2006.01) | |
| *C07D 209/08* | (2006.01) | |
| *C07D 277/62* | (2006.01) | |
| *C07D 209/30* | (2006.01) | |
| *C07D 209/32* | (2006.01) | |
| *C07D 209/86* | (2006.01) | |
| *C07D 295/185* | (2006.01) | |
| *C07D 211/96* | (2006.01) | |
| *C07D 295/26* | (2006.01) | |
| *C07D 213/42* | (2006.01) | |

(52) U.S. Cl.
CPC ......... *C07D 417/14* (2013.01); *C07D 471/04* (2013.01); *C07D 498/04* (2013.01); *C07C 2601/14* (2017.05); *C07C 2602/08* (2017.05)

(56) References Cited

U.S. PATENT DOCUMENTS

2018/0072997 A1* 3/2018 Bender .................... C12N 7/06
2018/0086697 A1* 3/2018 Bender ................ C07C 307/06

FOREIGN PATENT DOCUMENTS

| WO | WO 2014/110298 A1 | 7/2014 |
|---|---|---|
| WO | WO 2014/134566 A2 | 9/2014 |

* cited by examiner

INHIBITORS OF HUMAN IMMUNODEFICIENCY VIRUS REPLICATION

CROSS REFERENCE TO RELATED APPLICATION

This application is a § 371 of International Application No. PCT/US2016/028762, filed 22 Apr. 2016, which claims the benefit of U.S. Provisional Application No. 62/151,780, filed 23 Apr. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV.

It remains a major medical problem, with an estimated 34 million people infected worldwide at the end of 2011, 3.3 million of them under the age of 15. In 2011, there were 2.5 million new infections, and 1.7 million deaths from complications due to HIV/AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads >500 copies/mL (Oette, M, Kaiser, R, Daumer, M, et al. Primary HIV Drug Resistance and Efficacy of First-Line Antiretroviral Therapy Guided by Resistance Testing. J Acq Imm Def Synd 2006; 41(5):573-581). Among these patients, 76% had viruses that were resistant to one or more classes of antiretroviral agents. As a result, new drugs are needed that are easier to take, have high genetic barriers to the development of resistance and have improved safety over current agents. In this panoply of choices, novel MOAs that can be used as part of the preferred highly active antiretroviral therapy (HAART) regimen can still have a major role to play since they should be effective against viruses resistant to current agents.

Certain therapeutic compounds are disclosed in WO 2013/006738, WO 2014/110298, and WO 2014/134566.

What is now needed in the art are additional compounds which are novel and useful in the treatment of HIV. Additionally, these compounds may desirably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

In one aspect of the invention, there is provided a compound of Formula I, including pharmaceutically acceptable salts thereof:

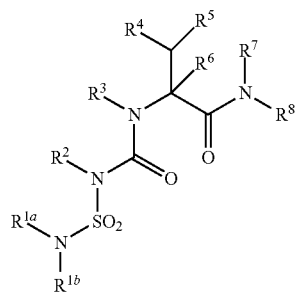

I wherein:
$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO($R^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —CH$_2$NH$_2$, -alkyl-heteroaryl, —CO-alkyl, CO($R^x$), —CON($R^y$)$_2$, —NHCON($R^y$)$_2$, —NHCO-alkyl, —NHCO$_2$alkyl, —NHSO$_2$-alkyl, —OCH$_2$-aryl, —SO$_2$-alkyl, —SO$_2$—N($R^y$)$_2$, and —SO$_2$-heterocyclyl; or $R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —CH$_2$NH$_2$, -alkyl-heteroaryl, —CO-alkyl, —CO($R^x$), —CON($R^y$)$_2$, —N($R^y$)CON($R^y$)$_2$, —N(R$^y$)CO-alkyl, —N(R$^y$)CO$_2$alkyl, —N(R$^y$)SO$_2$-alkyl, —OCH$_2$-aryl, —SO$_2$-alkyl, —SO$_2$—N(R$^y$)$_2$, and —SO$_2$-heterocyclyl;

R$^2$ is —H, C$_1$-C$_4$ alkyl or C$_3$-C$_4$ cycloalkyl;

R$^3$ is —H, C$_1$-C$_4$ alkyl or C$_3$-C$_4$ cycloalkyl;

R$^4$ is —H, alkyl, aryl, C$_5$-C$_{10}$ bicycloalkyl, C$_3$-C$_7$ cycloalkyl or heteroaryl with 0-4 groups independently selected from alkenoxy, alkenyl, alkoxy, alkoxycarbonyl, alkyl, benzyloxy, carboamide, cyano, halo, haloalkyl, haloalkyloxy, —NHCO(alkyl), —SO$_2$(R$^x$), —OH, and —CH$_2$OH;

R$^5$ and R$^6$ are independently H or alkyl, or R$^5$ and R$^6$ together with the atoms to which they are attached form a C$_3$-C$_4$ cycloalkyl;

R$^7$ is —H, alkyl, aryl, heterocyclyl, or C$_3$-C$_7$ cycloalkyl, wherein said aryl or heterocyclyl is substituted with 0-3 groups selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl;

R$^8$ is —H, alkyl, cycloalkyl, haloalkyl, halocycloalkyl alkenyl, or aryloxyalkyl;

or R$^7$ and R$^8$ together with the nitrogen atom to which they are attached form a heterocycle that is substituted with 0-4 groups independently selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl.

The invention also relates to pharmaceutical compositions comprising the compounds of the invention, including pharmaceutically acceptable salts thereof, and a pharmaceutically acceptable carrier, excipient, and/or diluent.

In addition, the invention provides one or more methods of treating HIV infection comprising administering a therapeutically effective amount of the compounds of the invention to a patient.

Also provided as part of the invention are one or more methods for making the compounds of the invention.

The present invention is directed to these, as well as other important ends, hereinafter described.

DETAILED DESCRIPTION OF THE INVENTION

The singular forms "a", "an", and "the" include plural reference unless the context dictates otherwise.

Unless otherwise expressly set forth elsewhere in the application, the following terms shall have the following meanings:

"Alkenyl" means a straight or branched alkyl group comprised of 2 to 10 carbons with at least one double bond and optionally substituted with 0-3 halo or alkoxy group.

"Alkenyloxy" means an alkenyl group attached to the parent structure by an oxygen atom.

"Alkoxy" means an alkyl group attached to the parent structure by an oxygen atom.

"Alkoxycarbonyl" means an alkoxy group attached to the parent structure by a carbonyl moiety.

"Alkyl" means a straight or branched saturated hydrocarbon comprised of 1 to 10 carbons, and preferably 1 to 6 carbons.

"Alkylthioxy" means an alkyl group attached to the parent structure through a sulfur atom.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of C$_3$ to C$_7$ alkyl group. Examples of aromatic group include, but are not limited to, phenyl, biphenyl, cyclopropylphenyl, indane, naphthalene, and tetrahydronaphthalene. The aryl group can be attached to the parent structure through any substitutable carbon atom in the group.

"Arylalkyl" is a C$_1$-C$_5$ alkyl group attached to 1 to 2 aryl groups and linked to the parent structure through the alkyl moiety. Examples include, but are not limited to, —(CH$_2$)$_n$Ph with n=1-5, —CH(CH$_3$)Ph, —CH(Ph)$_2$.

"Aryloxy" is an aryl group attached to the parent structure by oxygen.

"Azaindole" means one of the "CH" moieties in the 6-member ring of an indole is substituted with a nitrogen atom.

"Azaindoline" means one of the aromatic "CH" moieties of an indoline is substituted with a nitrogen atom.

"Azatetrahydroquinoline" means any aromatic CH moiety of tetrahydroquinoline is substituted with a nitrogen atom.

"Benzyloxy" means a benzyl group is attached to the parent structure through an oxygen atom. The phenyl group of the benzyl moiety could be optionally substituted by 1-3 moieties independently selected from alkyl, alkoxy, halo, haloalkyl, haloalkoxy and cyano.

"C$_x$-C$_y$" notation indicates a structural element comprised of carbons numbering between 'x' and 'y'. For example, "C$_5$-C$_{10}$ bicycloalkyl" means a bicyclic ring system comprised of 5 to 10 carbons, where the rings are attached in a fused, spiro or bridged manner; an example of C$_5$-C$_{10}$ bicycloalkyl include, but is not limited to, bicyclo[2.2.2]octane. Similarly, "C$_3$-C$_4$ cycloalkyl" is a subset of monocyclic ring system comprised of 3 to 4 carbons.

"Cycloalkyl" means a monocyclic ring system comprised of 3 to 7 carbons.

"Cyano" refers to —CN.

"Diazaindole" means any two "CH" moieties in the 6-member ring of an indole are substituted with nitrogen atoms.

"Diazaindoline" means any two aromatic "CH" moieties of an indoline are substituted with a nitrogen atom.

"Diazatetrahydroquinoline" means any two aromatic CH moieties of tetrahydroquinoline are substituted with nitrogen atoms.

"Halo" or "halogen" refers to —F, —Cl, —Br, or —I.

"Haloalkyl" means an alkyl group substituted by any combination of one to six halogen atoms.

"Haloalkoxy" or "Haloalkyloxy" means a haloalkyl group attached to the parent structure through an oxygen atom.

"Hydroxy" refers to —OH.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)_n$—$R^Z$ or —CH($CH_3$)—($R^Z$) where n=1-5 and that $R^Z$ is chosen from benzimidazole, imidazole, indazole, isooxazole, phenylpyrazole, pyridine, quinoline, thiazole, triazole, triazolone, oxadiazole.

"Tetrahydroquinoline" means 1,2,3,4-tetrahydroquinoline.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I, including pharmaceutically acceptable salts thereof:

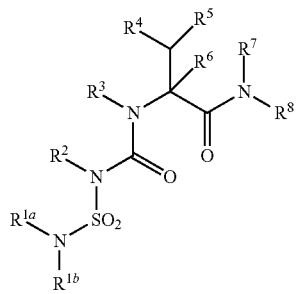

I wherein:

$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO($R^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —$CH_2NH_2$, -alkyl-heteroaryl, —CO-alkyl, CO($R^x$), —CON($R^y$)$_2$, —NHCON($R^y$)$_2$, —NHCO-alkyl, —NHCO$_2$alkyl, —NHSO$_2$-alkyl, —OCH$_2$-aryl, —SO$_2$-alkyl, —SO$_2$—N($R^y$)$_2$, and —SO$_2$-heterocyclyl; or $R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —CH$_2$NH$_2$, -alkyl-heteroaryl, —CO-alkyl, —CO(R$^x$), —CON(R$^y$)$_2$, —N(R$^y$)CON(R)$_2$, —N(R$^y$)CO-alkyl, —N(R$^y$)CO$_2$alkyl, —N(R$^y$)SO$_2$-alkyl, —OCH$_2$-aryl, —SO$_2$-alkyl, —SO$_2$—N(R$^y$)$_2$, and —SO$_2$-heterocyclyl;

R$^2$ is —H, C$_1$-C$_4$ alkyl or C$_3$-C$_4$ cycloalkyl;

R$^3$ is —H, C$_1$-C$_4$ alkyl or C$_3$-C$_4$ cycloalkyl;

R$^4$ is —H, alkyl, aryl, C$_5$-C$_{10}$ bicycloalkyl, C$_3$-C$_7$ cycloalkyl or heteroaryl with 0-4 groups independently selected from alkenoxy, alkenyl, alkoxy, alkoxycarbonyl, alkyl, benzyloxy, carboamide, cyano, halo, haloalkyl, haloalkyloxy, —NHCO(alkyl), —SO$_2$(R$^x$), —OH, and —CH$_2$OH;

R$^5$ and R$^6$ are independently H or alkyl, or R$^5$ and R$^6$ together with the atoms to which they are attached form a C$_3$-C$_4$ cycloalkyl;

R$^7$ is —H, alkyl, aryl, heterocyclyl, or C$_3$-C$_7$ cycloalkyl, wherein said aryl or heterocyclyl is substituted with 0-3 groups selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl;

R$^8$ is —H, alkyl, cycloalkyl, haloalkyl, halocycloalkyl alkenyl, or aryloxyalkyl;

or R$^7$ and R$^8$ together with the nitrogen atom to which they are attached form a heterocycle that is substituted with 0-4 groups independently selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl.

In another aspect of the invention, R$^7$ and R$^8$ may be the following:

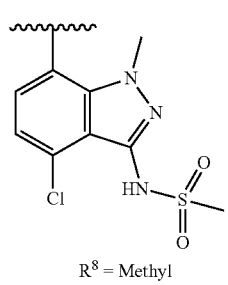

R$^8$ = Methyl

R$^x$ is dialkylamine or a nitrogen-containing heterocycle which is attached to the parent fragment through a nitrogen atom; and each R$^y$ is independently hydrogen, alkyl, haloalkyl or aryl.

In an aspect of the invention, there is provided a compound of Formula I, wherein R$^{1a}$ and R$^{1b}$ are each independently selected from hydrogen, alkyl, aryl, heteroaryl, arylalkyl, heteroarylalkyl, and -alkylCO(R$^x$), wherein the heteroaryl is attached to the parent structure through a carbon atom.

In an aspect of the invention, there is provided a compound of Formula I, wherein R$^{1a}$ and R$^{1b}$ are each independently selected from hydrogen, alkyl, phenyl, biphenyl, naphthalene, dihydroindene, pyridine, pyrimidine, quinoline, isoquinoline, benzothiazole, benzimidazole, 1,3-dihydrobenzo[c]thiophene 2,2-dioxide, —CH$_2$CO(R$^x$) and an alkyl moiety attached to any one of the following groups: phenyl, biphenyl, pyridiyl, quinoline, benzimidazole, imidazole, isothiazole, pyrrazole, thiazole, indazole, triazole, and triazolone.

In an aspect of the invention, there is provided a compound of Formula I, wherein R$^{1a}$ and R$^{1b}$ are each independently substituted by at least one member selected from alkyl, haloalkyl, alkoxy, haloalkoxy, halide, phenyl, thiazole, pyrrazole, phenoxy, oxazole, pyrrole, benzyloxy, pyridiylalkyl, methylcarbamate, cyano, acetamide, morpholin-4-ylsulfonyl, pyrrolidin-1-ylsulfonyl, piperidin-1-ylsulfonyl, —NHSO$_2$Me, —CONH$_2$, —NHCONMe$_2$, and —COCH$_3$.

In an aspect of the invention, there is provided a compound of Formula I, wherein R$^{1a}$ and R$^{1b}$ are each independently substituted by at least one member selected from alkyl, haloalkyl, alkoxy, haloalkoxy, halide, phenyl, thiazole, pyrrazole, phenoxy, oxazole, pyrrole, benzyloxy, pyridiylalkyl, methylcarbamate, cyano, acetamide, morpholin-4-ylsulfonyl, pyrrolidin-1-ylsulfonyl, piperidin-1-ylsulfonyl, —NHSO$_2$Me, —CONH$_2$, —NHCONMe$_2$, and —COCH$_3$.

In an aspect of the invention, there is provided a compound of Formula I, wherein R$^{1a}$ and R$^{1b}$ taken together form a heterocycle together with the nitrogen to which they are attached, and further wherein said heterocycle has 1-3 rings with a total of 4-14 carbon atoms and at least one internal nitrogen atom, and optionally at least one atom selected from oxygen and sulfur. In an aspect of the invention, there is provided a compound of Formula I, wherein the formed heterocycle will be selected from tetrahydroquinoline, azatetrahydroquinoline, diazatetrahydroquinoline, tetrahydroisoquinoline, indoline, azaindoline, diazaindoline, indole, azaindole, diazaindole, indazole, carbazole, azetidine, pyrrolidine, piperidine, piperizine, morpholine, 2,3-dihydro-1H-pyrrolo[3,4-c]pyridine, 2,3-dihydrobenzo[d]isothiazole 1,1-dioxide, 1H-pyrazolo[4,3-c]pyridine, 3,4-dihydro-2H-pyrido[3,2-b][1,4]oxazine, and spiro[cyclopropane-1,3'-indoline]. In an aspect of the invention, there is provided a compound of Formula I, wherein the formed heterocycle is substituted with at least one member selected from phenyl, aminoalkyl, alkyl, alkoxy, haloalkyl, haloalkoxy, halide, hydroxyl, pyridine, sulfonylalkyl, —CO$_2$NMe$_2$, and cyano.

In an aspect of the invention, there is provided a compound of Formula I, wherein the formed heterocycle is substituted with at least one member selected from phenyl, aminoalkyl, alkyl, alkoxy, haloalkyl, haloalkoxy, halide, hydroxyl, pyridine, sulfonylalkyl, —CO$_2$NMe$_2$, and cyano.

In an aspect of the invention, there is provided a compound of Formula I, wherein at least one of said R$^{1a}$ and R$^{1b}$ is phenyl. In an aspect of the invention, there is provided a compound of Formula I, wherein said phenyl is substituted with at least one member selected from alkyl, haloalkyl, alkoxy, haloalkoxy, halide, phenyl, thiazole, pyrrazole, phenoxy, oxazole, pyrrole, benzyloxy, pyridiylalkyl, methylcarbamate, cyano, acetamide, morpholin-4-ylsulfonyl, pyrrolidin-1-ylsulfonyl, piperidin-1-ylsulfonyl, —NHSO$_2$Me, —CONH$_2$, —NHCONMe$_2$, and —COCH$_3$.

In an aspect of the invention, there is provided a compound of Formula I, wherein R$^2$ and R$^3$ are each —H.

In an aspect of the invention, there is provided a compound of Formula I, wherein R$^4$ is aryl. In an aspect of the invention, there is provided a compound of Formula I, wherein said aryl is phenyl.

In an aspect of the invention, there is provided a compound of Formula I, wherein R$^4$ is aryl. In an aspect of the invention, there is provided a compound of Formula I, wherein said aryl is phenyl.

In an aspect of the invention, there is provided a compound of Formula I, wherein R$^8$ is alkyl.

In an aspect of the invention, there is provided a pharmaceutical composition comprising a compound of the invention, e.g., Formula I, II or III, and a pharmaceutically acceptable carrier, excipient and/or diluent.

In an aspect of the invention, there is provided a method of treating HIV infection comprising administering a therapeutically effective amount of a compound of the invention, e.g., Formula I, II or III, to a patient.

In an aspect of the invention, there is provided a compound of Formula II, including pharmaceutically acceptable salts thereof:

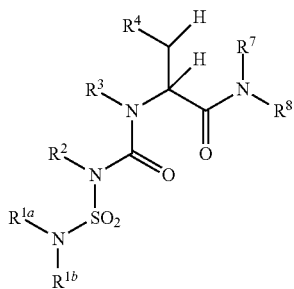

II

In an aspect of the invention, there is provided a compound of Formula II, wherein $R^4$ is aryl.

In an aspect of the invention, there is provided a compound of Formula II, wherein said aryl is phenyl.

In an aspect of the invention, there is provided a compound of Formula II, wherein $R^8$ is alkyl.

In an aspect of the invention, there is provided a compound of Formula III, including pharmaceutically acceptable salts thereof:

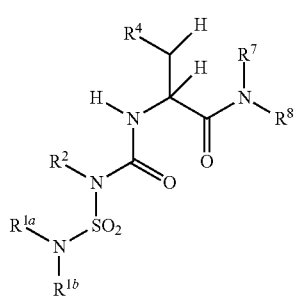

III wherein:
$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO($R^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —$CH_2NH_2$, -alkyl-heteroaryl, —CO-alkyl, CO($R^x$), —CON($R^y$)$_2$, —NHCON($R^y$)$_2$, —NHCO-alkyl, —NHCO$_2$alkyl, —NHSO$_2$-alkyl, —OCH$_2$-aryl, —SO$_2$-alkyl, —SO$_2$—N($R^y$)$_2$, and —SO$_2$-heterocyclyl; or
$R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —$CH_2NH_2$, -alkyl-heteroaryl, —CO-alkyl, —CO($R^x$), —CON($R^y$)$_2$, —N($R^y$)CON($R^y$)$_2$, —N($R^y$)CO-alkyl, —N($R^y$)CO$_2$alkyl, —N($R^y$)SO$_2$-alkyl, —OCH$_2$-aryl, —SO$_2$-alkyl, —SO$_2$—N($R^y$)$_2$, and —SO$_2$-heterocyclyl;
$R^2$ is —H, $C_1$-$C_2$ alkyl or $C_3$-$C_4$ cycloalkyl;
$R^3$ is —H, or $C_1$-$C_4$ alkyl;
$R^4$ aryl, $C_5$-$C_{10}$ bicycloalkyl, $C_3$-$C_7$ cycloalkyl or heteroaryl with 0-4 groups independently selected from alkoxy, alkyl, cyano, halo, haloalkyl, and haloalkyloxy;
$R^7$ is aryl, heterocyclyl, or $C_3$-$C_7$ cycloalkyl, wherein said aryl or heterocyclyl is substituted with 0-3 groups selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl;
$R^8$ is alkyl, cycloalkyl, haloalkyl, halocycloalkyl alkenyl, or aryloxyalkyl;
$R^x$ is dialkylamine or a nitrogen-containing heterocycle which is attached to the parent fragment through a nitrogen atom; and
each $R^y$ is independently hydrogen, alkyl, haloalkyl or aryl.

In an aspect of the invention, there is provided a compound of Formula II, wherein $R^2$ and $R^3$ are each —H.

wherein:
$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO($R^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —$CH_2NH_2$, -alkyl-heteroaryl, —CO-alkyl, CO($R^x$), —CON($R^y$)$_2$, —NHCON(R)$_2$, —NHCO-alkyl, —NHCO$_2$alkyl, —NHSO$_2$-alkyl, —OCH$_2$-aryl, —SO$_2$-alkyl, —SO$_2$—N($R^y$)$_2$, and —SO$_2$-heterocyclyl; or
$R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —$CH_2NH_2$, -alkyl-heteroaryl, —CO-alkyl, —CO($R^x$), —CON($R^y$)$_2$, —N($R^y$)CON($R^y$)$_2$, —N($R^y$)CO-alkyl, —N($R^y$)CO$_2$alkyl, —N($R^y$)SO$_2$-alkyl, —OCH$_2$-aryl, —SO$_2$-alkyl, —SO$_2$—N($R^y$)$_2$, and —SO$_2$-heterocyclyl;
$R^2$ is —H, or $C_1$-$C_2$ alkyl;
$R^4$ aryl, or heteroaryl with 0-3 groups independently selected from alkoxy, alkyl, cyano, or halo;
$R^7$ is aryl, heterocyclyl, wherein said aryl or heterocyclyl is substituted with 0-3 groups selected from —OH, —NHCOalkyl, —NHCON(alkyl)$_2$, —NHCO$_2$-alkyl, —CONH$_2$, —CN, alkoxy, alkyl, halo, haloalkoxy, and haloalkyl;
$R^8$ is alkyl, cycloalkyl, haloalkyl, halocycloalkyl alkenyl, or benzyloxyalkyl; $R^x$ is dialkylamine or a nitrogen-containing heterocycle which is attached to the parent fragment through a nitrogen atom; and
each $R^y$ is independently hydrogen, alkyl, haloalkyl or aryl.

In an aspect of the invention, there is provided a compound of Formula III, wherein $R^2$ is —H.

In an aspect of the invention, there is provided a compound of Formula III, wherein $R^4$ is aryl.

In an aspect of the invention, there is provided a compound of Formula III, wherein said aryl is phenyl.
In an aspect of the invention, there is provided a compound of Formula III, wherein $R^8$ is alkyl.
Preferred compounds of the invention, including pharmaceutically acceptable salts thereof, are selected from:
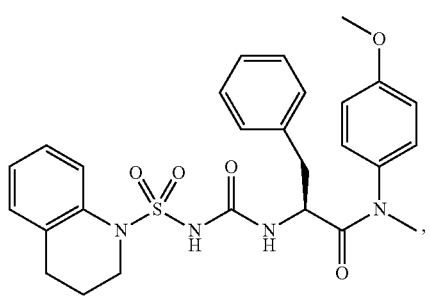
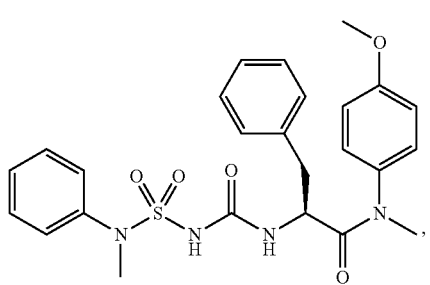
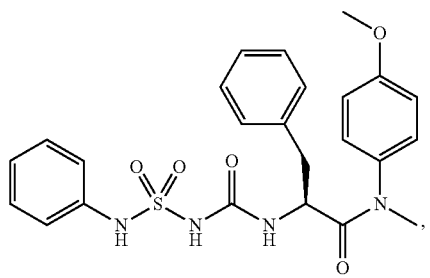
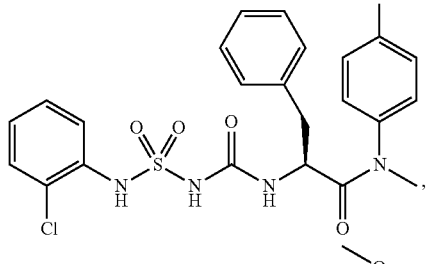
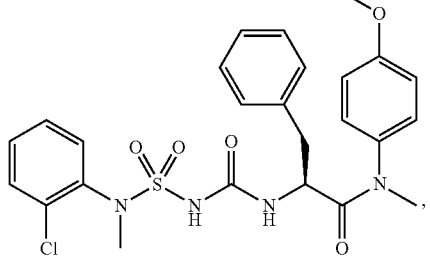
-continued
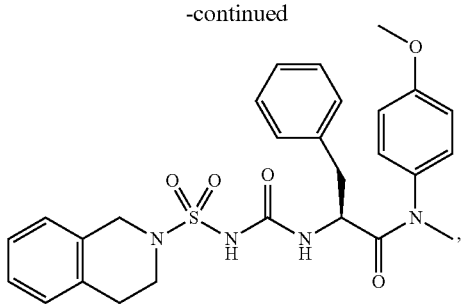
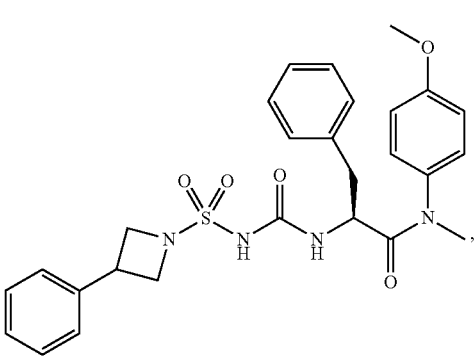
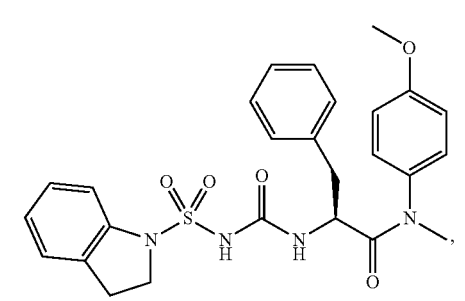
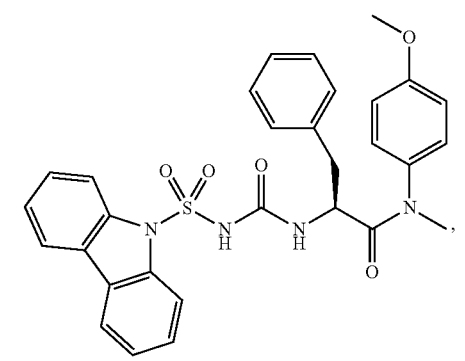
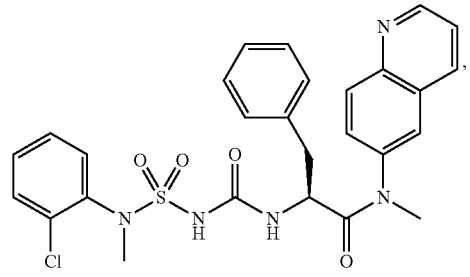

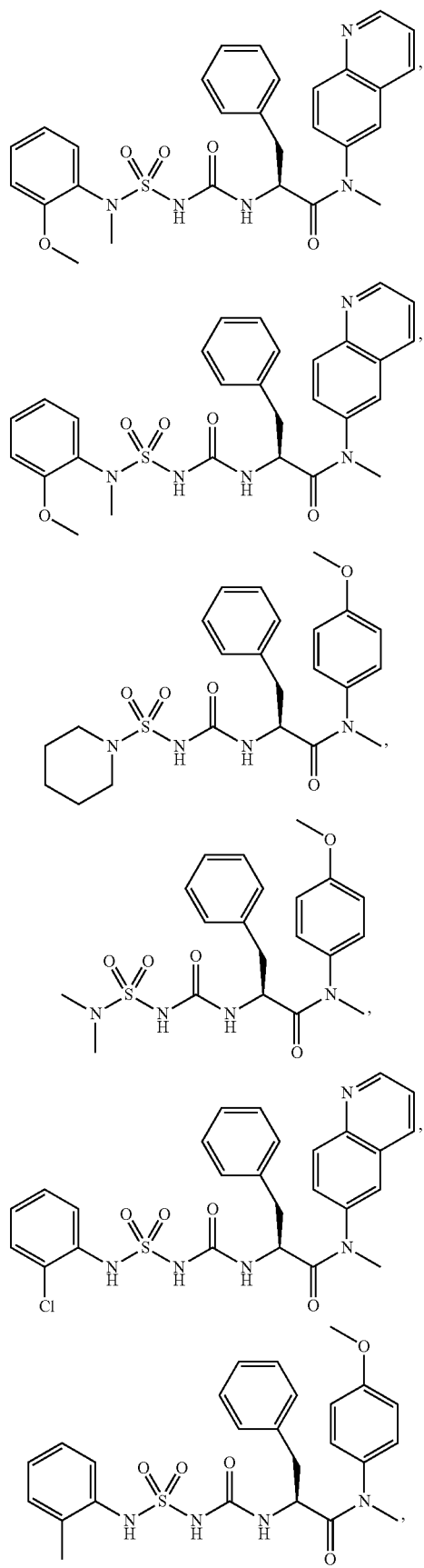
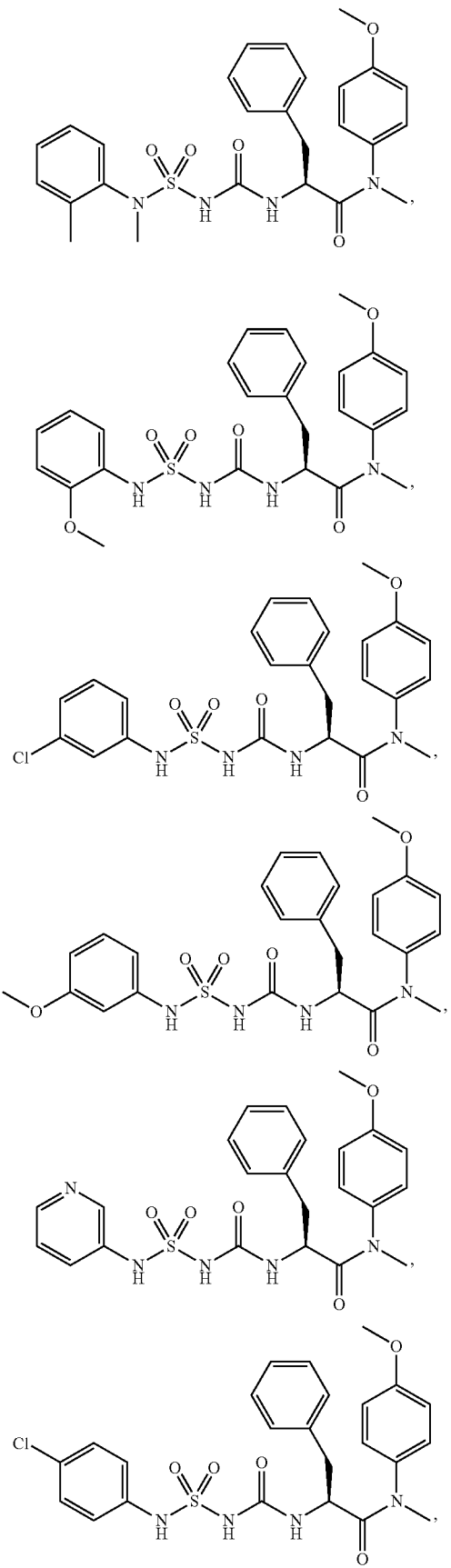

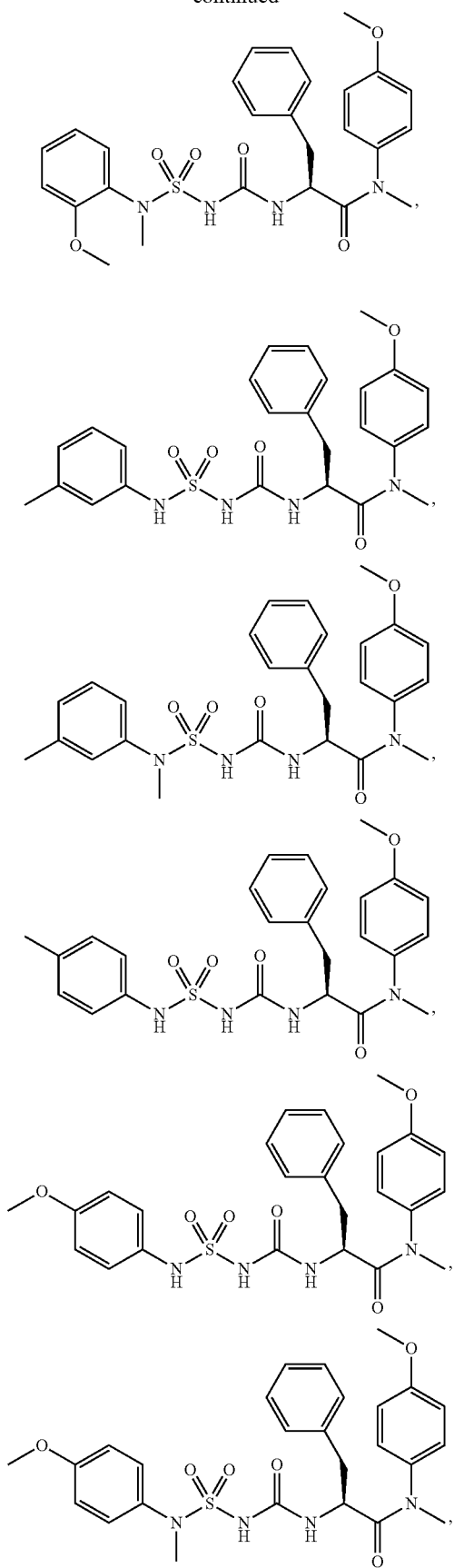
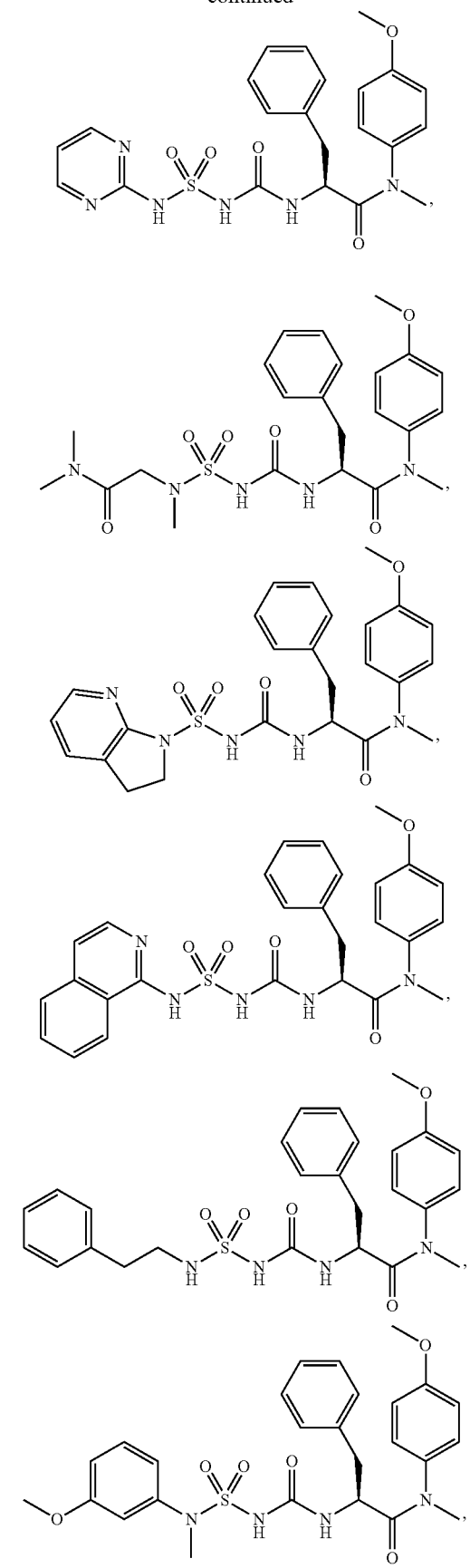

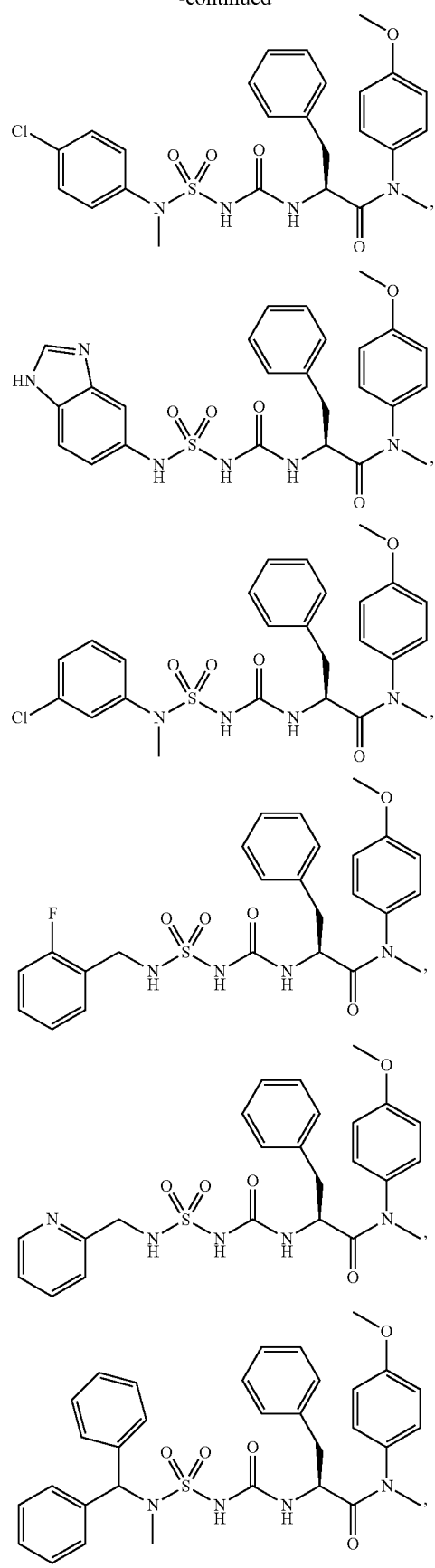
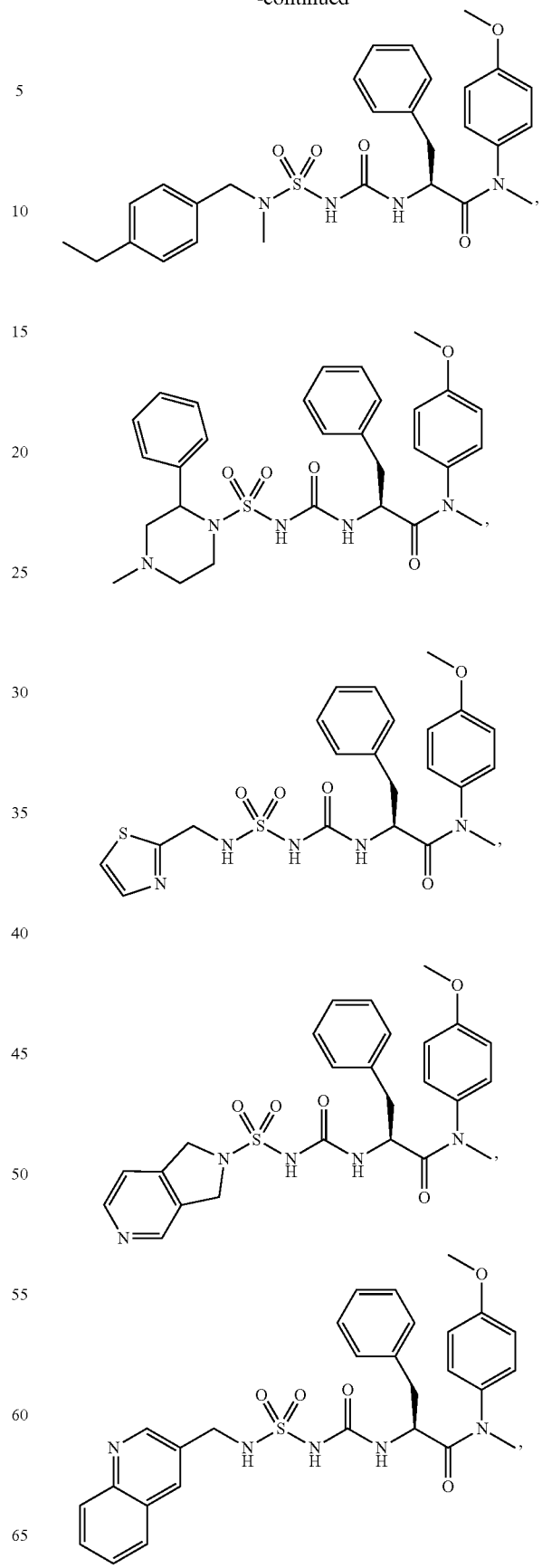

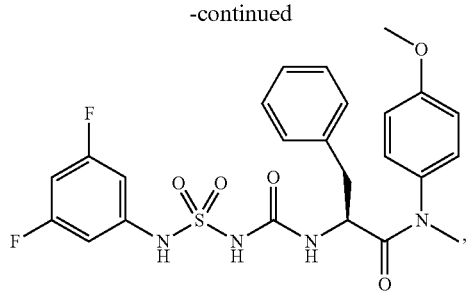
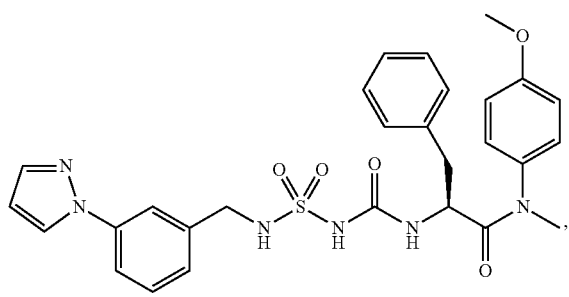
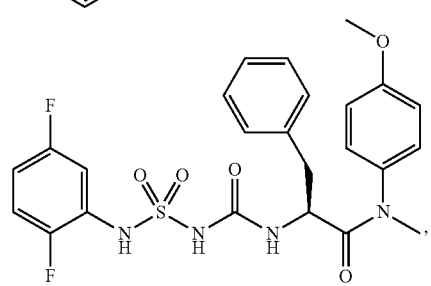
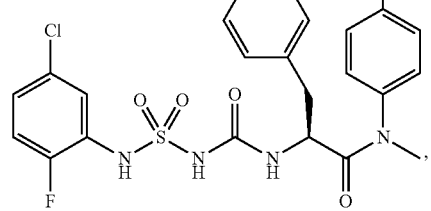
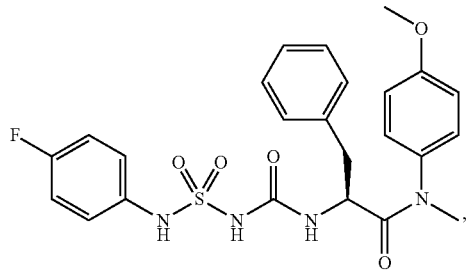
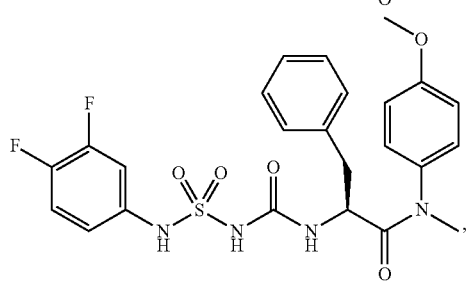
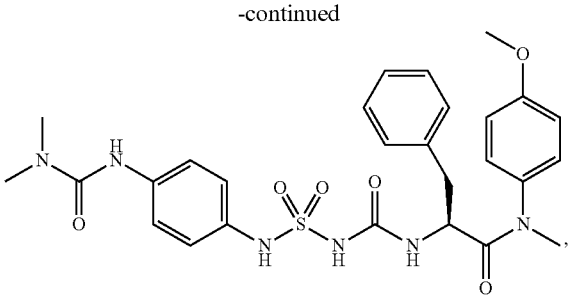
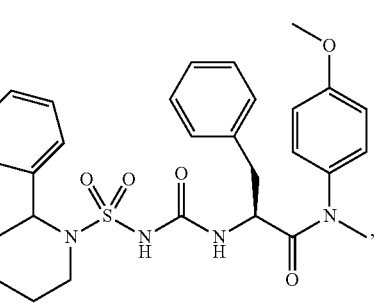
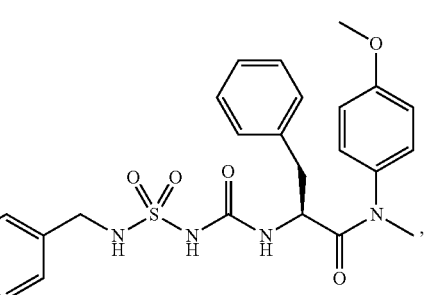
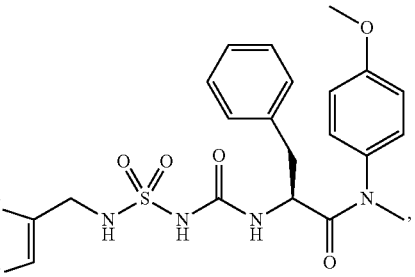
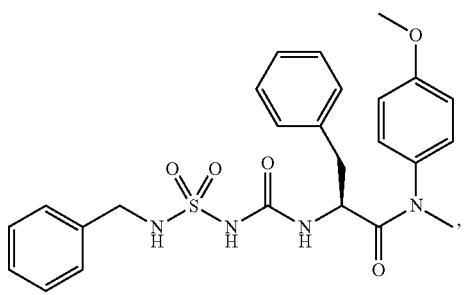

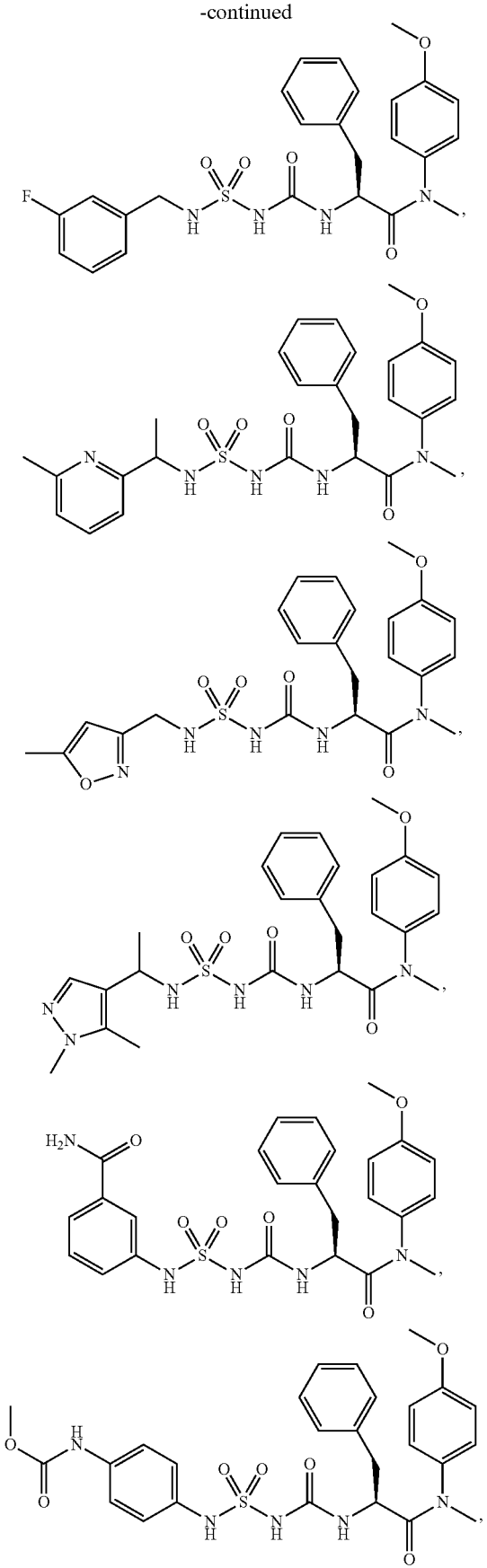
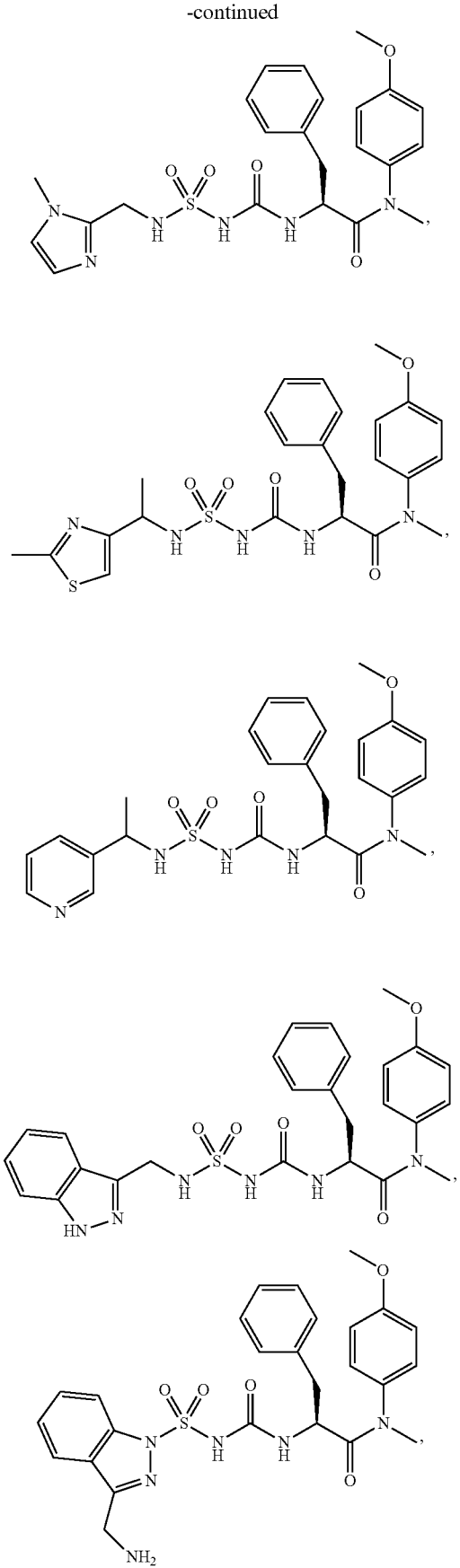

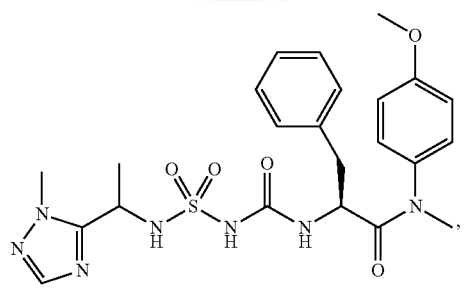
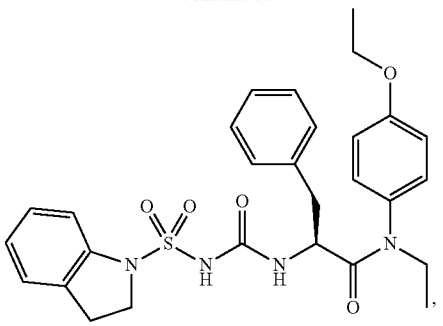
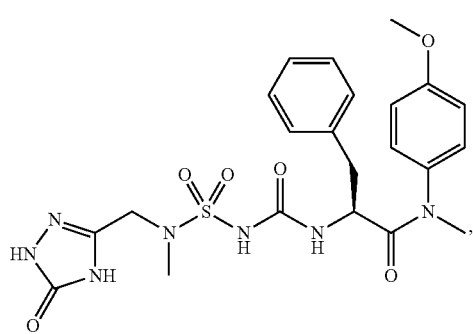
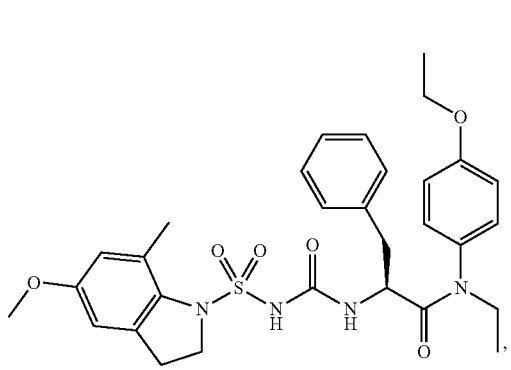
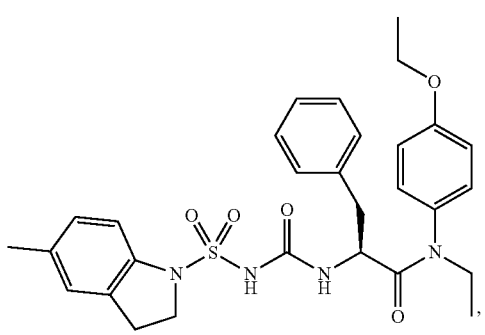
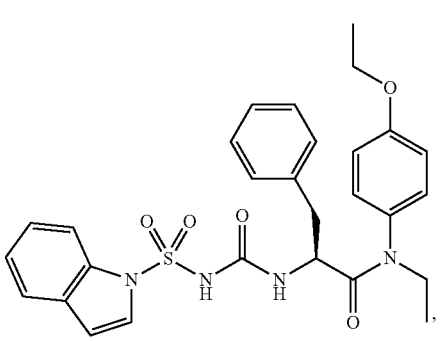
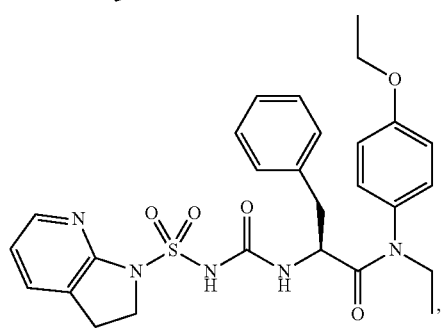
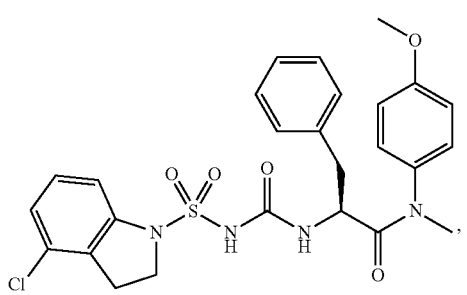
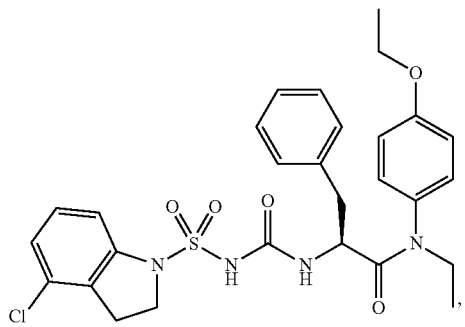
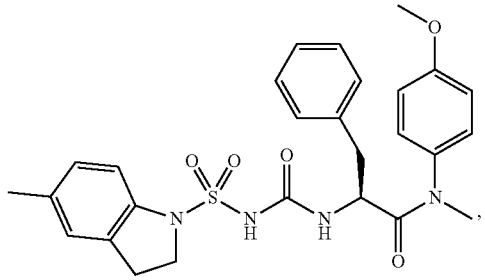

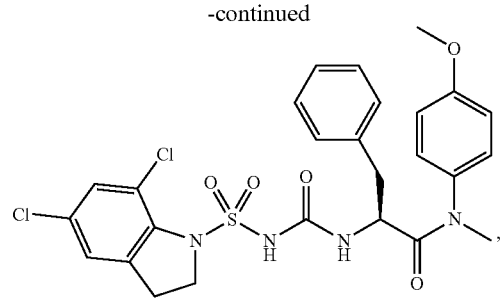
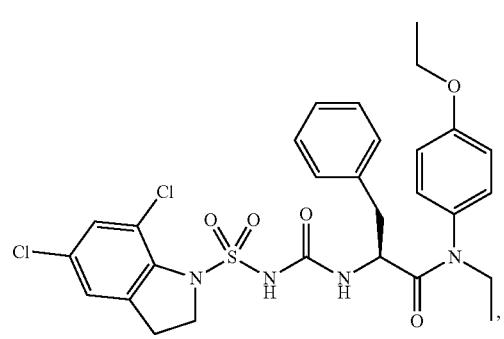
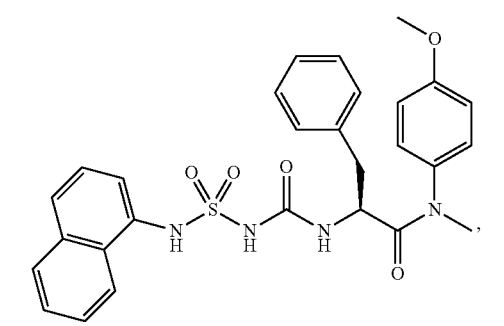
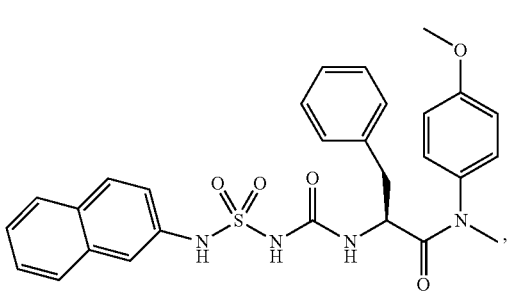
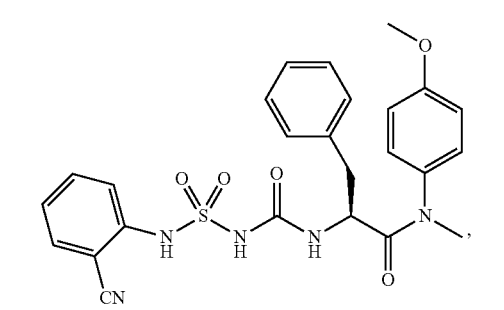
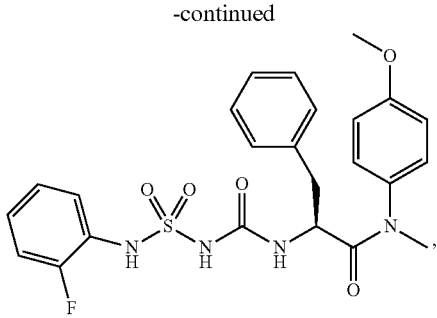
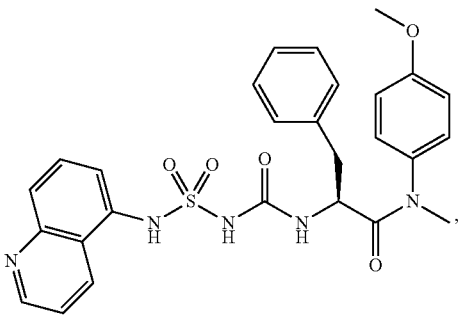
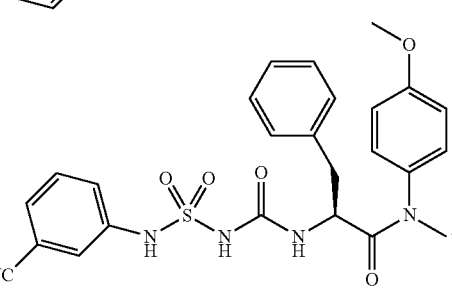
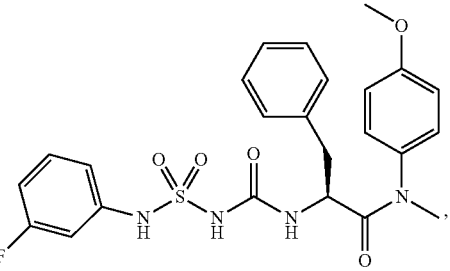
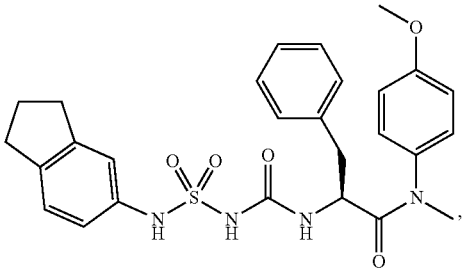
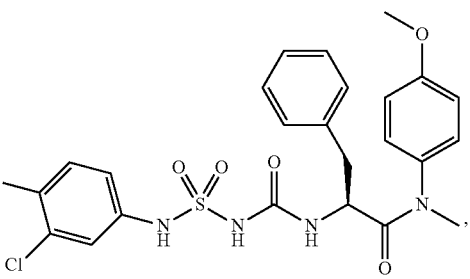

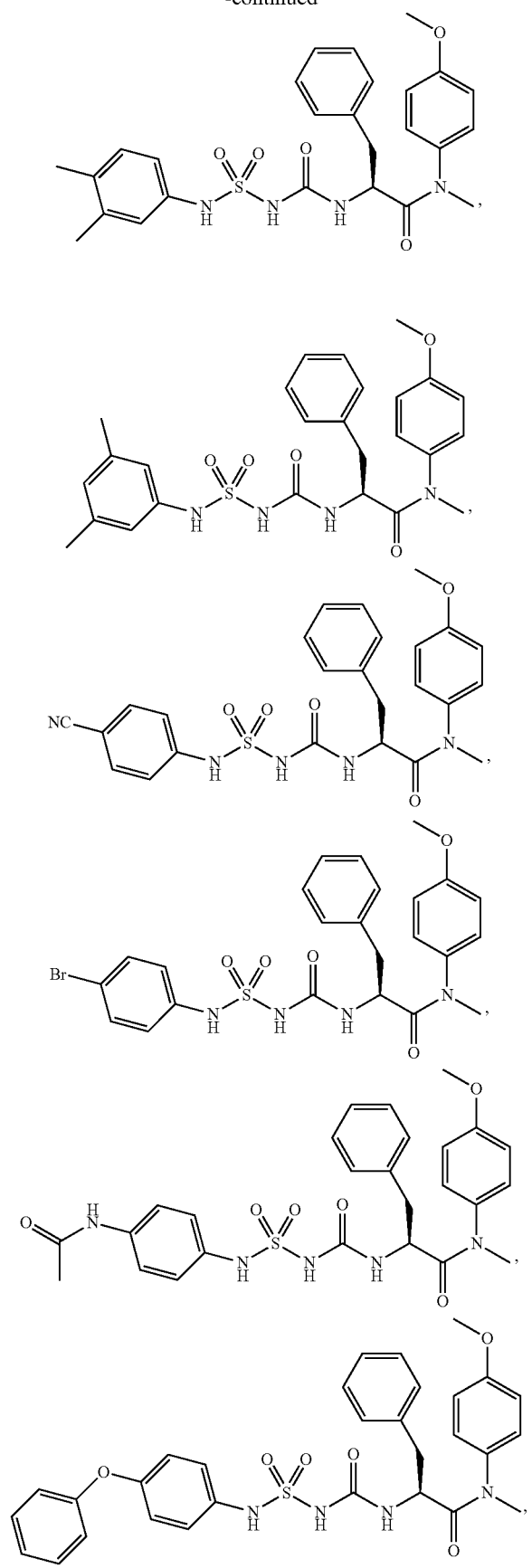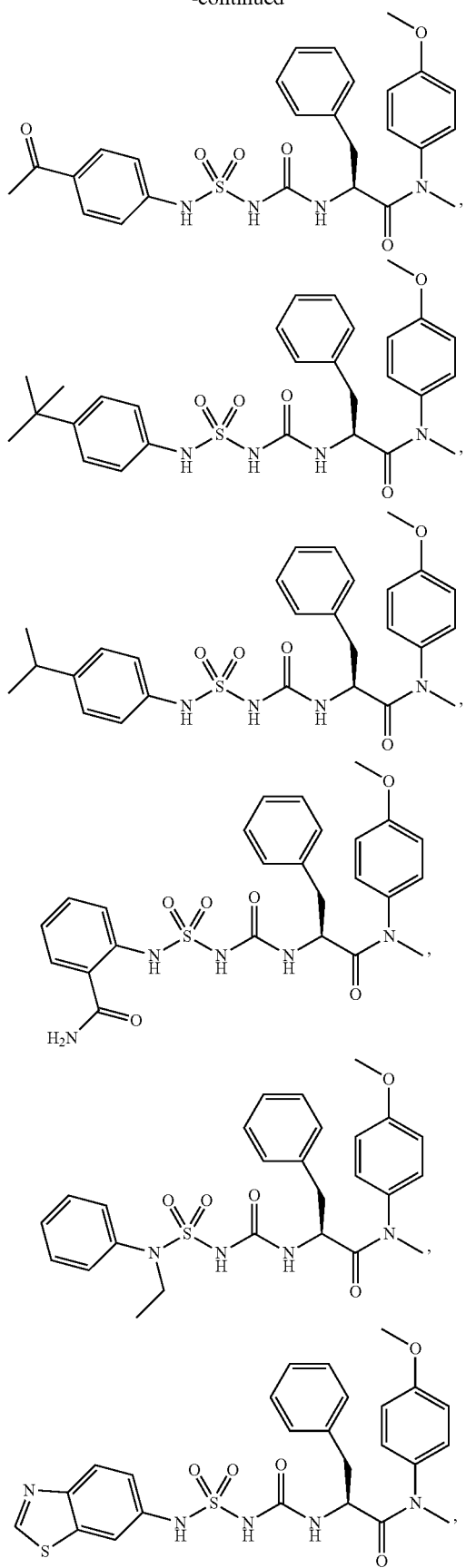

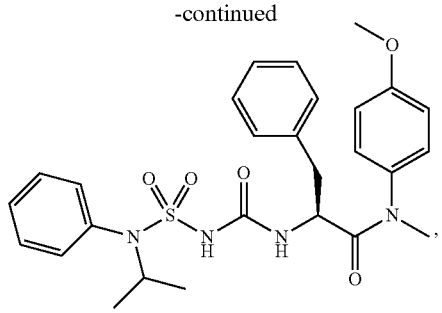
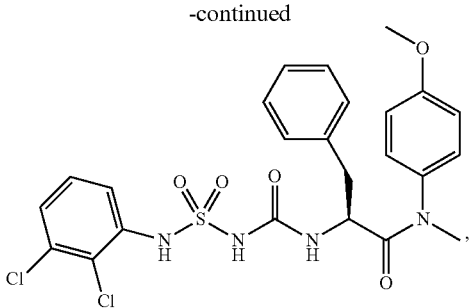
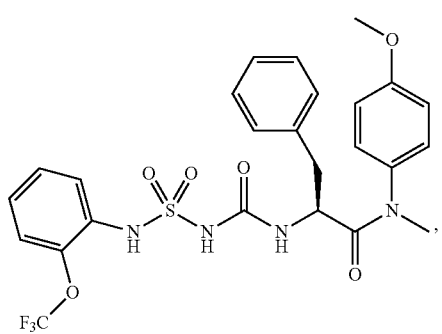
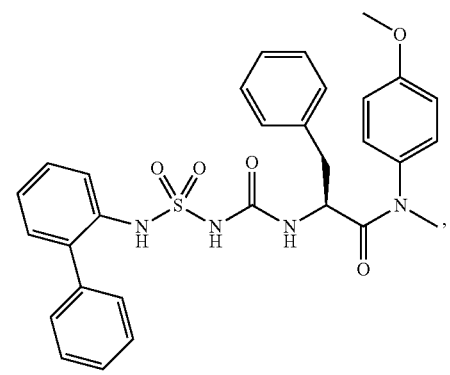
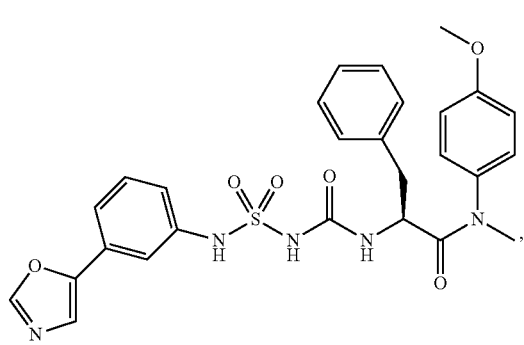
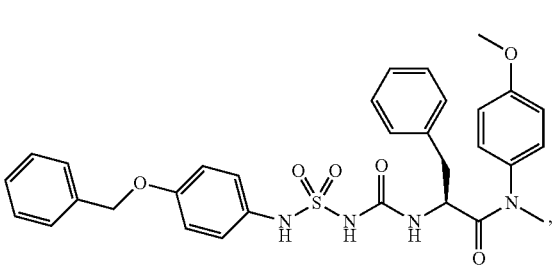
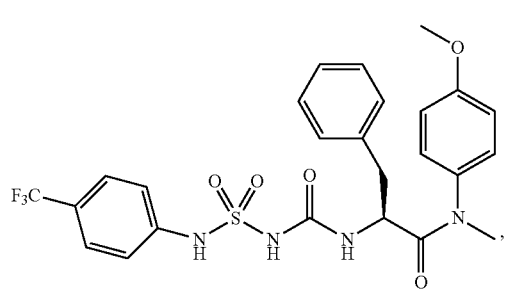
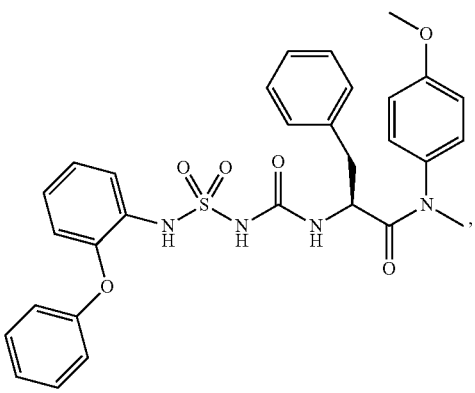
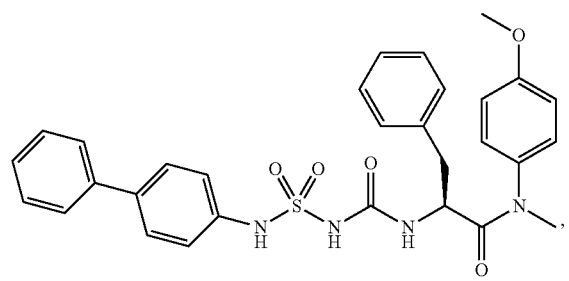
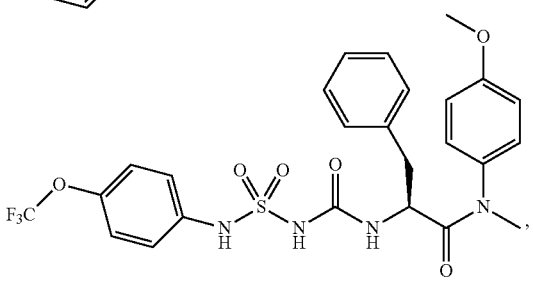

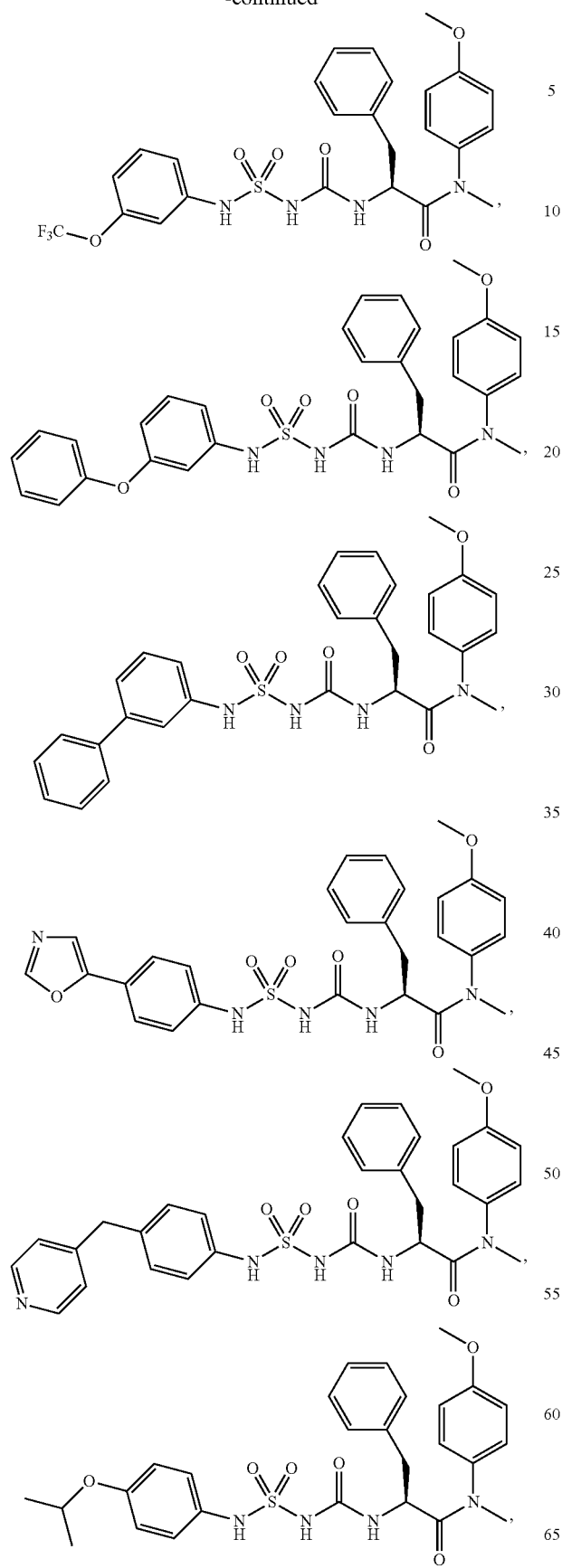
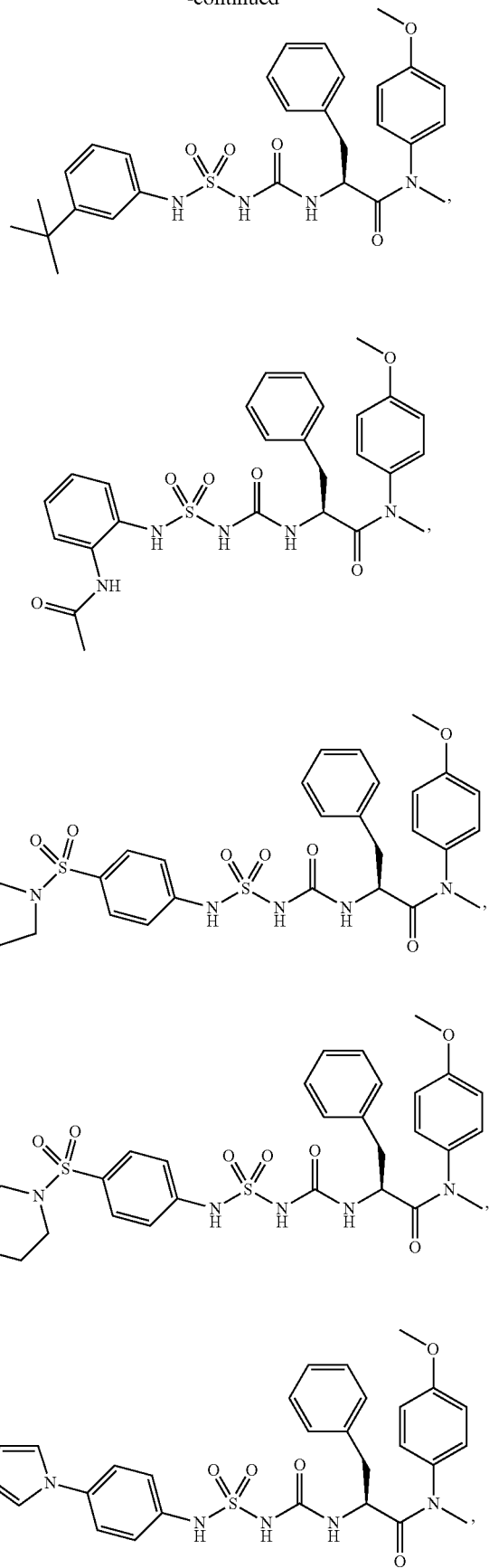

33
-continued
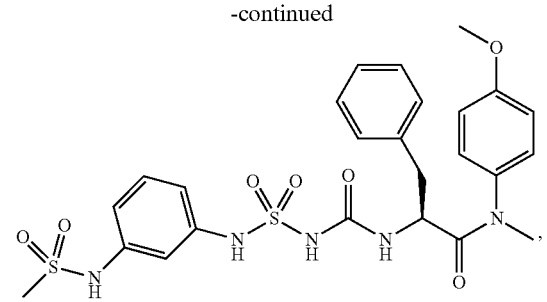
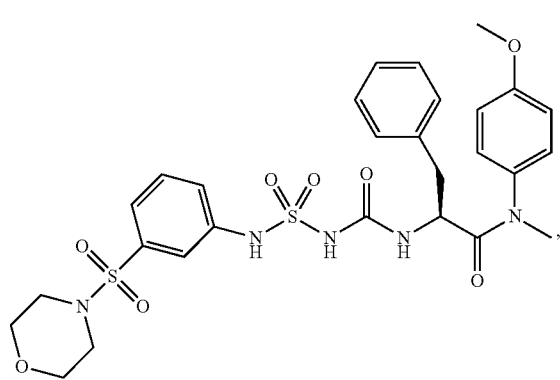
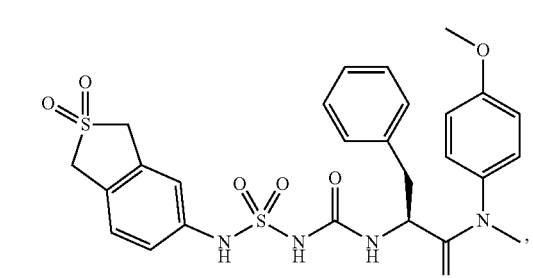
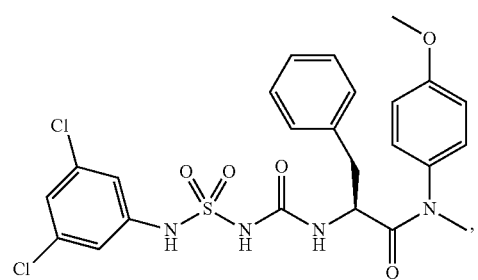
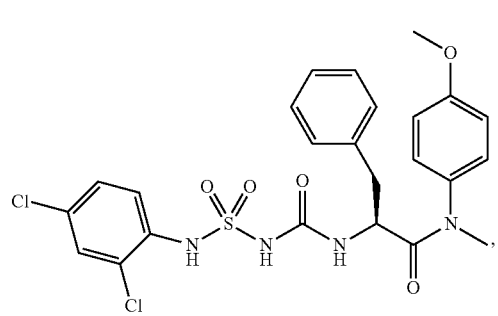
34
-continued
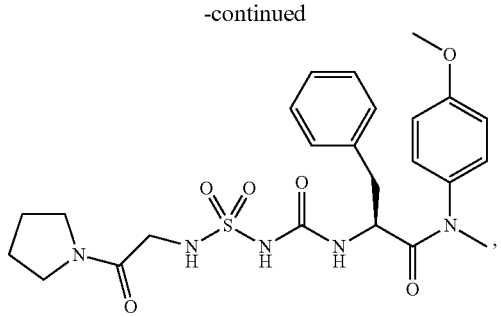
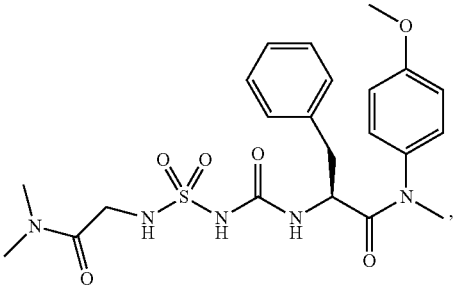
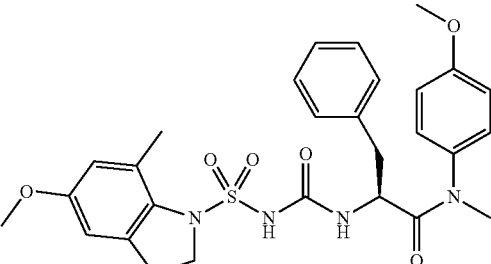
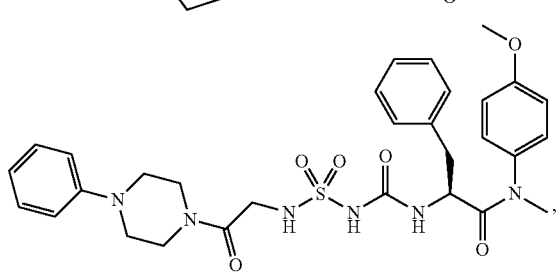
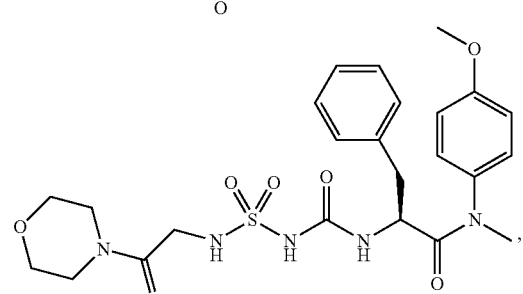
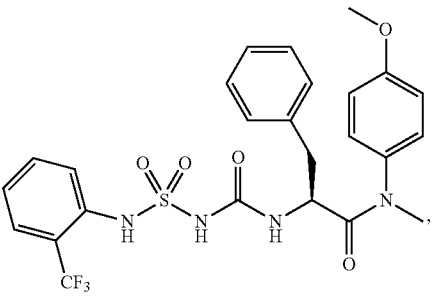

35
-continued
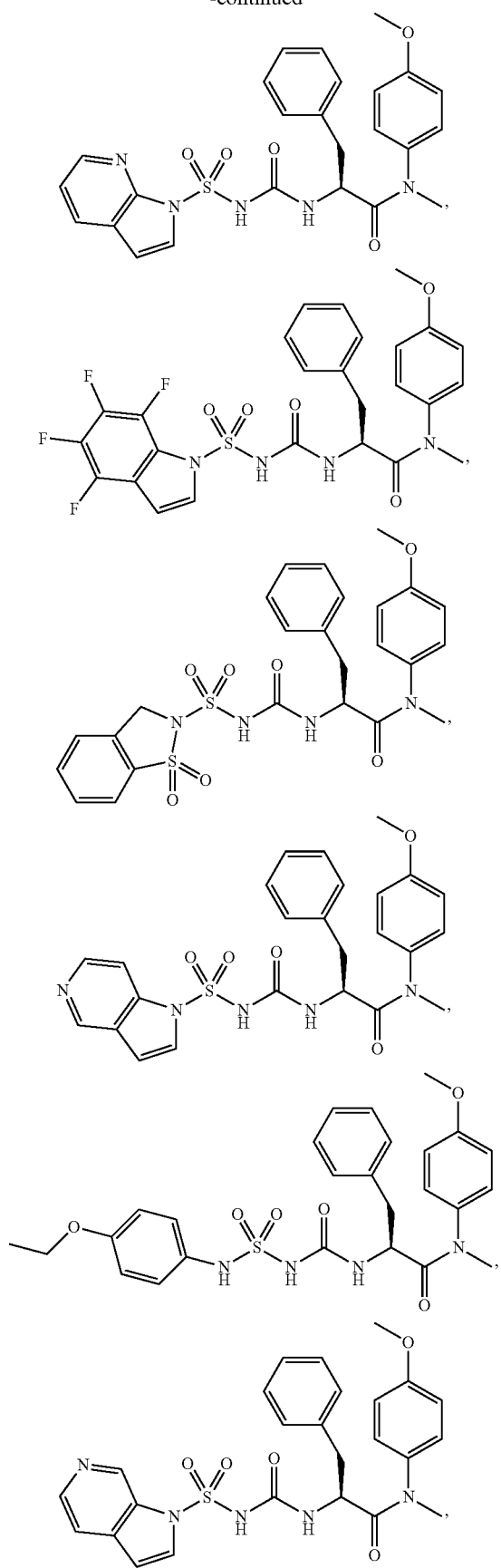
36
-continued
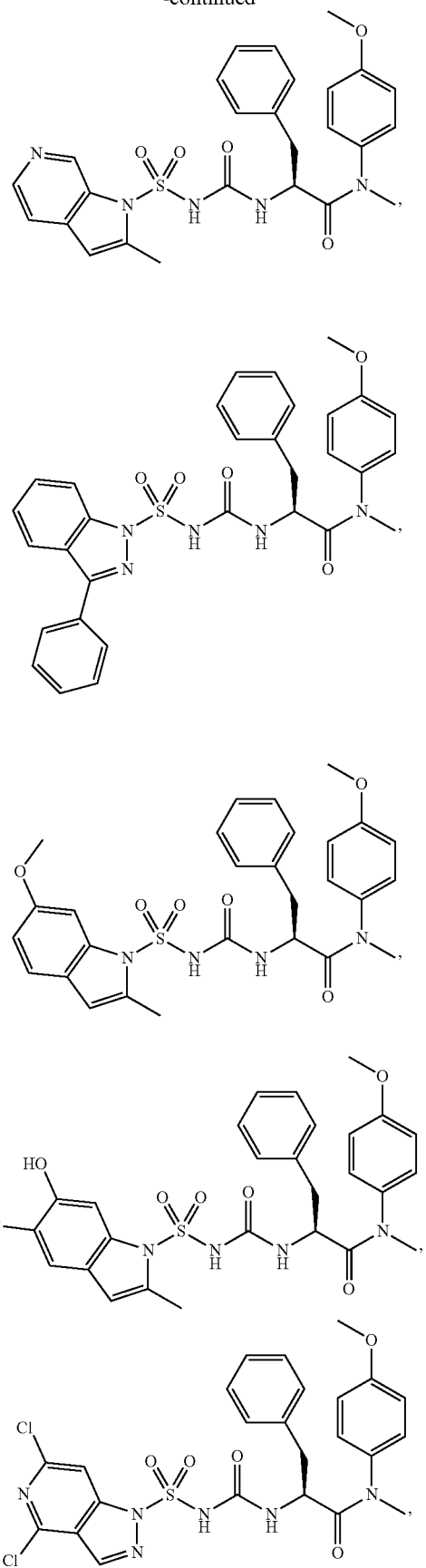

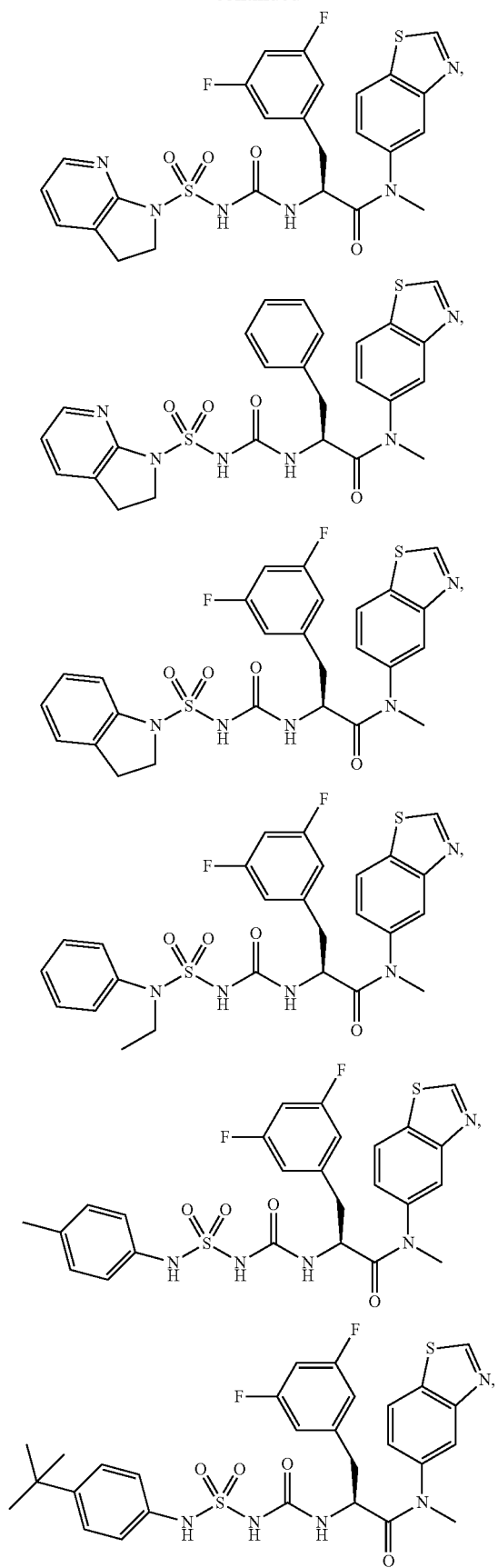
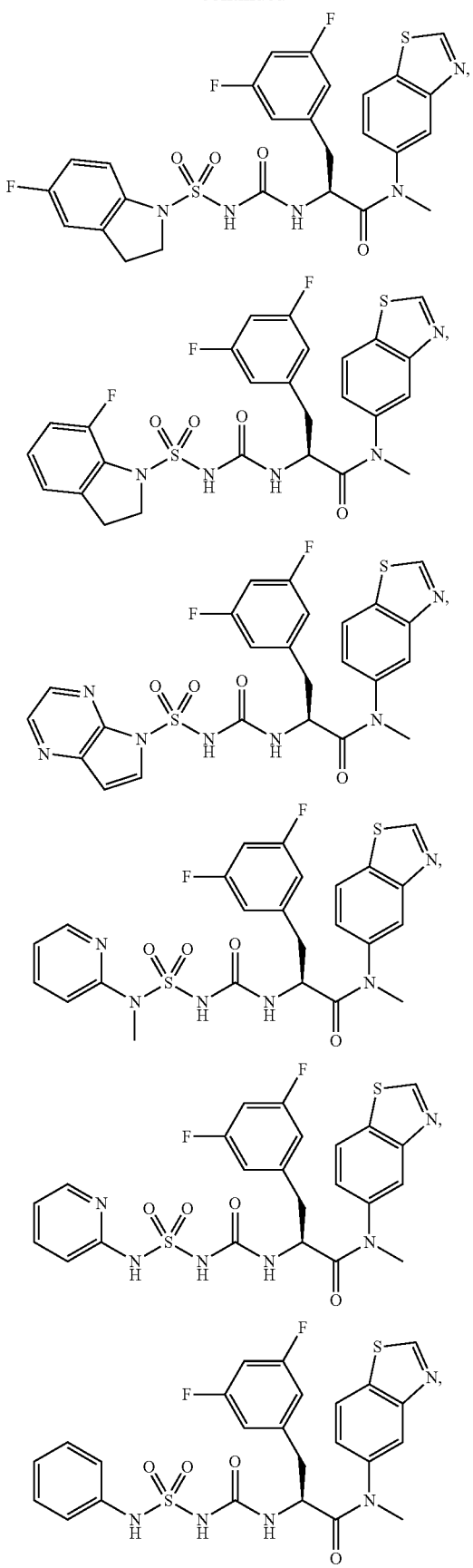

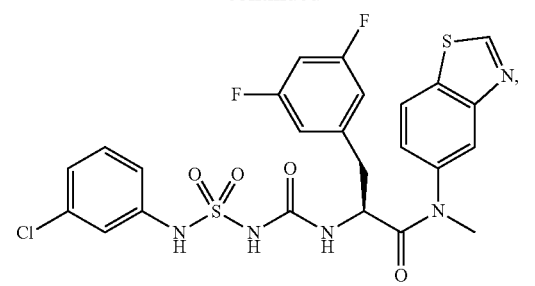
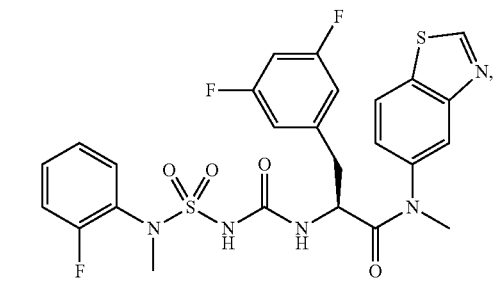
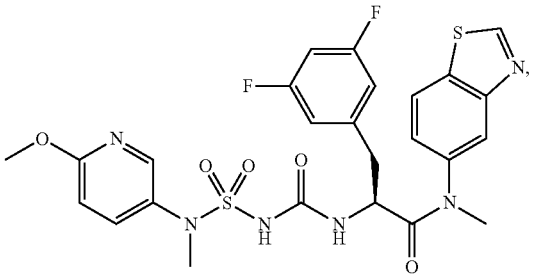
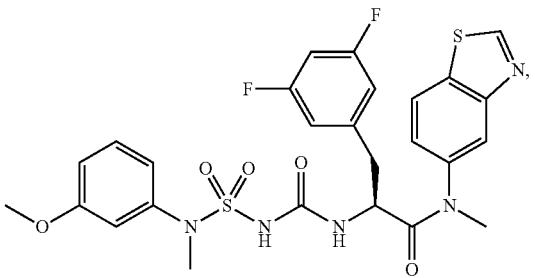
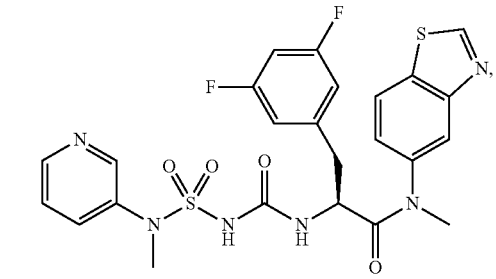
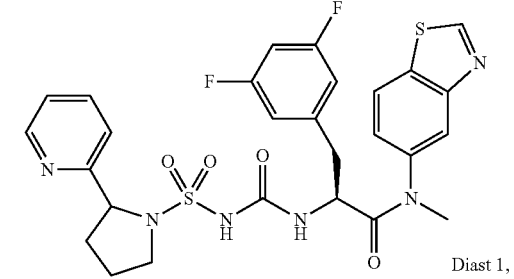
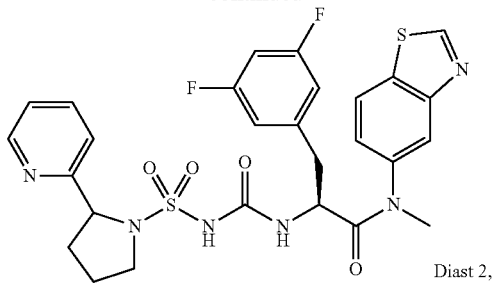
Diast 2,
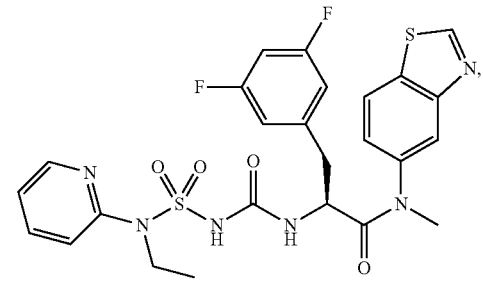
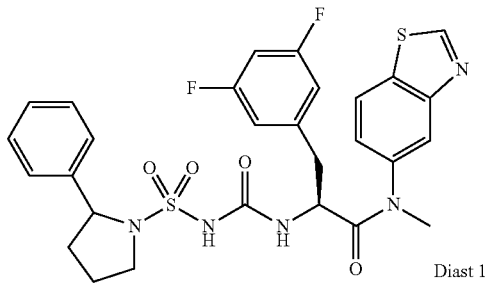
Diast 1,
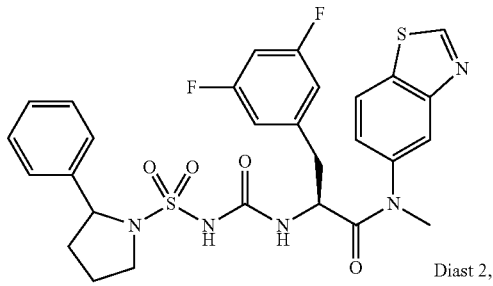
Diast 2,
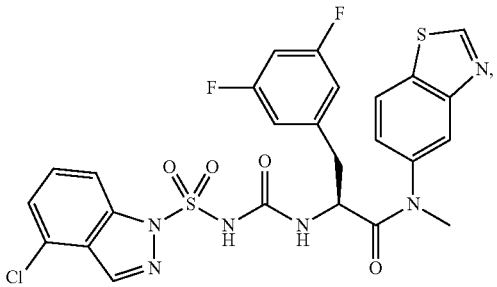
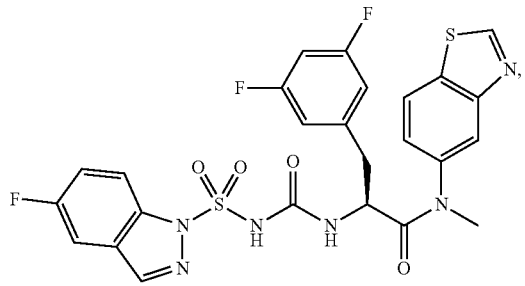

41
-continued
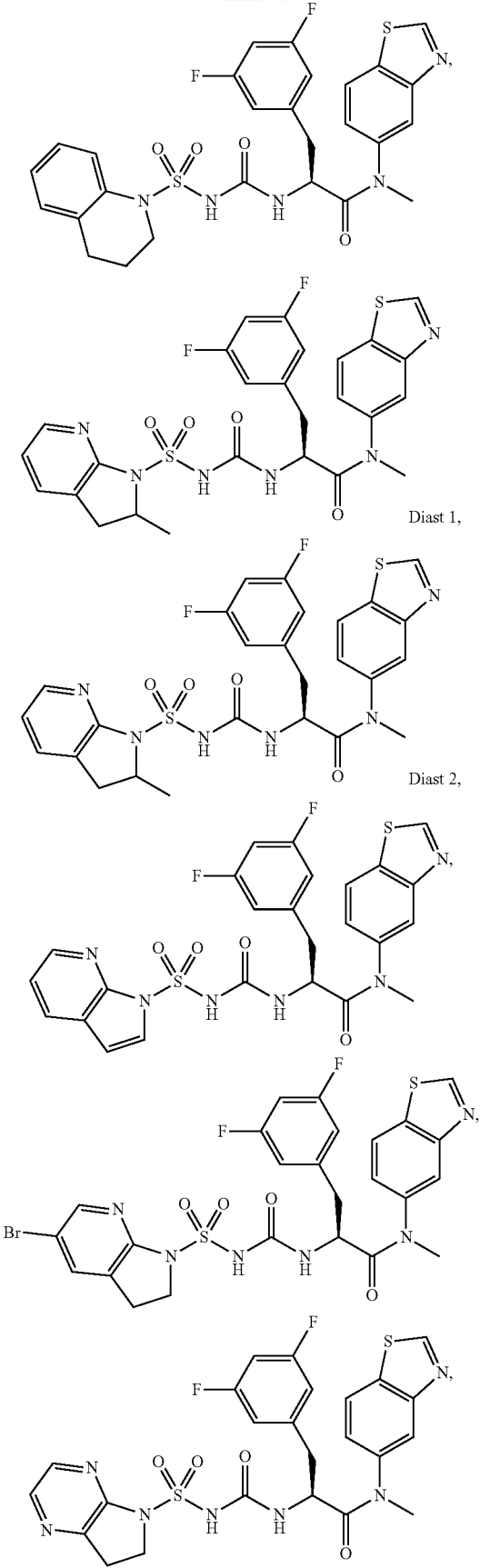
42
-continued
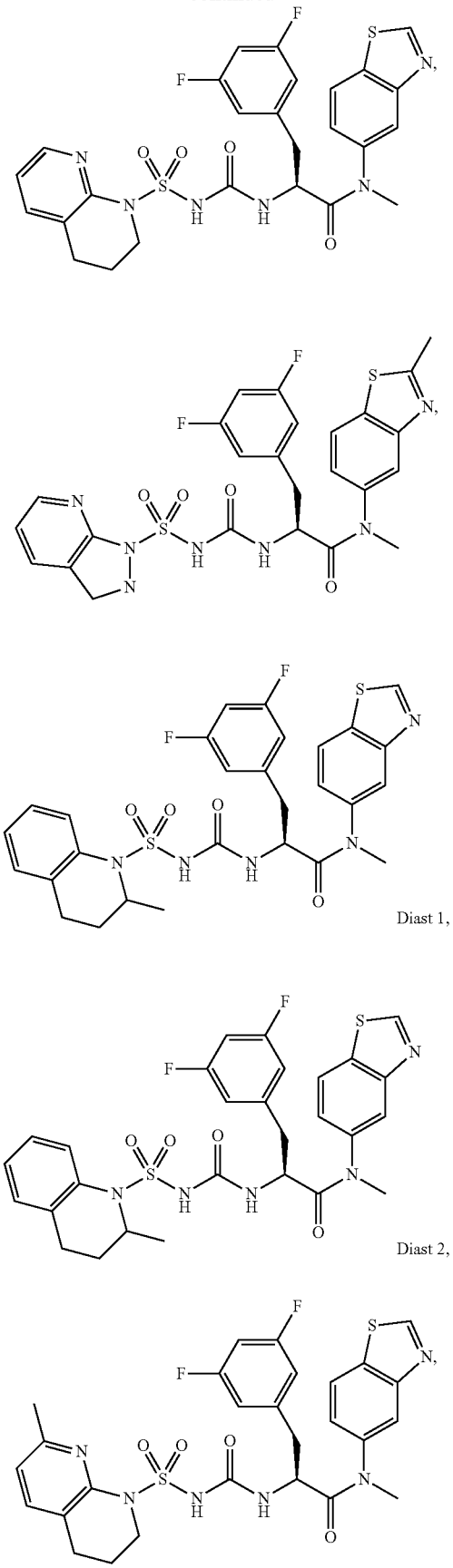

43
-continued
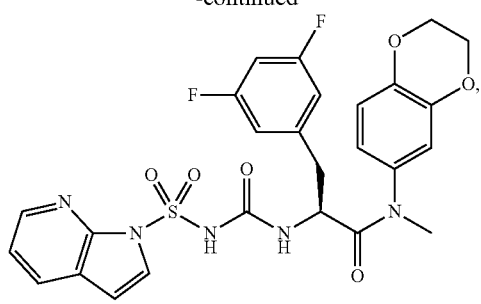
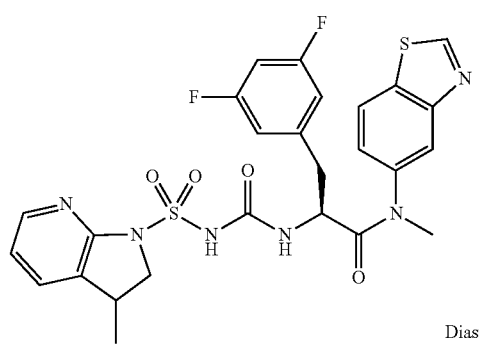
Diast 1,
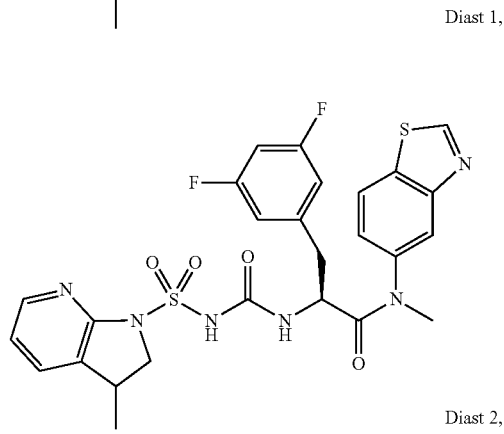
Diast 2,
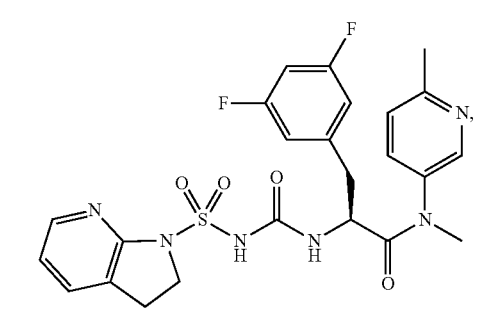
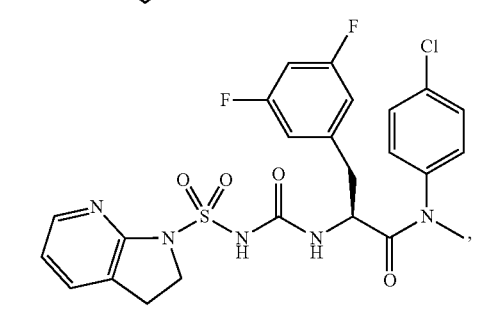
44
-continued
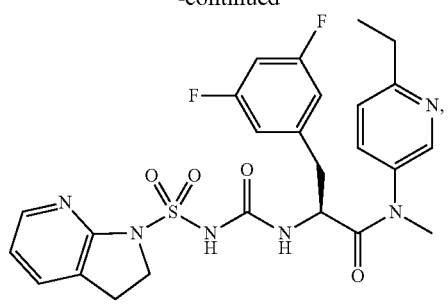
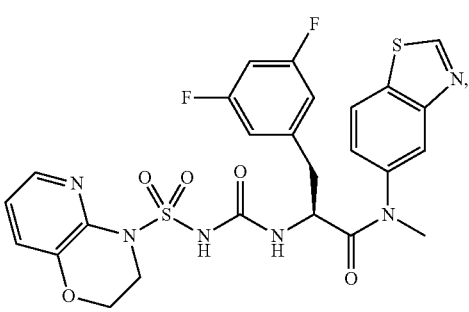
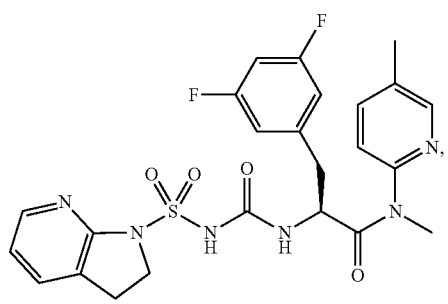
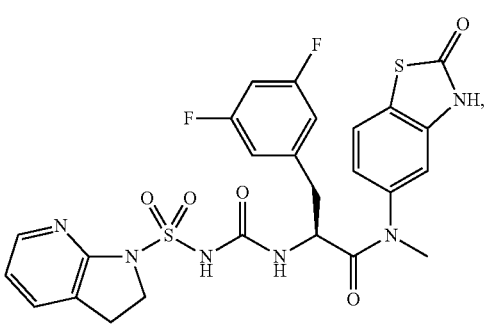
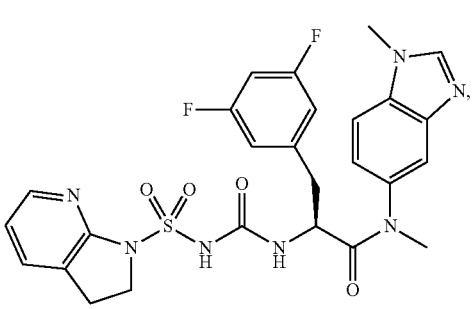

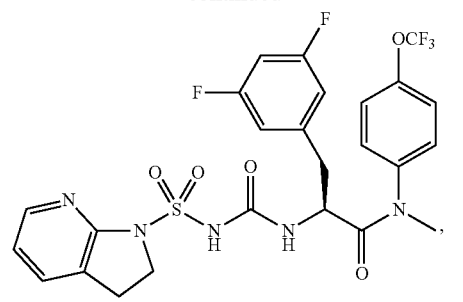
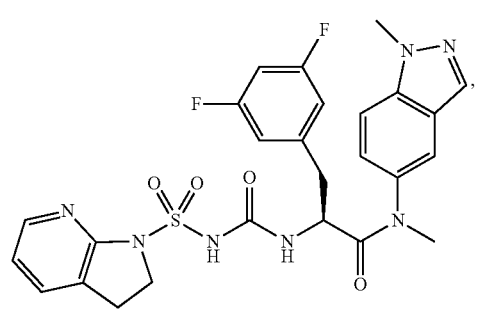
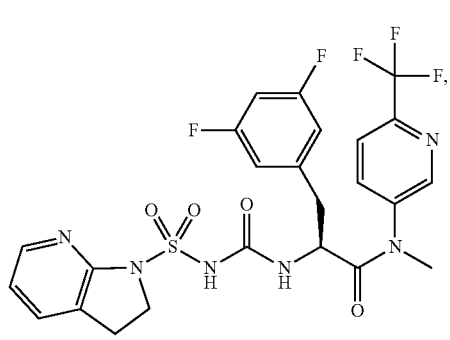
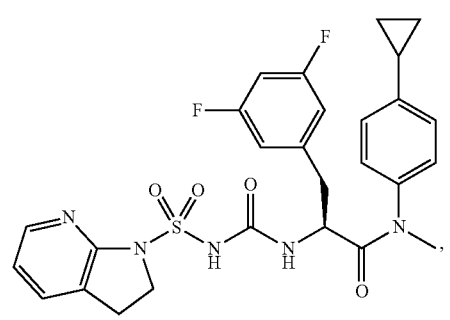
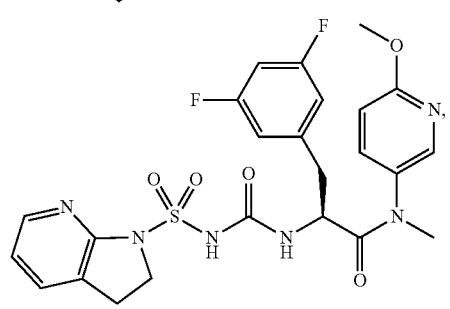
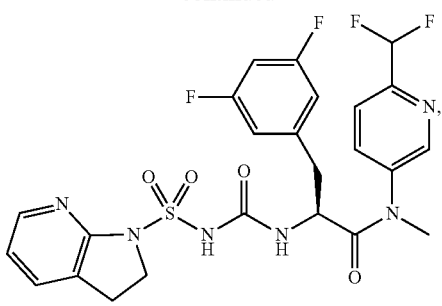
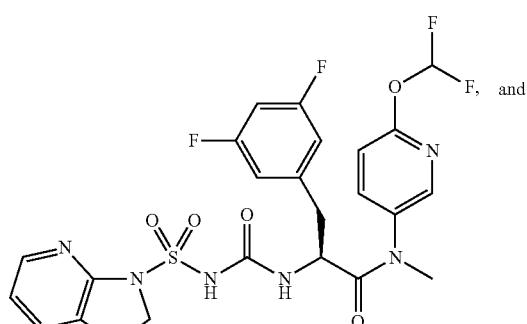
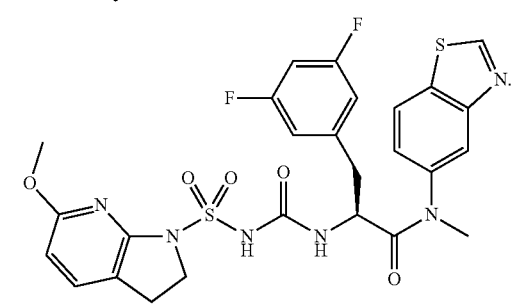
"Diast 1" and "Diast 2" refer to Diastereomer 1 and Diastereomer 2, respectively.
Other preferred compounds, including pharmaceutically acceptable salts thereof, are selected from:
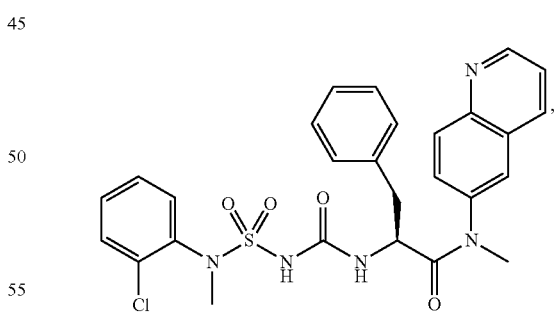
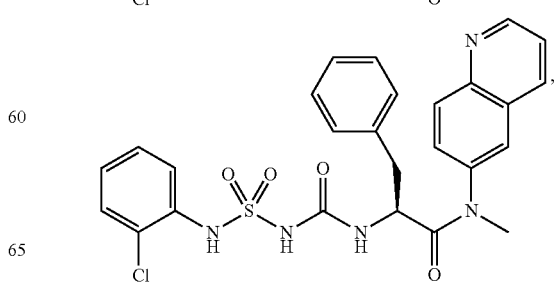

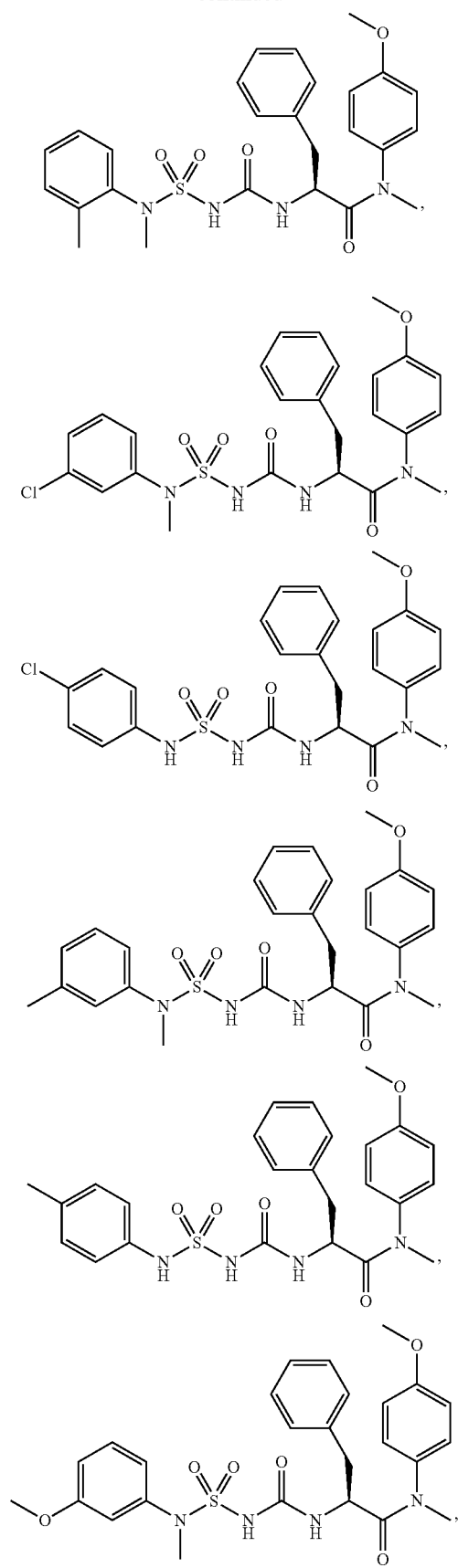
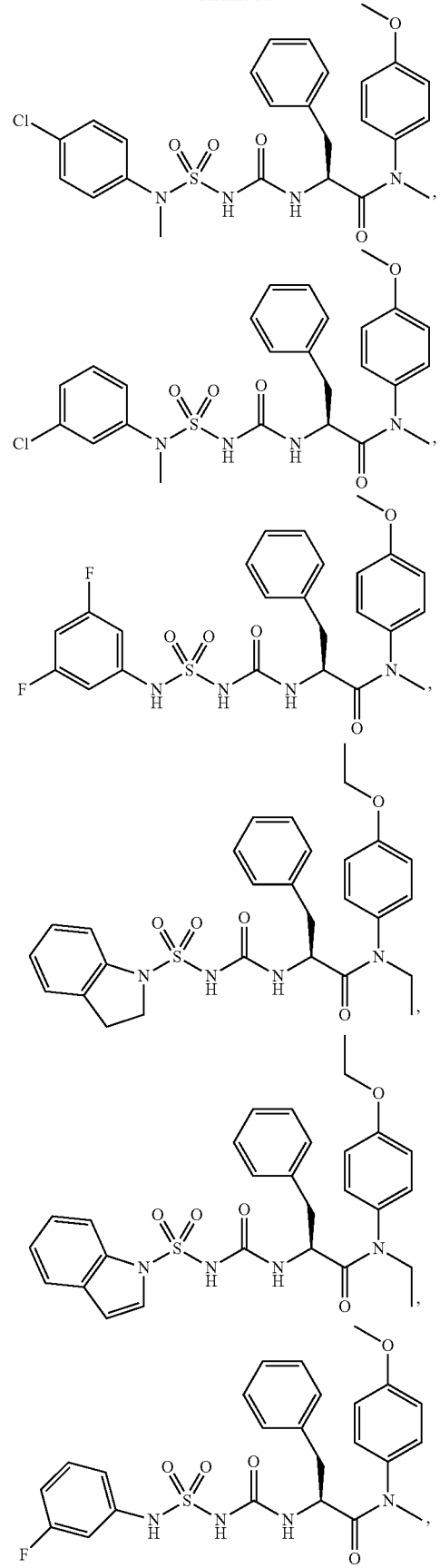

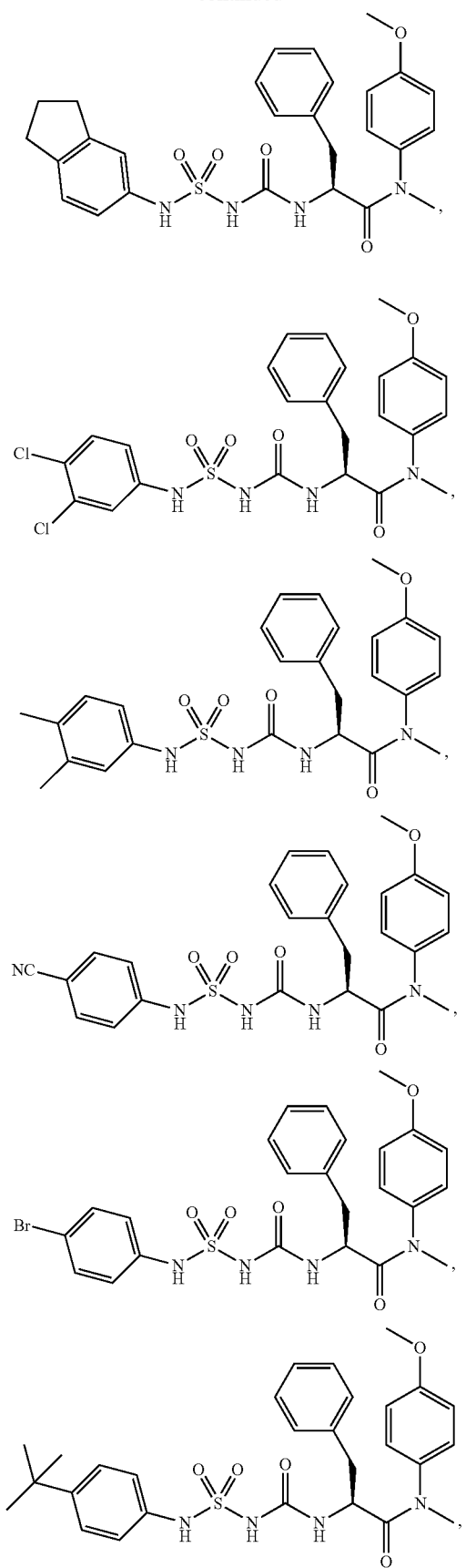
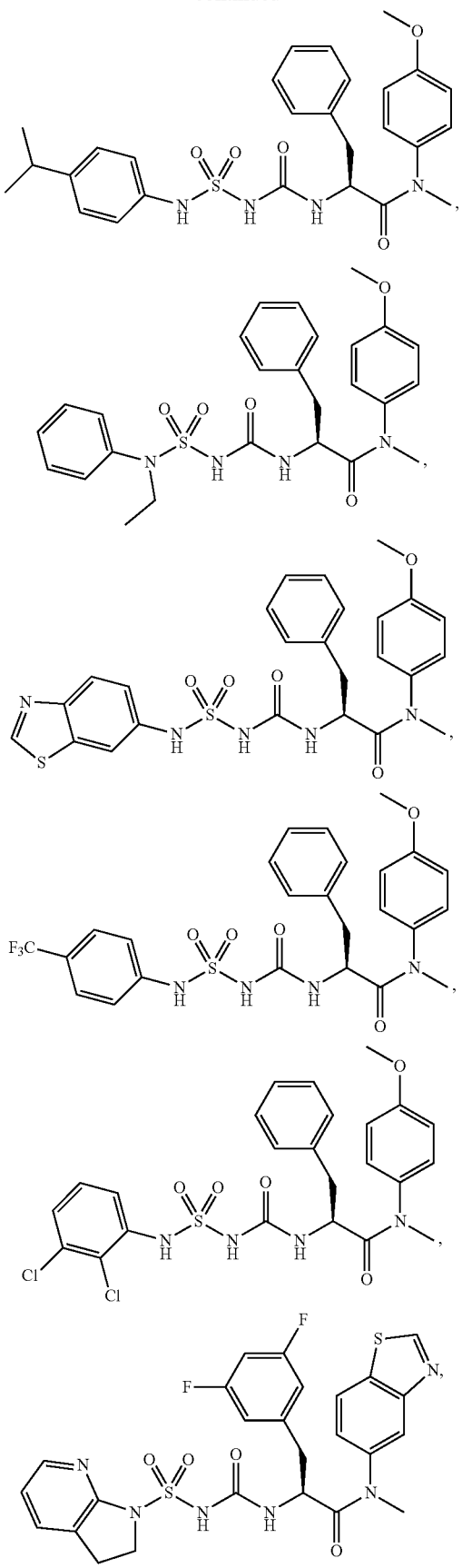

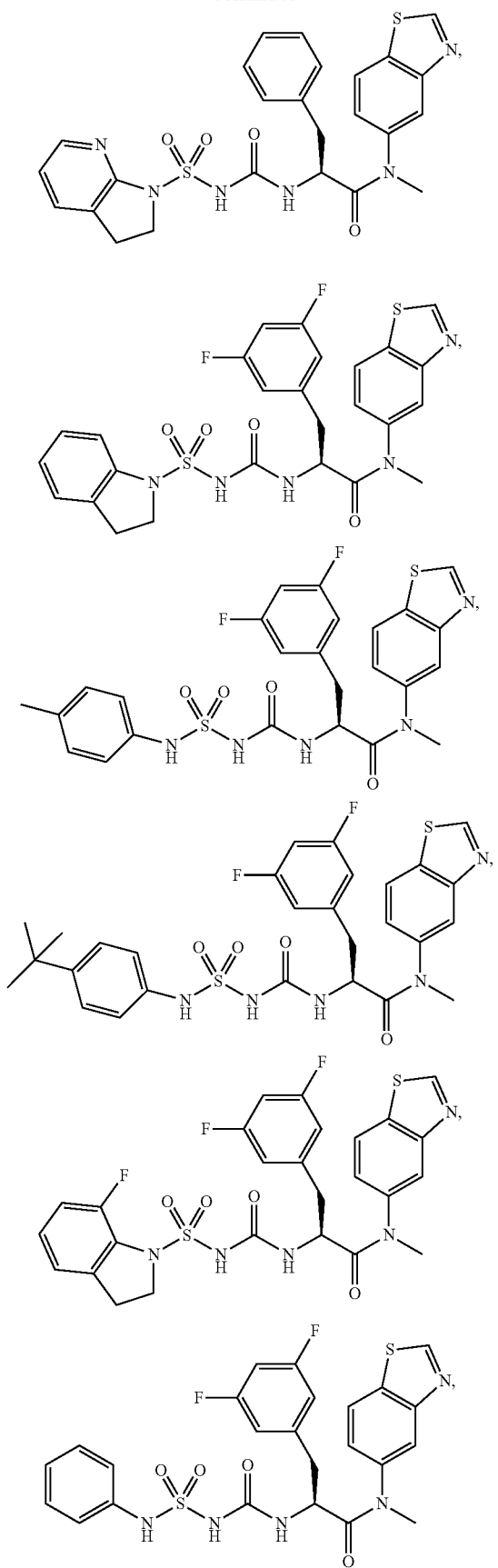
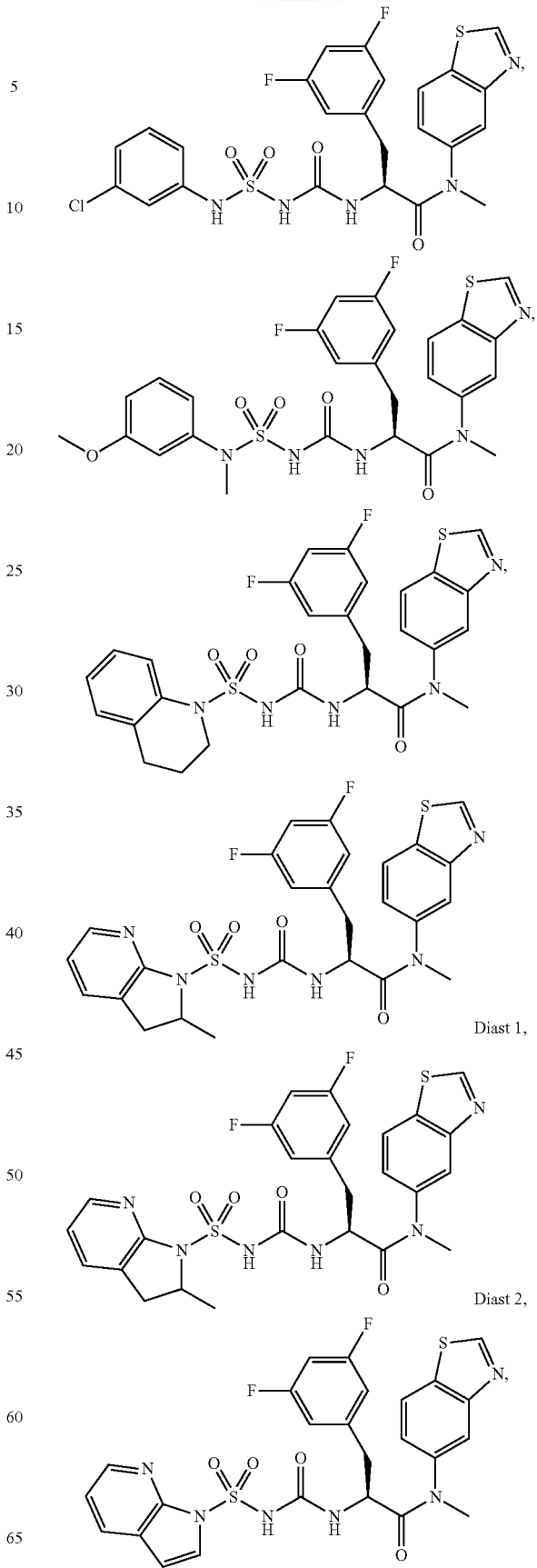

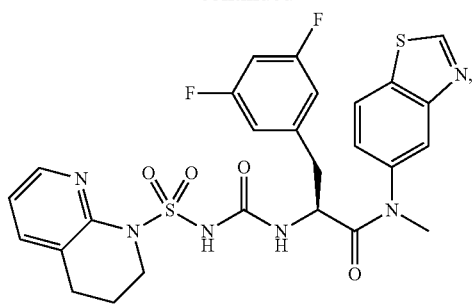
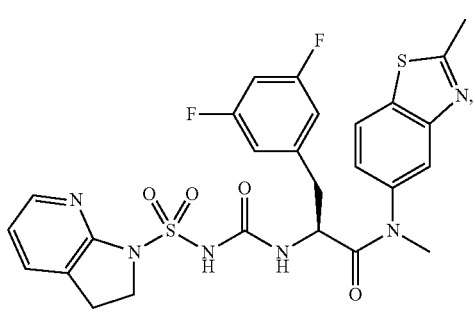
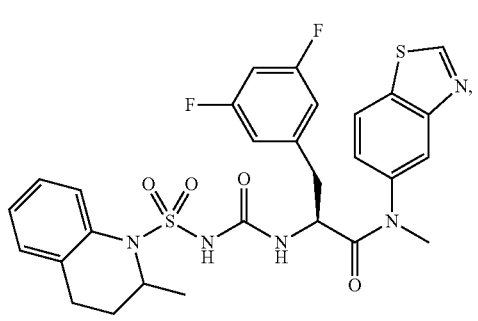
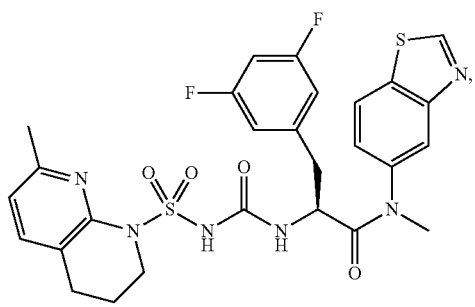
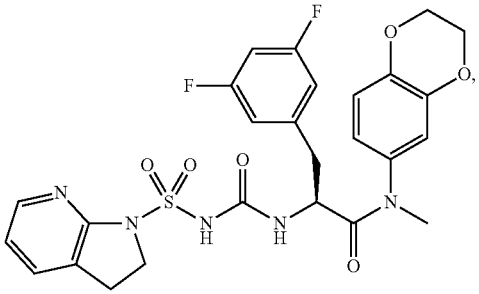
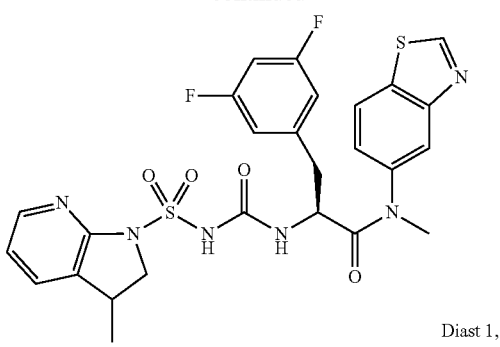
Diast 1,
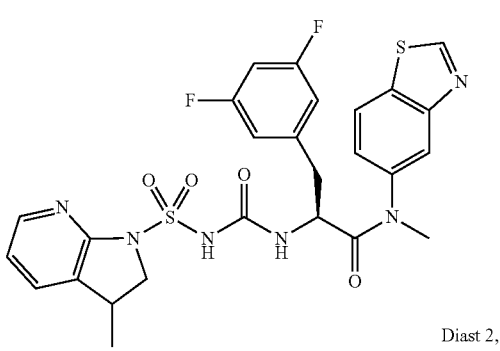
Diast 2,
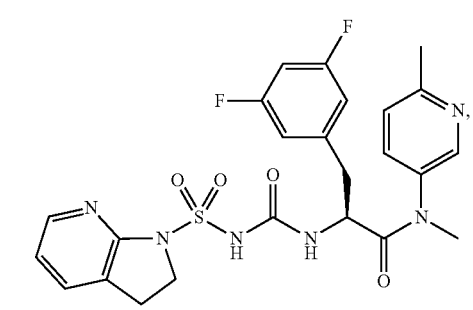
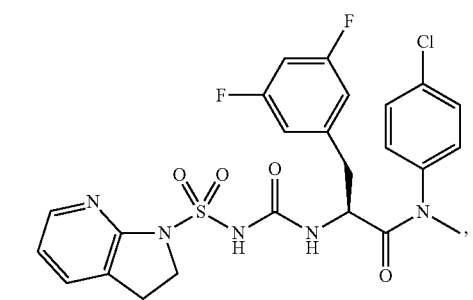
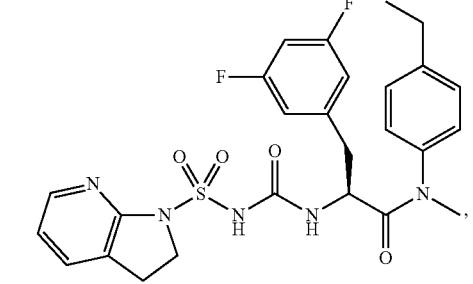

-continued

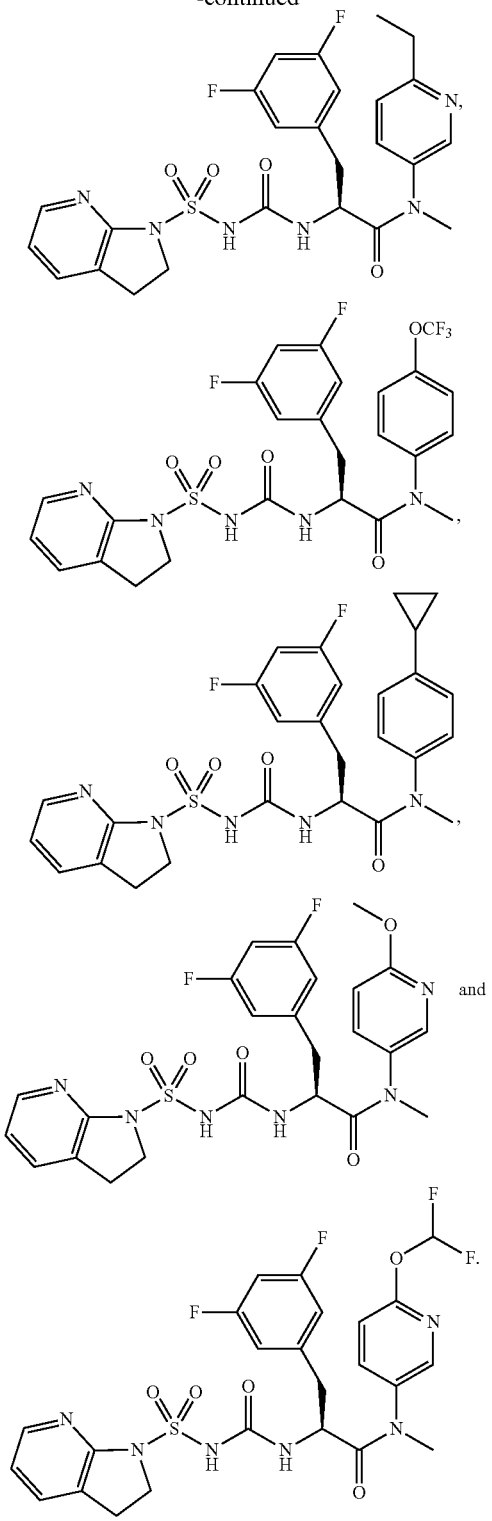

Pharmaceutical Compositions and Methods of Use

The compounds of the invention herein described and set forth are generally given as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 mg/kg body weight daily. Generally, more compound is required orally and less parenterally. The specific dosing regimen, however, will be determined by a physician using sound medical judgment.

The compounds of this invention desirably have activity against HIV. Accordingly, another aspect of the invention is a method for treating HIV infection in a human patient comprising administering a therapeutically effective amount of a compound of Formula I, including a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

"Combination," "coadministration," "concurrent" and similar terms referring to the administration of a compound of Formula I with at least one anti-HIV agent mean that the components are part of a combination antiretroviral therapy or HAART as understood by practitioners in the field of AIDS and HIV infection.

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| ANTIVIRALS | | |
|---|---|---|
| Drug Name | Manufacturer | Indication |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |

ANTIVIRALS

| Drug Name | Manufacturer | Indication |
|---|---|---|
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |

-continued

| ANTIVIRALS | | |
|---|---|---|
| Drug Name | Manufacturer | Indication |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |

ANTIVIRALS

| Drug Name | Manufacturer | Indication |
| --- | --- | --- |
| FESTINAVIR® | Oncolys BioPharma | HIV infection<br>AIDs<br>in development |
| CMX-157<br>Lipid conjugate of<br>nucleotide tenofovir | Chimerix | HIV infection<br>AIDs |
| GSK1349572<br>Integrase inhibitor | GSK | HIV infection<br>AIDs |

IMMUNOMODULATORS

| Drug Name | Manufacturer | Indication |
| --- | --- | --- |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
| --- | --- | --- |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

"Therapeutically effective" means the amount of agent required to provide a meaningful patient benefit as understood by practitioners in the field of AIDS and HIV infection. In general, the goals of therapeutically effective treatment include suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

Methods of Synthesis

The compounds of the invention according to the various aspects can be made by various methods available in the art, including those of the following schemes in the specific examples which follow. The structure numbering and variable numbering shown in the synthetic schemes may be distinct from, and should not be confused with, the structure or variable numbering in the claims or the rest of the specification. The variables in the schemes are meant only to illustrate how to make some of the compounds of the invention.

Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

EXAMPLES

The following examples are provided by way of illustration only, and should not be construed as limiting the scope of the invention.

Intermediate JB-1

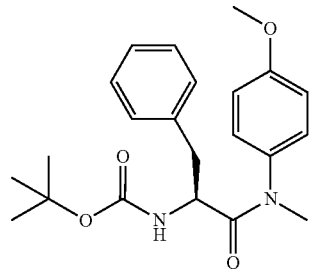 [SMILES: COc1ccc(N(C)C(=O)[C@H](Cc2ccccc2)NC(=O)OC(C)(C)C)cc1]

HATU (1.5 g, 4.0 mmol) was added to a stirred solution of 4-methoxy-N-methylaniline (500 mg, 3.64 mmol) and (S)-2-((tert-butoxycarbonyl)amino)-3-phenylpropanoic acid (1.06 g, 4.0 mmol) in DMF (20 mL) and DIPEA (1.3 mL, 7.3 mmol) and the reaction mixture was stirred at rt for 4 h. The reaction was concentrated and the residual crude oil was partitioned between EtOAc (~60 mL) and ½ sat. NaHCO$_3$ (aq) (~60 mL). The organic component was washed with brine (~40 mL), dried (MgSO$_4$), filtered, concentrated and purified using a Biotage Horizon (80 g SiO$_2$, 10-40% EtOAc/hexanes) to yield Intermediate JB-1 (1.34 g) as a clear amber viscous oil. LC-MS retention time=3.17 min; m/z=385.3 [M+H]$^+$. (Column: Phenonenex-Luna C18 2.0× 50 mm 3 μm. Solvent A=95% Water: 5% Acetonitrile: 10 mM NH$_4$OAc. Solvent B=5% Water: 95% Acetonitrile: 10 mM NH$_4$OAc. Flow Rate=0.8 mL/min. Start % B=0. Final % B=100. Gradient Time=4 min. Wavelength=220). $^1$H NMR (400 MHz, CDCl$_3$) δ 7.25-7.20 (m, 3H), 7.03-6.64 (m, 6H), 5.20 (d, J=8.8 Hz, 1H), 4.53 (app q, J=7.4 Hz, 1H), 3.83 (s, 3H), 3.18 (s, 3H), 2.89 (dd, J=13.1, 7.5 Hz, 1H), 2.71 (dd, J=13.1, 6.5 Hz, 1H), 1.39 (s, 9H).

Intermediate JB-2

A 4 M HCl (15 mL, 60.0 mmol) in 1,4-dioxane solution was added to a stirred solution of Intermediate JB-1 (1.34 g, 3.49 mmol) in THF (10 mL) and the reaction mixture was stirred at rt for 5 h. The reaction mixture was concentrated to dryness under vacuum to yield an HCl salt of the title compound (1.11 g) as a solidified foam which was used without additional purification. LC-MS retention time=2.33 min; m/z=285.2 [M+H]$^+$. (Column: Phenonenex-Luna C18 2.0×50 mm 3 μm. Solvent A=95% Water: 5% Acetonitrile: 10 mM NH$_4$OAc. Solvent B=5% Water: 95% Acetonitrile: 10 mM NH$_4$OAc. Flow Rate=0.8 mL/min. Start % B=0. Final % B=100. Gradient Time=4 min. Wavelength=220).

Intermediate JB-3

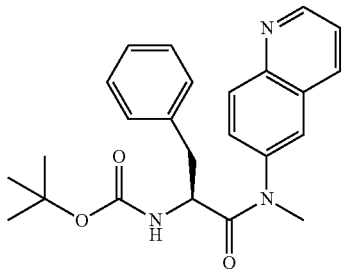 [SMILES: CN(C(=O)[C@H](Cc1ccccc1)NC(=O)OC(C)(C)C)c1ccc2ncccc2c1]

HATU (378 mg, 0.994 mmol) was added to a stirred solution of N-methylquinolin-6-amine (143 mg, 0.904 mmol) and (S)-2-((tert-butoxycarbonyl)amino)-3-phenylpropanoic acid (264 mg, 0.994 mmol) in DMF (6 mL) and DIPEA (0.32 mL, 1.8 mmol) and the reaction mixture was stirred at rt ON. The reaction mixture was concentrated, partitioned between EtOAc (~25 mL) and ½ sat NaHCO$_3$ (aq) (~20 mL) and the organic component was washed with brine (~15 mL), dried (MgSO$_4$), filtered and concentrated. The residue was then purified using a Biotage Horizon (24 g SiO$_2$, 30-60% EtOAc/hexanes) to yield the title compound (230 mg) as a clear amber viscous oil which solidified upon drying. LC-MS retention time=0.980 min; m/z=406.3 [M+H]$^+$. (Column: Waters Aquity BEH C18 2.1×50 mm 1.7 U. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^1$H NMR (400 MHz, CD$_3$OD) δ 8.97-8.93 (m, 1H), 8.36 (d, J=7.0 Hz, 1H), 8.05 (d, J=9.0 Hz, 1H), 7.67 (dd, J=8.4, 4.4 Hz, 1H), 7.58-7.13 (m, 5H), 6.90 (d, J=5.8 Hz, 2H), 4.40 (br. s., 1H), 3.30 (s, 3H), 3.06-2.92 (m, 1H), 2.74 (d, J=6.3 Hz, 1H), 1.41 (s, 9H).

Intermediate JB-4

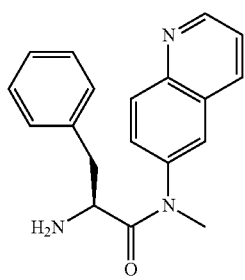 [SMILES: CN(C(=O)[C@@H](N)Cc1ccccc1)c1ccc2ncccc2c1]

A 4 M HCl (2.5 mL, 10 mmol) in 1,4-dioxane solution was added to a stirred solution of Intermediate JB-3 (225 mg, 0.555 mmol) in THF (2 mL) and the reaction mixture was stirred at rt ON. The reaction mixture was concentrated to dryness under vacuum to yield an HCl salt of the title compound (211 mg) as a solidified amber foam which was used without additional purification. LC-MS retention time=0.749 min; m/z=306.2 [M+H]$^+$. (Column: Waters Aquity BEH C18 2.1×50 mm 1.7 U. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate JB-5

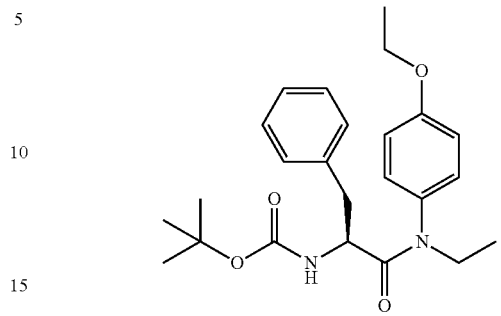

HATU (725 mg, 1.91 mmol) was added to a stirred solution of 4-ethoxy-N-ethylaniline (300 mg, 1.82 mmol) and (S)-2-((tert-butoxycarbonyl)amino)-3-phenylpropanoic acid (506 mg, 1.91 mmol) in DMF (10 mL) and DIPEA (0.63 mL, 3.6 mmol) and the reaction mixture was stirred at rt for 5 h. The reaction mixture was concentrated, partitioned between EtOAc (~60 mL) and sat. NaHCO$_3$ (aq) (~50 mL) and the organic component was washed with brine (~50 mL), dried (MgSO$_4$), filtered and concentrated. The residue was then purified using a Biotage Horizon (40 g SiO$_2$, 15-40% EtOAc/hexanes) to yield Intermediate JB-5 (632 mg) as a solidified off-white foam. LC-MS retention time=1.69 min; m/z=413.3 [M+H]$^+$. (Column: Phenomenex Luna 30×2.0 MM 3 u. Solvent A=90% Water: 10% Acetonitrile: 0.1% TFA. Solvent B=10% Water: 90% Acetonitrile: 0.1% TFA. Flow Rate=1 mL/min. Start % B=0. Final % B=100. Gradient Time=2 minutes. Wavelength=220). $^1$H NMR (400 MHz, CDCl$_3$) δ 7.26-7.19 (m, 3H), 7.04-6.77 (m, 6H), 5.19 (d, J=8.3 Hz, 1H), 4.48-4.37 (m, 1H), 4.10-4.01 (m, 2H), 3.80-3.70 (m, 1H), 3.60-3.48 (m, 1H), 2.91 (dd, J=13.2, 7.4 Hz, 1H), 2.71 (dd, J=12.5, 6.5 Hz, 1H), 1.44 (t, J=7.0 Hz, 3H), 1.38 (s, 9H), 1.05 (t, J=7.2 Hz, 3H).

Intermediate JB-6

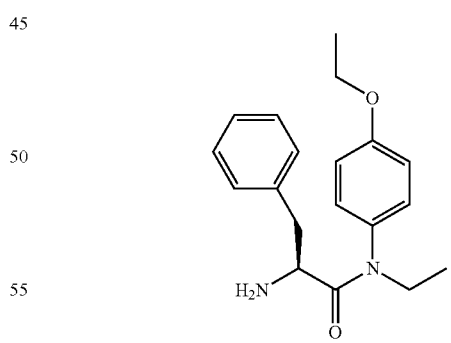

A solution of 4 M HCl (1.036 mL, 4.15 mmol) in 1,4-dioxane was added to a stirred solution of Intermediate JB-5 (684 mg, 1.66 mmol) in THF (2.2 mL) and the reaction mixture was stirred at rt for 5 h. Then additional 4 M HCl in 1,4-dioxane (1.5 mL) was added and stirring continued ON. The reaction mixture was concentrated and the residue was dried under high vacuum to yield and HCl salt of Intermediate JB-6 (632 mg) as a solidified foam. LC-MS retention time=1.24 min; m/z=313.3 [M+H]$^+$. (Column:

Phenomenex Luna 30×2.0 MM 3 u. Solvent A=90% Water: 10% Acetonitrile: 0.1% TFA. Solvent B=10% Water: 90% Acetonitrile: 0.1% TFA. Flow Rate=1 mL/min. Start % B=0. Final % B=100. Gradient Time=2 minutes. Wavelength=220). $^{1}$H NMR (400 MHz, CDCl$_{3}$) δ 7.35-7.25 (m, 5H), 7.10 (d, J=6.0 Hz, 2H), 6.77 (br. s., 2H), 4.15 (br. s., 1H), 3.99 (q, J=6.8 Hz, 2H), 3.79-3.70 (m, 1H), 3.57-3.47 (m, 1H), 3.27-3.11 (m, 2H), 1.41 (t, J=6.8 Hz, 3H), 1.06 (t, J=6.9 Hz, 3H).

Intermediate ZY-1

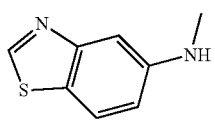

Paraformaldehyde (80 mg, 2.7 mmol) was added to a stirred solution of benzo[d]thiazol-5-amine (200 mg, 1.332 mmol) in MeOH (5 mL). The resulting suspension was then treated with 25% w/w NaOMe in MeOH (1.5 mL, 6.7 mmol) and the clear reaction mixture was stirred at 60° C. for 16 h. The reaction was allowed to cool to rt and then treated with NaBH$_{4}$ (126 mg, 3.33 mmol) and stirred at rt for 16 h. The reaction mixture was diluted with water (10 mL) and extracted with CHCl$_{3}$ (3×20 mL). The combined organic component was concentrated and purified using a Biotage Horizon (12 g SiO$_{2}$, 0-50% EtOAc/hexanes) to yield Intermediate ZY-1 (217 mg) as yellow gum. LC-MS retention time=0.67 min; m/z=165.05 [M+H]$^{+}$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^{1}$H NMR (400 MHz, CDCl$_{3}$) δ 8.92 (s, 1H), 7.69 (d, J=8.5 Hz, 1H), 7.31 (d, J=2.3 Hz, 1H), 6.82 (dd, J=8.8, 2.3 Hz, 1H), 3.93 (br. s., 1H), 2.94 (s, 3H).

Intermediate ZY-2

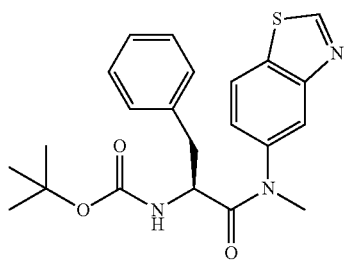 [SMILES: CN(C(=O)[C@H](Cc1ccccc1)NC(=O)OC(C)(C)C)c1ccc2scnc2c1]

HATU (1.90 g, 5.01 mmol) was added to a solution of Intermediate ZY-1 (685 mg, 4.17 mmol) and (S)-2-((tert-butoxycarbonyl)amino)-3-phenylpropanoic acid (1.33 g, 5.01 mmol) in DMF (20 mL) and DIPEA (2.18 mL, 12.5 mmol) and the reaction mixture was stirred at rt for 6 h. The crude reaction mixture was diluted with sat. aq. NaHCO$_{3}$ (20 mL) and extracted with EtOAc (3×50 mL). The combined organic component was washed with brine (~60 mL), dried (Na$_{2}$SO$_{4}$), filtered and concentrated. The crude material was then purified using a Biotage Horizon (12 g SiO$_{2}$, 0-40%-50% EtOAc/hexanes) to yield Intermediate ZY-2 (1.7 g) as a white solid. LC-MS retention time=1.19 min; m/z=412.0 [M+H]$^{+}$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^{1}$H NMR (400 MHz, CDCl$_{3}$) δ 9.07 (s, 1H), 7.90 (d, J=8.3 Hz, 1H), 7.38 (d, J=7.5 Hz, 1H), 7.27-7.19 (m, 3H), 6.94 (d, J=6.8 Hz, 3H), 5.22 (d, J=8.8 Hz, 1H), 4.58-4.48 (m, 1H), 3.26 (s, 3H), 2.93 (dd, J=12.9, 8.4 Hz, 1H), 2.78 (dd, J=12.4, 5.9 Hz, 1H), 1.40 (s, 9H).

Intermediate ZY-3

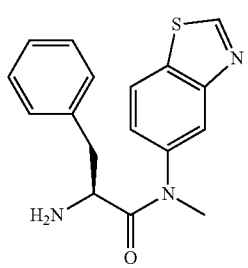 [SMILES: CN(C(=O)[C@@H](N)Cc1ccccc1)c1ccc2scnc2c1]

A solution of 4 M HCl (10 mL, 40.0 mmol) in 1,4-dioxane was added to a stirred solution of Intermediate ZY-2 (1.7 g, 4.13 mmol) in THF (10 mL) and the reaction mixture was stirred at rt for 16 h. The reaction mixture was concentrated, redissolved in EtOH/toluene, and then reconcentrated (3×) to yield an HCl salt of Intermediate ZY-3 (1.7 g, 4.42 mmol, 107% yield) as a pink sticky solid. LC-MS retention time=0.83 min; m/z=312.0 [M+H]$^{+}$. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). $^{1}$H NMR (400 MHz, CD$_{3}$OD) δ 9.42 (s, 1H), 8.10 (d, J=8.3 Hz, 1H), 7.39-7.08 (m, 6H), 6.91 (d, J=7.0 Hz, 2H), 4.10 (dd, J=8.0, 6.5 Hz, 1H), 3.63-3.56 (m, 2H), 3.11 (dd, J=13.4, 8.2 Hz, 1H), 2.92 (dd, J=13.3, 6.5 Hz, 1H), 2.87 (s, 3H).

Intermediate ZY-4

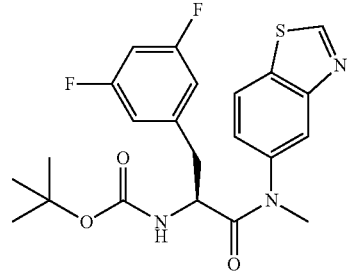 [SMILES: CN(C(=O)[C@H](Cc1cc(F)cc(F)c1)NC(=O)OC(C)(C)C)c1ccc2scnc2c1]

HATU (592 mg, 1.556 mmol) was added to a stirred solution of Intermediate ZY-1 (213 mg, 1.30 mmol) and (S)-2-((tert-butoxycarbonyl)amino)-3-(3,5-difluorophenyl) propanoic acid (469 mg, 1.56 mmol) in DMF (7 mL) and DIPEA (0.45 mL, 2.6 mmol) and the reaction mixture was stirred at rt for 16 h. The crude reaction mixture was diluted with sat. aq. NaHCO$_{3}$ (20 mL) and extracted with EtOAc (3×50 mL). The combined organic component was washed with brine (~60 mL), dried (Na₂SO₄), filtered and concentrated. The crude material was then purified using a Biotage Horizon (24 g SiO₂, 0-50% EtOAc/hexanes) yield Intermediate ZY-4 (581 mg) as a white solid. LC-MS retention time=1.23 min; m/z=448.0 [M+H]⁺. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220). ¹H NMR (400 MHz, CDCl₃) δ 9.10 (s, 1H), 7.98 (d, J=8.3 Hz, 1H), 7.68 (br. s., 1H), 7.05 (br. s., 1H), 6.68 (t, J=8.9 Hz, 1H), 6.44 (d, J=6.3 Hz, 2H), 5.25 (d, J=9.0 Hz, 1H), 4.54 (app q, J=7.3 Hz, 1H), 2.94-2.86 (m, 1H), 2.81 (s, 3H), 2.72 (dd, J=13.1, 6.5 Hz, 1H), 1.39 (s, 9H).

Intermediate ZY-5

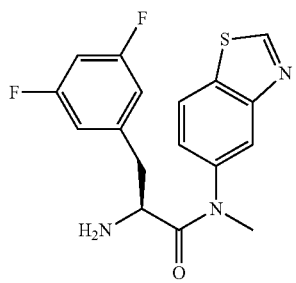 [SMILES: CN(C(=O)[C@@H](N)Cc1cc(F)cc(F)c1)c1ccc2scnc2c1]

TFA (1.0 mL, 13 mmol) was added to a stirred solution of Intermediate ZY-4 (0.58 g, 1.2 mmol) in DCM (2 mL) and the reaction mixture was stirred at rt for 16 h. The crude reaction mixture was concentrated and the residue was dissolved in MeOH/DCM and 4 M HCl in dioxane (2 mL) and reconcentrated. The residue was redissolved in EtOH/toluene, and then reconcentrated (3×) to yield an HCl salt of Intermediate ZY-5 (0.55 g) as a white solid. LC-MS retention time=0.83 min; m/z=348.1 [M+H]⁺. (Column: Waters Aquity BEH C18, 2.0×50 mm, 1.7-μm particles. Solvent A=100% Water: 0.05% TFA. Solvent B=100% Acetonitrile: 0.05% TFA. Flow Rate=0.8 mL/min. Start % B=2. Final % B=98. Gradient Time=1.5 min. Wavelength=220).

Intermediate VN-1

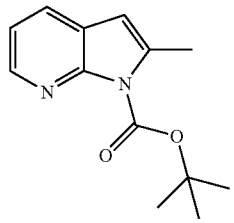 [SMILES: Cc1cc2cccnc2n1C(=O)OC(C)(C)C]

To a solution of 2-methyl-1H-pyrrolo[2,3-b]pyridine (0.5 g, 3.8 mmol) in THF (5 mL) was added DMAP (4.6 mg, 0.04 mmol) followed by the addition of di-tert-butyl dicarbonate (1.25 g, 5.73 mmol). The reaction mixture was stirred at ~25° C. under nitrogen for 3 h. Water (0.1 mL) was added to the reaction and stirring was continued at ~25° C. for 1 h. All solvents were removed in vacuo. The crude product was azeotroped with toluene (2×3 mL) to afford the title compound as a light yellow oil (quantitative yield). The product was used without further purification. ¹H NMR (400 MHz, CDCl₃) δ 8.42 (dd, J=4.8, 1.5 Hz, 1H), 7.73 (dd, J=7.7, 1.6 Hz, 1H), 7.13 (dd, J=7.7, 4.9 Hz, 1H), 6.29-6.16 (m, 1H), 2.59 (d, J=1.0 Hz, 3H), 1.69 (s, 9H).

Intermediate VN-2

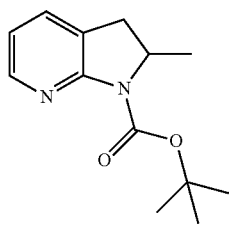 [SMILES: CC1Cc2cccnc2N1C(=O)OC(C)(C)C]

To a mixture of 10% palladium on carbon (0.412 g, 0.387 mmol) in MeOH (10 mL) in a Parr reaction vessel (500 mL) under nitrogen was added a solution of Intermediate VN-1 (0.90 g, 3.9 mmol) in MeOH (30 mL). The reaction vessel was vacuum flushed with nitrogen (3×) and then with hydrogen. The reaction was vigorously shaken at 60 psi at ~25° C. for 47 h. The reaction was filtered over a bed of Celite and concentrated in vacuo to afford a clear oil. The oil was loaded on an ISCO silica gel cartridge (120 g) eluting with 25% EtOAc/hexanes over 2592 mL of solvent to afford recovered starting material, 251.7 mg (first eluent) and the title compound, 484.2 mg, as a clear colorless oil (second eluent). ¹H NMR (400 MHz, CDCl₃) δ 8.25 (d, J=5.0 Hz, 1H), 7.41 (dq, J=7.3, 1.3 Hz, 1H), 6.83 (dd, J=7.3, 5.3 Hz, 1H), 4.57-4.40 (m, 1H), 3.36-3.19 (m, 1H), 2.65-2.46 (m, 1H), 1.57 (s, 9H), 1.32 (d, J=6.3 Hz, 3H).

Intermediate VN-3

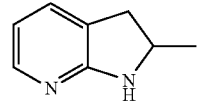

A solution Intermediate VN-2 (0.466 g, 1.989 mmol) in 4N HCl in dioxane (20 mL) was stirred at ~25° C. for 3 h. All solvents were removed in vacuo to afford an HCl salt of the title compound as a light yellow solid (quantitative yield). LC-MS retention time=1.67 min; m/z=135.04 [M+H]⁺; (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1-minute hold at 100% B. Oven temperature=40° C. Wavelength=220 nm). ¹H NMR (400 MHz, CDCl₃) δ 8.31 (br s, 1H), 7.42 (app br s., 1H), 7.40 (app br s, 1H), 6.56 (t, J=6.8 Hz, 1H), 4.46-4.32 (m, 1H), 3.36 (dd, J=17.6, 9.3 Hz, 1H), 2.77 (dd, J=17.7, 5.9 Hz, 1H), 1.43 (d, J=6.3 Hz, 3H).

Intermediate VN-4.1 and VN 4.2

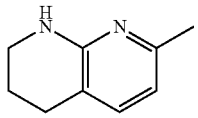 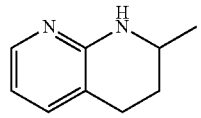

To a mixture of 10% palladium on carbon (0.369 g, 0.347 mmol) in MeOH (20 mL) under nitrogen in a 500 mL Parr reaction vessel was added 2-methyl-1,8-naphthyridine (0.500 g, 3.47 mmol). The reaction mixture was vacuum flushed with nitrogen (3×), then with hydrogen (3×) and vigorously shaken under hydrogen at 60 psi at ~25° C. for 23 h. The reaction was filtered through a pad of Celite and thoroughly washed with MeOH. The filtrated was concentrated in vacuo to afford a mixture of the title compounds (506.1 mg) as a white solid. $^1$H NMR indicated a mixture of two products in a ratio of 1:0.18 which was used without further purification. LC-MS retention time=1.70 min; m/z=149.06 $[M+H]^+$. (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). Major product: $^1$H NMR (400 MHz, DMSO-d6) δ 6.99 (d, J=7.3 Hz, 1H), 6.24 (d, J=7.0 Hz, 1H), 6.21 (br s, 1H), 3.26-3.19 (m, 2H), 2.59 (t, J=6.3 Hz, 2H), 2.16 (s, 3H), 1.74 (dt, J=11.7, 6.0 Hz, 2H). Minor product: $^1$H NMR (400 MHz, DMSO-d6) δ 7.76-7.69 (m, 1H), 7.12 (d, J=7.0 Hz, 1H), 6.39 (dd, J=7.2, 4.9 Hz, 1H), 3.49-3.33 (m, 1H), 2.70-2.61 (m, 2H), 1.89-1.78 (m, 1H), 1.47-1.33 (m, 1H), 1.15 (d, J=6.3 Hz, 3H).

Intermediate VN-5

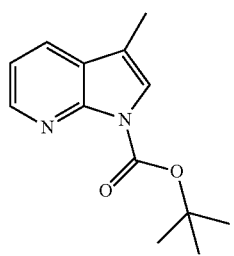 [SMILES: Cc1cn(C(=O)OC(C)(C)C)c2ncccc12]

To a solution of 3-methyl-1H-pyrrolo[2,3-b]pyridine (1 g, 8 mmol) in THF (15 mL) was added DMAP (9.2 mg, 0.08 mmol) followed by the addition of di-tert-butyl dicarbonate (2.48 g, 11.4 mmol). The reaction was stirred at ~25° C. under nitrogen for 20.5 h. Water (0.1 mL) was added to the reaction and stirring was continued at ~25° C. for 40 min. All solvents were removed in vacuo. The crude product was azeotroped with toluene (3×5 mL) to give the title compound as a tan solid (quantitative yield). The product was used without further purification. LC-MS retention time=3.11 min; m/z=255.10 $[M+Na]^+$. (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 8.37 (dd, J=4.6, 1.6 Hz, 1H), 7.98 (dd, J=7.8, 1.8 Hz, 1H), 7.55 (d, J=1.3 Hz, 1H), 7.27 (dd, J=7.8, 4.8 Hz, 1H), 2.23 (d, J=1.3 Hz, 3H), 1.60 (s, 9H).

Intermediate VN-6

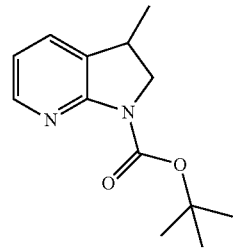 [SMILES: CC1CN(C(=O)OC(C)(C)C)c2ncccc21]

To a mixture of 10% palladium on carbon (0.779 g, 0.732 mmol) in MeOH (10 mL) in a 500 mL Parr reaction vessel under nitrogen was added a solution of Intermediate VN-5 (1.7 g, 7.3 mmol) in MeOH (40 mL). The reaction mixture was vacuum flushed with nitrogen (3×), then with hydrogen (3×) and vigorously shaken under hydrogen at 60 psi at ~25° C. for 24 h. The reaction was filtered over a plug of Celite, thoroughly washed with MeOH and concentrated in vacuo to afford a viscous oil. The crude oil was loaded on an ISCO silica gel cartridge (120 g) eluting with 25% EtOAc/hexanes over 1296 mL to afford recovered starting material (372.9 mg) as a white solid and the title compound (863.5 mg) as a clear colorless viscous oil. LC-MS retention time=2.32 min; m/z=257.11 $[M+Na]^+$. (Column: Phenomenex Luna C18 50×2.0 mm 3 m. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 8.06 (app d, J=4.8 Hz, 1H), 7.56 (dt, J=7.3, 1.3 Hz, 1H), 6.91 (dd, J=7.3, 5.0 Hz, 1H), 4.10 (dd, J=10.7, 9.7 Hz, 1H), 3.47-3.40 (m, 1H), 3.40-3.27 (m, 1H), 1.49 (s, 9H), 1.25 (d, J=6.8 Hz, 3H).

Intermediate VN-7 and Intermediate VN-8

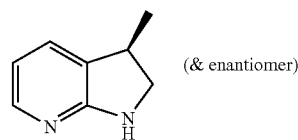

(Absolute stereochemcal assignment was not made)

A solution of Intermediate VN-6 (0.66 g, 2.8 mmol) in 4M HCl in dioxane (50 mL) was stirred at ~25° C. for 15.5 h. All solvents were removed in vacuo to afford a racemic mixture of an HCl salt of the title compounds (378 mg) as a light yellow solid. The racemic mixture was separated by preparatory chiral SFC using a ChiralCel OD-H, 21×250 mm, 5 μm column; Mobile phase: 10% EtOH (w/0.1% DEA)/90% $CO_2$; pressure 150 bar; temperature 40° C.; flow rate 40 mL/min; UV 310 nm; injection 0.2 mL (~25 mg/mL in MeOH); fraction collection: slope and level (make-up flow=6 mL/min IPA) to afford the individual title compounds: Intermediate VN-7 (first eluent) as an off-white solid (185 mg) (absolute stereochemistry not determined); ¹H NMR (400 MHz, DMSO-$d_6$) δ 7.67 (d, J=5.0 Hz, 1H), 7.23 (d, J=7.0 Hz, 1H), 6.41 (dd, J=7.0, 5.3 Hz, 1H), 6.24 (br s, 1H), 3.58 (t, J=9.0 Hz, 1H), 3.31-3.20 (m, 1H), 2.99 (ddd, J=9.0, 7.6, 1.8 Hz, 1H), 1.22 (d, J=7.0 Hz, 3H).

Intermediate VN-8 (second eluent) as an off-white solid (192 mg) (absolute stereochemistry not determined); ¹H NMR (400 MHz, DMSO-d6) δ 7.67 (d, J=5.0 Hz, 1H), 7.23 (d, J=7.0 Hz, 1H), 6.41 (dd, J=7.0, 5.3 Hz, 1H), 6.24 (br s, 1H), 3.63-3.52 (m, 1H), 3.32-3.18 (m, 1H), 2.98 (ddd, J=9.0, 7.5, 1.8 Hz, 1H), 1.21 (d, J=6.8 Hz, 3H), respectively.

Intermediate GW-1

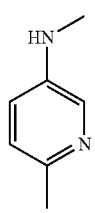

To a solution of 6-methylpyridin-3-amine (500 mg, 4.62 mmol) and formaldehyde (208 mg, 6.94 mmol) in methanol (10 mL) was added sodium methanolate (5.29 mL, 23.2 mmol) and the reaction mixture was heated to 50° C. for 16 h. The reaction mixture was cooled to rt, treated sodium tetrahydroborate (437 mg, 11.6 mmol) in two portions and stirred at rt for 6 h. Water (10 mL) was added slowly and the mixture was extracted by EtOAc (2×20 mL). The combined organic component was dried with $Na_2SO_4$, filtered, concentrated and purified using a Biotage Horizon (0-100% EtOAc, 10-20% MeOH/EtOAc) to afford the title compound (0.29 g) as a red oil. ¹H NMR (400 MHZ, $CDCl_3$-d) δ 7.97 (d, J=2.7 Hz, 1H), 6.98 (d, J=8.3 Hz, 1H), 6.85 (dd, J=8.3, 3.0 Hz, 1H), 2.86 (s, 3H), 2.46 (s, 3H).

Intermediate GW-2

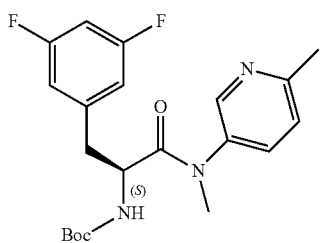

To a solution of (S)-2-((tert-butoxycarbonyl)amino)-3-(3,5-difluorophenyl)propanoic acid (0.715 g, 2.37 mmol) and Intermediate GW-1 (0.29 g, 2.4 mmol) in DMF (7 mL) was added DIPEA (0.83 mL, 4.8 mmol) and then HATU (0.95 g, 2.5 mmol) and the reaction mixture was stirred at rt for 2 h. The reaction mixture was partitioned between water (70 mL) and EtOAc (35 mL), the organic component was dried with $Na_2SO_4$, filtered, concentrated and purified with a Biotage Horizon (20-90% EtOAc/hexanes) to afford the title compound (0.67 g) as off-white foam. LC-MS retention time=3.48 min; m/z=428.07 [M+Na]⁺. (Column: Phenomenex-Luna 2.0×50 mm, 3 μm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, $CDCl_3$-d) δ 8.12 (s, 1H), 7.19 (d, J=8.0 Hz, 1H), 7.13 (d, J=7.0 Hz, 1H), 6.71 (m, 1H), 6.50 (d, J=6.3 Hz, 2H), 5.18 (m, 1H), 4.46 (d, J=7.8 Hz, 1H), 3.24 (s, 3H), 2.89 (dd, J=13.2, 7.8 Hz, 1H), 2.74 (dd, J=13.4, 6.8 Hz, 1H), 2.61 (s, 3H), 1.41 (s, 9H).

Intermediate GW-3

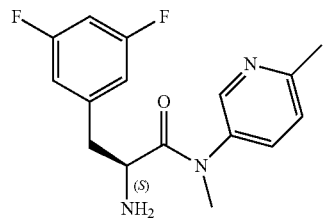

To a solution of Intermediate GW-2 (0.67 g, 1.7 mmol) in dioxane (6 mL) was added HCl (4N in dioxane) (1.50 mL, 49.6 mmol) and the reaction mixture was stirred at rt for 17 h. Methanol (2 mL) was added, the mixture was sonicated to make it a clear solution and the reaction mixture was stirred at rt for 8 h. The reaction mixture was concentrated and dried under high vacuum to afford an HCl salt of the title compound (0.62 g) as off-white solid. LC-MS retention time=2.26 min; m/z=306.06 [M+H]⁺. (Column: Phenomenex-Luna 2.0×50 mm, 3 μm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min: Detection: UV at 220 nm).

Intermediate GW-4

To a solution of 6-ethylpyridin-3-amine (500 mg, 4.09 mmol) and formaldehyde (184 mg, 6.14 mmol) in methanol (15 mL) was added sodium methanolate (4.7 mL, 20 mmol) and the reaction mixture was heated at 50° C. for 16 h. The reaction mixture was cooled to rt and sodium tetrahydroborate (387 mg, 10.2 mmol) was added in two portions and it was stirred at rt for 2 h. Water (10 mL) was added slowly and the mixture was extracted by EtOAc (2×20 mL). The combined organic component was dried with $Na_2SO_4$, filtered, concentrated and purified with a Biotage Horizon (20-70% EtOAc/hexanes) to afford the title compound (0.41 g) as brown oil. LC-MS retention time=2.30 min; m/z=137.05 [M+H]⁺. (Column: Phenomenex-Luna 2.0×50 mm, 3 μm particles; Mobile Phase A: 10% MeOH-90% $H_2O$-0.1% TFA; Mobile Phase B: 90% MeOH-10% $H_2O$-

0.1% TFA; Temperature: 40° C.; Gradient: 0-100% B over 4 min, then a 1-min hold at 100% B; Flow: 0.8 mL/min; Detection: UV at 220 nm). $^{1}$H NMR (400 MHZ, CDCl$_3$-d) δ 7.99 (s, 1H), 7.00 (d, J=8.3 Hz, 1H), 6.87 (d, J=11.2 Hz, 1H), 3.65 (br. s, 1H), 2.87 (s, 3H), 2.74 (q, J=7.6 Hz, 2H), 1.29 (t, J=7.6 Hz, 3H).

Intermediate GW-5

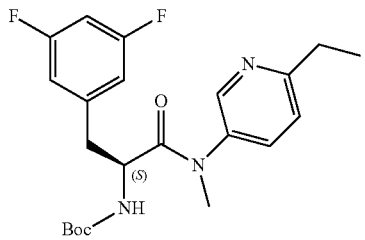

To a solution of (S)-2-((tert-butoxycarbonyl)amino)-3-(3,5-difluorophenyl)propanoic acid (0.55 g, 1.8 mmol) and Intermediate GW-4 (0.25 g, 1.8 mmol) in DMF (7 mL) was added DIPEA (0.64 mL, 3.7 mmol) and then HATU (0.73 g, 1.93 mmol) and the reaction mixture was stirred at rt for 16 h. The reaction mixture was partitioned between water (70 mL) and EtOAc (35 mL), the organic component was dried with Na$_2$SO$_4$, filtered, concentrated and purified with a Biotage Horizon (0-100% EtOAc/hexanes) to afford the title compound (0.42 g) as white oil. LC-MS retention time=3.54 min; m/z=442.09 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^{1}$H NMR (400 MHZ, CDCl$_3$-d) δ 8.16 (s, 1H), 7.20 (s, 2H), 6.70 (t, J=8.8 Hz, 1H), 6.47 (d, J=6.1 Hz, 2H), 5.22 (m, 1H), 4.47 (d, J=7.3 Hz, 1H), 3.25 (s, 3H), 2.90 (m, 3H), 2.72 (q, J=7.6 Hz, 1H), 1.41 (s, 9H), 1.35 (t, J=7.6 Hz, 3H)

Intermediate GW-6

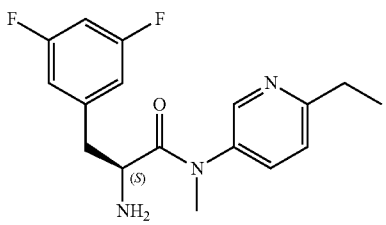

To a solution of Intermediate GW-5 (0.42 g, 1.0 mmol) in dioxane (1 mL) was added HCl (1.1 mL, 35.8 mmol, 4N in dioxane) and the solution was stirred at rt for 4 h. Methanol (1 mL) was added and the stirring was continued at rt for 16 h. The reaction mixture was concentrated to afford an HCl salt of the title compound (0.26 g). LC-MS retention time=2.37 min; m/z=320.12 [M+H]$^+$. (Column: Phenomenex-Luna 2.0×50 mm, 3 m particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-7

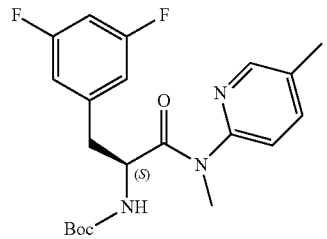

To a solution of (S)-2-((tert-butoxycarbonyl)amino)-3-(3,5-difluorophenyl)propanoic acid (0.617 g, 2.05 mmol) and N,5-dimethylpyridin-2-amine (0.25 g, 2.1 mmol) in DMF (7 mL) was added DIPEA (0.7 mL, 4 mmol) and then HATU (0.817 g, 2.15 mmol) and the reaction mixture was stirred at rt for 2 h. The reaction mixture was partitioned between water (70 mL) and EtOAc (35 mL). The organic component was dried with Na$_2$SO$_4$, filtered, concentrated and purified with a Biotage Horizon (0-100% EtOAc/hexanes) to afford the title compound (0.29 g) as light yellow oil. LC-MS retention time=3.88 min; m/z=406.12 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^{1}$H NMR (400 MHZ, CDCl$_3$-d) δ 8.36 (s, 1H), 7.61 (d, J=9.5 Hz, 1H), 7.05 (m, 1H), 6.65 (t, J=9.0 Hz, 1H), 6.54 (br. s, 1H), 5.32 (d, J=8.5 Hz, 1H), 4.75 (br. s, 1H), 3.34 (s, 3H), 3.06 (dd, J=13.5, 5.2 Hz, 1H), 2.99 (br. s, 1H), 2.40 (s, 3H), 1.44-1.39 (two s, 9H)

Intermediate GW-8

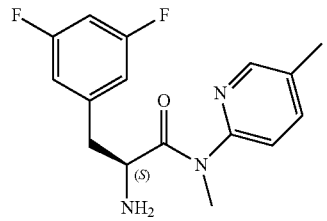

To a solution of Intermediate GW-7 (0.29 g, 0.72 mmol) in dioxane (2 mL) was added HCl (4N in dioxane) (1.1 mL, 4.4 mmol) and the reaction mixture was stirred at rt for 20 h. The solvent was evaporated and dried under high vacuum for 64 h to afford an HCl salt of the title compound (0.19 g) as pink solid. LC-MS retention time=2.75 min; m/z=328.04 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-4.1

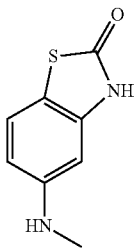

To a solution of 5-aminobenzo[d]thiazol-2(3H)-one (300 mg, 1.81 mmol) in methanol (10 mL) was added formaldehyde (108 mg, 3.61 mmol) and sodium methanolate (2.1 mL, 9.0 mmol) and the reaction mixture was heated to 60° C. for 16 h. The reaction mixture was cooled to rt and sodium tetrahydroborate (171 mg, 4.51 mmol) was added and it stirred at rt for 30 min. Then methanol (2 mL) was added to the reaction mixture and it was stirred at rt for 6 h. Silica gel was added to the reaction mixture, it was concentrated and the residue was dry loaded onto a Biotage Horizon (0-100% EtOAc/hexanes, 20% MeOH/EtOAc and 100% MeOH) for purification. The material collected was further purified by preparative HPLC to afford the title compound (140 mg) as off-white solid. LC-MS retention time=1.36 min; m/z=181.00 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 11.56 (s, 1H), 7.24 (d, J=8.6 Hz, 1H), 6.47 (d, J=8.5 Hz, 1H), 6.40 (s, 1H), 2.70 (s, 3H).

Intermediate GW-4.2

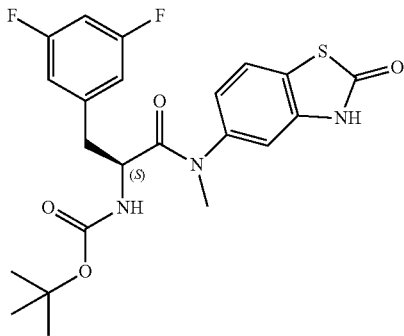

To a solution of (S)-2-((tert-butoxycarbonyl)amino)-3-(3,5-difluorophenyl)propanoic acid (143 mg, 0.48 mmol) Intermediate GW-4.1 and 2,2,2-trifluoroacetate (140 mg, 0.48 mmol) in DMF (4 mL) was added DIPEA (0.20 mL, 1.2 mmol) and then HATU (190 mg, 0.50 mmol) and the reaction mixture was stirred at rt for 16 h. The reaction mixture was partitioned between EtOAc (20 mL) and water (40 mL) and the organic component was dried with Na$_2$SO$_4$, filtered, concentrated and purified with a Biotage Horizon (10-100% EtOAc/hexanes) to afford the title compound (140 mg) as white foam. LC-MS retention time=3.83 min; m/z=486.02 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 12.07 (br. s, 1H), 7.69 (d, J=7.8 Hz, 1H), 7.13-7.00 (m, 4H), 6.50 (s, 1H), 4.19 (br. s, 1H), 3.18 (s, 3H), 2.84 (d, J=12.5 Hz, 1H), 2.73 (d, J=10.3 Hz, 1H), 1.28 (s, 9H).

Intermediate GW-4.3

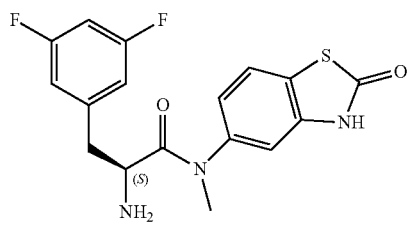

To a solution of Intermediate GW-4.2 (140 mg, 0.30 mmol) in dioxane (1 mL) was added HCl (4N in dioxane) (0.46 mL, 1.8 mmol) and the reaction mixture was stirred at rt for 16 h. Methanol (1 mL) was added and the stirring was continued for 8 h. The solvent was evaporated and dried under high vacuum to afford an HCl salt of the title compound (0.13 g) as light yellow solid. LC-MS retention time=2.91 min; m/z=364.02 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-5.1

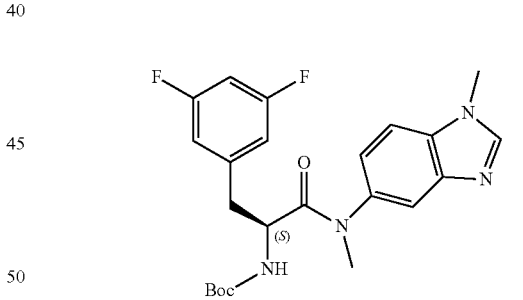

To a solution of (S)-2-((tert-butoxycarbonyl)amino)-3-(3,5-difluorophenyl)propanoic acid (1278 mg, 4.24 mmol) and N,1-dimethyl-1H-benzo[d]imidazol-5-amine (570 mg, 3.54 mmol) in DCM (20 mL) was added N-ethoxycarbonyl-2-ethoxy-1,2-dihydroquinoline (1.05 g, 4.24 mmol) and the reaction mixture was stirred at rt for 17 h. The solvent was evaporated and the residue was purified with a Biotage Horizon (30-100% Hexane/EtOAc, 10-20% MeOH/EtOAc) to afford the title (0.13 g) compound as pink solid. LC-MS retention time=3.29 min; m/z=467.08 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min: Detection: UV at 220 nm). $^1$H NMR (400 MHZ, DMSO-d6) δ 8.32 (s, 1H), 7.71 (d, J=8.2 Hz, 2H), 7.28 (d, J=7.3 Hz, 1H), 7.12 (d, J=8.3 Hz, 1H), 6.95 (t, J=9.2 Hz, 1H), 6.34 (d, J=7.0 Hz, 2H), 4.25-4.14 (m, 1H), 3.90 (s, 3H), 3.23 (s, 3H), 2.86 (d, J=13.1 Hz, 1H), 2.68 (t, J=10.3 Hz, 1H), 1.28 (s, 9H).

Intermediate GW-5.2

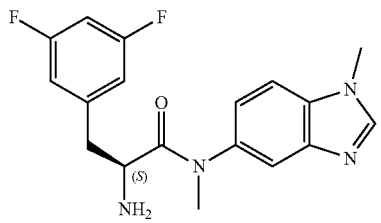

To a solution of Intermediate GW-5.1 (0.13 g, 0.29 mmol) in dioxane (2 mL) was added HCl (4N in dioxane) (0.9 mL, 3.6 mmol) and the reaction mixture was stirred at rt for 4 h, The reaction mixture was treated with methanol (0.5 mL) and stirred for an additional 4 h. The solvent was evaporated and the residue was dried under high vacuum to afford an HCl salt of the title compound (0.12 g) as light yellow solid. LC-MS retention time=1.97 min; m/z=345.19 [M+H]$^+$. (Column: Phenomenex-Luna 2.0×50 mm, 3 µm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min; Detection: UV at 220 nm).

Intermediate GW-6.1

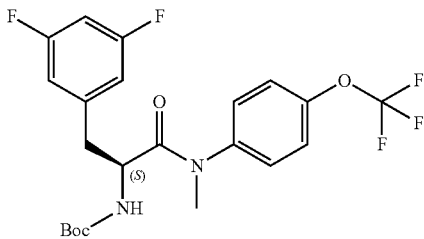

To a solution of (S)-2-((tert-butoxycarbonyl)amino)-3-(3,5-difluorophenyl)propanoic acid (0.79 g, 2.6 mmol) in DMF (6 mL) was added N-methyl-4-(trifluoromethoxy)aniline (0.500 g, 2.62 mmol), DIPEA (0.91 mL, 5.2 mmol) and HATU (1.04 g, 2.75 mmol) and the reaction mixture was stirred at rt for 2 h. The reaction mixture was partitioned between water (60 mL) and EtOAc (30 mL). The organic component was dried with $Na_2SO_4$, filtered, concentrated and purified with a Biotage Horizon (0-100% EtOAc/hexanes) to afford the title compound (0.80 g) as pink solid. LC-MS retention time=4.25 min; m/z=375.14 [M-Boc+H]$^+$. (Column: Phenomenex-Luna 2.0×50 mm, 3 µm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 7.55 (s, 4H), 7.25 (d, J=7.7 Hz, 1H), 7.02 (m, 1H), 6.42 (m, 2H), 4.10 (m, 1H), 3.19 (s, 3H), 2.80-2.65 (m, 2H), 1.30 (s, 9H).

Intermediate GW-6.2

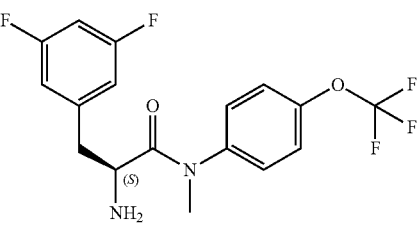

To a solution of Intermediate GW-6.1 (0.800 g, 1.68 mmol) in dioxane (3 mL) was added HCl (4N in dioxane) (3.1 mL, 12.4 mmol) and the reaction mixture was stirred at rt for 17 h. The reaction mixture was concentrated and dried under high vacuum to afford an HCl salt of the title compound (0.65 g) as white solid. LC-MS retention time=3.31 min; m/z=375.15 [M+H]$^+$. (Column: Phenomenex-Luna 2.0×50 mm, 3 µm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min; Detection: UV at 220 nm).

Intermediate GW-7.1

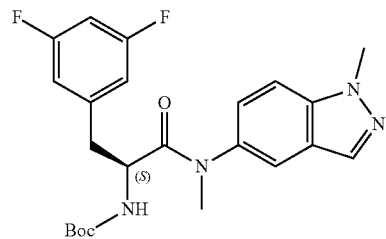

To a solution of (S)-2-((tert-butoxycarbonyl)amino)-3-(3,5-difluorophenyl)propanoic acid (0.82 g, 2.7 mmol) and N,1-dimethyl-1H-indazol-5-amine (0.44 g, 2.7 mmol) in DMF (7 mL) was added DIPEA (0.95 mL, 5.5 mmol) and then HATU (1.09 g, 2.87 mmol) and the reaction mixture was stirred at rt for 19 h. The reaction mixture was partitioned between water (70 mL) and EtOAc (35 mL), the organic component was dried with $Na_2SO_4$, filtered, concentrated and purified with a Biotage Horizon to afford the title compound (1.14 g) as pink foam. LC-MS retention time=3.69 min; m/z=467.07 [M+Na]$^+$. (Column: Phenomenex-Luna 2.0×50 mm, 3 µm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 8.10 (s, 1H), 7.77 (d, J=8.8 Hz, 2H), 7.71 (s, 1H), 7.08 (d, J=8.0 Hz, 1H), 6.95 (t, J=9.6 Hz, 1H), 6.65-6.39 (m, 2H), 4.09 (m overlapped with s, 4H), 3.21 (s, 3H), 2.87 (d, J=10.5 Hz, 1H), 2.70 (t, J=9.3 Hz, 1H), 1.28 (two s, 9H).

Intermediate GW-7.2

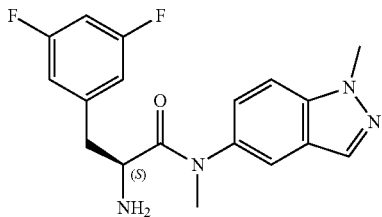

To a solution of Intermediate GW-7.1 (1.14 g, 2.56 mmol) in dioxane (4 mL) was added HCl (4N in dioxane) (2.4 mL, 9.6 mmol) and the reaction mixture was stirred at rt for 1 h. Precipitate was redissolved with the addition of methanol (1 mL) and the stirring was continued for 24 h. The reaction was concentrated and dried under high vacuum to afford an HCl salt of the title compound (1.03 g) as light brown solid. LC-MS retention time=2.67 min; m/z=345.10 [M+H]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-8.1

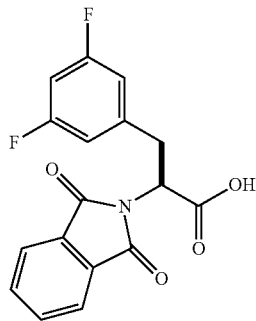 [SMILES: O=C(O)[C@H](Cc1cc(F)cc(F)c1)N1C(=O)c2ccccc2C1=O]

A mixture of (S)-2-amino-3-(3,5-difluorophenyl)propanoic acid (1.72 g, 8.55 mmol) and isobenzofuran-1,3-dione (1.27 g, 8.55 mmol) in DMF (12 mL) in a microwave vial (20 mL) was heated at 155° C. for 1 h in a microwave reactor. The crude mixture was poured into water (50 mL) and stirred for 30 min. The solids were collected by filtration, washed with water and dried under high vacuum overnight to afford the title compound (2.3 g) as light brown solid. LC-MS retention time=3.57 min; m/z=354.07 [M+Na]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 13.45 (br. s, 1H), 7.87 (s, 4H), 7.02-6.94 (m, 3H), 5.23 (d, J=4.8 Hz, 0.5H), 5.20 (d, J=4.8 Hz, 0.5H), 3.53 (d, J=4.5 Hz, 0.5H), 3.50 (d, J=4.5 Hz, 0.5H), 3.35 (m, 1H, overlapped with water peak).

Intermediate GW-8.2

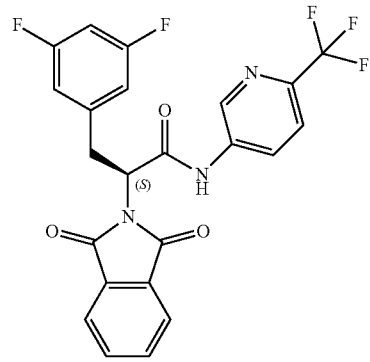

A solution of Intermediate GW-8.1 (500 mg, 1.51 mmol) in SOCl$_2$ (1.1 mL, 15 mmol) was heated at 45° C. for 2.5 h. The reaction mixture was concentrated and azeotroped with DCM (3×10 mL) and dried under high vacuum overnight to afford crude intermediate (S)-3-(3,5-difluorophenyl)-2-(1,3-dioxoisoindolin-2-yl)propanoyl chloride (0.49 g) as white solid. To a solution of crude (S)-3-(3,5-difluorophenyl)-2-(1,3-dioxoisoindolin-2-yl)propanoyl chloride (440 mg, 1.26 mmol) and 6-(trifluoromethyl)pyridin-3-amine (204 mg, 1.26 mmol) in DMF (6 mL) was added DIPEA (0.44 mL, 2.5 mmol) and the reaction mixture was stirred at rt for 2 h. The reaction mixture was partitioned between water (60 mL) and EtOAc (30 mL), the organic component was separated and dried with Na$_2$SO$_4$, filtered, concentrated and purified with a Biotage Horizon (10-100% EtOAc/hexanes) to afford the title compound (0.39 g) as white solid. LC-MS retention time=3.92 min; m/z=476.11 [M+H]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 10.50 (s, 1H), 8.86 (s, 1H), 8.30 (d, J=10.8 Hz, 1H), 7.88 (m, 5H), 7.01 (m, 1H), 6.94 (d, J=8.5 Hz, 2H), 5.35 (d, J=4.8 Hz, 0.5H), 5.33 (d, J=4.8 Hz, 0.5H), 3.65 (d, J=4.5 Hz, 0.5H), 3.62 (d, J=4.5 Hz, 0.5H), 3.29 (m, 1H).

Intermediate GW-8.3

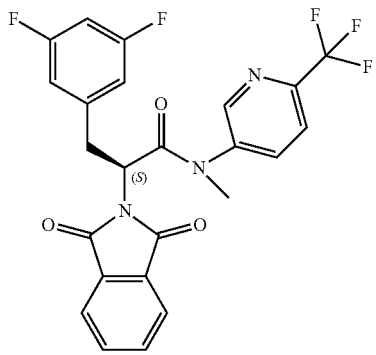

To a solution of Intermediate GW-8.2 (0.39 g, 0.8 mmol) in DMF (6 mL) was added 60% NaH (0.036 g, 0.9 mmol) as a dispersion in mineral oil and the reaction mixture was stirred for 5 min, then iodomethane (0.06 mL, 0.9 mmol) was added and the reaction mixture was stirred at rt for 23 h. The reaction was quenched with sat. NH₄Cl (5 mL) and water (5 mL) and extracted with EtOAc (2×20 mL). The combined organic components was dried with Na₂SO₄, filtered, concentrated and purified with a Biotage (0-80% EtOAc/hexanes) to afford the title compound (0.19 g) as colorless oil. LC-MS retention time=3.73 min; m/z=490.13 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 8.61 (s, 1H), 7.96 (d, J=8.8 Hz, 1H), 7.80 (m, 2H), 7.66 (br. s, 3H), 6.96 (t, J=9.6 Hz, 1H), 6.83 (d, J=6.7 Hz, 2H), 5.30 (br. s, 1H), 3.47 (d, J=4.5 Hz, 0.5H), 3.43 (d, J=4.5 Hz, 0.5H), 3.19 (s, 3H), 3.16 (t, J=11.3 Hz, 1H).

Intermediate GW-8.4

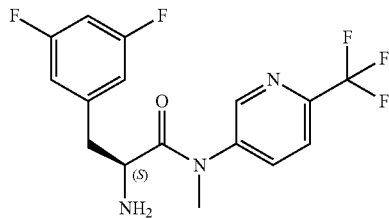

To a solution of Intermediate GW-8.3 (0.19 g, 0.4 mmol) in ethanol (6 mL) was added hydrazine hydrate (0.10 mL, 2.3 mmol) and the reaction mixture was heated to 50° C. for 5 h. The cooled reaction mixture was filtered and the filtrate was concentrated, azeotroped with ethanol (2×10 mL) and dried under high vacuum for 72 h to afford the title compound (0.14 g) as sticky solid. LC-MS retention time=2.87 min; m/z=360.11 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-9.1

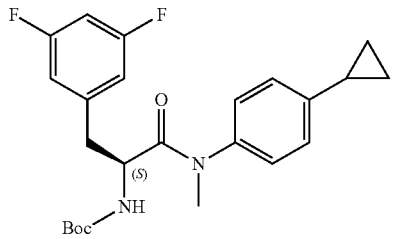

To a solution of (S)-2-((tert-butoxycarbonyl)amino)-3-(3,5-difluorophenyl)propanoic acid (1.02 g, 3.4 mmol) and 4-cyclopropyl-N-methylaniline (0.50 g, 3.4 mmol) in DMF (7 mL) was added DIPEA (1.2 mL, 6.8 mmol) and then HATU (1.36 g, 3.6 mmol) and the reaction mixture was stirred at rt for 24 h. The reaction mixture was partitioned between EtOAc (35 mL) and water (70 mL), the organic component was separated, dried with Na₂SO₄, filtered, concentrated and purified with a Biotage Horizon (0-50% EtOAc/hexanes) to afford the title compound (1.03 g) as light brown solid. LC-MS retention time=4.24 min; m/z=453.20 [M+Na]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 7.26 (m, 4H), 7.14 (d, J=8.6 Hz, 1H), 7.00 (t, J=9.3 Hz, 1H), 6.35 (m, 2H), 4.23-4.11 (m, 1H), 3.16 (two s, 3H), 2.75-2.60 (m, 2H), 2.00 (m, 1H), 1.30 (s, 7.5H), 1.10 (s, 1.5H), 1.00 (m, 2H), 0.72 (m, 2H).

Intermediate GW-9.2

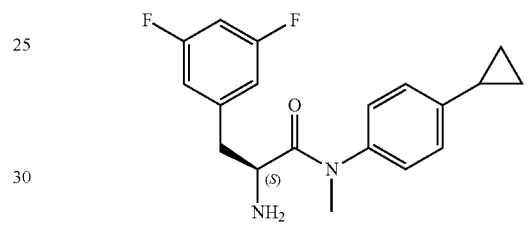

To a solution of Intermediate GW-9.1 (1.03 g, 2.39 mmol) in dioxane (5 mL) was added HCl (4N in dioxane) (3.63 mL, 14.4 mmol) and the reaction mixture was stirred at rt for 5 h. Methanol (5 drops) was added and the stirring continued at rt for 39 h. The reaction mixture was concentrated and dried under high vacuum overnight to afford an HCl salt of the title compound (0.87 g) as brown solid. LC-MS retention time=3.38 min; m/z=331.17 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-10.1

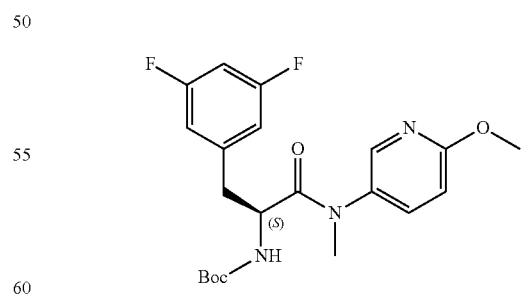

To a solution of (S)-2-((tert-butoxycarbonyl)amino)-3-(3,5-difluorophenyl)propanoic acid (0.57 g, 1.88 mmol) and 6-methoxy-N-methylpyridin-3-amine (0.26 g, 1.9 mmol) in DMF (7 mL) was added DIPEA (0.66 mL, 3.8 mmol) and then HATU (0.75 g, 2.0 mmol) and the reaction mixture was stirred at rt for 2 h. The reaction mixture was partitioned between water (70 mL) and EtOAc (35 mL), the organic component was dried with Na$_2$SO$_4$, filtered, concentrated and purified with a Biotage Horizon (0-100% EtOAc) to afford the title compound (0.73 g) as pink foam. LC-MS retention time=3.93 min; m/z=444.10 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 7.73 (s, 1H), 7.09 (s, 1H), 6.71 (d, J=8.8 Hz, 1H), 6.65 (m, 1H), 6.49 (d, J=6.0 Hz, 2H), 5.33 (m, 1H), 4.43 (m, 1H), 3.92 (s, 3H), 3.17 (s, 3H), 2.87 (dd, J=13.3, 7.5 Hz, 1H), 2.72 (dd, J=13.3, 7.5 Hz, 1H), 1.36 (s, 9H)

Intermediate GW-10.2

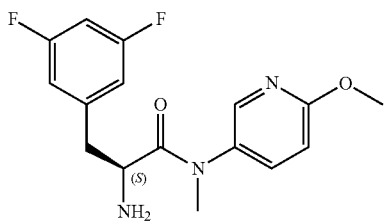

To a solution of Intermediate GW-10.1 (0.73 g, 1.7 mmol) in dioxane (6 mL) was added HCl (4N in dioxane) (1.6 mL, 6.4 mmol) and the reaction mixture was stirred at rt for 18 h. Methanol (2 mL) was added, the reaction was sonicated to get a clear solution and the stirring was continued for 5 h. The reaction mixture was concentrated and dried under high vacuum overnight to afford an HCl salt of the title compound (0.68 g) as brown solid. LC-MS retention time=2.92 min; m/z=322.08 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-11.1

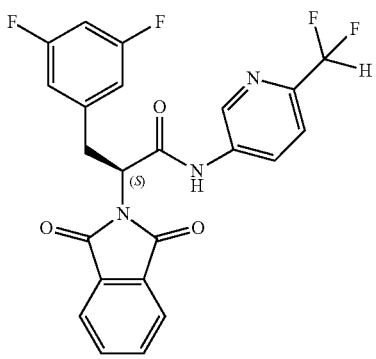

To a solution of (S)-3-(3,5-difluorophenyl)-2-(1,3-dioxoisoindolin-2-yl)propanoyl chloride (1.21 g, 3.47 mmol) and 6-(difluoromethyl)pyridin-3-amine (0.500 g, 3.47 mmol) in DMF (6 mL) was added DIPEA (1.2 mL, 6.94 mmol) and the reaction mixture was stirred at rt for 2 h. The reaction mixture was partitioned between water (60 mL) and EtOAc (30 mL), the organic component was dried with Na$_2$SO$_4$, filtered, concentrated and purified with a Biotage Horizon (10-100% EtOAc/hexanes) to afford the title compound (0.9 g) as white solid. LC-MS retention time=3.79 min; m/z=458.13 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).). $^1$H NMR (400 MHZ, DMSO-d6) δ 10.37 (s, 1H), 8.80 (s, 1H), 8.20 (d, J=8.5 Hz, 1H), 7.88 (s, 4H), 7.70 (d, J=8.8 Hz, 1H), 7.06-6.92 (m, 4H), 5.32 (dd, J=13.8, 4.5 Hz, 1H), 3.63 (dd, J=13.8, 4.5 Hz, 1H), 3.30 (m, 1H).

Intermediate GW-11.2

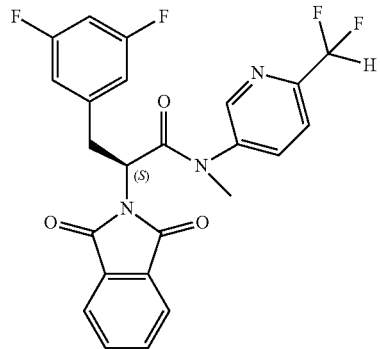

To a solution of Intermediate GW-11.1 (0.90 g, 2.0 mmol) in DMF (20 mL) was added 60% NaH (0.087 g, 2.17 mmol) as a dispersion in mineral oil and the reaction mixture was stirred for 5 min. Then iodomethane (0.14 mL, 2.2 mmol) was added and the stirring was continued at rt for 23 h. The reaction mixture was quenched with sat. aq. NH$_4$Cl (10 mL) and water (100 mL) and extracted by EtOAc (2×20 mL). The combined organic component was dried with Na$_2$SO$_4$, filtered, concentrated and purified with a Biotage Horizon (0-60% EtOAc/hexanes, 60-100% EtOAc/hexanes) to afford the title compound (0.7 g) as white solid. LC-MS retention time=3.58 min; m/z=494.11 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-11.3

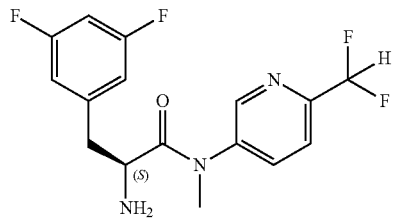

To a solution of Intermediate GW-11.2 (0.44 g, 0.93 mmol) in ethanol (10 mL) was added hydrazine hydrate (0.27 mL, 5.6 mmol) and the reaction mixture was heated to 50° C. for 5 h. The reaction mixture was filtered and the filtrate was concentrated, azeotroped with ethanol (2×10 mL) and dried under high vacuum for 64 h to afford the title compound (0.29 g) as white solid. LC-MS retention time=2.56 min; m/z=364.13 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-12.1

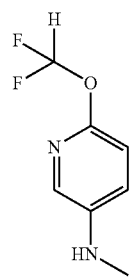

To a solution of 6-(difluoromethoxy)pyridin-3-amine (250 mg, 1.56 mmol) and formaldehyde (70 mg, 2.34 mmol) in methanol (8 mL) was added sodium methanolate (1.8 mL, 7.8 mmol) and the reaction mixture was heated to 50° C. for 18 h. The reaction mixture was cooled to rt, sodium tetrahydroborate (148 mg, 3.90 mmol) was added in two portions, and it was stirred at rt for 3 h. Water (5 mL) was added slowly and the mixture was extracted with EtOAc (2×20 mL), the combined organic component was dried with Na$_2$SO$_4$, filtered, concentrated and purified with a Biotage Horizon (20-100% EtOAc/hexanes) to afford the title compound (0.23 g) as colorless oil. LC-MS retention time=1.94 min; m/z=175.05 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 7.51 (d, J=2.7 Hz, 1H), 7.46 (t, J=74.1 Hz, 1H), 7.10 (dd, J=8.8, 3.1 Hz, 1H), 6.85 (d, J=8.8 Hz, 1H), 5.81 (m, 1H), 2.69 (d, J=5.2 Hz, 3H).

Intermediate GW-12.2

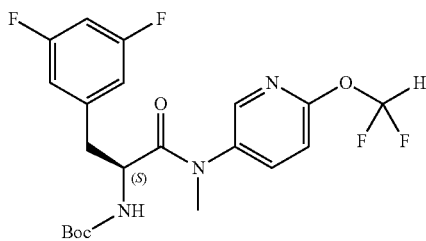

To a solution of (S)-2-((tert-butoxycarbonyl)amino)-3-(3,5-difluorophenyl)propanoic acid (398 mg, 1.32 mmol) and Intermediate GW-12.1 (0.23 g, 1.3 mmol) in DMF (5 mL) was added DIPEA (0.50 mL, 2.6 mmol) and then HATU (527 mg, 1.39 mmol) and the reaction mixture was stirred at rt for 18 h. The reaction mixture was partitioned between water (50 mL) and EtOAc (25 mL), the organic component was dried with Na$_2$SO$_4$, filtered, concentrated and purified with a Biotage Horizon to afford the title compound (0.48 g) as colorless oil. LC-MS retention time=4.00 min; m/z=480.13 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 8.36-8.27 (two s, 1H), 7.92 (m, 1H), 7.74 (t, J=72.5 Hz, 1H), 7.27-7.21-7.04 (m, 3H), 6.63 (m, 2H), 4.11 (m, 1H), 3.16 (s, 3H), 2.86 (d, J=3.6 Hz, 1H), 2.73 (d, J=3.6 Hz, 1H), 1.26 (s, 9H).

Intermediate GW-12.3

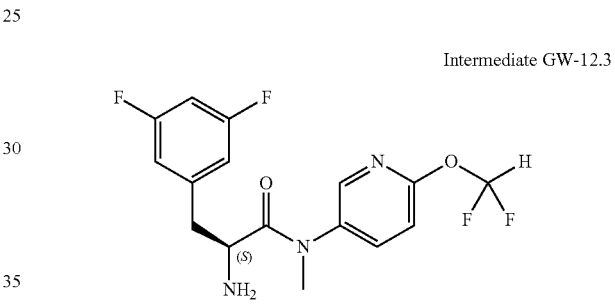

Intermediate GW-12.3

To a solution of Intermediate GW-12.2 (0.48 g, 1.1 mmol) in dioxane (4 mL) was added HCl (4N in dioxane) (1.6 mL, 6.4 mmol) and the reaction mixture was stirred at rt for 5 h. The reaction mixture was concentrated and dried under high vacuum overnight to afford an HCl salt of the title compound (0.51 g) as glassy brown solid. LC-MS retention time=2.92 min; m/z=358.14 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-13.1

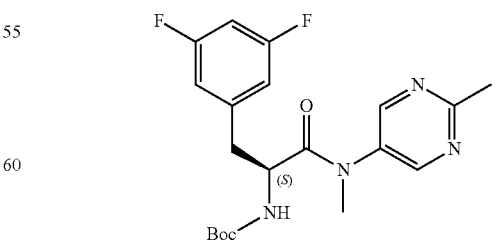

To a solution of (S)-2-((tert-butoxycarbonyl)amino)-3-(3,5-difluorophenyl)propanoic acid (1003 mg, 3.33 mmol) and N,2-dimethylpyrimidin-5-amine (410 mg, 3.33 mmol) in DMF (5 mL) was added DIPEA (1.2 mL, 6.7 mmol) and HATU (1329 mg, 3.50 mmol) and the reaction mixture was stirred at rt for 4 h. The reaction mixture was partitioned between water (50 mL) and EtOAc (25 mL), the organic component was dried with Na₂SO₄, filtered, concentrated and purified with a Biotage Horizon (70-100% EtOAc/hexanes) to afford the title compound (0.6 g) as white solid. LC-MS retention time=3.60 min; m/z=429.17 [M+Na]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 8.77-8.61 (two s, 2H), 7.33 (m, 1H), 7.05-6.69 (m, 3H), 4.12 (m, 1H), 3.17 (s, 3H), 2.89 (m, 1H), 2.75 (m, 1H), 2.62 (s, 3H), 1.24 (s, 9H).

Intermediate GW-13.2

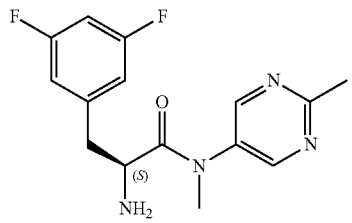

To a solution of Intermediate GW-13.1 (0.60 g, 1.5 mmol) in dioxane (5 mL) was added HCl (4N in dioxane) (2.2 mL, 8.8 mmol) and the reaction mixture was stirred at rt for 19 h. The reaction mixture was concentrated and dried under high vacuum overnight to afford an HCl salt of the title compound (0.55 g) as light brown solid. LC-MS retention time=2.29 min; m/z=307.15 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-14.1

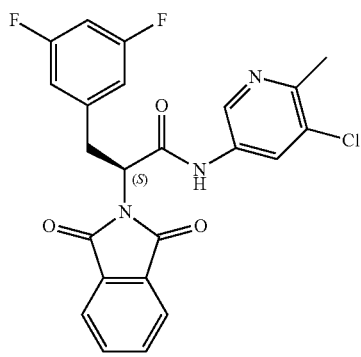

To a solution of (S)-3-(3,5-difluorophenyl)-2-(1,3-dioxoisoindolin-2-yl)propanoyl chloride (1.08 g, 3.09 mmol) and 5-chloro-6-methylpyridin-3-amine (440 mg, 3.09 mmol) in DMF (5 mL) was added DIPEA (1.1 mL, 6.2 mmol) and the reaction mixture was stirred at rt for 16 h. The reaction mixture was partitioned between water (50 mL) and EtOAc (25 mL), the organic component was dried with Na₂SO₄, concentrated and purified with a Biotage Horizon (10-100% EtOAc/hexanes) to afford the title compound (0.66 g) as white solid. LC-MS retention time=3.64 min; m/z=456.11 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).). ¹H NMR (400 MHZ, DMSO-d6) δ 10.22 (s, 1H), 8.54 (d, J=2.3 Hz, 1H), 8.11 (d, J=2.3 Hz, 1H), 7.87 (m, 4H), 7.00 (m, 1H), 6.92 (d, J=6.3 Hz, 2H), 5.30 (m, 1H), 3.61 (dd, J=13.8, 4.5 Hz, 1H), 3.28 (m, 1H), 2.51 (s, 3H, overlapped with DMSO).

Intermediate GW-14.2

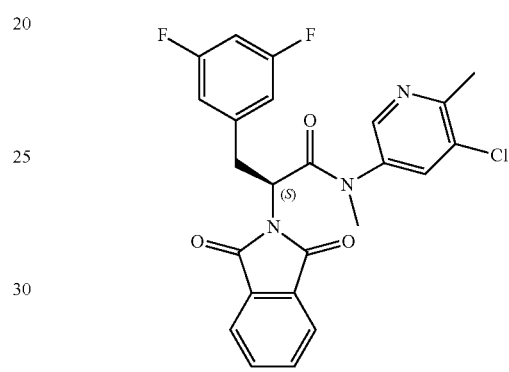

To a solution of Intermediate GW-14.1 (0.66 g, 1.5 mmol) in DMF (10 mL) was added 60% NaH (0.064 g, 1.59 mmol) as a dispersion in mineral oil and the reaction mixture was stirred at rt for 5 min. Then iodomethane (0.10 mL, 1.6 mmol) was added and the reaction mixture was stirred at rt for 17 h and then heated to 60° C. for 1 h. To the cooled reaction mixture, sat. aq. NH₄Cl (5 mL) was added slowly and followed by water (100 mL) and then it was extracted by EtOAc (2×20 mL). The combined organic component was dried with Na₂SO₄, concentrated and purified with a Biotage Horizon (0-70% EtOAc/hexanes) to afford the title compound (0.14 g) as white solid. LC-MS retention time=3.80 min; m/z=470.07 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-14.3

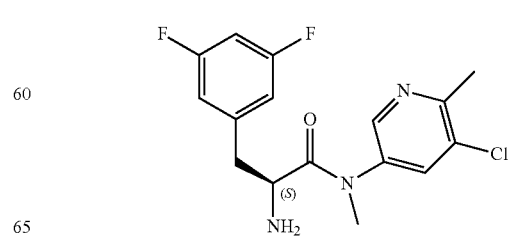

To a solution of Intermediate GW-14.2 (0.16 g, 0.34 mmol) in ethanol (5 mL) was added hydrazine hydrate (0.10 mL, 2.0 mmol) and the reaction mixture was heated to 50° C. for 5 h. The reaction mixture was filtered and the filtrate was concentrated, azeotroped with ethanol (2×10 mL) and dried under high vacuum overnight to afford the title compound (90 mg) as white solid. LC-MS retention time=2.95 min; m/z=340.09 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-15.1

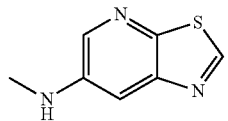

To a solution of thiazolo[5,4-b]pyridin-6-amine (0.50 g, 3.3 mmol) and formaldehyde (0.149 g, 4.96 mmol) in MeOH (20 mL) was added sodium methanolate (3.78 mL, 16.5 mmol) and the reaction mixture was heated to 50° C. for 18 h. The reaction mixture was cooled to rt, treated sodium tetrahydroborate (0.313 g, 8.27 mmol) in two portions and stirred at rt for 2 h. Water (5 mL) was added slowly, the reaction mixture was partially concentrated and then extracted with EtOAc (20 mL). The organic component was dried with Na$_2$SO$_4$, filtered, concentrated and purified by Biotage Horizon (20-100% EtOAc/hexanes) to afford the title compound (0.36 g) as pink solid. LC-MS retention time=1.04 min; m/z=166.03 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 9.36 (s, 1H), 8.15 (d, J=2.5 Hz, 1H), 7.41 (d, J=2.5 Hz, 1H), 6.25 (m, 1H), 2.78 (d, J=5.0 Hz, 3H).

Intermediate GW-15.2

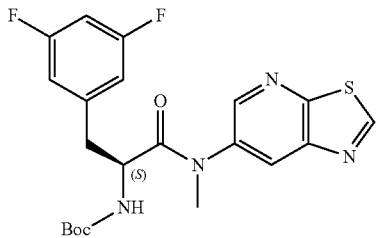

To a solution of (S)-2-((tert-butoxycarbonyl)amino)-3-(3, 5-difluorophenyl)propanoic acid (656 mg, 2.18 mmol) in DMF (2 mL) was added Intermediate GW-15.1 (360 mg, 2.18 mmol), DIPEA (0.76 mL, 4.4 mmol) and HATU (870 mg, 2.29 mmol) and the reaction mixture was stirred at rt for 16 h. The reaction mixture was partitioned between water (20 mL) and EtOAc (10 mL), the organic component was dried with Na$_2$SO$_4$, filtered, concentrated and purified with a Biotage Horizon (0-80% EtOAc/hexanes) to afford the title compound (0.54 g) as light yellow foam. LC-MS retention time=3.71 min; m/z=471.11 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 9.63 (s, 1H), 8.61 (s, 1H), 8.45 (s, 1H), 7.28-6.99 (m, 2H), 6.58 (m, 2H), 4.15 (m, 1H), 3.26 (two s, 3H), 2.93 (m, 1H), 2.76 (m, 1H), 1.18 (s, 9H).

Intermediate GW-15.3

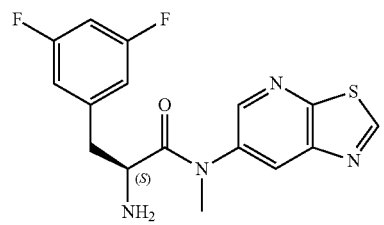

To a solution of Intermediate GW-15.2 (500 mg, 1.12 mmol) in dioxane (5 mL) was added HCl (4N in dioxane) (3.40 mL, 13.6 mmol) and methanol (5 drops) and the reaction mixture was stirred at rt for 5 h. The reaction mixture was concentrated and dried under high vacuum overnight to afford an HCl salt of the title compound (0.42 g) as orange solid. LC-MS retention time=2.27 min; m/z=349.10 [M+H]$^+$. (Column: Phenomenex-Luna C18 2.0×50 mm, 3 μm particles; Mobile Phase A: 5% ACN-95% H$_2$O-0.1% TFA; Mobile Phase B: 95% ACN-5% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate VN-17.1

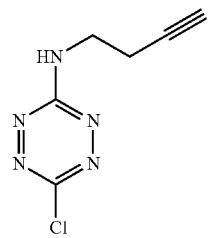

To a solution of 3,6-dichloro-1,2,4,5-tetrazine (2.67 g, 17.7 mmol) in methyl tert-butyl ether (125 mL) at ~25° C. under nitrogen was added but-3-yn-1-amine hydrochloride (1.87 g, 17.7 mmol), followed by the addition of N,N-diisopropylethylamine (12.4 mL, 70.7 mmol) and the reaction mixture was stirred at ~25° C. under nitrogen for 26 h. Silica gel (~5 g) was added to the reaction and all solvents were removed in vacuo. The silica gel mesh was loaded on an ISCO silica gel cartridge (220 g) eluting with 25% EtOAc/hexanes over 2592 mL to afford the title compound (853.3 mg) as a deep red/orange viscous oil. $^1$H NMR (400 MHz, CDCl$_3$) δ 6.12 (br s, 1H), 3.80 (q, J=6.3 Hz, 2H), 2.63 (td, J=6.3, 2.6 Hz, 2H), 2.10 (t, J=2.6 Hz, 1H).

Intermediate VN-17.2

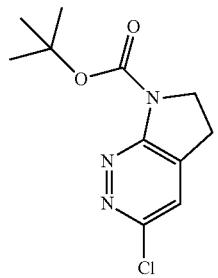 [SMILES: CC(C)(C)OC(=O)N1CCc2cc(Cl)nnc21]

To a solution of Intermediate VN-17.1 (0.85 g, 4.6 mmol) in THF (70 mL) was added BOC-anhydride (4.04 g, 18.5 mmol), followed by the addition of DMAP (0.085 g, 0.694 mmol). The reaction was stirred at ~25° C. under nitrogen for 4 days. All solvents were removed in vacuo. The residue was taken up in $CH_2Cl_2$ (3 mL) and loaded on an ISCO silica gel cartridge (120 g) eluting with 50% EtOAc/hexanes over 2592 mL to afford the title compound (366.1 mg) as a tan solid. LC-MS retention time=2.82 min; m/z=278.10 [M+Na]+. (Column: Phenomenex Luna C18 50×2.0 mm 3 m. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 7.61 (s, 1H), 3.96 (t, J=8.4 Hz, 2H), 3.15-3.02 (m, 2H), 1.50 (s, 9H).

Intermediate VN-17.3

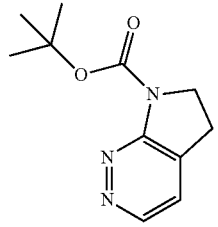 [SMILES: CC(C)(C)OC(=O)N1CCc2ccnnc21]

A mixture of Intermediate VN-17.2 (0.366 g, 1.43 mmol) and 10% palladium on carbon (0.152 g, 0.143 mmol) in MeOH (25 mL) in a 500 mL Parr reaction vessel was exposed to hydrogen at 60 psi. The reaction mixture was shaken vigorously at ~25° C. for 1 h. The reaction was removed from the hydrogen and filtered via a syringe with a Whatman Puradisc 13 mm syringe filter (0.45 mm pore size) and concentrated in vacuo to afford the title compound (quantitative yield) as a pink foam. The product was used without further purification. LC-MS retention time=2.10 min; m/z=244.12 [M+Na]+. (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 9.02 (d, J=5.3 Hz, 1H), 7.96 (d, J=5.0 Hz, 1H), 4.04 (t, J=8.3 Hz, 2H), 3.28 (t, J=8.2 Hz, 2H), 1.53 (s, 9H).

Intermediate VN-17.4

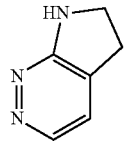

A solution of Intermediate VN-17.3 (0.330 g, 1.491 mmol) in 4N HCl in dioxane (25 mL) was stirred at ~25° C. for 16 h. All solvents were removed in vacuo to afford the title compound (quantitative yield) as a tan solid. LC-MS retention time=0.49 min; m/z=not observed. (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 9.38 (br s, 1H), 8.32 (d, J=4.3 Hz, 1H), 7.58-7.36 (m, 1H), 3.77 (t, J=7.9 Hz, 2H), 3.29-3.18 (m, 2H).

Intermediate VN-17.5

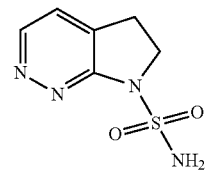 [SMILES: NS(=O)(=O)N1CCc2ccnnc21]

To a solution of sulfurisocyanatidic chloride (0.093 mL, 1.07 mmol) in $CH_2Cl_2$ (0.5 mL) at 0° C. under nitrogen was added 2-methylpropan-2-ol (0.102 mL, 1.07 mmol) dropwise. The reaction was stirred at 0° C. for 25 min, then a solution of Intermediate VN-17.4 (0.140 g, 0.888 mmol) and triethylamine (0.50 mL, 3.6 mmol) in $CH_2Cl_2$ (5 mL) was added dropwise. The reaction was removed from the cold bath and stirred at ~25° C. under nitrogen for 24 h. All solvents were removed in vacuo. The residue was taken up in MeOH (8 mL) and purified on a prep-HPLC (Column: SunFire Prep C18 OBD 30×100 mm 5 μm. Solvent A=90% Water: 10% MeOH: 0.1% TFA. Solvent B=10% Water: 90% MeOH: 0.1% TFA. Flow Rate=30 mL/min. Start % B=25. Final % B=65. Gradient Time=20 minutes, Stop time=20 min. Wavelength=220 nm) to afford a tan/brown viscous oil (170.8 mg). LC/MS indicated it is mainly a mixture of tert-butyl (5H-pyrrolo[2,3-c]pyridazin-7(6H)-yl)sulfonylcarbamate and the title compound product. The mixture was taken up in 25% TFA/$CH_2Cl_2$ (8 mL) and stirred at ~25° C. for 2 h. All solvents were removed in vacuo to afford the title compound (150 mg) as a brown solid. LC-MS retention time=0.49 min; m/z=201.05 [M+H]+. (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 8.81 (d, J=4.8 Hz, 1H), 7.64 (s, 2H), 7.61-7.55 (m, 1H), 3.94 (t, J=8.2 Hz, 2H), 3.23-3.13 (m, 2H).

Intermediate GW-16.1

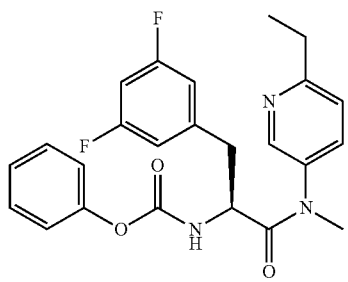 [SMILES: CCc1ccc(N(C)C(=O)[C@H](Cc2cc(F)cc(F)c2)NC(=O)Oc2ccccc2)cn1]

To a solution of Intermediate GW-6 (200 mg, 0.51 mmol) in THF (12 mL) was added phenyl chloroformate (80 mg, 0.51 mmol) and then TEA (0.20 mL, 1.5 mmol) and the reaction mixture was stirred at rt for 17 h. The reaction mixture was concentrated and purified with a Biotage Horizon (10-100% EtOAc/hexanes) to afford the title compound (0.15 g) as colorless oil. LC-MS retention time=3.76 min; m/z=440.15 [M+H]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, CDCl$_3$-d) δ 8.32-8.15 (two s, 1H), 7.31 (m, 3H), 7.16 (m, 2H), 7.05 (d, J=7.8 Hz, 2H), 6.70 (m, 1H), 6.48 (m, 3H), 4.56 (dd, J=16.1, 7.3 Hz, 1H), 3.27 (s, 3H), 2.98 (dd, J=13.6, 7.3 Hz, 1H), 2.86 (m, 3H), 1.31 (t, J=7.7 Hz, 3H).

Intermediate VN-19.1

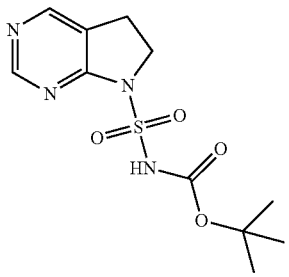 [SMILES: CC(C)(C)OC(=O)NS(=O)(=O)N1CCc2cncnc21]

To a solution of 2-methylpropan-2-ol (1.10 g, 14.8 mmol) in diethyl ether (60 mL) at −78° C. under nitrogen was added sulfurisocyanatidic chloride (1.29 mL, 14.8 mmol) dropwise. The reaction was removed from the cold bath and stirred at ~25° C. for 5.5 h. All solvents were removed in vacuo to afford tert-butyl chlorosulfonylcarbamate. The crude tert-butyl chlorosulfonylcarbamate was added dropwise to a solution of 6,7-dihydro-5H-pyrrolo[2,3-d]pyrimidine, TFA (1.16 g, 4.93 mmol) and triethylamine (3.44 mL, 24.7 mmol) in THF (25 mL) at 0° C. under nitrogen. The reaction was stirred at 0° C. for 30 min, then at ~25° C. for 20 h. All solvents were removed in vacuo. The residue was taken up in water (50 mL) and EtOAc (50 mL). The separated aqueous component was extracted further with EtOAc (2×50 mL). The combined organic components were dried over MgSO$_4$, filtered, and concentrated in vacuo. The residue was recrystallized from EtOAc/MeOH to afford the title compound (120 mg) as a white crystalline solid which was used without further purification. $^1$H NMR suggests a mixture of the title compound and tert-butyl (7H-pyrrolo[2,3-d]pyrimidin-7-yl)sulfonylcarbamate. LC-MS retention time=2.73 min; m/z=201.04 [M-Boc+H]$^+$. (Column: Phenomenex Luna C18 50×2.0 mm 3 µm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 8.69 (s, 1H), 8.44 (s, 1H), 4.19 (t, J=8.5 Hz, 2H), 3.17 (t, J=8.7 Hz, 2H), 1.27 (s, 9H). Indole minor product: $^1$H NMR (400 MHz, DMSO-d6) δ 9.20 (s, 1H), 9.04 (s, 1H), 7.84 (d, J=4.0 Hz, 1H), 6.87 (d, J=4.0 Hz, 1H), 1.19 (s, 9H).

Intermediate VN-19.2.1 and VN-19.2.2

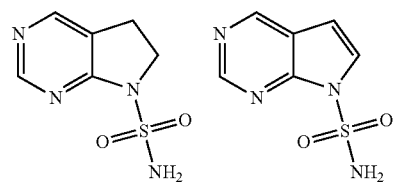

A solution of a mixture of Intermediate VN-19.1 and tert-butyl (7H-pyrrolo[2,3-d]pyrimidin-7-yl)sulfonylcarbamate (0.120 g, 0.400 mmol) in 25% TFA/CH$_2$Cl$_2$ (6 mL) was stirred at ~25° C. for 3 h. All solvents were removed in vacuo. The residue was taken up in MeOH (10 mL) and concentrated in vacuo to dryness (3×). The residue was then taken up in toluene (10 mL) and concentrated in vacuo to dryness (3×) to afford a mixture of the title compounds as a white solid (quantitative yield, 1:0.4 mole ratio) which was used without further purification. LC-MS retention time=0.53 and 0.94 min; m/z=not observed. (Column: Phenomenex Luna C18 50×2.0 mm 3 µm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1 minute hold at 100% B. Oven temperature=40° C. Wavelength=220 nm). $^1$H NMR (400 MHz, DMSO-d6) δ 8.78 (s, 1H), 8.41 (s, 1H), 7.84 (s, 2H), 4.02 (t, J=8.5 Hz, 2H), 3.14 (t, J=8.4 Hz, 2H). Indole minor product: $^1$H NMR (400 MHz, DMSO-d6) δ 9.17 (s, 1H), 9.01 (s, 1H), 8.73 (s, 2H), 7.79 (d, J=3.8 Hz, 1H), 6.82 (d, J=4.0 Hz, 1H).

Intermediate GW-17.1

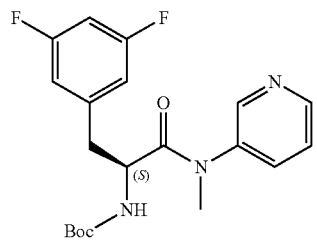

To a solution of (S)-2-((tert-butoxycarbonyl)amino)-3-(3,5-difluorophenyl)propanoic acid (0.697 g, 2.31 mmol) and N-methylpyridin-3-amine (0.250 g, 2.31 mmol) in DMF (5 mL) was added DIPEA (0.808 mL, 4.62 mmol) and then HATU (0.923 g, 2.43 mmol) and the reaction mixture was stirred at rt for 17 h. The reaction mixture was partitioned between water (50 mL) and EtOAc (25 mL), the organic component was dried with Na$_2$SO$_4$, concentrated and purified with a Biotage Horizon (20-100% EtOAc/hexanes) to afford the title compound (0.27 g) as white foam. LC-MS retention time=3.36 min; m/z=292.16 [M+H]$^+$ (− Boc). (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min: Detection: UV at 220 nm). $^1$H NMR (400 MHZ, DMSO-d$_6$) δ 8.58 (m, 2H), 7.80 (m, 1H), 7.54 (m, 1H), 7.30 (m, 1H), 7.04 (m, 2H), 6.53 (m, 1H), 4.15 (m, 1H), 3.20 (s, 3H), 2.84-2.72 (m, 2H), 1.29 (two s, 9H).

Intermediate GW-17.2

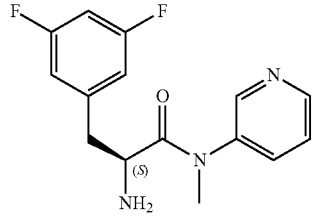

To a solution of Intermediate GW-17.1 (0.27 g, 0.69 mmol) in dioxane (2 mL) was added HCl (4N in dioxane) (1 mL, 4 mmol) and the reaction mixture was stirred at rt for 4 h. Methanol (1 mL) was added and the stirring was continued at rt for 16 h. The reaction mixture was concentrated and dried under high vacuum overnight to afford an HCl salt of the title compound (0.23 g) as orange solid. LC-MS retention time=2.15 min; m/z=292.16 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-18.1

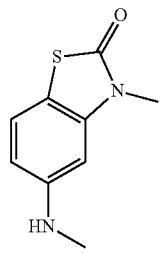

To a suspension of 5-amino-3-methylbenzo[d]thiazol-2(3H)-one (690 mg, 3.83 mmol) and formaldehyde (172 mg, 5.74 mmol) in methanol (20 mL) was added sodium methanolate (4.4 mL, 19 mmol) and the reaction mixture was heated to 50° C. for 16 h. The reaction mixture was cooled to rt, treated sodium tetrahydroborate (362 mg, 9.57 mmol) in two portions and stirred at rt for 3 h. The reaction mixture was concentrated, the mixture was dry-loaded with silica gel to a Biotage Horizon (0-80% EtOAc/hexanes) for purification to afford the title compound (0.54 g) as white solid. LC-MS retention time=1.84 min; m/z=195.11 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 8.50 (d, J=8.5 Hz, 1H), 6.45 (dd, J=8.5, 2.3, 1H), 6.40 (d, J=2.3 Hz, 1H), 5.91 (m, 1H), 3.34 (s, 3H, overlapped with water peak), 2.72 (d, J=5.0 Hz, 3H).

Intermediate GW-18.2

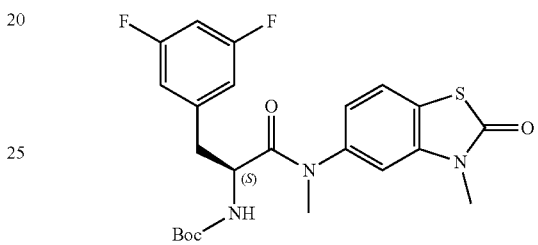

To a solution of (S)-2-((tert-butoxycarbonyl)amino)-3-(3,5-difluorophenyl)propanoic acid (0.392 g, 1.30 mmol) and Intermediate GW-18.1 (0.23 g, 1.2 mmol) in DMF (5 mL) was added DIPEA (0.40 mL, 2.4 mmol) and HATU (0.495 g, 1.30 mmol) and the reaction mixture was stirred at rt for 3 h. The reaction mixture was partitioned between water (50 mL) and EtOAc (25 mL), the organic component was dried with Na$_2$SO$_4$, concentrated and purified twice with a Biotage Horizon (120 g SiO$_2$, 0-70% EtOAc/hexanes and then 10-70% EtOAc/hexanes) to afford the title compound (0.21 g) as white foam. LC-MS retention time=3.92 min; m/z=500.15 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 7.82-7.74 (m, 1H), 7.47-7.36 (two s, 1H), 7.22 (d, J=8.0 Hz, 1H), 7.09-7.00 (m, 2H), 6.67-6.55 (m, 2H), 4.23 (m, 1H), 3.40 (s, 3H), 3.23-3.19 (two s, 3H), 2.89 (m, 1H), 2.71 (m, 1H), 1.28 (s, 9H).

Intermediate GW-18.3

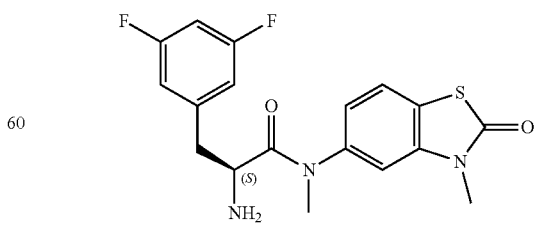

To a solution of Intermediate GW-18.2 (210 mg, 0.44 mmol) in dioxane (2 mL) was added HCl (4N in dioxane)

(0.67 mL, 2.7 mmol) and the reaction mixture was stirred at rt for 24 h. The reaction mixture was concentrated and dried under high vacuum overnight to afford an HCl salt of the title compound (0.19 g) as light pink solid. LC-MS retention time=2.67 min; m/z=378.10 [M+H]⁺. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-19.1

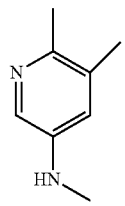

To a suspension of 5,6-dimethylpyridin-3-amine (650 mg, 5.32 mmol) and formaldehyde (240 mg, 7.98 mmol) in methanol (20 mL) was added sodium methanolate (6.08 mL, 26.6 mmol) and the reaction mixture was heated to 50° C. for 16 h. The reaction mixture was cooled to rt, treated sodium tetrahydroborate (503 mg, 13.3 mmol) in two portions and stirred at rt for 3 h. The reaction mixture was concentrated and dry-loaded with silica gel to a Biotage Horizon (20-100% EtOAc/hexanes then 0-20% MeOH/EtOAc) for purification, the title compound (0.40 g) was obtained as white solid. LC-MS retention time=1.44 min; m/z=137.13 [M+H]⁺. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 7.63 (d, J=2.7 Hz, 1H), 6.68 (d, J=2.5H, 1H), 5.50 (m, 1H), 2.66 (d, 5.0 Hz, 3H), 2.25 (s, 3H), 2.14 (s, 3H).

Intermediate GW-19.2

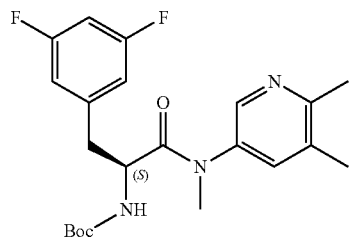

To a solution of (S)-2-((tert-butoxycarbonyl)amino)-3-(3,5-difluorophenyl)propanoic acid (0.885 g, 2.94 mmol) and Intermediate GW-19.1 (0.40 g, 2.9 mmol) in DMF (5 mL) was added DIPEA (1.02 mL, 5.87 mmol) and then HATU (1.17 g, 3.08 mmol) and the reaction mixture was stirred at rt for 4 h. The reaction mixture was partitioned between water (50 mL) and EtOAc (25 mL), the organic component was dried with Na$_2$SO$_4$, filtered, concentrated and purified with a Biotage Horizon (20-100% EtOAc/hexanes) to afford the title compound (0.80 g) as white solid. LC-MS retention time=3.27 min; m/z=442.20 [M+Na]⁺. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 8.32-8.25 (two s, 1H), 7.36 (s, 1H), 7.25 (d, J=8.0 Hz, 1H), 7.08 (m, 1H), 6.71-6.56 (m, 2H), 4.06 (m, 1H), 3.18-3.13 (two s, 3H), 2.83 (m, 1H), 2.72 (m, 1H), 2.45 (s, 3H), 2.26 (s, 3H), 1.29 (s, 9H).

Intermediate GW-193

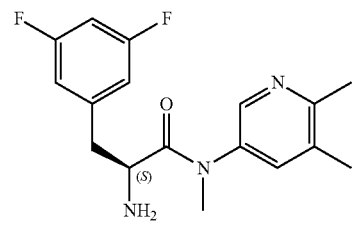

To a solution of Intermediate GW-19.2 (0.800 g, 1.90 mmol) in dioxane (6 mL) was added HCl (4N in dioxane) (2.90 mL, 11.6 mmol) and the reaction mixture was stirred at rt for 20 h. Most of the solvent was removed and then HCl (4N in dioxane) (2.90 mL, 95 mmol) was added and the reaction mixture was stirred at rt for 2 h. Methanol (2 mL) was added, stirred for 1 h, additional methanol (2 mL) was added and the stirring was continued at rt for 20 h. The reaction mixture was concentrated and dried under high vacuum to afford an HCl salt of the title compound (0.7 g) as white solid. LC-MS retention time=2.20 min; m/z=320.19 [M+H]⁺. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate VN-28.1

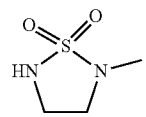

To a solution of N¹-methylethane-1,2-diamine (2.0 g, 27 mmol) in pyridine (30 mL) was added sulfuric diamide (3.10 g, 32.4 mmol). The reaction was heated at 120° C. under nitrogen for 24 h. All solvents were removed in vacuo. The residue was partitioned between saturated NaCl (aq, 25 mL) and EtOAc (125 mL) and organic component was washed with 1N HCl (aq, 50 mL) and saturated NaCl (aq, 25 mL). The organic component was dried over MgSO$_4$, filtered, and concentrated in vacuo to afford the title compound as a yellow viscous oil (799.4 mg). The product was used without further purification. ¹H NMR (400 MHz, CDCl$_3$) δ 4.48 (br s, 1H), 3.59-3.45 (m, 2H), 3.44-3.33 (m, 2H), 2.75 (s, 3H).

Intermediate VN-29

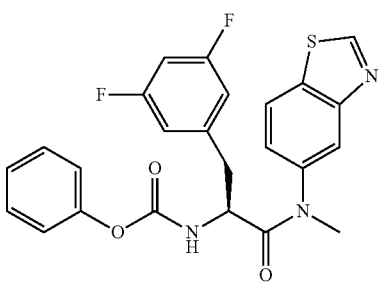 [SMILES: CN(C(=O)[C@H](Cc1cc(F)cc(F)c1)NC(=O)Oc1ccccc1)c1ccc2scnc2c1]

To a stirred solution of an HCl salt of Intermediate ZY-5 (0.50 g, 1.3 mmol) in THF (30 mL) was added phenyl chloroformate (0.16 mL, 1.3 mmol) and triethylamine (0.55 mL, 3.9 mmol) and the reaction mixture was stirred at room temperature overnight. The reaction mixture concentrated to dryness, diluted with DCM (4 mL) and purified using a Biotage Horizon (80 g SiO$_2$, 40% EtOAc/hexanes) to yield the title compound (545 mg) as white foam. LC-MS retention time=3.89 min; m/z=468.11 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHz, DMSO-d6) δ 9.50 (s, 1H), 8.28 (d, J=8.5 Hz, 2H), 8.07 (s, 1H), 7.45 (d, J=8.3 Hz, 1H), 7.38-7.29 (m, 2H), 7.22-7.14 (m, 1H), 7.02 (t, J=9.3 Hz, 1H), 6.92 (d, J=7.8 Hz, 2H), 6.50 (d, J=6.8 Hz, 2H), 4.22 (br. s., 1H), 3.27 (s, 3H), 3.08-2.92 (m, 1H), 2.88-2.73 (m, 1H).

Intermediate GW-20.1

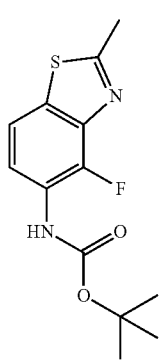 [SMILES: Cc1nc2c(F)c(NC(=O)OC(C)(C)C)ccc2s1]

To a solution of tert-butyl (2-methylbenzo[d]thiazol-5-yl) carbamate (1.28 g, 4.84 mmol) in acetonitrile (50 mL) was added selectfluor (3.43 g, 9.68 mmol) and the reaction mixture was stirred at rt for 19 h. The reaction mixture was partitioned between EtOAc (20 mL) and water (20 mL), the organic component was dried with Na$_2$SO$_4$, filtered and purified with a Biotage Horizon (0-40% EtOAc/hexanes) to afford the title compound (0.33 g) as white solid. LC-MS retention time=3.86 min; m/z=283.13 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 9.06 (s, 1H), 7.76 (d, J=8.6 Hz, 1H), 7.54 (t, J=7.3 Hz, 1H), 2.82 (s, 3H), 1.48 (two s, 9H).

Intermediate GW-20.2

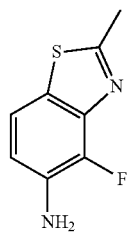

To a solution of Intermediate GW-20.1 (0.33 g, 1.2 mmol) in dioxane (2 mL) was added HCl (4N in dioxane) (1.1 mL, 4.4 mmol) and the reaction mixture was stirred at rt for 5 h, methanol (1 mL) was added and the stirring was continued at rt for 7 h. Additional HCl (4N in dioxane) (1.06 mL, 4.24 mmol) was added and the stirring was continued at rt for 16 h. The reaction mixture was concentrated and dried under high vacuum to afford the title compound (0.29 g) as brown solid. LC-MS retention time=2.24 min; m/z=183.03 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Intermediate GW-20.3

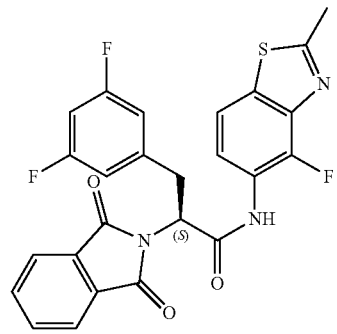

To a solution of Intermediate GW-8.1 (338 mg, 1.02 mmol) and Intermediate GW-20.2 (260 mg, 1.02 mmol) in DMF (1 mL) was added DIPEA (0.62 mL, 3.6 mmol) and HATU (407 mg, 1.09 mmol) and the reaction mixture was stirred at rt for 3 h. the reaction mixture was partitioned between water (10 mL) and EtOAc (5 mL), the organic component was dried with Na$_2$SO$_4$, filtered and purified with a Biotage Horizon (0-70% EtOAc/hexanes) to afford impure title compound (0.28 g, with impurity). The material was purified again with a Biotage Horizon (10-70% EtOAc/hexanes, 120 g column) to afford the title compound (0.12 g) as green oil. LC-MS retention time=3.86 min; m/z=496.14 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-

0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 10.08 (s, 1H), 7.86 (m, 5H), 7.45 (m, 1H), 6.94 (m, 3H), 5.33 (dd, J=9.0, 6.5 Hz, 1H), 3.64 (dd, J=13.8, 4.5 Hz, 1H), 3.40 (m, 1H), 2.83 (s, 3H).

Intermediate GW-20.4

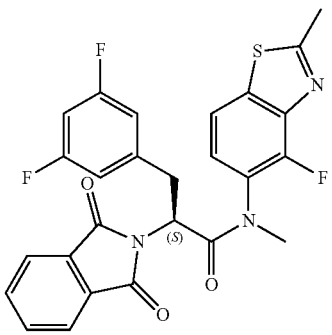

To a solution of Intermediate GW-20.3 (0.15 g, 0.30 mmol) in DMF (5 mL) was added 60% NaH (0.013 g, 0.33 mmol) as a dispersion in mineral oil and the reaction mixture was stirred at rt for 3 min. Then iodomethane (0.02 mL, 0.33 mmol) was added and the stirring was continued at rt for 17 h. The reaction mixture was partitioned between water (50 mL) and EtOAc (25 mL), the organic component was dried with Na₂SO₄, filtered, concentrated and purified with a Biotage Horizon (0-80% EtOAc/hexanes) to afford the title compound (60 mg) as white solid. LC-MS retention time=3.92 min; m/z=510.12 [M+H]⁺. (Column: Phenomenex-Luna 2.0×50 mm, 3 µm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-20.5

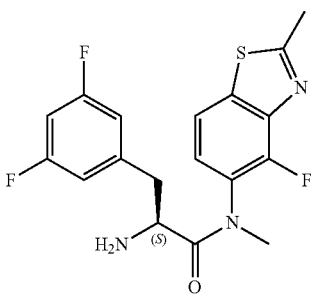

To a solution of Intermediate GW-20.4 (60 mg, 0.12 mmol) in ethanol (3 mL) was added hydrazine hydrate (0.030 mL, 0.71 mmol) and the reaction mixture was heated to 50° C. for 5 h. The solvent was concentrated and the residue was azeotroped with ethanol (2×10 mL) and dried under high vacuum overnight to afford the title compound (40 mg) white solid. LC-MS retention time=2.69 min; m/z=380.20 [M+H]⁺. (Column: Phenomenex C18 2.0×50 mm, 3 µm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-21.1

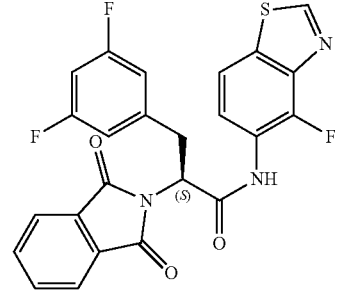

To a solution of Intermediate GW-8.1 (838 mg, 2.53 mmol) and 4-fluorobenzo[d]thiazol-5-amine (610 mg, 2.53 mmol) in DMF (6 mL) was added DIPEA (1.5 mL, 8.9 mmol) and HATU (1010 mg, 2.66 mmol) and the reaction mixture was stirred at rt for 3 h. The reaction mixture was partitioned between water (60 mL) and EtOAc (30 mL), the organic component was dried with Na₂SO₄, filtered and purified with a Biotage Horizon (0-70% EtOAc/hexanes) to afford the title compound (0.62 g) as colorless oil. LC-MS retention time=2.52 min; m/z=482.15 [M+H]⁺. (Column: Phenomenex C18 2.0×50 mm, 3 m particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 10.16 (s, 1H), 9.44 (s, 1H), 7.97 (d, J=8.8 Hz, 1H), 7.88 (m, 4H), 7.53 (t, J=6.7 Hz, 1H), 6.97 (m, 3H), 5.34 (dd, J=13.8, 4.5 Hz, 1H), 3.64 (dd, J=13.8, 4.5 Hz, 1H), 3.38 (m, 1H).

Intermediate GW-21.2

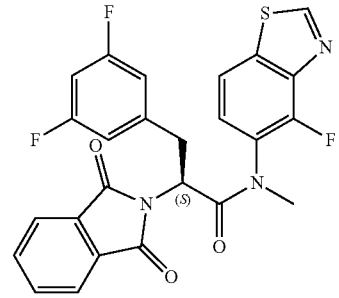

To a solution of Intermediate GW-21.1 (0.62 g, 1.3 mmol) in DMF (12 mL) was added 60% NaH (0.057 g, 1.42 mmol) as a dispersion in mineral oil and the reaction mixture was stirred for 3 min. Then iodomethane (0.090 mL, 1.4 mmol) was added and the reaction mixture was stirred at rt for 16 h. It was partitioned between water (120 mL) and EtOAc (60 mL), the organic component was dried with Na₂SO₄, filtered and purified with a Biotage Horizon (0-80% EtOAc/hexanes) to afford the title compound (0.32 g) as colorless oil. LC-MS retention time=2.35 min; m/z=496.15 [M+Na]⁺. (Column: Phenomenex C18 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-21.3

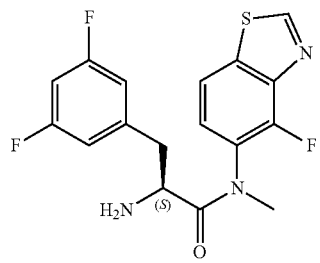

To a solution of Intermediate GW-21.2 (320 mg, 0.65 mmol) in ethanol (10 mL) was added hydrazine hydrate (0.19 mL, 3.88 mmol) and the reaction mixture was heated to 50° C. for 5.5 h. The reaction mixture was filtered and the filtrate was azeotroped with ethanol (2×10 mL), dried under high vacuum overnight and purified with a Biotage Horizon (0-100% MeOH/EtOAc) to afford the title compound (60 mg) as solid. LC-MS retention time=1.79 min; m/z=366.25 [M+H]⁺. (Column: Phenomenex C18 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-22.1

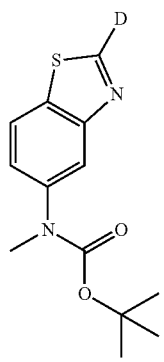 [SMILES: [2H]c1nc2cc(N(C)C(=O)OC(C)(C)C)ccc2s1]

To a solution of tert-butyl benzo[d]thiazol-5-yl(methyl)carbamate (0.88 g, 3.3 mmol) in THF (40 mL) was added n-butyllithium (2.5M in hexanes) (2.26 mL, 5.66 mmol) at −78° C. and the reaction mixture was stirred for 30 min. Then D20 (0.72 mL, 39.9 mmol) was added, the bath was removed and the reaction mixture was stirred at rt for 17 h. The reaction mixture was concentrated and partitioned between water (20 mL) and EtOAc (20 mL), the organic component was dried with Na₂SO₄, filtered and purified with a Biotage Horizon (10-80% EtOAc/hexanes) to afford the title compound (0.48 g) as yellow solid. LC-MS retention time=2.63 min; observed m/z=210.20 [M-tBu+H]⁺. (Column: Phenomenex C18 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d6) δ 8.12 (d, J=9.0 Hz, 1H), 7.99 (s, 1H), 7.44 (d, J=10.8 Hz, 1H), 3.34 (s, 3H), 1.41 (s, 9H).

Intermediate GW-22.2

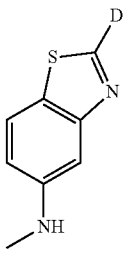

To a mixture of Intermediate GW-22.1 (0.46 g, 1.73 mmol) in dioxane (4 mL) was added HCl (4N in dioxane) (2.63 mL, 10.52 mmol) and the clear solution was stirred at rt for 17 h. The reaction mixture was concentrated and dried under high vacuum for 64 h to afford an HCl salt of the title compound (0.4 g) as beige solid. LC-MS retention time=1.81 min; m/z=166.07 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm). ¹H NMR (400 MHZ, DMSO-d₆) δ 9.36 (s, 1H), 8.15 (d, J=2.5 Hz, 1H), 7.41 (d, J=2.5 Hz, 1H), 6.25 (m, 1H), 2.78 (d, J=5.0 Hz, 3H).

Intermediate GW-22.3

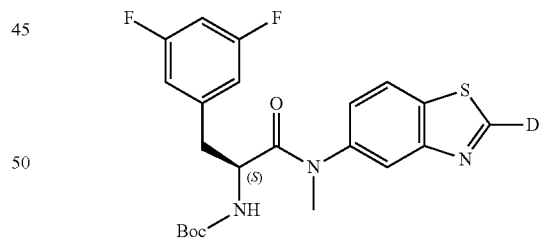

To a solution of (S)-2-((tert-butoxycarbonyl)amino)-3-(3,5-difluorophenyl)propanoic acid (0.523 g, 1.74 mmol) and Intermediate GW-22.2 (0.35 g, 1.7 mmol) in DMF (5 mL) was added DIPEA (0.76 mL, 4.3 mmol) and then HATU (0.69 g, 1.8 mmol) and the reaction mixture was stirred at rt for 3 h. The reaction mixture was partitioned between water (50 mL) and EtOAc (20 mL) and the organic component was dried with Na₂SO₄, filtered and purified with a Biotage Horizon (0-80% EtOAc/hexanes) to afford the title compound (0.50 g) as light yellow foam. LC-MS retention time=3.85 min; m/z=471.21 [M+Na]⁺. (Column: Phenomenex-Luna 2.0×50 mm, 3 μm particles; Mobile Phase A: 10% MeOH-90% H₂O-0.1% TFA; Mobile Phase B: 90%

MeOH-10% H₂O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, DMSO-d6) δ 8.32 (d, J=8.6 Hz, 1H), 8.12 (s, 1H), 7.49 (d, J=8.5 Hz, 1H), 7.22 (d, J=8.3 Hz, 1H), 6.97 (m, 1H), 6.48-6.38 (m, 2H), 4.30-4.16 (m, 1H), 3.26 (s, 3H), 2.89 (d, J=16.6 Hz, 1H), 2.71 (m, 1H), 1.27 (s, 9H).

Intermediate GW-22.4

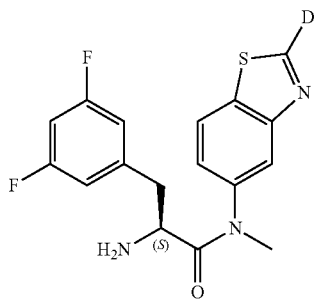

To a solution of Intermediate GW-22.3 (0.500 g, 1.12 mmol) in dioxane (3 mL) was added HCl (4N in dioxane) (1.69 mL, 6.76 mmol) and the reaction mixture was stirred at rt for 17 h. Methanol (1 mL) was added and the reaction mixture was stirred at rt for 5 h. The reaction mixture was concentrated and dried under high vacuum overnight to afford an HCl salt of the title compound (0.43 g) as light yellow solid. LC-MS retention time=2.83 min; m/z=349.13 [M+H]⁺. (Column: Phenomenex-Luna 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Intermediate GW-23.1

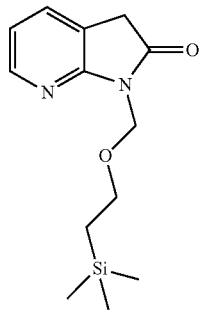 [SMILES: C[Si](C)(C)CCOCN1C(=O)Cc2cccnc21]

To a solution of 1H-pyrrolo[2,3-b]pyridin-2(3H)-one (2.00 g, 14.9 mmol) in DMF (30 mL) and THF (30 mL) under nitrogen at 0° C. was added sodium hydride, 60% in mineral oil (0.600 g, 15.0 mmol). The reaction mixture was stirred at 0° C. for 1 h. Then (2-(chloromethoxy)ethyl)trimethylsilane (3.17 mL, 17.9 mmol) was added dropwise over 3 min and the reaction was allowed to warm up to rt without removing the cold bath over 21 h. The reaction mixture was partitioned between water (50 mL) and EtOAc (50 mL), the aqueous was extracted with EtOAc (2×50 mL), the combined organic component was washed with water (2×50 mL), brine (50 mL), dried over MgSO₄, filtered, concentrated and purified with a Biotage Horizon (25% EtOAc/hexanes) to afford the title compound (2.26 g) as viscous orange oil. LC-MS retention time=3.49 min; m/z=265.20 [M+H]⁺. (Column: Phenomenex C18 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1-minute hold at 100% B. Oven temperature=40° C. Wavelength=220 nm). $^1$H NMR (400 MHZ, DMSO-d6) δ 8.15 (d, J=5.0 Hz, 1H), 7.65 (d, J=7.3 Hz, 1H), 7.05 (dd, J=7.2, 5.4 Hz, 1H), 5.07 (s, 2H), 3.69 (s, 2H), 3.59 (t, J=8.0 Hz, 2H), 0.85 (t, J=8.0 Hz, 2H), −0.06 (s, 9H).

Intermediate GW-23.2

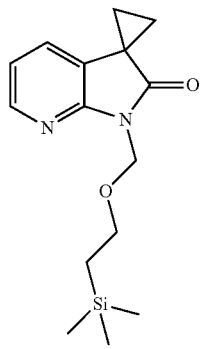 [SMILES: C[Si](C)(C)CCOCN1C(=O)C2(CC2)c2cccnc21]

To a solution of Intermediate GW-23.1 (2.21 g, 8.38 mmol) in DMF (40 mL) at rt under nitrogen was added sodium hydride, 60% in mineral oil (0.670 g, 16.8 mmol). The reaction mixture was stirred at rt under nitrogen for 1.5 h. To the reaction mixture was added 1,2-dibromoethane (0.722 mL, 8.38 mmol) dropwise over 3 min and the reaction mixture was stirred at rt for 2 h. The reaction mixture was partitioned between water (50 mL) and EtOAc (50 mL) and the aqueous component was extracted by EtOAc (2×25 mL). The combined organic component was washed with water (2×25 mL), brine (25 mL), dried over MgSO₄, filtered, concentrated and purified with a Biotage Horizon (120 g column, 25% EtOAc/hexanes) to afford the title compound (1.87 g) as light yellow viscous oil. $^1$H NMR (400 MHZ, DMSO-d6) δ 8.15 (dd, J=5.1, 1.4 Hz, 1H), 7.46 (dd, J=7.3, 1.5 Hz, 1H), 7.05 (dd, J=7.3, 5.3 Hz, 1H), 5.15 (s, 2H), 3.60 (t, J=1.0 Hz, 2H), 1.77-1.69 (m, 2H), 1.65-1.56 (m, 2H), 0.85 (t, J=8.0 Hz, 2H), −0.08 (s, 9H).

Intermediate GW-23.3

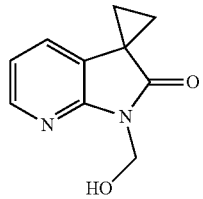 [SMILES: O=C1N(CO)c2ncccc2C12CC2]

A solution of Intermediate GW-23.2 (1.87 g, 6.44 mmol) in 25% TFA/CH$_2$Cl$_2$ (60 mL) was stirred at rt for 1.5 h. The reaction mixture was cooled to 0° C., carefully made basic with a solution of saturated NaHCO$_3$ (aq), and extracted with CH$_2$Cl$_2$ (2×50 mL). The combined organic component was dried over MgSO$_4$, filtered and concentrated to afford an off-white solid. The solid was re-crystallized from EtOAc to afford the title compound (0.85 g) as pink crystals. LC-MS retention time=1.60 min; m/z=161.0 [M-MeOH+H]$^+$. (Column: Phenomenex Luna C18 50×2.0 mm 3 µm. Solvent A=95% Water: 5% AcCN: 10 mM NH$_4$OAc. Solvent B=5% Water: 95% AcCN: 10 mM NH$_4$OAc. Flow Rate=0.8 mL/min. Start % B=0. Final % B=100. Gradient Time=4 minutes, then a 1-minute hold at 100% B. Oven temperature=40° C. Wavelength=220 nm). $^1$H NMR (400 MHZ, DMSO-d6) δ 8.15 (dd, J=5.3, 1.5 Hz, 1H), 7.44 (dd, J=7.5, 1.5 Hz, 1H), 7.03 (dd, J=7.3, 5.3 Hz, 1H), 6.31 (t, J=6.9 Hz, 1H), 5.16 (d, J=7.0 Hz, 2H), 1.75-1.67 (m, 2H), 1.62-1.55 (m, 2H). $^{13}$C NMR (101 MHz, DMSO-d6) δ 175.9, 155.2, 145.3, 127.1, 124.6, 118.1, 61.2, 26.2, 18.8.

Intermediate GW-23.4

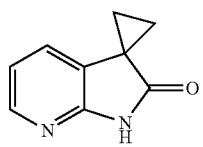 [SMILES: O=C1Nc2ncccc2C12CC2]

To a suspension of Intermediate GW-23.3 (0.500 g, 2.63 mmol) in MeOH (50 mL) was added 6N HCl (aq) (100 mL). The suspension became a homogeneous solution with stirring at rt for 5 d. The reaction mixture was concentrated and the residue was partitioned between EtOAc (25 mL) and a solution of saturated NaHCO$_3$ (aq, 25 mL). The aqueous component was further extracted with EtOAc (2×25 mL) and the combined organic components were dried over MgSO$_4$, filtered, concentrated and purified twice with a Biotage Horizon (120 g column, 75% EtOAc/hexanes and then 120 g column, 50% EtOAc/hexanes). The resulting mixture was dissolved in MeOH (18 mL) and purified by preparative HPLC (Column: XTERRA 30×100 mm S5. Solvent A=90% Water: 10% MeOH: 0.1% TFA. Solvent B=10% Water: 90% MeOH: 0.1% TFA. Flow Rate=40 mL/min. Start % B=0. Final % B=100. Gradient Time=10 minutes, then a 2-minute hold at 100% B. Wavelength=220 nm) to afford the title compound (0.247 g) as white solid. LC-MS retention time=1.29 min; m/z=161.1 [M+H]$^+$. (Column: Phenomenex Luna C18 50×2.0 mm 3 µm. Solvent A=95% Water: 5% AcCN: 10 mM NH$_4$OAc. Solvent B=5% Water: 95% AcCN: 10 mM NH$_4$OAc. Flow Rate=0.8 mL/min. Start % B=0. Final % B=100. Gradient Time=4 minutes, then a 1-minute hold at 100% B. Oven temperature=40° C. Wavelength=220 nm). $^1$H NMR (400 MHZ, DMSO-d6) δ 11.18 (br s, 1H), 8.04 (dd, J=5.3, 1.5 Hz, 1H), 7.36 (dd, J=7.3, 1.5 Hz, 1H), 6.93 (dd, J=7.3, 5.3 Hz, 1H), 1.68-1.60 (m, 2H), 1.55-1.47 (m, 2H).

Intermediate GW-23.5

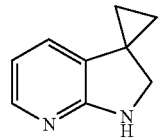 [SMILES: c1cnc2c(c1)C1(CC1)CN2]

To a solution of Intermediate GW-23.4 (0.050 g, 0.31 mmol) in THF (1 mL) at rt was added 1M lithium aluminum hydride in THF (0.624 mL, 0.624 mmol) dropwise over 1 min. The reaction was stirred at rt for 18.5 h. The reaction was carefully quenched with EtOAc (2 mL) followed by water (2 mL). To the resulting slurry was added a solution of Rochelle's salt (aq, 10 mL) and the mixture was extracted with EtOAc (3×25 mL). The combined organic component was dried over MgSO$_4$, filtered, concentrated and purified with a Biotage Horizon (24 g column, 75% EtOAc/hexanes) to afford the title compound (22.5 mg) as white solid. LC-MS retention time=1.93 min; m/z=147.1 [M+H]$^+$. (Column: Phenomenex Luna C18 50×2.0 mm 3 µm. Solvent A=95% Water: 5% AcCN: 10 mM NH$_4$OAc. Solvent B=5% Water: 95% AcCN: 10 mM NH$_4$OAc. Flow Rate=0.8 mL/min. Start % B=0. Final % B=100. Gradient Time=4 minutes, then a 1-minute hold at 100% B. Oven temperature=40° C. Wavelength=220 nm). $^1$H NMR (400 MHZ, DMSO-d6) δ 7.61 (dd, J=5.3, 1.5 Hz, 1H), 6.83-6.77 (m, 1H), 6.46 (br s, 1H), 6.35 (dd, J=7.0, 5.3 Hz, 1H), 3.45 (d, J=1.5 Hz, 2H), 0.96-0.93 (m, 2H), 0.93-0.91 (m, 2H). $^{13}$C NMR (101 MHz, DMSO-d6) δ 164.7, 144.9, 127.6, 124.7, 112.1, 51.8, 22.4, 17.2.

Intermediate AW-2

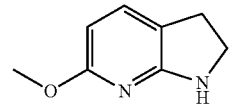

Step 1.

To a solution of 6-methoxy-1H-pyrrolo[2,3-b]pyridine (180 mg, 1.215 mmol) and DMAP (14.8 mg, 0.121 mmol) in THF (5 mL) was added BOC$_2$O (0.338 mL, 1.46 mmol). The resulting solution was stirred at rt for 1 h and then sealed and heated in an oil bath at 70° C. for 2 h. The solvent was removed in vacuo and the residue was purified by flash silica chromatography (40 g Silica gel cartridge), eluting with gradient 0~35% EtOAc-hexanes to afford tert-butyl 6-methoxy-1H-pyrrolo[2,3-b]pyridine-1-carboxylate (300 mg). LC-MS retention time=1.87 min; m/z=271.07 [M+Na]+ (Start % B=0, Final % B=100, Gradient Time=2 min, Flow Rate=1 mL/min, Wavelength=220, Solvent Pair=Water: Acetonitrile 10 mM Ammonium Acetate, Solvent A=95% Water: 5% Acetonitrile 10 mM Ammonium Acetate, Solvent B=5% Water: 95% Acetonitrile 10 mM Ammonium Acetate, Column=Phenomenex Luna C18 2.0× 30 mm 3 µm, Oven Temp.=40° C.).

Step 2.

To a solution of tert-butyl 6-methoxy-1H-pyrrolo[2,3-b]pyridine-1-carboxylate (298 mg, 1.20 mmol) in methanol (10 mL), 10% Pd/C (64 mg, 0.060 mmol) was added. The resulting mixture was placed under 1 atm of H$_2$ (balloon)

and stirred at rt for 4 h. The reaction mixture was filtered through a pad of Celite, washed with MeOH and concentrated in vacuo. The residue was purified by flash silica chromatography (40 g Silica gel cartridge), eluting with gradient 0~35% EtOAc-hexanes to afford tert-butyl-1-carboxylate protected Intermediate AW-2 (278 mg) as a white solid. $^1$H NMR (500 MHZ, CDCl$_3$) δ 7.32 (d, J=8.0 Hz, 1H), 6.30 (d, J=8.0 Hz, 1H), 4.04 (t, J=8.7 Hz, 2H), 3.96 (s, 3H), 2.97 (t, J=8.7 Hz, 2H), 1.61 (s, 9H).

Step 3.

To a solution of tert-butyl-1-carboxylate protected Intermediate AW-2 (275 mg, 1.10 mmol) in methanol (1 mL) was added HCl (4N in dioxane) (5.5 mL, 22 mmol) and the reaction mixture was stirred at rt for 6 h. The solvents were evaporated in vacuo. The residue was triturated with ether (10 mL), filtered, washed with ether, and dried in vacuo to afford an HCl salt of Intermediate AW-2 (170 mg) as an off-white solid. LC-MS retention time=1.19 min; m/z=151.03 [M+H]+ (Start % B=0, Final % B=100, Gradient Time=2 min, Flow Rate=1 mL/min, Wavelength=220, Solvent Pair=Water: Acetonitrile 10 mM Ammonium Acetate, Solvent A=95% Water: 5% Acetonitrile 10 mM Ammonium Acetate, Solvent B=5% Water: 95% Acetonitrile 10 mM Ammonium Acetate, Column=Phenomenex Luna C18 2.0×30 mm 3 μm, Oven Temp.=40° C.).

Intermediate AW-3

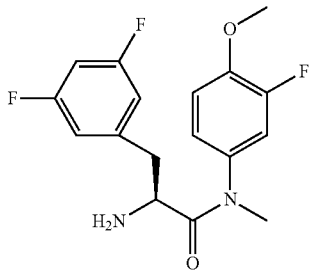 [SMILES: COc1ccc(N(C)C(=O)[C@@H](N)Cc2cc(F)cc(F)c2)cc1F]

Step 1.

To a mixture of 3-fluoro-4-methoxyaniline (3.00 g, 21.3 mmol) and paraformaldehyde (1.28 g, 42.5 mmol) in MeOH (100 mL) was added sodium methoxide (19.4 mL, 85.0 mmol). The reaction mixture was sealed and heated at 55° C. for 2 h. After cooling to rt, sodium borohydride (2.01 g, 53.1 mmol) was then added in small portions. The final mixture was stirred at rt ON. The solvent was removed in vacuo and the residue was taken up in EtOAc (100 mL) and washed with water (150 mL). The aqueous component was saturated with NaCl and extracted with EtOAc (100 mL). The combined organic components were washed with brine (50 mL), dried over MgSO$_4$, filtered, and concentrated in vacuo. The residue was taken up into DCM (10 mL) and purified by FCC (80 g silica gel cartridge), eluting with gradient 5%~50% EtOAc-hexanes to afford 3-fluoro-4-methoxy-N-methylaniline (3.08 g) as a light yellow oil. LC-MS retention time=1.34 min; m/z=153.42 [M−H]−. (Start % B=0, Final % B=100, Gradient Time=2 min, Flow Rate=1 mL/min, Wavelength=220, Solvent Pair=Water: Acetonitrile 10 mM Ammonium Acetate, Solvent A=95% Water: 5% Acetonitrile 10 mM Ammonium Acetate, Solvent B=5% Water: 95% Acetonitrile 10 mM Ammonium Acetate, Column=Phenomenex Luna C18 2.0×30 mm 3 μm, Oven Temp.=40° C.).

Step 2.

To a solution of (S)-2-((tert-butoxycarbonyl)amino)-3-(3,5-difluorophenyl)propanoic acid (971 mg, 3.22 mmol), 3-fluoro-4-methoxy-N-methylaniline (500 mg, 3.22 mmol) and HATU (1.35 g, 3.54 mmol) in DMF (15 mL) was added DIPEA (2.25 mL, 12.9 mmol) dropwise. The reaction solution was stirred at rt ON, diluted with EtOAc (50 mL) and poured into water (100 mL). The separated aqueous component was saturated with NaCl, extracted with EtOAc (20 mL). The combined organic components were washed with brine, dried over MgSO$_4$, filtered and evaporated in vacuo. The residue was taken up into DCM (20 mL) and purified by FCC (220 g silica gel cartridge), eluting with gradient 35%~65% EtOAc-hexanes to afford (S)-tert-butyl (3-(3,5-difluorophenyl)-1-((3-fluoro-4-methoxyphenyl)(methyl)amino)-1-oxopropan-2-yl)carbamate (1.26 g) as a white foam. LC-MS retention time=1.30 min; m/z=439.05 [M+H]+. (Start % B=0, Final % B=98, Gradient Time=1.5 min, Flow Rate=0.8 mL/min, Wavelength=220, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm 1.7 m, Oven Temp.=40° C.).

Step 3.

A mixture of (S)-tert-butyl (3-(3,5-difluorophenyl)-1-((3-fluoro-4-methoxyphenyl)(methyl)amino)-1-oxopropan-2-yl)carbamate (1.26 g, 2.88 mmol) and 4 M HCl in 1,4-dioxane (5.76 mL, 23.0 mmol) was stirred at rt for 1 h. The reaction mixture was concentrated and then dried it in vacuo to afford an HCl salt of the title compound (1.10 g) as an off-white foam. LC-MS retention time=0.90 min; m/z=339.20 [M+H]+. (Start % B=0, Final % B=98, Gradient Time=1.5 min, Flow Rate=0.8 mL/min, Wavelength=220, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm 1.7 m, Oven Temp.=40° C.). $^1$HNMR (500 MHZ, methanol-d$_4$) δ 7.17 (t, J 8.9 Hz, 1H), 7.01-6.71 (m, 3H), 6.60 (d, J 6.3 Hz, 2H), 4.17 (t, J=7.1 Hz, 1H), 3.94 (s, 3H), 3.26 (s, 3H), 3.11 (dd, J=13.7, 7.6 Hz, 1H), 2.97 (dd, J=13.8, 6.7 Hz, 1H).

Intermediate AW-4

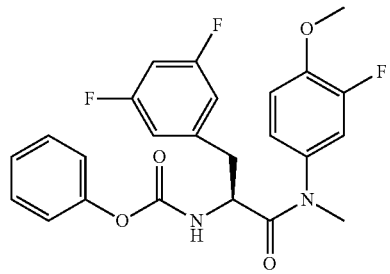 [SMILES: COc1ccc(N(C)C(=O)[C@H](Cc2cc(F)cc(F)c2)NC(=O)Oc2ccccc2)cc1F]

To an ice bath cooled solution of phenyl chloroformate (0.034 mL, 0.26 mmol) in DCM (2.5 mL) was added a solution of an HCl salt of Intermediate AW-3 (101 mg, 0.261 mmol) and TEA (0.109 mL, 0.784 mmol) in DCM (2.5 mL) dropwise through an addition funnel. The resulting solution was stirred at 0° C. for 30 min, then at rt for 30 min. The mixture was cooled to 0° C., additional phenyl chloroformate (0.034 mL, 0.26 mmol) was added and stirring continued at rt ON. The reaction mixture was diluted with DCM (5 mL), washed with water, brine and 1 M NaOH, dried over MgSO₄, filtered and evaporated in vacuo to afford the title compound (122 mg) as an off-white gum which was used without further purification. LC-MS retention time=1.73 min; m/z=459.20 [M+H]+. (Start % B=0, Final % B=100, Gradient Time=2 min, Flow Rate=1 mL/min, Wavelength=220, Solvent Pair=Water: Acetonitrile 10 mM Ammonium Acetate, Solvent A=95% Water: 5% Acetonitrile 10 mM Ammonium Acetate, Solvent B=5% Water: 95% Acetonitrile 10 mM Ammonium Acetate, Column=Phenomenex Luna C18 2.0×30 mm 3 μm, Oven Temp.=40° C.).

Intermediate ZY-24.1

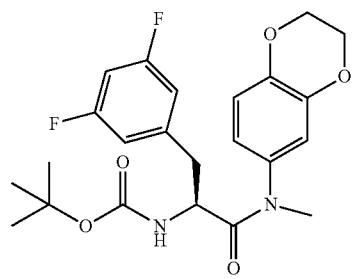 [SMILES: CN(C(=O)[C@H](Cc1cc(F)cc(F)c1)NC(=O)OC(C)(C)C)c1ccc2c(c1)OCCO2]

HATU (127 mg, 0.33 mmol) was added to a mixture of (S)-2-((tert-butoxycarbonyl)amino)-3-(3,5-difluorophenyl)propanoic acid (100 mg, 0.33 mmol) and N-methyl-2,3-dihydrobenzo[b][1,4]dioxin-6-amine (50 mg, 0.30 mmol) in DMF (2 mL) and DIPEA (0.16 mL, 0.91 mmol) and the reaction mixture was stirred at rt for 2 h. The reaction was filtered, and purified by preparative HPLC to afford the title compound (125 mg). LC-MS retention time=1.94 min; m/z=449.2 [M+H]⁺. (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm).

Intermediate ZY-24.2

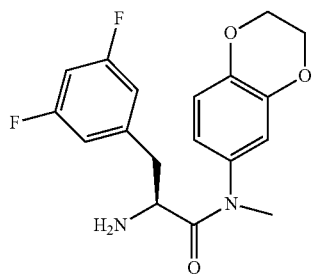 [SMILES: CN(C(=O)[C@@H](N)Cc1cc(F)cc(F)c1)c1ccc2c(c1)OCCO2]

A solution of 4 M HCl in dioxane (1.5 mL, 6.00 mmol) was added to a solution of Intermediate ZY-24.1 (125 mg, 0.28 mmol) in MeOH (1.5 mL) and the reaction mixture was stirred at rt for 16 h. The reaction was concentrated and the residue was azeotroped with EtOH and dried to afford an HCl salt of the title compound (119 mg) as yellow solid. LC-MS retention time=0.87 min; m/z=349.2 [M+H]⁺. (Column: Waters Aquity BEH C18 2.1×50 mm 1.7 U. Solvent A=100% Water: 0.05% TFA. Solvent B=100% Acetonitrile: 0.05% TFA. Flow Rate=0.8 mL/min. Gradient: 2-98% B. Gradient Time=1.5 min. Wavelength=220).

Intermediate ZY-25.1

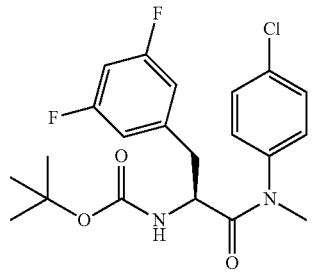 [SMILES: CN(C(=O)[C@H](Cc1cc(F)cc(F)c1)NC(=O)OC(C)(C)C)c1ccc(Cl)cc1]

HATU (148 mg, 0.39 mmol) was added to a mixture of (S)-2-((tert-butoxycarbonyl)amino)-3-(3,5-difluorophenyl)propanoic acid (117 mg, 0.39 mmol) and 4-chloro-N-methylaniline (50 mg, 0.35 mmol) in DMF (2 mL) and DIPEA (0.18 mL, 1.1 mmol) and the reaction mixture was stirred at rt for 2 h. The reaction was filtered, and purified by preparative HPLC to afford the title compound (108.7 mg). LC-MS retention time=2.37 min; m/z=425.0 [M+H]⁺. (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm).

Intermediate ZY-25.2

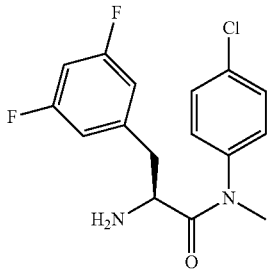 [SMILES: CN(C(=O)[C@@H](N)Cc1cc(F)cc(F)c1)c1ccc(Cl)cc1]

A solution of 4M HCl in dioxane (1.5 mL, 6.0 mmol) was added to a solution of Intermediate ZY-25.1 (108 mg, 0.25 mmol) in MeOH (1.5 mL) and the reaction mixture was stirred at rt for 16 h. The reaction was concentrated and the residue was azeotroped with EtOH and dried to afford an HCl salt of title the compound (108 mg) as yellow solid. LC-MS retention time=0.91 min; m/z=325.1 [M+H]⁺. (Column: Waters Aquity BEH C18 2.1×50 mm 1.7 U. Solvent A=100% Water: 0.05% TFA. Solvent B=100% Acetonitrile: 0.05% TFA. Flow Rate=0.8 mL/min. Gradient: 2-98% B. Gradient Time=1.5 min. Wavelength=220).

Intermediate BB-1.1

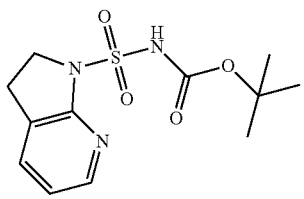 [SMILES: CC(C)(C)OC(=O)NS(=O)(=O)N1CCc2cccnc21]

To a stirred solution of tert-butanol (1.59 mL, 16.7 mmol) in DCM (20 mL) at 0° C. was slowly added sulfurisocyanatidic chloride (2.36 g, 16.7 mmol) under nitrogen atmosphere and stirred for 15 min. A DCM (5 mL) solution of 2,3-dihydro-1H-pyrrolo[2,3-b]pyridine (2.00 g, 16.7 mmol) and TEA (7.0 ml, 40 mmol) was added to the above reaction mixture and stirred for 30 min at 0° C. and at room temperature for 1 h. The reaction mixture was diluted with ice cold saturated aqueous solution of NaHCO$_3$ (50 mL) and extracted with DCM (2×50 mL). The combined organic layer was washed with brine (75 mL), dried (Na$_2$SO$_4$), filtered and concentrated. The crude product was purified by combiflash chromatography (24 g Redisep® SiO$_2$ column, eluting with 30% EtOAc in n-hexanes) to afford the title compound (1.6 g) as a viscous liquid. LC-MS retention time=1.69 min; m/z=300.2 [M+H]$^+$. Column: KINETIX C18, 75×3 mm 2.6 micron; Flow: 1 mL/min; Mobile Phase A: 1% HCOOH in Water; Mobile Phase B: ACN; 20% B to 100% B over 4 minutes, then hold a 0.6 min. at 100% B of flow rate 1.5 ml/min; Detection: UV at 220 nm.

Intermediate BB-1.2

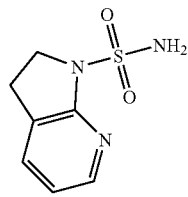 [SMILES: NS(=O)(=O)N1CCc2cccnc21]

To a stirred solution of Intermediate BB-1.1 (2.00 g, 6.68 mmol) in dioxane (20 mL) was added 4M HCl in dioxane (16.70 mL, 66.8 mmol) and stirred at RT for 5 h. The reaction mixture was evaporated under reduced pressure; the crude product was quenched with aqueous sodium bicarbonate solution (50 mL) and then extracted with ethyl acetate (100 mL). The combined organic layer was dried over Na$_2$SO$_4$, filtered and evaporated under reduced pressure to give Intermediate BB-1.2 (1.15 g) as pale yellow solid. LC-MS retention time=0.73 min; m/z=200 [M+H]$^+$.]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHz, DMSO-d$_6$) δ ppm 8.07-8.05 (m, 1H), 7.59-7.57 (m, 1H), 6.93 (dd, J=9.0, 5.2 Hz, 1H), 3.87 (t, J=8.0 Hz, 2H), 3.05 (t, J=8.0 Hz, 2H).

Intermediate BB-2.1

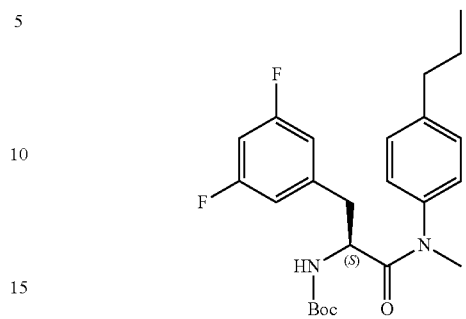

To a stirred solution of (S)-2-((tert-butoxycarbonyl) amino)-3-(3,5-difluorophenyl)propanoic acid (200 mg, 0.66 mmol) in DMF (5 mL) was added HATU (380 mg, 0.1 mmol), DIPEA (0.39 mL, 1.99 mmol) and the reaction mixture was stirred for 30 min. N-methyl-4-propylaniline (120 mg, 0.8 mmol) was added to the above reaction mixture and stirred at room temperature for 16 h. The reaction mixture was then diluted with water (20 mL) and extracted with EtOAc (3×25 mL). The combined organic layer was washed with 10% aqueous NaHCO$_3$ solution (25 mL), water (25 mL), brine (25 mL) dried (Na$_2$SO$_4$), filtered, concentrated and the crude product was purified by combiflash chromatography (24 g Redisep® SiO$_2$ column, eluting with 0-15% EtOAc in hexanes) to afford the title compound (0.25 g) as an off white solid. LC-MS retention time=1.33 min; m/z=377.2 [M-isobutylene+H]$^+$. Column: Acquity BEH C8 (2.1×50 mm) 1.7µ: Flow rate: 0.8 mL/min; Mobile Phase A: 5 mM NH$_4$OAc in water (pH=3.5): ACN (95:5); Mobile Phase B: 5 mM NH$_4$OAc in water: ACN (5:95); 5% B to 95% B over 1.1 minutes and then hold a 0.6 min. at 95% B of flow rate 0.8 mL/min; Detection: UV at 220 nm. $^1$H NMR (300 MHZ, DMSO-d$_6$) δ 7.35 (d, J=8.4 Hz, 2H), 7.31 (d, J=9.0 Hz, 2H), 7.13 (d, J=8.3 Hz, 1H), 6.99 (t, J=9.0 Hz, 1H), 6.34 (d, J=7.2 Hz, 2H), 4.17 (m, 1H), 3.17 (s, 3H), 2.77-2.58 (m, 4H), 1.70-1.59 (m, 2H), 1.30 (s, 9H), 0.92 (t, J=7.4 Hz, 3H).

Intermediate BB-2.2

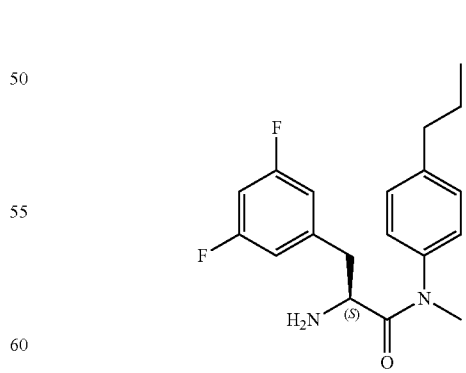

To a stirred solution of Intermediate BB-2.1 (250 mg, 0.58 mmol) in DCM (10 mL) was added HCl in dioxane (4M, 457 µL, 1.83 mmol) and the reaction mixture was stirred at room temperature for 4 h. The reaction mixture was concentrated to dryness; the residue was triturated with hexane (2×25 mL)

to afford the title compound (0.2 g) as an off white solid. LC-MS retention time=2.93 min; m/z=333.2 [M+H]⁺. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-2.3

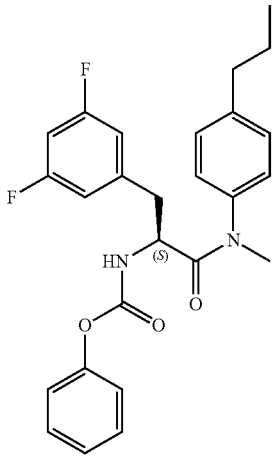

To a stirred solution of Intermediate BB-2.2 (100 mg, 0.3 mmol) and pyridine (0.05 mL, 0.6 mmol) in DCM (5 mL) was added phenyl chloroformate (0.05 mL, 0.36 mmol) at 0° C. and the reaction mixture was stirred at room temperature for 16 h. The reaction mixture was diluted with water (20 mL) and extracted with DCM (2×20 mL). The combined organic layer was washed with 1.5 N HCl solution (25 mL), dried (Na$_2$SO$_4$), filtered, concentrated and the crude product was purified by combiflash chromatography (4 g Redisep® SiO$_2$ column, eluting with 25% EtOAc in n-hexanes) to afford the title compound (80 mg) as an off white solid. LC-MS retention time=3.46 min; m/z=453.2 [M+H]⁺. Column: KINETIX XB-C18, 75×3 mm, 2.6 μm; Flow rate: 0.7 mL/min; Mobile Phase A: 5 mM CH$_3$CO$_2$NH$_4$ in 98% Water/2% ACN; Mobile Phase B: 10 mM CH$_3$CO$_2$NH$_4$ in 2% Water/98% ACN; 20% B to 100% B over 4 min, then hold for 0.6 min at 100% B with flow rate of 1.5 mL/min; Detection: UV at 220 nm. ¹H NMR (400 MHz, CDCl$_3$) δ 7.38-7.30 (m, 2H), 7.22-7.16 (m, 3H), 7.07 (d, J=7.5 Hz, 2H), 6.93 (d, J=7.8 Hz, 2H), 6.67 (tt, J=8.9, 2.4 Hz, 1H), 6.41 (d, J=6.0 Hz, 2H), 5.76 (d, J=8.8 Hz, 1H), 4.73-4.63 (m, 1H), 3.28 (s, 3H), 2.92 (dd, J=13.4, 6.4 Hz, 1H), 2.74 (dd, J=13.5, 7.5 Hz, 1H), 2.60 (t, J=7.2 Hz, 2H), 1.65 (m, 2H), 0.96 (t, J=7.4 Hz, 3H).

Intermediate BB-3.1

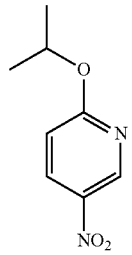

To a stirred solution 2-chloro-5-nitropyridine (3.5 g, 22 mmol) in 2-propanol (20 mL) and DMF (25 mL) was added NaH (1.32 g, 33.1 mmol, 60% in mineral oil) and stirred at 0° C. for 20 min. and warmed to room temperature and stirred for 1 h. The reaction mixture was quenched with saturated NH$_4$Cl solution (100 mL), extracted with EtOAc (2×60 mL) and the combined organic layer was washed with brine (100 mL), dried (Na$_2$SO$_4$), filtered and concentrated. The crude product was purified by combiflash chromatography (80 g Redisep® SiO$_2$ column, eluting with 8% EtOAc in n-hexanes) to afford the title compound (1.65 g) as a pale yellow liquid. LC-MS retention time=2.64 min; m/z=182 [M−H]. Column: KINETIX XB-C18, 75×3 mm, 2.6 μm; Flow rate: 1 mL/min; Mobile Phase A: 5 mM CH$_3$CO$_2$NH$_4$ in 98% Water/2% ACN; Mobile Phase B: 10 mM CH$_3$CO$_2$NH$_4$ in 2% Water/98% ACN; 20% B to 100% B over 4 min, then hold for 0.6 min at 100% B with flow rate of 1.5 mL/min; Detection: UV at 220 nm. ¹H NMR (300 MHZ, DMSO-d$_6$) δ 9.07 (d, J=3.0 Hz, 1H), 8.44 (dd, J=9.1, 3.0 Hz, 1H), 6.95 (d, J=9.1 Hz, 1H), 5.37 (sep, J=6.3 Hz, 1H), 1.34 (d, J=6.4 Hz, 6H).

Intermediate BB-3.2

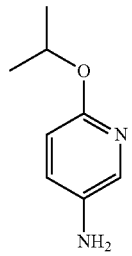

To a stirred solution of Intermediate BB-3.1 (1.65 g, 9.06 mmol) in methanol (60 mL) was added 10% palladium on carbon (0.241 g, 2.264 mmol) and stirred under hydrogen atmosphere for 16 h. The reaction mixture was filtered over Celite pad and the filtrate evaporated under reduced pressure to afford the title compound (1.15 g) as black liquid. LC-MS retention time=0.99 min; m/z=153.2 [M+H]⁺. Column: KINETIX XB-C18, 75×3 mm, 2.6 μm; Flow rate: 1 mL/min; Mobile Phase A: 1% HCO$_2$H in water; Mobile Phase B: ACN; 20% B to 100% B over 4 min, then hold for 0.6 min at 100% B with flow rate of 1.5 mL/min; Detection: UV at 220 nm. ¹H NMR (300 MHZ, DMSO-d$_6$) δ 7.48 (d, J=3.0 Hz, 1H), 6.97 (dd, J=8.7, 3.0 Hz, 1H), 6.46 (d, J=8.7 Hz, 1H), 5.01 (sep, J=6.2 Hz, 1H), 4.68 (s, 2H), 1.21 (d, J=6.0 Hz, 6H).

Intermediate BB-3.3

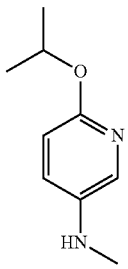

To a stirred solution of Intermediate BB-3.2 (1.65 g, 10.8 mmol) in THF (10 mL) was added LDA (8.13 mL, 16.3 mmol) at −78° C. under nitrogen and the reaction mixture was stirred at same temperature for 1 h. Then methyl iodide (0.74 mL, 11.93 mmol) was added and reaction mixture was allowed to stir at room temperature for 16 h. Then the reaction mixture quenched with saturated NH$_4$Cl solution (50 mL), extracted with EtOAc (2×60 mL) and the combined organic layer was washed with brine (100 mL), dried (Na$_2$SO$_4$), filtered and concentrated. The crude product was purified by combiflash chromatography (80 g Redisep® SiO$_2$ column, eluting with 15% EtOAc in n-hexanes) to afford the title compound (0.68 g) as a pale yellow liquid. LC-MS retention time=2.44 min; m/z=167.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, DMSO-d$_6$) δ 7.42 (d, J=2.6 Hz, 1H), 6.97 (dd, J=8.7, 3.0 Hz, 1H), 6.52 (d, J=8.7 Hz, 1H), 5.25 (m, 1H), 5.03 (sep, J=6.1 Hz, 1H), 2.64 (d, J=5.3 Hz, 3H), 1.22 (d, J=6.0 Hz, 6H).

Intermediate BB-3.4

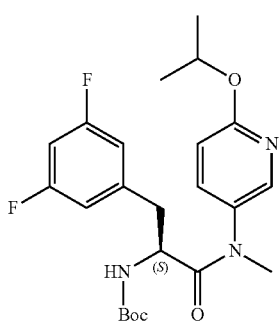

To a solution of (S)-2-((tert-butoxycarbonyl)amino)-3-(3,5-difluorophenyl)propanoic acid (453 mg, 1.504 mmol) in DCM (5 mL) at 0° C. was added Intermediate BB-3.3 (250 mg, 1.50 mmol), pyridine (0.608 mL, 7.52 mmol) and POCl$_3$ (0.280 mL, 3.01 mmol) and the reaction mixture was allowed to room temperature and stirred for 1 h. The reaction mixture was diluted with water (25 mL), extracted with EtOAc (2×25 mL) and the combined organic layer was washed with brine (50 mL)), dried (Na$_2$SO$_4$), filtered and concentrated. The crude product was purified by combiflash chromatography (12 g Redisep® SiO$_2$ column, eluting with 28% EtOAc in n-hexanes) to afford the title compound (0.35 g) as a brown color solid. LC-MS retention time=3.35 min; m/z=450.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, DMSO-d$_6$) δ 8.13 (d, J=2.5 Hz, 1H), 7.65 (dd, J=8.8, 2.8 Hz, 1H), 7.20 (d, J=8.0 Hz, 1H), 7.01 (t, J=9.5 Hz, 1H), 6.85 (d, J=8.5 Hz, 1H), 6.53 (d, J=6.5 Hz, 2H), 5.26 (sep, J=6.3 Hz, 1H), 4.10-4.03 (m, 1H), 3.14 (s, 3H), 2.82 (dd, J=13.2, 3.6 Hz, 1H), 2.70 (dd, J=18.2, 10.0 Hz, 1H), 1.31 (d, J=6.0, 6H), 1.28 (s, 9H).

Intermediate BB-3.5

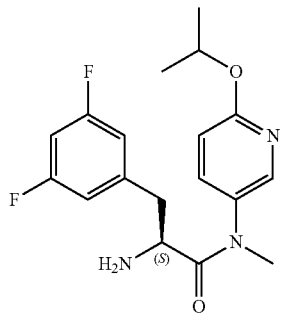

HCl in dioxane (4M solution, 0.118 mL, 3.89 mmol) was added to the Intermediate BB-3.4 (350 mg, 0.779 mmol) and the reaction mixture was stirred at room temperature for 2 h. The crude reaction mixture was concentrated to dryness; the residue was basified with saturated aq. NaHCO$_3$ (25 mL) solution and extracted with EtOAc (2×25 mL). The combined organic layer was dried (Na$_2$SO$_4$), filtered, concentrated and the crude product was purified by combiflash chromatography (12 g Redisep® SiO$_2$ column, eluting with 2% MeOH in Chloroform) to afford the title compound (0.260 g) as a red liquid. LC-MS retention time=1.08 min; m/z=350.3 [M+H]$^+$. Column: Acquity BEH C8 (2.1×50 mm) 1.7μ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold a 0.6 min. at 90% B of flow rate 0.5 mL/min; Detection: UV at 220 nm. $^1$H NMR (300 MHZ, DMSO-d$_6$) δ 7.95 (d, J=2.6 Hz, 1H), 7.49 (dd, J=8.7, 2.6 Hz, 1H), 7.03 (t, J=9.4, 2H), 6.80 (d, J=8.7 Hz, 1H), 6.62-6.57 (m, 2H), 5.23 (sep, J=6.3 Hz, 1H), 3.30-3.25 (m, 1H), 3.10 (s, 3H), 2.73 (dd, J=13.2, 6.0 Hz, 1H), 2.50 (m, 1H), 1.74 (br. s., 2H), 1.30 (d, J=6.0 Hz, 6H).

Intermediate BB-3.6

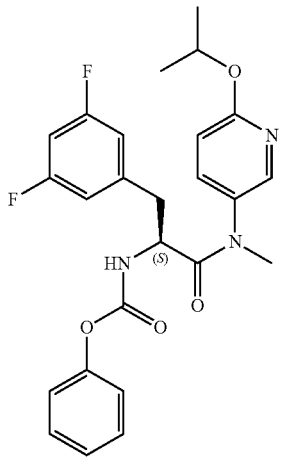

To a stirred solution of Intermediate BB-3.5 (150 mg, 0.429 mmol) in DCM (5 mL) was added pyridine (0.174 mL, 2.15 mmol), phenyl chloroformate (0.065 mL, 0.515 mmol) at 0° C. and the reaction mixture was stirred at room temperature for 2 h. The reaction mixture was diluted with water (25 mL) and extracted with DCM (2×25 mL). The combined organic layer was washed with 1.5N HCl solution (40 mL), dried ($Na_2SO_4$), filtered, concentrated and the crude product was purified by combiflash chromatography (12 g Redisep® $SiO_2$ column, eluting with 20% EtOAc in n-hexanes) to afford the title compound (180 mg) as a red liquid. LC-MS retention time=3.49 min; m/z=470.2 [M+H]$^+$. Column: KINETIX XB-C18, 75×3 mm, 2.6 µm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm.

Intermediate BB-4.1

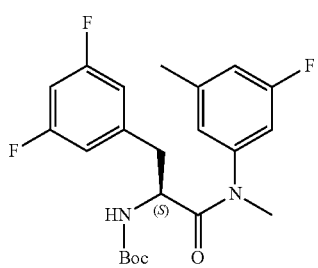

To a stirred solution of (S)-2-((tert-butoxycarbonyl) amino)-3-(3,5-difluorophenyl)propanoic acid (200 mg, 0.66 mmol) in DCM (5 mL) was added 3-fluoro-N,5-dimethylaniline (139 mg, 0.996 mmol), N-ethoxycarbonyl-2-ethoxy-1,2-dihydroquinoline (226 mg, 0.913 mmol) and the reaction mixture was stirred at room temperature for 16 h. The reaction mixture was concentrated and the crude product was purified by combiflash chromatography (40 g Redisep® $SiO_2$ column, eluting with 20% EtOAc in hexanes) to afford the title compound (0.25 g) as an off white solid. LC-MS retention time=3.18 min; m/z=367.2 [M-isobutylene+H]$^+$. Column: KINETIX XB-C18, 75×3 mm, 2.6 µm; Flow rate: 1 mL/min; Mobile Phase A: 5 mM $NH_4OAc$ in 98% Water/2% ACN; Mobile Phase B: 5 mM $NH_4OAc$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, CDCl$_3$) δ 6.87 (d, J=8.8 Hz, 1H), 6.69 (tt, J=9.0, 2.2 Hz, 1H), 6.50 (br. s., 2H), 6.40 (br. s., 2H), 5.17 (br. s., 1H), 4.50 (d, J=5.8 Hz, 1H), 3.17 (s, 3H), 2.88 (dd, J=13.0, 8.3 Hz, 1H), 2.77-2.68 (m, 1H), 2.32 (s, 3H), 1.40 (br. s., 9H).

Intermediate BB-4.2

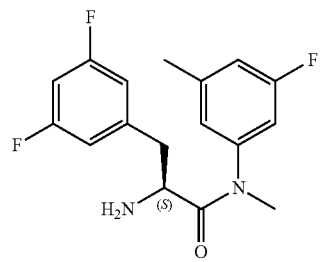

To a solution of Intermediate BB-4.1 (250 mg, 0.59 mmol) in DCM (10 mL) was added HCl in dioxane (4M, 0.15 mL, 0.59 mmol) and the reaction mixture was stirred at room temperature for 4 h. The reaction mixture was concentrated to dryness; the residue was triturated with n-hexane (2×25 mL) to afford the title compound (0.2 g) as an off white solid. LC-MS retention time=2.83 min; m/z=323.2 [M+H]$^+$. Column: KINETIX XB-C18, 75×3 mm, 2.6 µm; Flow rate: 1 mL/min; Mobile Phase A: 5 mM $NH_4OAc$ in 98% Water/2% ACN; Mobile Phase B: 5 mM $NH_4OAc$ in 2% Water/98% ACN; 20% B to 100% B over 4 min, then hold for 0.6 min at 100% B with flow rate of 1.5 mL/min; Detection: UV at 220 nm.

Intermediate BB-4.3

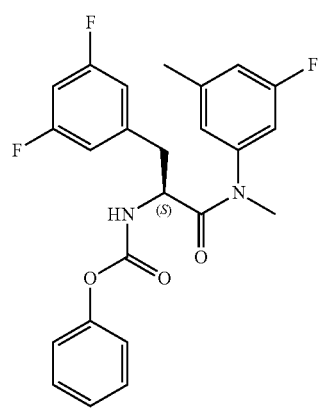

To a stirred solution of Intermediate BB-4.2 (100 mg, 0.3 mmol) and pyridine (0.05 mL, 0.6 mmol) in DCM (5 mL) was added phenyl chloroformate (0.05 mL, 0.36 mmol) at 0° C. and the reaction mixture was stirred at room temperature for 16 h. The reaction mixture was diluted with water (20 mL) and extracted with DCM (2×20 mL). The Combined organic layer was washed with 1.5 N HCl solution (25 mL), dried (Na$_2$SO$_4$), filtered and concentrated. The crude product was purified by combiflash chromatography (4 g Redisep® SiO$_2$ column, eluting with 30% EtOAc in n-hexanes) to afford the title compound (80 mg) as an off white solid. LC-MS retention time=1.32 min; m/z=443.4 [M+H]$^+$. Column: Acquity BEH C8 (2.1×50 mm) 1.7μ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold a 0.6 min. at 90% B of flow rate 0.5 mL/min; Detection: UV at 220 nm. $^1$H NMR (400 MHZ, CDCl$_3$) δ 7.38-7.32 (m, 2H), 7.23-7.17 (m, 1H), 7.09 (d, J=7.5 Hz, 2H), 6.89 (d, J=9.3 Hz, 1H), 6.73 (tt, J=9.0, 2.3 Hz, 1H), 6.53 (d, J=5.8 Hz, 2H), 6.47 (br. s., 2H), 5.72 (d, J=8.0 Hz, 1H), 4.65 (dd, J=15.2, 8.0 Hz, 1H), 3.23 (s, 3H), 2.97 (dd, J=13.2, 7.8 Hz, 1H), 2.82 (dd, J=13.2, 6.4 Hz, 1H), 2.31 (s, 3H).

Intermediate BB-5.1

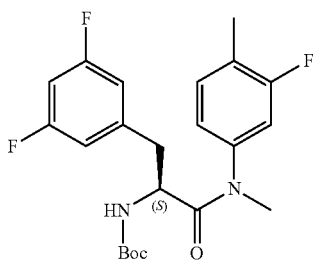

To a stirred solution of (S)-2-((tert-butoxycarbonyl)amino)-3-(3,5-difluorophenyl)propanoic acid (250 mg, 0.83 mmol) in DCM (5 mL) was added 3-fluoro-N,4-dimethylaniline (139 mg, 0.996 mmol), N-ethoxycarbonyl-2-ethoxy-1,2-dihydroquinoline (226 mg, 0.913 mmol) and the reaction mixture was stirred at room temperature for 16 h. The reaction mixture was concentrated and the crude product was purified by combiflash chromatography (40 g Redisep® SiO$_2$ column, eluting with 20% EtOAc in hexanes) to afford the title compound (0.27 g) as an off white solid. LC-MS retention time=3.35 min; m/z=423.2 [M+H]$^+$. Column: KINETIX XB-C18, 75×3 mm, 2.6 μm; Flow rate: 1 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm.

Intermediate BB-5.2

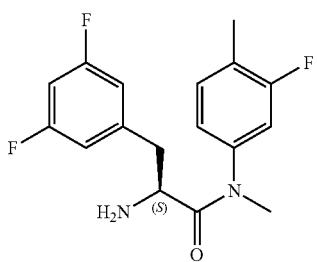

To a stirred solution of Intermediate BB-5.1 (250 mg, 0.59 mmol) in DCM (10 mL) was added HCl in dioxane (4M, 0.15 mL, 0.59 mmol) and stirred at room temperature for 4 h. The reaction mixture was concentrated to dryness; the residue was triturated with n-hexane (2×25 mL) to afford the title compound (0.2 g) as an off white solid. LC-MS retention time=2.93 min; m/z=323.2 [M+H]$^+$. Column: KINETIX XB-C18, 75×3 mm, 2.6 μm; Flow rate: 1 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm.

Intermediate BB-5.3

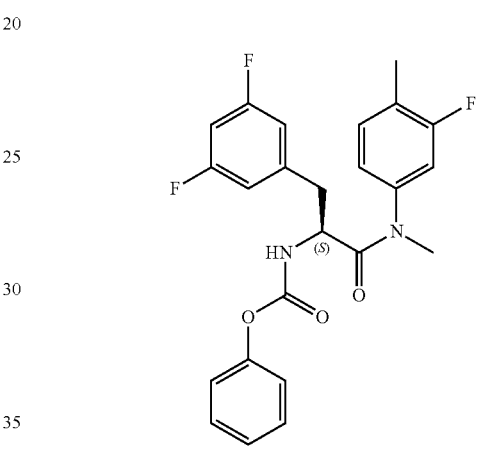

To a stirred solution of Intermediate BB-5.2 (100 mg, 0.300 mmol) and pyridine (0.05 mL, 0.6 mmol) in DCM (5 mL) was added phenyl chloroformate (0.050 mL, 0.36 mmol) at 0° C. and the reaction mixture was stirred at room temperature for 16 h. The reaction mixture was diluted with water (20 mL) and extracted with DCM (2×20 mL). The combined organic layer was washed with 1.5 N HCl solution (25 mL), dried (Na$_2$SO$_4$), filtered and concentrated. The crude product was purified by combiflash chromatography (4 g Redisep® SiO$_2$ column, eluting with 30% EtOAc in n-hexanes) to afford the title compound (80 mg) as an off white solid. LC-MS retention time=3.39 min; m/z=443.2 [M+H]$^+$. Column: KINETIX XB-C18, 75×3 mm, 2.6 μm; Flow rate: 1 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm. $^1$H NMR (300 MHZ, CDCl$_3$) δ 7.36-7.30 (m, 2H), 7.24-7.15 (m, 2H), 7.10 (d, J=7.9 Hz, 2H), 6.78-6.68 (m, 2H), 6.55-6.48 (m, 3H), 5.78 (d, J=8.7 Hz, 1H), 4.70 (dd, J=15.6, 7.2 Hz, 1H), 3.25 (s, 3H), 2.97 (dd, J=13.4, 7.8 Hz, 1H), 2.84 (dd, J=13.4, 6.6 Hz, 1H), 2.27 (d, J=1.9 Hz, 3H)

Intermediate BB-6.1

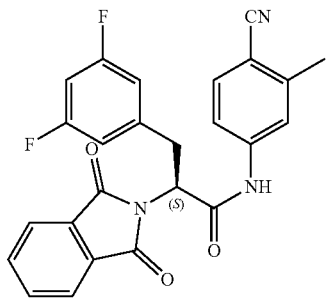

To a stirred solution of Intermediate GW-8.1 (0.400 g, 1.21 mmol), 4-amino-2-methylbenzonitrile (0.191 g, 1.45 mmol) and pyridine (0.586 mL, 7.24 mmol) in DCM (8 mL) was added $POCl_3$ (0.338 mL, 3.62 mmol) at 0° C. and the reaction mixture was stirred at room temperature for 16 h. The reaction mixture was diluted with 10% aqueous solution of $NaHCO_3$ (25 mL) and extracted with DCM (2×25 mL). The combined organic layer was dried ($Na_2SO_4$), filtered, concentrated and the crude product was washed with mixture of diethyl ether and DCM (7:3) and dried under vacuum to afford the title compound (0.35 g) as an off white solid. LC-MS retention time=3.02 min; m/z=446.2 $[M+H]^+$. Column: KINETIX XB-C18, 75×3 mm, 2.6 μm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm. $^1H$ NMR (300 MHz, DMSO-$d_6$) δ 10.24 (s, 1H), 7.87 (s, 4H), 7.72 (d, J=9.3 Hz, 1H), 7.64 (d, J=7.5 Hz, 2H), 7.03-6.82 (m, 3H), 5.27 (dd, J=10.76, 4.72 Hz, 1H), 3.59 (dd, J=13.79, 4.72 Hz, 1H), 3.28 (dd, J=13.79, 4.72 Hz, 1H), 2.42 (s, 3H).

Intermediate BB-6.2

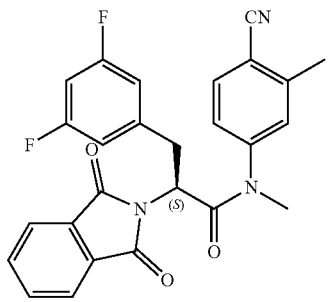

To a stirred solution of Intermediate BB-6.1 (0.35 g, 0.79 mmol) in DMF (8 mL) was added portion wise NaH (0.063 g, 60% in mineral oil, 1.6 mmol) at 0° C. and stirred for 10 min. Methyl iodide (0.197 mL, 3.14 mmol) was added at 0° C. and stirred further at room temperature for 16 h. The reaction mixture was diluted with ice cold saturated aqueous solution of $NH_4Cl$ (50 mL) and extracted with EtOAc (2×50 mL). The combined organic layer was washed with brine (75 mL), dried ($Na_2SO_4$), filtered, concentrated and the crude product was purified by combiflash chromatography (24 g Redisep® $SiO_2$ column, eluting with 25% EtOAc in n-hexanes) to afford the title compound (0.25 g) as a pale yellow solid. LC-MS retention time=3.31 min; m/z=460.2 $[M+H]^+$. Column: KINETIX XB-C18, 75×3 mm, 2.6 μm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm. $^1H$ NMR (300 MHz, DMSO-$d_6$) δ 7.84-7.76 (m, 2H), 7.67 (dd, J=5.4, 3.02 Hz, 2H), 7.50 (d, J=7.6 Hz, 1H), 7.22 (d, J=9.4 Hz, 1H), 7.12 (br. s., 1H), 6.94 (t, J=9.4 Hz, 1H), 6.82 (d, J=6.8 Hz, 2H), 5.28 (dd, J=10.4, 5.2 Hz, 1H), 3.47 (dd, J=13.8, 4.8 Hz, 1H), 3.18 (s, 3H), 3.08 (dd, J=13.8, 10.4 Hz, 1H), 1.99 (s, 3H).

Intermediate BB-6.3

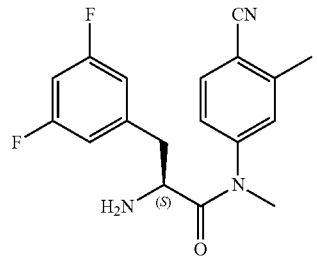

To a stirred solution of Intermediate BB-6.2 (0.17 g, 0.37 mmol) in ethanol (4 mL) in a sealed tube was added 40% aqueous solution of methylamine (0.144 g, 1.85 mmol) and the resultant reaction mixture was stirred at 65° C. for 16 h. The reaction mixture was cooled to room temperature; ethanol was removed under reduced pressure and the residue was diluted with water (25 mL) and extracted with EtOAc (2×25 mL). The combined organic layer was dried ($Na_2SO_4$), filtered, concentrated and the crude product was purified by combiflash chromatography (12 g Redisep® $SiO_2$ column, eluting with 3% MeOH in chloroform) to afford the title compound (100 mg) as a yellow solid. LC-MS retention time=0.98 min; m/z=330.3 $[M+H]^+$. Column: Acquity BEH C8 (2.1×50 mm) 1.7μ: Flow rate: 0.5 mL/min; Mobile Phase A: 5 mM $NH_4OAc$ in water: ACN (95:5); Mobile Phase B: 5 mM $NH_4OAc$ in water: ACN (5:95); 20% B to 90% B over 1.1 minutes and then hold a 0.6 min. at 90% B of flow rate 0.5 mL/min; Detection: UV at 220 nm.

Intermediate BB-6.4

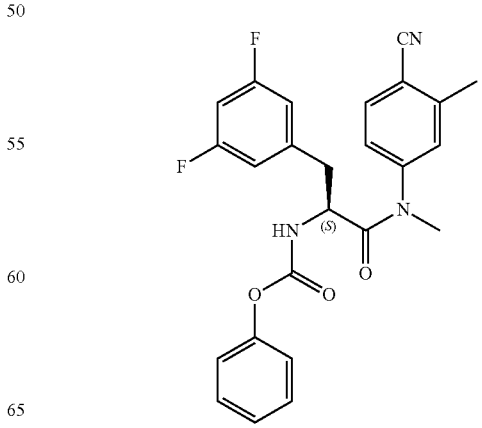

To a stirred solution of Intermediate BB-6.3 (40 mg, 0.12 mmol) and pyridine (0.020 mL, 0.24 mmol) in DCM (4 mL) was added phenyl chloroformate (0.019 mL, 0.146 mmol) at 0° C. and the reaction mixture stirred at room temperature for 16 h. The reaction mixture was diluted with water (20 mL) and extracted with DCM (2×20 mL). The combined organic layer was washed with 1.5N HCl solution (25 mL), dried (Na₂SO₄), filtered and concentrated. The crude product was purified by combiflash chromatography (4 g Redisep® SiO₂ column, eluting with 25% EtOAc in n-hexanes) to afford the title compound (33 mg) as an off white solid. LC-MS retention time=3.17 min; m/z=450.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-7.1

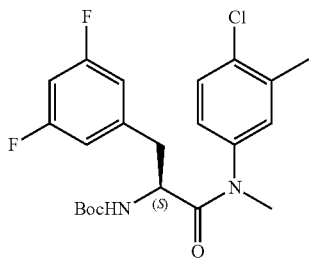

To a stirred solution of (S)-2-((tert-butoxycarbonyl)amino)-3-(3,5-difluorophenyl)propanoic acid (0.25 g, 0.83 mmol) and 4-chloro-N-3-dimethylaniline (0.142 g, 0.913 mmol) in DCM (5 mL) was added N-ethoxycarbonyl-2-ethoxy-1,2-dihydroquinoline (0.226 g, 0.913 mmol) and the reaction mixture was stirred at room temperature for 16 h. Then the reaction mixture was concentrated to dryness and the crude product was purified by combiflash chromatography (120 g Redisep® SiO₂ column, eluting with 30% EtOAc in n-hexanes) to afford the title compound (0.23 g) as a pale yellow oil. LC-MS retention=3.39 min; m/z=439 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, DMSO-d₆) δ 7.51 (d, J=9.0 Hz, 1H), 7.35-7.11 (m, 3H), 7.03 (t, J=9.4 Hz, 1H), 6.54 (br. s., 2H), 4.13 (br. s., 1H), 3.13 (s, 3H), 2.83 (m, 1H), 2.75-2.63 (m, 1H), 2.33 (s, 3H), 1.28 (s, 9H).

Intermediate BB-7.2

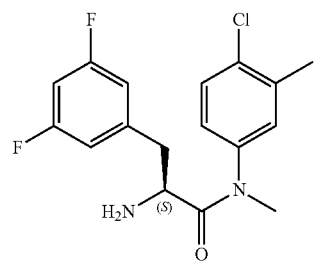

To a solution of Intermediate BB-7.1 (0.230 g, 0.524 mmol) in dioxane (1 mL) was added 4M HCl in dioxane (2 mL, 8 mmol) and stirred at room temperature for 3 h. The reaction mixture was concentrated to dryness; the residue was basified with 10% NaHCO₃ solution (30 mL) and extracted with EtOAc (3×10 mL). The combined organic layer was washed with brine, dried (Na₂SO₄), filtered and concentrated to dryness to afford the title compound (0.15 g) as pale yellow oil. LC-MS retention time=2.6 min; m/z=339.0 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-7.3

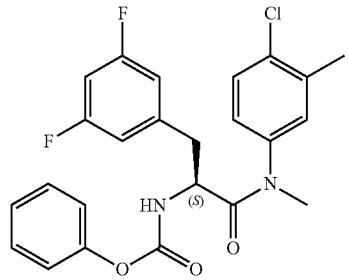

To a stirred solution of Intermediate BB-7.2 (0.100 g, 0.295 mmol) and pyridine (0.048 mL, 0.59 mmol) in DCM (2 mL) at 0° C. was added phenyl chloroformate (0.04 mL, 0.3 mmol) and the reaction mixture was stirred at room temperature for 16 h. The reaction mixture was diluted with water (30 mL), extracted with DCM (3×10 mL) and the combined organic layer was washed with 10% HCl solution (15 mL), brine (15 mL), dried (Na₂SO₄), filtered and concentrated. The crude product was purified by combiflash chromatography (4 g Redisep® SiO₂ column, eluting with 30% EtOAc in n-hexanes) to afford the title compound (0.11 g) as a pale yellow oil. LC-MS Retention time=1.41 min; m/z=459.2 [M+H]⁺. Column: Acquity BEH C8 (2.1×50 mm) 1.7μ; Flow rate: 0.5 mL/min; Mobile Phase A: 5 mM NH₄OAc in water: ACN (95:5); Mobile Phase B: 5 mM NH₄OAc in water: ACN (5:95); 20% B to 90% B over 1.1 minutes and then hold a 0.6 min. at 90% B of flow rate 0.5 mL/min; Detection: UV at 220 nm. ¹H NMR (300 MHZ, DMSO-d₆) δ 8.28 (d, J=7.7 Hz, 1H), 7.57-7.43 (m, 1H), 7.42-7.29 (m, 3H), 7.27-7.03 (m, 3H), 7.10 (t, J=9.0 Hz, 1H), 6.96 (d, J=7.8 Hz, 2H), 6.63 (d, J=6.4 Hz, 2H), 4.21 (br. s., 1H), 3.15 (s, 3H), 3.00-2.90 (m, 1H), 2.88-2.75 (m, 1H), 2.30 (s, 3H).

Intermediate BB-8.1

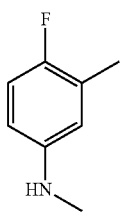

To a stirred suspension of sodium methoxide (4.32 g, 80 mmol) in MeOH (10 mL) was added 4-fluoro-3-methylaniline (2.0 g, 16 mmol) and stirred for 15 min. The resulting solution was poured into a suspension of paraformaldehyde (0.672 g, 22.37 mmol) in MeOH (10 mL) and the reaction mixture was stirred at room temperature for 16 h. NaBH$_4$ (0.605 g, 15.98 mmol) was added and the reaction mixture was refluxed for 3 h. The reaction mixture was concentrated to dryness; the residue was added 1N KOH solution (15 mL) and extracted with EtOAc (3×20 mL). The combined organic layer was washed with water (20 mL), brine (20 mL), dried (Na$_2$SO$_4$), filtered and concentrated. LC-MS Retention Time=2.13 min; m/z=140 [M+H]$^+$. Column: KINETIX XB-C18, 75×3 mm, 2.6 µm; Flow rate: 1 mL/min: Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, DMSO-d$_6$) δ 6.83 (t, J=9.3 Hz, 1H), 6.41-6.22 (m, 2H), 5.39 (d, J=4.9 Hz, 1H), 2.62 (d, J=5.3 Hz, 3H), 2.13 (s, 3H).

Intermediate BB-8.2

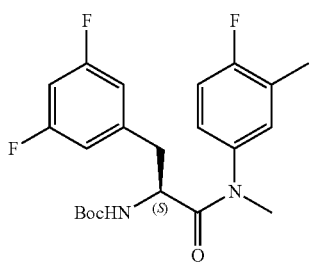

To a stirred solution of (S)-2-((tert-butoxycarbonyl) amino)-3-(3,5-difluorophenyl)propanoic acid (0.25 g, 0.83 mmol) and Intermediate BB-8.1 (0.127 g, 0.913 mmol) in DCM (5 mL) was added N-ethoxycarbonyl-2-ethoxy-1,2-dihydroquinoline (0.226 g, 0.913 mmol) and the reaction mixture was stirred at RT for 16 h. Then the reaction mixture was concentrated to dryness and the crude product was purified by combiflash chromatography (12 g Redisep® SiO$_2$ column, eluting with 30% EtOAc in n-hexanes) to afford the title compound (0.23 g) as a pale yellow oil. LC-MS retention time=1.36 min; m/z=423.2 [M+H]$^+$. Column: Acquity BEH C8 (2.1×50 mm) 1.7µ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold for 0.6 min. at 90% B of flow rate 0.5 mL/min; Detection: UV at 220 nm. $^1$H NMR (400 MHZ, DMSO-d$_6$) δ 7.30-7.11 (m, 4H), 7.03 (t, J=9.5 Hz, 1H), 6.53 (d, J=7.0 Hz, 2H), 4.12 (br. s., 1H), 3.12 (s, 3H), 2.83 (m, 1H), 2.74 (m, 1H), 2.24 (s, 3H), 1.29 (s, 9H).

Intermediate BB-8.3

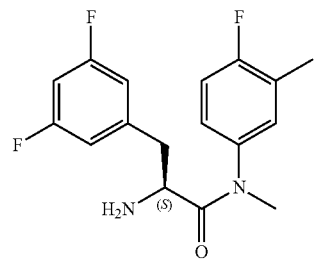

To a stirred solution of Intermediate BB-8.2 (0.230 g, 0.544 mmol) in dioxane 91 mL) was added 4M HCl in dioxane (2 mL, 8 mmol) and the reaction mixture was stirred at room temperature for 3 h. The reaction mixture was concentrated to dryness; the residue was treated with aqueous 10% NaHCO$_3$ solution (15 mL) and extracted with EtOAc (3×10 mL). The combined organic layer was washed with brine (15 mL), dried (Na$_2$SO$_4$), filtered and concentrated to afford the title compound (0.16 g) as yellow liquid. LC-MS retention time=0.99 min; m/z=323.4 [M+H]$^+$. Column: Acquity BEH C8 (2.1×50 mm) 1.7µ: Flow rate: 0.5 mL/min; Mobile Phase A: 0.1% TFA in water; Mobile Phase B: ACN; 2% B to 98% B over 1.0 minutes, then hold a 0.6 min. at 98% B of flow rate 0.5 mL/min; Detection: UV at 220 nm. $^1$H NMR (300 MHZ, DMSO-d$_6$, D20 exchange) δ 7.13 (t, J=9.1 Hz, 1H), 7.05-6.95 (m, 1H), 6.95-6.85 (br. s., 1H), 6.73 (br. s., 1H), 6.57 (d, J=6.8 Hz, 2H), 3.32 (t, J=7.0 Hz, 1H), 3.03 (s, 3H), 2.70 (dd, J=13.2, 7.2 Hz, 1H), 2.54 (dd, J=13.2, 7.2 Hz, 1H), 2.16 (s, 3H).

Intermediate BB-8.4

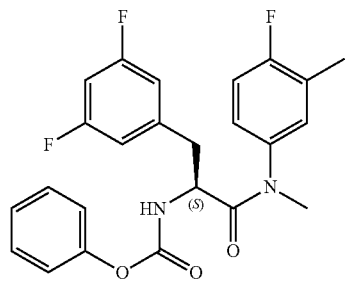

To a stirred cooled solution of Intermediate BB-8.3 (0.090 g, 0.28 mmol) and pyridine (0.045 mL, 0.56 mmol) in DCM (2 mL) at 0° C. was added phenyl chloroformate (0.039 mL, 0.31 mmol) and the reaction mixture was stirred at room temperature for 16 h. The reaction mixture was diluted with water (30 mL), extracted with DCM (3×10 mL) and the combined organic layer was washed with 10% HCl solution (15 mL), brine (15 mL), dried (Na$_2$SO$_4$), filtered and concentrated. The crude product was purified by combiflash chromatography (4 g Redisep® SiO$_2$ column, eluting with 30% EtOAc in n-hexanes) to afford the title compound (0.08 g) as a pale yellow oil. LC-MS retention time=3.24 min; m/z=443.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, DMSO-d$_6$) δ 8.26 (d, J=7.9 Hz, 1H), 7.41-7.30 (m, 2H), 7.26-7.03 (m, 5H), 6.97 (d, J=7.6 Hz, 2H), 6.62 (d, J=6.8 Hz, 2H), 4.23-4.12 (m, 1H), 3.15 (s, 3H), 2.95 (dd, J=13.2, 4.5 Hz, 1H), 2.87-2.71 (m, 1H), 2.21 (s, 3H).

Intermediate BB-9.1

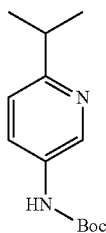

To a stirred solution of 5-(di-Boc-amino)-2-chloropyridine (4.00 g, 12.2 mmol) in THF (200 mL) and NMP (58.5 mL, 608 mmol) was added iron(III)acetylacetonate (2.58 g, 7.30 mmol) at −30° C. followed by isopropyl magnesium chloride (85 mL, 170 mmol) and the reaction mixture was allowed to warm to 0° C. and stirred for 1 h. The reaction mixture was quenched with saturated NH$_4$Cl solution (100 mL), extracted with EtOAc (2×60 mL) and the combined organic layer was washed with brine (100 mL), dried (Na$_2$SO$_4$), filtered and concentrated. The crude product was purified by combiflash chromatography (80 g Redisep® SiO$_2$ column, eluting with 10% EtOAc in n-hexanes) to afford the title compound (2.2 g) as a pale yellow solid. LC-MS retention time=2.38 min; m/z=237.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, DMSO-d$_6$) δ 9.41 (br. s., 1H), 8.48 (d, J=2.5 Hz, 1H), 7.77 (dd, J=8.4, 2 Hz, 1H), 7.16 (d, J=8.5 Hz, 1H), 2.93 (spt, J=6.9 Hz, 1H), 1.51 (s, 9H), 1.22-1.16 (d, J=7.4 Hz, 6H).

Intermediate BB-9.2

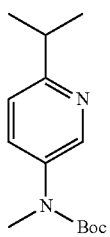

To a stirred solution of Intermediate BB-9.1 (0.500 g, 2.12 mmol) in DMF (5 mL) was added NaH (0.127 g, 60% in mineral oil, 3.17 mmol) at 0° C. and stirred for 10 min. Methyl iodide (0.265 mL, 4.23 mmol) was added at 0° C. and the reaction mixture was stirred further at room temperature for 16 h. The reaction mixture was diluted with ice cold saturated solution of NH$_4$Cl (50 mL) and extracted with EtOAc (2×50 mL). The combined organic layer was washed with brine (75 mL), dried (Na$_2$SO$_4$), filtered and concentrated. The crude product was purified by combiflash chromatography (24 g Redisep® SiO$_2$ column, eluting with 10% EtOAc in n-hexanes) to afford the title compound (0.45 g) as a colorless liquid. LC-MS retention time=2.76 min; m/z=251.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, DMSO-d$_6$) δ 8.41 (d, J=2.0 Hz, 1H), 7.62 (dd, J=8.3, 2.8 Hz, 1H), 7.25 (d, J=8.0 Hz, 1H), 3.19 (s, 3H), 3.00 (sep, J=6.8 Hz, 1H), 1.40 (s, 9H), 1.23 (d, J=6.5 Hz, 6H).

Intermediate BB-9.3

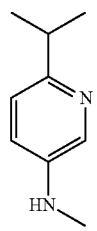

HCl in dioxane (2.0 mL, 65.8 mmol, 4M solution) was added to the Intermediate BB-9.2 (0.45 g, 1.8 mmol) and the reaction mixture was stirred at room temperature for 2 h. The crude reaction mixture was concentrated to dryness, basified with saturated aq. NaHCO$_3$ (25 mL) solution and extracted with EtOAc (2×25 mL). The combined organic layer was dried (Na$_2$SO$_4$), filtered and concentrated to afford the title compound (0.26 g) as a pale yellow gummy solid, which was used to the next step without further purification. LC-MS retention time=1.92 min; m/z=151.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, DMSO-d$_6$) δ 7.84 (d, J=2.5 Hz, 1H), 6.96 (d, J=8.5 Hz, 1H), 6.82 (dd, J=8.4, 2.8 Hz, 1H), 5.58 (d, J=5.0 Hz, 1H), 2.84 (sep, J=7.0 Hz, 1H), 2.67 (d, J=5.2 Hz, 3H), 1.17 (d, J=6.5 Hz, 6H).

Intermediate BB-9.4

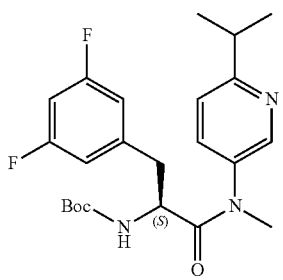

To a stirred solution of (S)-2-((tert-butoxycarbonyl)amino)-3-(3,5-difluorophenyl)propanoic acid (450 mg, 1.49 mmol) and Intermediate BB-9.3 (224 mg, 1.49 mmol) in DMF (4 mL) was added HATU (1136 mg, 2.99 mmol) and DIPEA (0.058 mL, 0.33 mmol) and the reaction mixture was stirred at room temperature for 16 h. The reaction mixture was diluted with water (25 mL), extracted with EtOAc (2×25 mL) and the combined organic layer was washed with brine (50 mL)), dried ($Na_2SO_4$), filtered and concentrated. The crude product was purified by combiflash chromatography (12 g Redisep® $SiO_2$ column, eluting with 30% EtOAc in n-hexanes) to afford the title compound (0.26 g) as a brown color solid. LC-MS retention time=3.19 min; m/z=434.2 $[M+H]^+$. Column: KINETIX XB-C18, 75×3 mm, 2.6 µm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm.

Intermediate BB-9.5

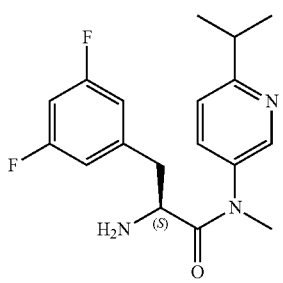

HCl in dioxane (5.0 mL, 165 mmol, 4M solution) was added to the Intermediate BB-9.4 (0.26 g, 0.6 mmol) and the reaction mixture stirred at room temperature for 2 h. The crude reaction mixture was concentrated to dryness; the residue was basified with saturated aq. $NaHCO_3$ (25 mL) solution and extracted with EtOAc (2×25 mL). The combined organic layer was dried ($Na_2SO_4$), filtered, concentrated and the crude product was purified by combiflash chromatography (12 g Redisep® $SiO_2$ column, eluting with 2% MeOH in chloroform) to afford the title compound (0.2 g) as a brown color solid. LC-MS retention time=2.16 min; m/z=334.2 $[M+H]^+$. Column: KINETIX XB-C18, 75×3 mm, 2.6 µm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm.

Intermediate BB-9.6

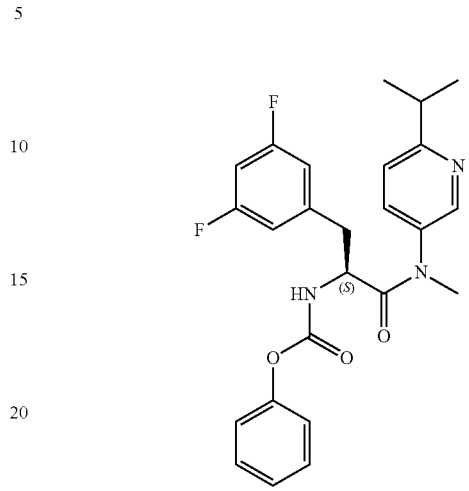

To a stirred solution of Intermediate BB-9.5 (100 mg, 0.3 mmol) and pyridine (0.036 mL, 0.45 mmol) in DCM (5 mL) was added phenyl chloroformate (0.042 mL, 0.33 mmol) at 0° C. and the reaction mixture stirred at room temperature for 16 h. The reaction mixture was diluted with water (25 mL) and extracted with DCM (2×25 mL). The combined organic layer was washed with 1.5N HCl solution (40 mL), dried ($Na_2SO_4$), filtered and concentrated. The crude product was purified by combiflash chromatography (12 g Redisep® $SiO_2$ column, eluting with 50% EtOAc in n-hexanes) to afford the title compound (100 mg) as a pale yellow solid. LC-MS retention time=3.31 min; m/z=454.2 $[M+H]^+$. Column: KINETIX XB-C18, 75×3 mm, 2.6 µm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm. $^1H$ NMR (400 MHZ, DMSO-$d_6$) δ 8.50 (br. s., 1H), 8.30 (d, J=8.0 Hz, 1H), 7.71 (d, J=8.0 Hz, 1H), 7.40 (d, J=8.4 Hz, 1H), 7.34 (t, J=8.0 Hz, 2H), 7.18 (t, J=7.2 Hz, 1H), 7.05 (t, J=9.2 Hz, 1H), 6.96 (d, J=7.6 Hz, 2H), 6.52 (d, J=7.0 Hz, 2H), 4.12 (br. s., 1H), 3.21 (s, 3H), 3.13-3.01 (m, 1H), 2.95-2.85 (m, 1H), 2.85-2.75 (m, 1H) 1.25 (d, J=7.0 Hz, 6H).

Intermediate BB-10.1

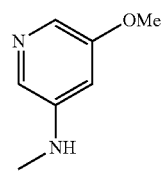

To a suspension of sodium methoxide (2.176 g, 10.07 mmol) in methanol (5 mL) was added 5-methoxypyridin-3-amine (0.250 g, 2.01 mmol) and stirred for 15 min. The resulting solution was poured into a suspension of paraformaldehyde (0.085 g, 2.82 mmol) in methanol (5 mL) and the reaction mixture was stirred at room temperature for 16 h.

NaBH₄ (0.114 g, 3.02 mmol) was added and the reaction mixture was stirred for 2 h. The reaction mixture was concentrated and the residue was diluted with ice cold water (30 mL) and extracted with EtOAc (3×20 mL). The combined organic layer was dried (Na₂SO₄), filtered, concentrated and the crude product was purified by combiflash chromatography (12 g Redisep® SiO₂ column, eluting with 2% MeOH in chloroform) to afford the title compound (0.24 g) as a pale yellow solid. LC-MS retention time=1.02 min; m/z=139.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, DMSO-d₆) δ 7.56 (d, J=2.5 Hz, 1H), 7.49 (d, J=2.5 Hz, 1H), 6.41 (t, J=2.3 Hz, 1H), 5.89 (d, J=4.5 Hz, 1H), 3.75 (s, 3H), 2.68 (d, J=5.0 Hz, 3H).

Intermediate BB-10.2

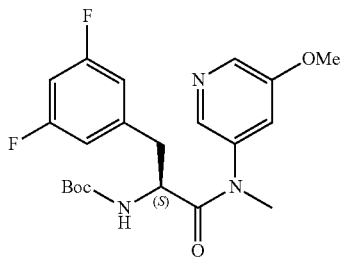

To a stirred solution of Intermediate BB-10.1 (92 mg, 0.66 mmol) and (S)-2-((tert-butoxycarbonyl)amino)-3-(3,5-difluorophenyl)propanoic acid (200 mg, 0.664 mmol) in DMF (4 mL) was added DIPEA (0.058 mL, 0.33 mmol) and HATU (505 mg, 1.33 mmol) and the reaction mixture was stirred at room temperature for 16 h. The reaction mixture was diluted with water (25 mL) and extracted with EtOAc (3×10 mL). The combined organic layer was dried (Na₂SO₄), filtered, concentrated and the crude product was purified by combiflash chromatography (12 g Redisep® SiO₂ column, eluting with 40% EtOAc in n-hexanes) to afford the title compound (105 mg) as a brown color solid. LC-MS retention time=2.72 min; m/z=422.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-10.3

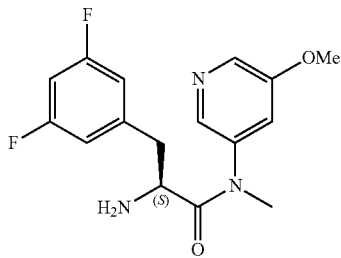

HCl in dioxane (5.0 mL, 17 mmol, 4M solution) was added to the Intermediate BB-10.2 (260 mg, 0.617 mmol) and the reaction mixture was stirred at room temperature for 2 h. The reaction mixture was concentrated to dryness; the residue was basified with saturated aq. NaHCO₃ (25 mL) solution and extracted with EtOAc (2×25 mL). The combined organic layer was dried (Na₂SO₄), filtered, concentrated and the crude product was purified by combiflash chromatography (12 g Redisep® SiO₂ column, eluting with 2% MeOH in chloroform) to afford the title compound (0.2 g) as a brown color gummy solid. LC-MS retention time=1.55 min; m/z=322.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-10.4

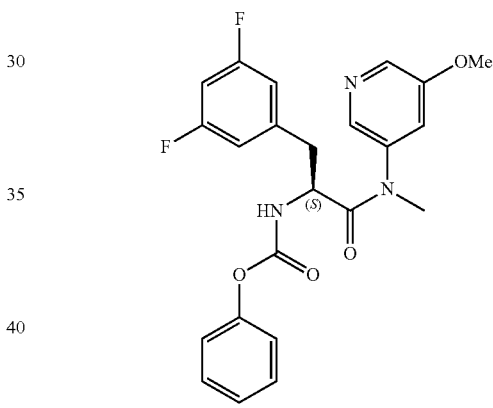

To a stirred solution of Intermediate BB-10.3 (100 mg, 0.311 mmol) and pyridine (0.038 mL, 0.47 mmol) in DCM (5 mL) was added phenyl chloroformate (0.043 mL, 0.342 mmol) at 0° C. and the reaction mixture was stirred at room temperature for 16 h. The reaction mixture was diluted with water (25 mL) and extracted with DCM (2×25 mL). The combined organic layer was washed with 1.5N HCl solution (40 mL), dried (Na₂SO₄), filtered, concentrated and the crude product was purified by combiflash chromatography (12 g Redisep® SiO₂ column, eluting with 50% EtOAc in n-hexanes) to afford the title compound (100 mg) as a pale yellow solid. LC-MS retention time=2.98 min; m/z=442.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, DMSO-d₆) δ 8.31 (d, J=7.5 Hz, 1H), 8.11 (d, J=2.0 Hz, 1H), 7.44-7.31 (m, 3H), 7.18 (t, J=7.2 Hz, 1H), 7.08 (t, J=9.3 Hz, 1H), 6.95 (d, J=8.0 Hz, 2H), 6.67 (br. s., 2H), 4.23 (br. s., 1H), 3.82 (s, 3H), 3.21 (s., 3H), 3.12-3.05 (m, 1H), 2.87-2.80 (m, 1H).

Intermediate BB-11.1

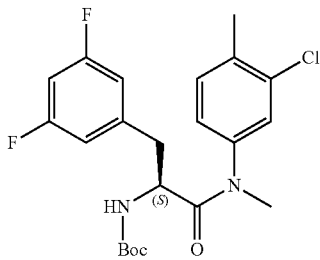

To a stirred solution of (S)-2-((tert-butoxycarbonyl) amino)-3-(3,5-difluorophenyl)propanoic acid (250 mg, 0.83 mmol) in DCM (5 mL) was added 3-fluoro-N,5-dimethylaniline (155 mg, 0.996 mmol), N-ethoxycarbonyl-2-ethoxy-1,2-dihydroquinoline (226 mg, 0.913 mmol) and the reaction mixture was stirred at room temperature for 16 h. The reaction mixture was concentrated and the crude product was purified by combiflash chromatography (40 g Redisep® SiO$_2$ column, eluting with 20% EtOAc in n-hexanes) to afford the title compound (0.25 g) as an off white solid. LC-MS retention time=1.46 min; m/z=439.2 [M+H]$^+$. Column: Acquity BEH C8 (2.1×50 mm) 1.7μ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold a 0.6 min. at 90% B of flow rate of 0.5 mL/min; Detection: UV at 220 nm. $^1$H NMR (400 MHZ, CDCl$_3$) δ 7.24 (d, J=8.3 Hz, 1H), 6.80-6.66 (m, 3H), 6.50 (d, J=6.5 Hz, 2H), 5.19 (d, J=8.0 Hz, 1H), 4.52-4.40 (m, 1H), 3.19 (s, 3H), 2.87 (dd, J=13.2, 8.0 Hz, 1H), 2.72 (dd, J=13.2, 6.0 Hz, 1H), 2.39 (s, 3H), 1.41 (br. s., 9H).

Intermediate BB-11.2

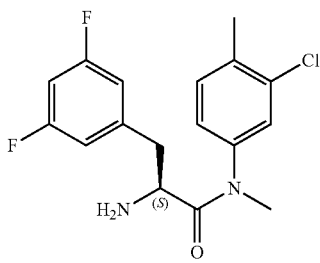

To a stirred solution of Intermediate BB-11.1 (250 mg, 0.57 mmol) in DCM (10 mL) was added HCl in dioxane (0.15 mL, 0.57 mmol, 4M in dioxane) and stirred at room temperature for 4 h. The reaction mixture was concentrated to dryness; the residue was triturated with n-hexane (2×25 mL) to afford the title compound (0.210 g) as an off white solid. LC-MS retention time=3.13 min; m/z=339.2 [M+H]$^+$. Column: KINETIX XB-C18, 75×3 mm, 2.6 jam; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, DMSO-d$_6$) δ 8.47 (br. s., 2H), 7.41 (d, J=7.9 Hz, 1H), 7.23-7.01 (m, 3H), 6.63 (d, J=6.8 Hz, 2H), 3.98 (br. s., 1H), 3.14 (s, 3H), 2.95-2.89 (m, 2H), 2.34 (s, 3H).

Intermediate BB-11.3

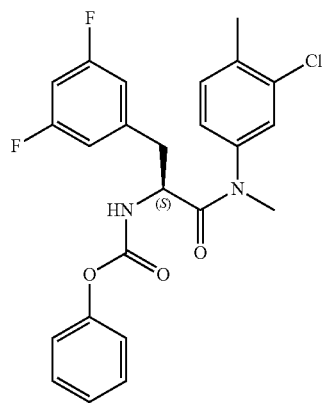

To a stirred solution of Intermediate BB-11.2 (100 mg, 0.295 mmol) and pyridine (0.05 mL, 0.6 mmol) in DCM (5 mL) was added phenyl chloroformate (0.050 mL, 0.36 mmol) at 0° C. and the reaction mixture was stirred at room temperature for 16 h. The reaction mixture was diluted with water (20 mL) and extracted with DCM (2×20 mL). The combined organic layer was washed with 1.5N HCl solution (25 mL), dried (Na$_2$SO$_4$), filtered and concentrated. The crude product was purified by combiflash chromatography (4 g Redisep® SiO$_2$ column, eluting with 30% EtOAc in n-hexanes) to afford the title compound (110 mg) as an off white solid. LC-MS retention time=3.48 min; m/z=459.2 [M+H]$^+$. Column: KINETIX XB-C18, 75×3 mm, 2.6 μm; Flow rate: 0.7 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm. $^1$H NMR (300 MHZ, CDCl$_3$) δ 7.41-7.32 (m, 2H), 7.26-7.18 (m, 2H), 7.10 (d, J=7.9 Hz, 2H), 6.88 (d, J=7.9 Hz, 1H), 6.79-6.69 (m, 2H), 6.54 (d, J=6.0 Hz, 2H), 5.75 (d, J=8.3 Hz, 1H), 4.62 (dd, J=20.0, 10.8 Hz, 1H), 3.24 (s, 3H), 2.96 (dd, J=17.6, 10.4 Hz, 1H), 2.82 (dd, J=16.8, 8.4 Hz, 1H), 2.39 (s, 3H).

Intermediate BB-12.1

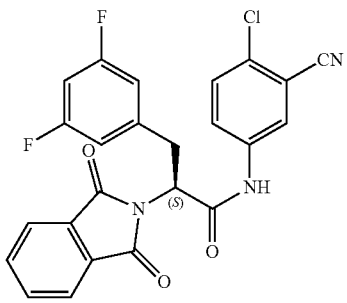

To a stirred solution of Intermediate GW-8.1 (0.25 g, 0.755 mmol), 3-amino-6-chlorobenzonitrile (0.138 g, 0.906 mmol) and pyridine (0.366 mL, 4.53 mmol) in DCM (8 mL)

was added POCl₃ (0.211 mL, 2.26 mmol) at 0° C. and the reaction mixture was stirred at room temperature for 16 h. The reaction mixture was diluted with 10% aqueous solution of NaHCO₃ (25 mL) and extracted with DCM (2×25 mL). The combined organic layer was dried (Na₂SO₄), filtered and concentrated. The crude product was purified by combiflash chromatography (24 g Redisep® SiO₂ column, eluting with 25% EtOAc in n-hexanes) to afford the title compound (0.275 g) as yellow solid. LC-MS retention time=3.32 min; m/z=466.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, CDCl₃) δ 8.60 (s, 1H), 7.93 (d, J=2.5 Hz, 1H), 7.88-7.85 (m, 2H), 7.79-7.76 (m, 2H), 7.70 (d, J=2.5 Hz, 1H), 7.45 (d, J=8.5 Hz, 1H), 6.74 (d, J=5.5 Hz, 1H), 6.65-6.59 (m, 1H), 5.20 (dd, J=9.0, 7.5 Hz, 1H), 3.61-3.58 (m, 2H).

Intermediate BB-12.2

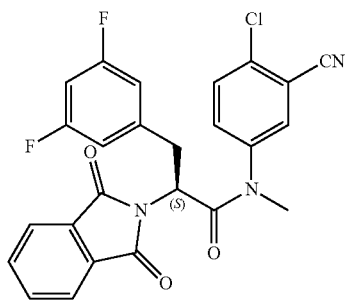

To a stirred solution of Intermediate BB-12.1 (0.25 g, 0.54 mmol) in DMF (8 mL) was added portion wise NaH (0.026 g, 60% in mineral oil, 0.64 mmol) at 0° C. and stirred for 10 min. Methyl iodide (0.05 mL, 0.805 mmol) was added at 0° C. and stirred further at room temperature for 16 h. The reaction mixture was diluted with ice cold saturated aqueous solution of NH₄Cl (50 mL) and extracted with EtOAc (2×50 mL). The combined organic layer was washed with brine (75 mL), dried (Na₂SO₄), filtered, concentrated and the crude product was purified by combiflash chromatography (24 g Redisep® SiO₂ column, eluting with 25% EtOAc in n-hexanes) to afford the title compound (0.175 g) as a pale yellow solid. LC-MS retention time=2.88 min; m/z=480.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-12.3

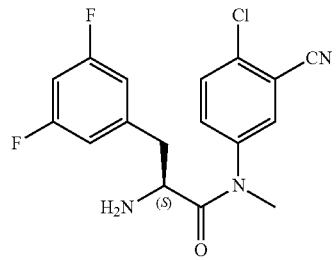

To a stirred solution of Intermediate BB-12.2 (0.175 g, 0.365 mmol) in ethanol (4 mL) in a sealed tube was added 40% aqueous solution of methylamine (0.227 mL, 1.82 mmol) and the resultant reaction mixture was stirred at 65° C. for 16 h. The reaction mixture was concentrated under reduced pressure; the residue was diluted with water (25 mL) and extracted with EtOAc (2×25 mL). The combined organic layer was dried (Na₂SO₄), filtered, concentrated and the crude product was purified by combiflash chromatography (12 g Redisep® SiO₂ column, eluting with 3% MeOH in chloroform) to afford the title compound (80 mg) as a yellow solid. LC-MS retention time=1.04 min; m/z=350.2 [M+H]⁺. Column: Acquity BEH C8 (2.1×50 mm) 1.7μ: Flow rate: 0.5 mL/min; Mobile Phase A: 5 mM NH₄OAc in water: ACN (95:5); Mobile Phase B: 5 mM NH₄OAc in water: ACN (5:95); 20% B to 90% B over 1.1 minutes and then hold a 0.6 min. at 90% B of flow rate 0.5 mL/min; Detection: UV at 220 nm.

Intermediate BB-12.4

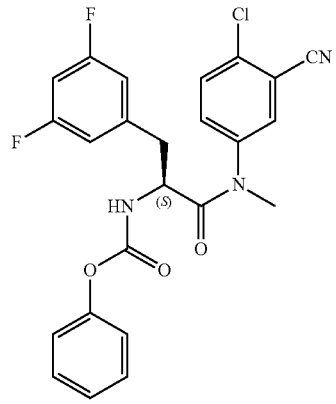

To a stirred solution of Intermediate BB-12.3 (75 mg, 0.21 mmol) and pyridine (0.035 mL, 0.43 mmol) in DCM (4 mL) was added phenyl chloroformate (0.03 mL, 0.236 mmol) at 0° C. and the reaction mixture stirred at room temperature for 16 h. The reaction mixture was diluted with water (20 mL) and extracted with DCM (2×20 mL). The combined organic layer was washed with 1.5N HCl solution (25 mL), dried (Na₂SO₄), filtered, concentrated and the crude product was purified by combiflash chromatography (4 g Redisep® SiO₂ column, eluting with 25% EtOAc in n-hexanes) to afford the title compound (33 mg) as an off white solid. LC-MS retention time=2.9 min; m/z=470.2 [M+H]⁺. Column: KINETIX XB-C18, 75×3 mm, 2.6 µm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-13

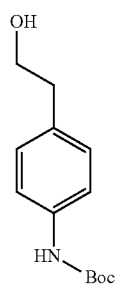

To a solution of 2-(4-aminophenyl)ethanol (1 g, 7.29 mmol) in EtOAc (15 mL) was added Boc-anhydride (1.862 mL, 8.02 mmol) and the reaction mixture was stirred at room temperature for 16 h. The reaction mixture was evaporated under reduced pressure and triturated with hexane (30 mL) to afford the title compound (1.65 g) as a white solid. LC-MS retention time=1.84 min; m/z=238.2 [M+H]⁺. Column: KINETIX XB-C18, 75×3 mm, 2.6 µm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (300 MHZ, CDCl₃) δ 7.29 (d, J=8.4 Hz, 2H), 7.17 (d, J=8.7 Hz, 2H), 6.46 (br. s., 1H), 3.84 (q, J=6.4 Hz, 2H), 2.84 (t, J=6.4 Hz, 2H), 1.53 (s, 9H).

Intermediate BB-14.1

To a stirred solution of oxalyl chloride (0.83 mL, 9.4 mmol) in DCM (15 mL) was added DMSO (1.84 mL, 26 mmol) at −78° C. and then added Intermediate BB-13 (1.4 g, 5.9 mmol) in DCM (10 mL) and stirred at the same temperature for 2 h and then slowly allowed to warm to room temperature and quenched with TEA (4.11 mL, 29.5 mmol). The reaction mixture was diluted with saturated NH₄Cl solution (150 mL), extracted with DCM (2×75 mL), dried over Na₂SO₄, filtered and concentrated. The crude aldehyde was dissolved in DCM (20 mL) and added DAST (1.559 mL, 11.80 mmol) at 0° C. and stirred at room temperature for 30 min. The reaction mixture was quenched with cold water (100 mL), extracted with EtOAc (2×100 mL), washed with brine (75 mL), dried (Na₂SO₄), filtered, concentrated and the crude product was purified by combi-flash chromatography (24 g Redisep® SiO₂ column, eluting with 12% EtOAc in n-hexanes) to afford the title compound (0.56 g) as a colorless liquid. LC-MS retention time=2.85 min; m/z=256.2 [M−H]⁺. Column: KINETIX XB-C18, 75×3 mm, 2.6 µm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHz, CDCl₃) δ 7.32 (d, J=8.4 Hz, 2H), 7.16 (d, J=8.4 Hz, 2H), 6.45 (br. s., 1H), 5.87 (tt, J=56.8, 4.8 Hz, 1H), 3.08 (dt, J=17.19, 4.77 Hz, 2H), 1.55 (s, 9H).

Intermediate BB-14.2

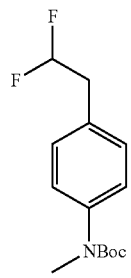

To a stirred solution of Intermediate BB-14.1 (470 mg, 1.83 mmol) in DMF (10 mL) added NaH (110 mg, 2.74 mmol, 60% in mineral oil) and stirred at 0° C. for 15 min. Methyl iodide (0.171 mL, 2.74 mmol) was added and stirring continued at room temperature for 30 min. The reaction mixture was diluted with saturated NH₄Cl solution (50 mL) and extracted with EtOAc (2×50 mL). The combined organic layer was dried (Na₂SO₄), filtered and concentrated to afford the title compound (0.38 g) as a pale yellow liquid, which was used to the next step without further purification. LC-MS retention time=1.25 min; m/z=216 [M-isobutylene+H]⁺. Column: Acquity BEH C8 (2.1×50 mm) 1.7µ: Flow rate: 0.5 mL/min; Mobile Phase A: 10 mM NH₄OAc in water: ACN (95:5); Mobile Phase B: 10 mM NH₄OAc in water: ACN (5:95); 20% B to 90% B over 1.1 minutes and then hold a 0.6 min. at 90% B of flow rate 0.5 mL/min; Detection: UV at 220 nm.

Intermediate BB-14.3

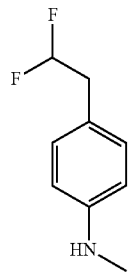

HCl in dioxane (4M solution, 5 mL, 20 mmol) was added to the Intermediate BB-14.2 (550 mg, 2.03 mmol) and the reaction mixture was stirred at room temperature for 2 h. The crude reaction mixture was concentrated to dryness; the residue was basified with saturated aq. NaHCO$_3$ (25 mL) solution and extracted with EtOAc (2×25 mL). The combined organic layer was dried (Na$_2$SO$_4$), filtered and concentrated to afford the title compound (0.26 g) as a pale yellow liquid, which was used to the next step without further purification. LC-MS retention time=2.74 min; m/z=172.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, CDCl$_3$) δ 7.09 (d, J=8.4 Hz, 2H), 6.57 (d, J=8.4 Hz, 2H), 5.84 (tt, J=57, 4.8 Hz, 1H), 3.05 (dt, J=17.19, 4.77 Hz, 2H), 2.85 (s, 3H).

Intermediate BB-14.4

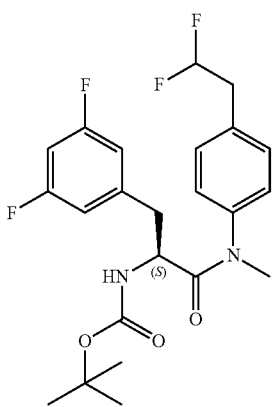

To a stirred solution of Intermediate BB-14.3 (200 mg, 1.17 mmol), (S)-2-((tert-butoxycarbonyl)amino)-3-(3,5-difluorophenyl)propanoic acid (352 mg, 1.17 mmol) in DMF (5 mL) was added HATU (888 mg, 2.34 mmol), DIPEA (1.020 mL, 5.84 mmol) and the reaction mixture was stirred at room temperature for 3 h. The reaction mixture was diluted with water (25 mL), extracted with EtOAc (2×25 mL) and the combined organic layer was washed with brine (50 mL), dried (Na$_2$SO$_4$), filtered and concentrated. The crude product was purified by combiflash chromatography (12 g Redisep® SiO$_2$ column, eluting with 28% EtOAc in n-hexanes) to afford the title compound (0.38 g) as a pale yellow liquid. LC-MS retention time=2.48 min; m/z=399.2 [M-isobutylene+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, CDCl$_3$) δ 7.31 (d, J=8.3 Hz, 2H), 6.97 (d, J=7.6 Hz, 2H), 6.71-6.62 (m, 1H), 6.40 (d, J=6.0 Hz, 2H), 5.97 (tt, J=56.4, 4.8 Hz, 1H), 5.25 (d, J=8.3 Hz, 1H), 4.65 (dd, J=15.6, 6.9 Hz, 1H), 3.25 (s, 3H), 3.20 (dt, J=17.4, 4.2 Hz, 2H), 2.84 (dd, J=13.2, 6.8 Hz, 1H), 2.64 (dd, J=13.2, 6.8 Hz, 1H), 1.40 (s, 9H).

Intermediate BB-14.5

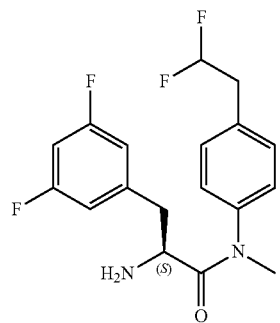

HCl in dioxane (4M solution, 0.125 mL, 4.18 mmol) was added to the Intermediate BB-14.4 (380 mg, 0.836 mmol) in DCM (10 mL) and stirred at room temperature for 2 h. The crude reaction mixture was concentrated to dryness; the residue was basified with saturated aq. NaHCO$_3$ (25 mL) solution and extracted with EtOAc (2×25 mL). The combined organic layer was dried (Na$_2$SO$_4$), filtered and concentrated. The crude product was purified by combiflash chromatography (12 g Redisep® SiO$_2$ column, eluting with 2% MeOH in Chloroform) to afford the title compound (0.25 g) as a brown color solid. LC-MS retention time=2.95 min; m/z=355.2 [M+H]$^+$ (Agilent 6330 Ion Trap). Column: KINETIX XB-C18, 75×3 mm, 2.6 μm; Flow rate: 1 mL/min; Mobile Phase A: 10 mM HCOONH$_4$ in Water; Mobile Phase B: ACN; 20% B to 100% B over 4 min, then hold for 0.6 min at 100% B with flow rate of 1.5 mL/min; Detection: UV at 220 nm. $^1$H NMR (400 MHZ, CDCl$_3$) δ 7.29 (d, J=8.0 Hz, 2H), 6.91 (d, J=8.0 Hz, 2H), 6.65 (tt, J=9.0, 2.3 Hz, 1H), 6.42 (d, J=6.0 Hz, 2H), 5.93 (tt, J=56.0, 4.0 Hz, 1H), 3.54 (t, J=7.0 Hz, 1H), 3.22 (s, 3H), 3.15 (dt, J=17.2, 4.4 Hz, 2H), 2.88 (dd, J=13.1, 6.5 Hz, 1H), 2.57 (dd, J=13.3, 7.3 Hz, 1H).

Intermediate BB-14.6

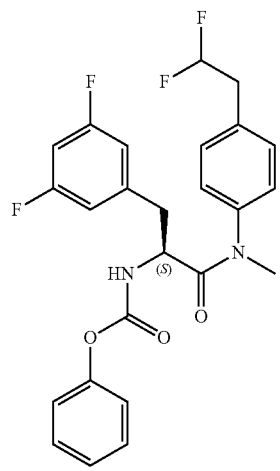

To a stirred solution of Intermediate BB-14.5 (200 mg, 0.564 mmol) in DCM (10 mL) was added pyridine (0.228 mL, 2.82 mmol) and phenyl chloroformate (0.106 mL, 0.677 mmol) at 0° C. and the reaction mixture was allowed to stir at room temperature for 16 h. The reaction mixture was diluted with water (25 mL) and extracted with DCM (2×25 mL). The combined organic layer was washed with 1.5N HCl solution (40 mL), dried (Na₂SO₄), filtered and concentrated. The crude product was purified by combiflash chromatography (12 g Redisep® SiO₂ column, eluting with 15% EtOAc in n-hexanes) to afford the title compound (260 mg) as a pale yellow solid. LC-MS retention time=3.34 min; m/z=475.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Intermediate BB-15.1

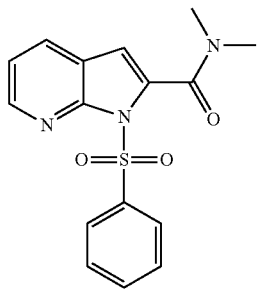 [SMILES: CN(C)C(=O)c1cc2cccnc2n1S(=O)(=O)c1ccccc1]

To a stirred solution of 1-(phenylsulfonyl)-1H-pyrrolo[2,3-b]pyridine-2-carboxylic acid (3.60 g, 11.9 mmol) in DMF (30 mL) was added DIPEA (6.24 mL, 35.7 mmol), HATU (6.79 g, 17.8 mmol) and dimethylamine (8.9 mL, 17.8 mmol). Resulting reaction mixture was allow to stir at room temperature for 16 h. The reaction mixture was poured in ice water (50 mL) and extracted with ethyl acetate (3×30 mL), organic layer washed with water (3×50 mL), brine (2×30 mL). The combined organic layer was dried over Na₂SO₄ and concentrated to obtain the title compound (4 g) as an off white solid. LC-MS retention time=0.64 min; m/z=330.4 [M+H]⁺. Column: ACQUITY BEH C8 (2.1×50 mm) 1.7μ: Flow: 0.7 mL/min; Mobile Phase A: 0.1% TFA in water; Mobile Phase B: 0.1% TFA in ACN; 2% B to 98% B over 1.0 min., then hold a 0.6 min. at 98% B of flow rate 0.7 ml/min; Detection: UV at 220 nm.

Intermediate BB-15.2

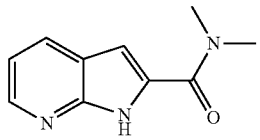

N,N-dimethyl-1H-pyrrolo[2,3-b]pyridine-2-carboxamide

To a stirred solution of Intermediate BB-15.1 (4.00 g, 12.1 mmol) in THF (40 mL) was added potassium tert-butoxide (12.1 mL, 12.1 mmol. 1.0 M) and stirred for 1 h. The reaction mixture was filtered, washed with diethyl ether to give title compound (2.4 g) as an off white solid. LC-MS retention time=0.43 min; m/z=190.2 [M+H]⁺. Column: Acquity BEH C8 (2.1×50 mm) 1.7μ: Flow rate: 0.5 mL/min; Mobile Phase A: 5 mM NH₄OAc in water: ACN (95:5); Mobile Phase B: 5 mM NH₄OAc in water: ACN (5:95); 20% B to 90% B over 1.1 min., and then hold a 0.6 min. at 90% B of flow rate 0.5 mL/min; Detection: UV at 220 nm.

Intermediate BB-16.1

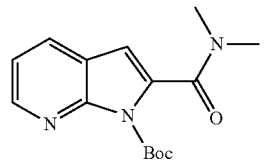 [SMILES: CN(C)C(=O)c1cc2cccnc2n1C(=O)OC(C)(C)C]

To a stirred solution of N,N-dimethyl-1H-pyrrolo[2,3-b]pyridine-2-carboxamide (2.4 g, 12.68 mmol) in acetonitrile (25 mL) was added 4-dimethylaminopyridine (0.155 g, 1.27 mmol), Boc₂O (4.42 mL, 19.03 mmol) and stirred for 16 h. The reaction mixture was concentrated under reduced pressure to give crude compound which was dissolved in ethyl acetate (50 mL), organic layer washed with water (2×30 mL), sat. NH₄Cl (2×40 mL), dried over sodium sulphate, concentrated to give title compound (1.3 g) as a yellow solid. LC-MS retention time=0.83 min; m/z=290.2 [M+H]⁺. Column: Acquity BEH C8 (2.1×50 mm) 1.7μ: Flow rate: 0.5 mL/min; Mobile Phase A: 5 mM NH₄OAc in water: ACN (95:5); Mobile Phase B: 5 mM NH₄OAc in water: ACN (5:95); 20% B to 90% B over 1.1 min., and then hold a 0.6 min. at 90% B of flow rate 0.5 mL/min; Detection: UV at 220 nm. ¹H NMR (300 MHz, CDCl₃) δ ppm 8.57 (dd, J=4.72, 1.70 Hz, 1H), 7.90 (dd, J=7.74, 1.70 Hz, 1H), 7.24 (dd, J=7.93, 4.91 Hz, 1H), 6.56 (s, 1H), 3.14 (s, 3H), 3.00 (s, 3H), 1.62 (s, 9H).

Intermediate BB-16.2

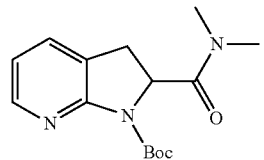 [SMILES: CN(C)C(=O)C1Cc2cccnc2N1C(=O)OC(C)(C)C]

To a stirred solution of Intermediate BB-16.1 (800 mg, 2.77 mmol) in ethanol (10 mL) was added 10% palladium on carbon (400 mg, 0.376 mmol) under inert atmosphere and then stirred under hydrogen bladder pressure for 16 h. The reaction mass was concentrated to dryness and the crude product was purified by combiflash chromatography (12 g Redisep® SiO₂ column, eluting with 0-10% MeOH in DCM) to afford the title compound (600 mg). LC-MS retention time=0.66 min; m/z=292.2 [M+H]⁺. Column: Acquity BEH C8 (2.1×50 mm) 1.7μ: Flow rate: 0.5 mL/min; Mobile Phase A: 5 mM NH₄OAc in water: ACN (95:5); Mobile Phase B: 5 mM NH₄OAc in water: ACN (5:95); 20% B to 90% B over 1.1 minutes and then hold a 0.6 min. at 90% B of flow rate 0.5 mL/min; Detection: UV at 220 nm.

Intermediate BB-16.3

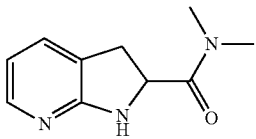

To a solution of Intermediate BB-16.2 (600 mg, 2.06 mmol) in dioxane (5 mL) was added 4M hydrochloric acid in 1,4-dioxane (2.57 mL, 10.3 mmol) and the resulting solution was stirred at room temperature for 2 h. The reaction mixture was concentrated under reduced pressure to give Intermediate BB-16.3, hydrochloride (500 mg) as an off white solid. LC-MS retention time=0.49 min; m/z=192.1 [M+H]$^+$. Column: Acquity BEH C8 (2.1×50 mm) 1.7μ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold a 0.6 min. at 90% B of flow rate 0.5 mL/min; Detection: UV at 220 nm.

Intermediate BB-16.4

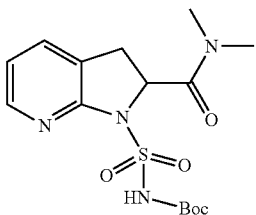 [SMILES: CN(C)C(=O)C1Cc2cccnc2N1S(=O)(=O)NC(=O)OC(C)(C)C]

To a stirred solution of tert-butyl alcohol (0.25 mL, 2.6 mmol) in DCM (5 mL) was added to a solution of chlorosulfonyl isocyanate (0.23 mL, 2.6 mmol) in DCM (5 mL) and stirred for 1 h. Then a solution of Intermediate BB-16.3, hydrochloride (500 mg, 2.61 mmol) and TEA (1.09 mL, 7.84 mmol) in DCM (5 mL) was added to the above stirred reaction mixture and stirred further for 1 h at 0° C. and then at room temperature for 16 h. The reaction mixture was then diluted with water (20 mL) and extracted with DCM (3×25 mL). The combined organic layers was washed with 10% aqueous NaHCO$_3$ solution (25 mL), water (25 mL), brine (25 mL), dried (Na$_2$SO$_4$), filtered and concentrated. The crude product was purified by combiflash chromatography (12 g Redisep® SiO$_2$ column, eluting with 0-10% MeOH in CHCl$_3$) to afford the title compound (0.5 g) as an off white solid. LC-MS retention time=0.48 min; m/z=371.3 [M+H]$^+$. Column: Acquity BEH C8 (2.1×50 mm) 1.7μ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold a 0.6 min. at 90% B of flow rate 0.5 mL/min; Detection: UV at 220 nm.

Intermediate BB-16.5

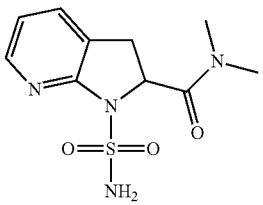 [SMILES: CN(C)C(=O)C1Cc2cccnc2N1S(N)(=O)=O]

To a stirred solution of Intermediate BB-16.4 (500 mg, 1.35 mmol) in DCM (10 mL) was added HCl in dioxane (4M, 0.34 mL, 1.4 mmol) and the reaction mixture was stirred at room temperature for 1 h. The reaction mixture was concentrated to dryness and the residue was triturated with hexane (2×25 mL) to afford the title compound (0.4 g) as an off white solid. LC-MS retention time=0.65 min; m/z=271.2 [M+H]$^+$. Column: KINETIX XB-C18, 75×3 mm, 2.6 μm; Flow rate: 0.7 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm.

Intermediate BB-17.1

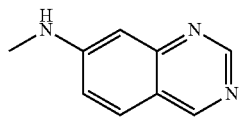

To the solution of 7-bromoquinazoline (0.500 g, 2.39 mmol) and methylamine (7.00 mL, 2.39 mmol) in a pressure tube was added CuI (0.046 g, 0.24 mmol) and the reaction vessel was sealed and stirred at 100° C. for 16 h. The reaction mixture was diluted with water (25 mL) and extracted with EtOAc (3×25 mL). The combined organic layer was washed with water (50 mL), brine (50 mL), dried (Na$_2$SO$_4$), filtered and concentrated.

The crude product was purified by combiflash chromatography (12 g Redisep® SiO$_2$ column, eluting with 70% EtOAc in n-hexanes) to afford the title compound (0.12 g) as a pale green solid. LC-MS retention time=1.24 min; m/z=160.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, CDCl$_3$) δ 9.20 (s, 1H), 9.08 (s, 1H), 7.83 (d, J=9.1 Hz, 1H), 7.31 (d, J=2.6 Hz, 1H), 6.73 (d, J=2.6 Hz, 1H), 4.24 (br. s., 1H), 2.99 (d, J=5.3 Hz, 3H).

Intermediate BB-17.2

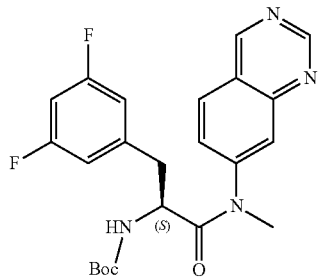

To a solution of (S)-2-((tert-butoxycarbonyl)amino)-3-(3,5-difluorophenyl)propanoic acid (0.300 g, 0.996 mmol) in DMF (3 mL) was added DIPEA (0.52 mL, 3 mmol) and HATU (0.757 g, 2 mmol) at 0° C. and stirred for 5 min. Intermediate BB-17.1 (0.174 g, 1.1 mmol) was added and the reaction mixture was stirred at room temperature for 16 h. The reaction mixture was diluted with water (30 mL), extracted with EtOAc (3×30 mL) and the combined organic layer was washed with water (30 mL), brine (30 mL), dried (Na$_2$SO$_4$), filtered and concentrated. The crude product was purified by combiflash chromatography (12 g Redisep® SiO$_2$ column, eluting with 50% EtOAc in n-hexanes) to afford the title compound (0.25 g) as a pale yellow oil. LC-MS retention time=2.77 min; m/z=443.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-17.3

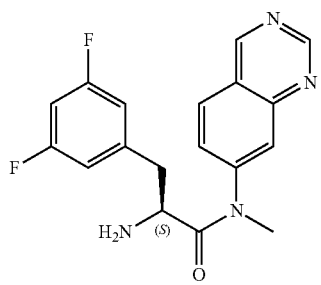

To a solution of Intermediate BB-17.2 (0.10 g, 0.23 mmol) in dioxane (0.5 mL) was added 4M HCl in dioxane (1 mL, 4 mmol) and the reaction mixture was stirred at room temperature for 3 h. The reaction mixture was concentrated to dryness; the residue was basified with 10% aqueous NaHCO$_3$ solution (15 mL) and extracted with EtOAc (3×10 mL). The combined organic layer was washed with water (15 mL), brine (15 mL), dried (Na$_2$SO$_4$), filtered and concentrated to obtain the title compound (50 mg) as pale yellow oil. LC-MS retention time=0.56 min; m/z=343.2 [M+H]$^+$. Column: Acquity BEH C8 (2.1×50 mm) 1.7µ: Flow rate: 0.5 mL/min; Mobile Phase A: 5 mM NH$_4$OAc in water: ACN (95:5); Mobile Phase B: 5 mM NH$_4$OAc in water: ACN (5:95); 20% B to 90% B over 1.1 minutes and then hold a 0.6 min. at 90% B of flow rate 0.5 mL/min; Detection: UV at 220 nm. $^1$H NMR (400 MHZ, CDCl$_3$) δ 9.39 (s, 1H), 9.32 (s, 1H), 8.09 (d, J=8.8 Hz, 1H), 7.43 (br. s., 1H), 7.38-7.29 (m, 1H), 6.74 (tt, J=8.9, 2.3 Hz, 1H), 6.50 (br. s., 2H), 3.55 (br. s., 1H), 3.32 (s, 3H), 2.98 (m, 1H), 2.73-2.59 (m, 1H).

Intermediate BB-17.4

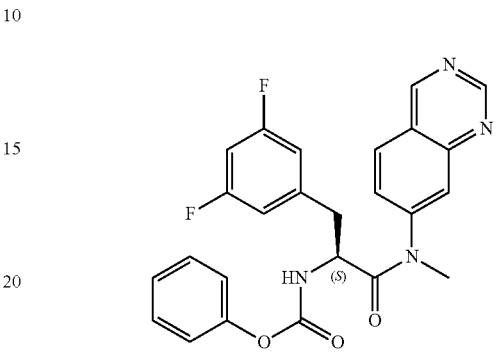

To a stirred solution of Intermediate BB-17.3 (0.1 g, 0.292 mmol) and pyridine (0.047 mL, 0.584 mmol) in DCM (2 mL) at 0° C. was added phenyl chloroformate (0.040 mL, 0.321 mmol) and the reaction mixture was stirred at room temperature for 16 h. The reaction mixture was diluted with water (20 mL) and extracted with DCM (3×20 mL). The combined organic layer was washed with 1.5N HCl solution (15 mL), water (15 mL), brine (15 mL), dried (Na$_2$SO$_4$), filtered and concentrated. The crude product was purified by combiflash chromatography (4 g Redisep® SiO$_2$ column, eluting with 4% MeOH in CHCl$_3$) to afford the title compound (0.1 g) as pale yellow oil. LC-MS retention time=2.99 min; m/z=463.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-18.1

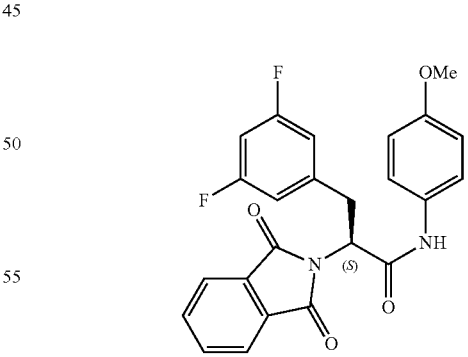

To a solution of Intermediate GW-8.1 (1.0 g, 3.0 mmol), HATU (1.4 g, 3.6 mmol) and DIPEA (1.3 mL, 7.5 mmol) in DMF (20 mL) was added 4-methoxyaniline (0.4 g, 3.3 mmol) and the reaction mixture was stirred at room temperature for 16 h. The reaction mass quenched into water (50 mL), extracted with EtOAc (2×30 mL) and the combined organic layer was washed with water (50 mL), brine (50 mL), dried (Na$_2$SO$_4$), filtered and concentrated. The crude product was purified by combiflash chromatography (40 g Redisep® SiO₂ column, eluting with 40-45% EtOAc in n-hexanes) to afford the title compound (1.0 g) as a colorless liquid. LC-MS retention time=1.16 min; m/z=437.4 [M+H]$^+$. Column: XBridge BEH C18 (2.1×50 mm) 2.5μ: Flow rate: 0.5 mL/min; Mobile Phase A: 5 mM NH₄OAc in water: ACN (95:5); Mobile Phase B: 5 mM NH₄OAc in water: ACN (5:95); 20% B to 90% B over 1.1 minutes and then hold a 0.6 min. at 90% B of flow rate 0.5 mL/min; Detection: UV at 220 nm. $^1$H NMR (400 MHZ, DMSO-d₆) δ 9.82 (s, 1H), 7.86 (d, J=1.5 Hz, 4H), 7.43 (d, J=9.0 Hz, 2H), 7.02-6.95 (m, 1H), 6.94-6.87 (m, 4H), 5.21 (dd, J=11.3, 4.8 Hz, 1H), 3.72 (s, 3H), 3.62 (dd, J=14.1, 4.5 Hz, 2H).

Intermediate BB-18.2

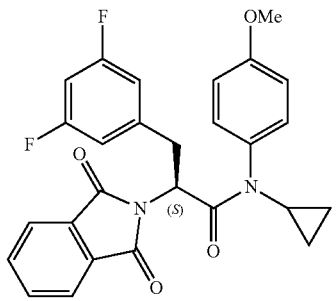

To a solution of Intermediate BB-18.1 (500 mg, 1.5 mmol) in toluene (5 mL) was added cyclopropyl boronic acid (197 mg, 2.30 mmol), cesium carbonate (187 mg, 0.57 mmol), diacetoxycopper.H₂O (208 mg, 1.15 mmol), pyridine (0.3 mL, 3.44 mmol) and the resulting reaction mixture was allowed to stir at 90° C. for 36 h under oxygen bladder. The reaction mixture was quenched into water (50 mL), extracted with EtOAc (2×30 mL) and the combined organic layer was washed with water (50 mL), brine (50 mL), dried (Na₂SO₄), filtered and concentrated. The crude product was purified by combiflash chromatography (24 g Redisep® SiO₂ column, eluting with 40-50% EtOAc in n-hexanes) to afford the title compound (0.5 g) as a pale yellow solid. LC-MS retention time=1.58 min; m/z=477.5 [M+H]$^+$. Column: ACQUITY BEH C18 (2.1×50 mm) 1.7μ: Flow: 0.7 mL/min; Mobile Phase A: 0.1% TFA in water; Mobile Phase B: 1% TFA in ACN; 2% B to 98% B over 1.0 minutes, then hold a 0.6 min. at 98% B of flow rate 0.7 mL/min; Detection: UV at 220 nm.

Intermediate BB-18.3

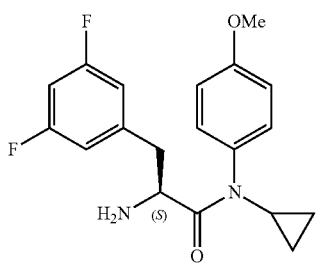

To a solution of Intermediate BB-18.2 (500 mg, 1.05 mmol) in ethanol (20 mL) was added hydrazine monohydrate (525 mg, 10.49 mmol) and the resultant solution was heated to 90° C. and stirred for 4 h. The reaction mixture was cooled RT, solid precipitated out was filtered off and the filtrate was concentrated to give crude product which was triturated with n-hexane, filtered and dried under vacuum to afford the title compound (0.5 g) as a pale yellow solid. LC-MS Retention time=1.04 min; m/z=347.5 [M+H]$^+$. Column: ACQUITY BEH C18 (2.1×50 mm) 1.7μ: Flow: 0.7 mL/min; Mobile Phase A: 0.1% TFA in water; Mobile Phase B: 0.1% TFA in ACN; 2% B to 98% B over 1.0 minutes, then hold a 0.6 min. at 98% B of flow rate 0.7 mL/min; Detection: UV at 220 nm.

Intermediate BB-18.4

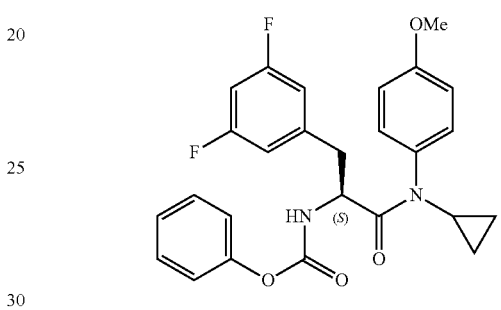

To a solution of Intermediate BB-18.3 (350 mg, 1.01 mmol) in DCM (20 mL) was added pyridine (0.25 mL, 3.03 mmol) followed by phenyl chloroformate (190 mg, 1.21 mmol) and stirred at room temperature for 16 h. The reaction mixture was concentrated and the crude product was quenched with ice cold water to afford solid product which was filtered, dried, triturated with n-hexane to afford the title compound (250 mg) as pale yellow solid. LC-MS Retention time=1.12 min; m/z=467.5 [M+H]$^+$. Column: ACQUITY BEH C18 (2.1×50 mm) 1.7μ: Flow: 0.7 mL/min; Mobile Phase A: 0.1% TFA in water; Mobile Phase B: ACN; 2% B to 98% B over 1.0 minutes, then hold a 0.6 min. at 98% B of flow rate 0.7 mL/min; Detection: UV at 220 nm.

Intermediate BB-19.1

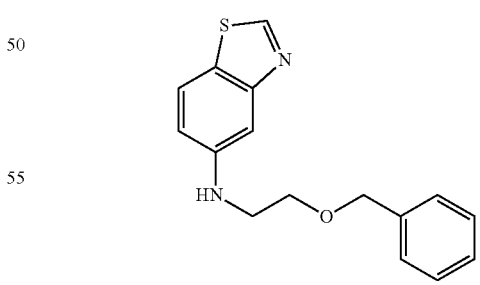

To a stirred solution of benzo[d]thiazol-5-amine (250 mg, 1.66 mmol) in acetonitrile (5 mL) were added the K₂CO₃ (276 mg, 2.00 mmol) in portion wise over the period of 10 min at 0° C. and the reaction mixture heated at 65° C. for 30 min. Then the temperature was brought to 30° C., ((2-bromoethoxy)methyl)benzene (0.290 mL, 1.83 mmol) was added the resulting reaction mixture was refluxed for 24 h.

The reaction mixture was concentrated to dryness; the crude material dissolved in water (30 mL), washed with ether (2×30 mL) to remove organic impurities and the aqueous layer neutralized with 1.5N HCl to pH 7 and extracted with ether (3×50 mL). The combined organic layer was washed with water (30 mL), brine (30 mL), dried (Na$_2$SO$_4$), filtered, concentrated and the crude product was purified by silica gel chromatography (24 g Redisep® column, eluting with 30% EtOAc in n-hexane) to afford the title compound (285 mg) as light brown solid. LC-MS Retention Time=2.56 min; m/z=285.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, CDCl$_3$) δ 8.90 (s, 1H), 7.70 (d, J=8 Hz, 1H), 7.36-7.25 (m, 6H), 6.83 (dd, J=8.8, 2.0 Hz, 1H), 4.57 (s, 2H), 4.24 (br s, 1H), 3.76 (t, J=5.2 Hz, 2H), 3.42 (m, 2H).

Intermediate BB-19.2

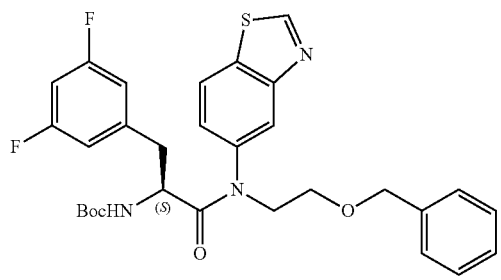

To a stirred solution of (S)-2-((tert-butoxycarbonyl)amino)-3-(3,5-difluorophenyl)propanoic acid (500 mg, 1.66 mmol) in DMF (2.5 mL) was added HATU (947 mg, 2.49 mmol), DIPEA (0.870 mL, 4.98 mmol) and the reaction mixture stirred at room temperature for 15 min. Then added Intermediate BB-19.1 (519 mg, 1.83 mmol) and the reaction mixture was stirred for 16 h. The reaction mixture was diluted with water (25 mL) and extracted with DCM (2×20 mL). The combined organic layer was washed with 1.5N HCl solution (25 mL), water (25 mL), brine (25 mL), dried (Na$_2$SO$_4$), filtered, concentrated and the crude product was purified by silica gel chromatography (24 g Redisep® column, eluting with 30% EtOAc in n-hexanes) to afford the title compound (825 mg) as pale brown solid. LC-MS retention time=3.71 min; m/z=568.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-19.3

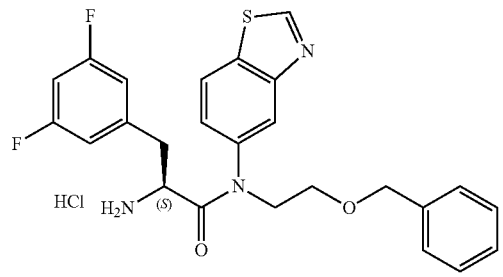

To a stirred solution of Intermediate BB-19.2 (300 mg, 0.528 mmol) in DCM (5 mL) was added 4M HCl in dioxane (0.661 mL, 2.64 mmol) and stirred at room temperature for 16 h. The reaction mixture was concentrated to dryness; the residue was triturated with diethyl ether (3×50 mL) and the resulting solid was allowed to settle and the supernatant was decanted to afford the an HCl salt of the title compound (245 mg) as a brown solid. LC-MS retention time=2.68 min; m/z=468.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-19.4

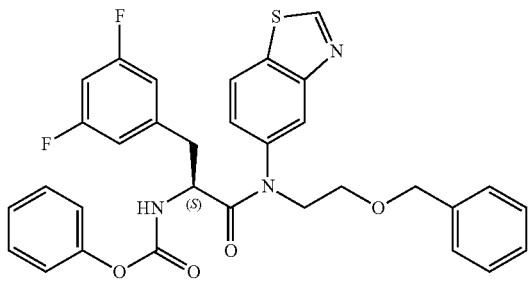

To a stirred cooled solution of Intermediate BB-19.3 hydrochloride (0.12 g, 0.24 mmol) and pyridine (0.039 mL, 0.48 mmol) in DCM (2 mL) at 0° C. was added phenyl chloroformate (0.034 mL, 0.26 mmol) and the reaction mixture was stirred at room temperature for 16 h. The reaction mixture was diluted with water (30 mL) and extracted with DCM (3×10 mL). The combined organic layer was washed with 1.5N HCl solution (15 mL), brine (15 mL), dried (Na$_2$SO$_4$), filtered and concentrated. The crude product was purified by combiflash chromatography (4 g Redisep® SiO$_2$ column, eluting with 30% EtOAc in n-hexanes) to afford the title compound (85 mg) as a pale yellow oil. LC-MS Retention time=3.38 min; m/z=588.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-20.1

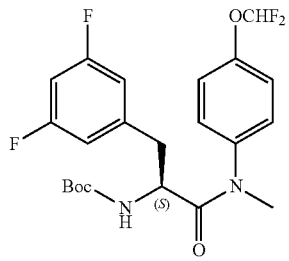

To a stirred solution of (S)-2-((tert-butoxycarbonyl)amino)-3-(3,5-difluorophenyl)propanoic acid (3.13 g, 10.4 mmol) and 4-(difluoromethoxy)-N-methyl aniline (1.20 g, 6.93 mmol) in DCM (25 mL) was added N-ethoxycarbinyl-2-ethoxy-1,2-dihydroquinoline (5.14 g, 20.8 mmol), reaction mixture was stirred at room temperature for 16 h. The reaction mixture was concentrated to dryness and the crude product was purified by combiflash chromatography (24 g Redisep® SiO$_2$ column, eluting with 10% EtOAc in n-hexanes) to afford the title compound (2.3 g) as a colorless gummy solid. LC-MS retention time=3.13 min; m/z=457.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, CDCl$_3$) δ 7.13 (d, J=8.0 Hz, 2H), 6.94 (d, J=6.0 Hz, 2H), 6.69-6.61 (m, 1H), 6.54 (t, J=73.6 Hz, 1H), 6.45 (d, J=6.0 Hz, 2H), 5.19 (d, J=9.5 Hz, 1H), 4.51 (dd, J=14.4, 6.8 Hz, 1H), 3.21 (s, 3H), 2.84 (dd, J=13.1, 7.5 Hz, 1H), 2.68 (dd, J=13.1, 6.5 Hz, 1H), 1.46 (s, 9H).

Intermediate BB-20.2

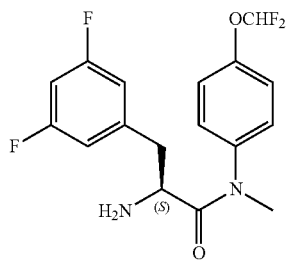

HCl in dioxane (4M solution, 16.1 mL, 46 mmol) was added to Intermediate BB-20.1 (2.10 g, 4.60 mmol) and the reaction mixture was stirred at room temperature for 2 h. The crude reaction mixture was concentrated to dryness; the residue was basified with saturated aq. NaHCO$_3$ (50 mL) solution and extracted with EtOAc (2×50 mL). The combined organic layer was dried (Na$_2$SO$_4$), filtered, concentrated and the crude product was purified by combiflash chromatography (24 g Redisep® SiO$_2$ column, eluting with 2% MeOH in Chloroform) to afford the title compound (1.3 g) as a brown color gummy solid. LC-MS retention time=2.30 min; m/z=357.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, CDCl$_3$) δ 7.15 (d, J=9.0 Hz, 2H), 6.92 (d, J=6.0 Hz, 2H), 6.68 (t, J=8.8 Hz, 1H), 6.53 (t, J=73.2 Hz, 1H), 6.48 (d, J=6.8 Hz, 2H), 3.54 (t, J=6.9 Hz, 1H), 3.22 (s, 3H), 2.91 (dd, J=13.0, 7.0 Hz, 1H), 2.61 (dd, J=13.0, 7.0 Hz, 1H).

Intermediate BB-20.3

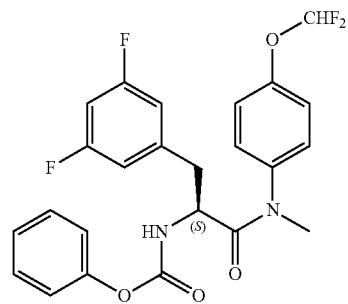

To a stirred solution of Intermediate BB-20.2 (1.30 g, 3.65 mmol) and pyridine (0.443 mL, 5.47 mmol) in DCM (15 mL) was added phenyl chloroformate (0.551 mL, 4.38 mmol) at 0° C. and the reaction mixture was stirred at room temperature for 16 h. The reaction mixture was diluted with water (50 mL) and extracted with DCM (2×50 mL). The combined organic layer was washed with 1.5N HCl solution (50 mL), dried (Na$_2$SO$_4$), filtered and concentrated. The crude product was purified by combiflash chromatography (24 g Redisep® SiO$_2$ column, eluting with 50% EtOAc in n-hexanes) to afford the title compound (1.3 g) as a pale yellow solid. LC-MS retention time=2.83 min; m/z=477.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, CDCl$_3$) δ 7.39-7.31 (m, 2H), 7.24-7.17 (t, J=7.4 Hz, 1H), 7.11 (d, J=8.8 Hz, 2H), 7.07 (d, J=7.6 Hz, 2H), 6.95 (br. s., 2H), 6.51 (t, J=73.6 Hz, 1H), 6.49 (d, J=6.0 Hz, 2H), 5.74 (d, J=9.0 Hz, 1H), 4.64 (dd, J=14.8, 6.4 Hz, 1H), 3.25 (s, 3H), 2.95 (dd, J=13.2, 7.6 Hz, 1H), 2.81 (dd, J=13.2, 6.4 Hz, 1H).

Intermediate BB-21.1

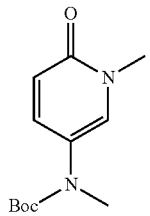

To a stirred solution of tert-butyl (1-methyl-6-oxo-1,6-dihydropyridin-3-yl)carbamate (1.00 g, 4.46 mmol) in DMF (10 mL) at 0° C. was added portion wise 60% NaH (0.446 g, 11.2 mmol, dispersion in mineral oil) and the reaction mixture was stirred at room temperature for 20 min. Methyl iodide (0.418 mL, 6.69 mmol) was added drop wise at the same temperature and the reaction mixture was stirred at room temperature for 16 h. The reaction mixture was diluted with water (50 mL) and extracted with EtOAc (3×30 mL). The combined organic layer was washed with water (50 mL), brine (50 mL), dried ($Na_2SO_4$), filtered and concentrated to afford the title compound (1 g) as pale yellow oil. LC-MS retention time=1.34 min; m/z=239.2 [M+H]$^+$. Column: KINETIX XB-C18, 75×3 mm, 2.6 μm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, DMSO-$d_6$) δ ppm 7.75 (d, J=2.6 Hz, 1H), 7.38 (dd, J=9.8, 3.0 Hz, 1H), 6.34 (d, J=9.4 Hz, 1H), 3.33 (s, 3H), 3.07 (s, 3H), 1.37 (s, 9H).

Intermediate BB-21.2

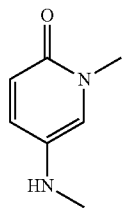

To a stirred solution of Intermediate BB-21.1 (1.0 g, 4.2 mmol) in dioxane (2 mL) was added 4 M HCl in dioxane (6.0 mL, 4.2 mmol) and stirred at room temperature for 3 h. The reaction mixture was concentrated to dryness; the residue was triturated with diethyl ether (3×50 mL) and the resulting solid was allowed to settle and the supernatant was decanted to afford the title compound as an off white solid (0.5 g) as an off white solid. LC-MS retention time=0.45 min; m/z=139.2 [M+H]$^+$. Column: KINETIX XB-C18, 75×3 mm, 2.6 μm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, DMSO-$d_6$) δ ppm 11.67-10.44 (br. s., 1H), 8.03 (d, J=2.5 Hz, 1H), 7.64 (dd, J=10.0, 3.0 Hz, 1H), 6.56 (d, J=9.5 Hz, 1H), 3.46 (s, 3H), 2.80 (s, 3H).

Intermediate BB-21.3

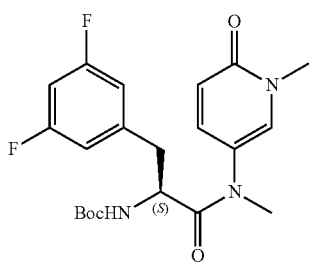

To a stirred solution of (S)-2-((tert-butoxycarbonyl) amino)-3-(3,5-difluorophenyl)propanoic acid (0.250 g, 0.830 mmol) in DMF (2 mL) at 0° C. was added HATU (0.38 g, 1 mmol) and DIPEA (0.73 mL, 4.2 mmol) and the reaction mixture was stirred for 30 min. Intermediate BB-21.2 (0.17 g, 0.91 mmol) was added to the reaction mixture and it was stirred at room temperature for 16 h. The reaction mixture was diluted with water (20 mL) and extracted with EtOAc (3×25 mL). The combined organic layer was washed with 10% $NaHCO_3$ solution (20 mL), water (25 mL), brine (25 mL), dried ($Na_2SO_4$), filtered and concentrated to afford the title compound (0.31 g) as a dark blue oil. LC-MS retention time=2.10 min; m/z=422.2 [M+H]$^+$. Column: KINETIX XB-C18, 75×3 mm, 2.6 μm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm.

Intermediate BB-21.4

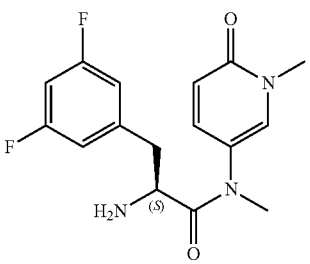

To a stirred solution of Intermediate BB-21.3 (0.30 g, 0.71 mmol) in dioxane (1 mL) at 0° C. was added 4M HCl in dioxane (3.0 mL, 0.71 mmol) and the reaction mixture was stirred at room temperature for 3 h. The reaction mixture was concentrated to dryness; and the residue was triturated with diethyl ether (3×50 mL). The resulting solid was allowed to settle and the supernatant was decanted to afford the title compound (0.21 g) as a brown solid. LC-MS retention time=0.92 min; m/z=322.2 [M+H]$^+$. Column: KINETIX XB-C18, 75×3 mm, 2.6 μm; Flow rate: 1 mL/min; Mobile Phase A: 10 mM $HCOONH_4$ in 98% Water/2% ACN; Mobile Phase B: 10 mM $HCOONH_4$ in 2% Water/98% ACN; 20% B to 100% B over 4 min, then hold for 0.6 min at 100% B with flow rate of 1.5 mL/min; Detection: UV at 220 nm.

Intermediate BB-22.1

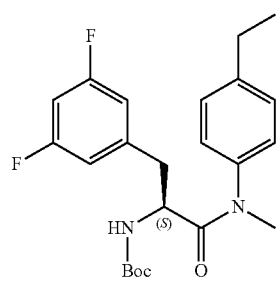

To a stirred solution of (S)-2-((tert-butoxycarbonyl) amino)-3-(3,5-difluorophenyl)propanoic acid (4.46 g, 14.8 mmol) in DMF (100 mL) was added HATU (8.44 g, 22.2 mmol), TEA (4.12 mL, 29.6 mmol) and the reaction mixture was stirred for 30 min. N-methyl-4-ethylaniline (2.00 g, 14.8 mmol) was added to the above reaction mixture and stirred at room temperature for 16 h. The reaction mixture was then diluted with water (50 mL) and extracted with EtOAc (3×50 mL). The combined organic layer was washed with 10% aqueous NaHCO$_3$ solution (50 mL), brine (50 mL), dried (Na$_2$SO$_4$), filtered and concentrated. The crude product was purified by combiflash chromatography (40 g Redisep® SiO$_2$ column, eluting with 0-15% EtOAc in hexanes) to afford the title compound (2.5 g) as an off white solid. LC-MS retention time=3.7 min; m/z=419.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-22.2

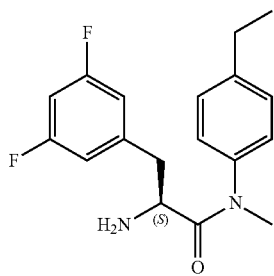

To a stirred solution of Intermediate BB-22.1 (4.0 g, 9.6 mmol) in DCM (25 mL) was added HCl in dioxane (4M, 10 mL, 38.2 mmol) and the reaction mixture was stirred at room temperature for 4 h. The reaction mixture was concentrated to dryness; the residue was triturated with hexane (2×25 mL) to afford the title compound (3.0 g) as an off white solid. LC-MS retention time=1.03 min; m/z=319.2 [M+H]$^+$. Column: Acquity BEH C8 (2.1×50 mm) 1.7µ: Flow rate: 0.8 mL/min; Mobile Phase A: 5 mM NH$_4$OAc in water: ACN (95:5); Mobile Phase B: 5 mM NH$_4$OAc in water: ACN (5:95); 5% B to 99% B over 1.1 minutes and then hold a 0.6 min. at 95% B of flow rate 0.8 mL/min; Detection: UV at 220 nm.

Intermediate BB-23.1

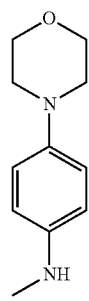

To a solution of 4-morpholinoaniline (1.50 g, 8.42 mmol) in methanol (10 mL) was added sodium methoxide (2.20 mL, 10.1 mmol), paraformaldehyde (0.278 g, 9.26 mmol) and the reaction mixture was at room temperature for 10 h. To this stirred reaction mixture was added sodium borohydride (0.480 g, 12.6 mmol) and stirred further at room temperature for 2 h. The reaction mixture was diluted with aqueous saturated solution of NH$_4$Cl (50 mL) and extracted with EtOAc (2×50 mL). The combined organic layer was washed with brine (75 mL), dried (Na$_2$SO$_4$), filtered and concentrated to afford the title compound (1.3 g) as a black solid. LC-MS retention time=0.99 min; m/z=193.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHz, DMSO-d$_6$) δ 6.77 (d, J=9.04 Hz, 2H), 6.48 (d, J=9.04 Hz, 2H), 5.13 (br. s., 1H), 3.70 (t, J=4.8 Hz, 4H), 2.89 (t, J=4.8 Hz, 4H), 2.62 (s, 3H).

Intermediate BB-23.2

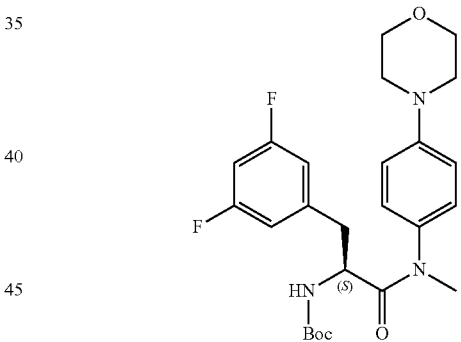

To a stirred solution of (S)-2-((tert-butoxycarbonyl) amino)-3-(3,5-difluorophenyl)propanoic acid (2.59 g, 8.58 mmol) in DMF (20 mL) was added Intermediate BB-23.1 (1.50 g, 7.80 mmol), HATU (4.45 g, 11.70 mmol) followed by DIPEA (6.81 mL, 39.0 mmol) and the reaction mixture was stirred at room temperature for 3 h. The reaction mixture was diluted with water (25 mL), extracted with EtOAc (2×25 mL) and the combined organic layer was washed with brine (50 mL), dried (Na$_2$SO$_4$), filtered and concentrated to afford the title compound (2.5 g) as a brown color solid. The crude was taken to next reaction without any further purification. LC-MS retention time=2.8 min; m/z=476.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-23.3

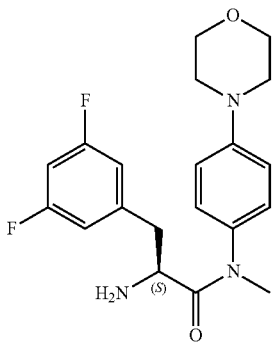

HCl in dioxane (4M solution, 13.0 mL, 52.6 mmol) was added to the Intermediate BB-23.2 (2.5 g, 5.3 mmol) and the reaction mixture stirred at room temperature for 2 h. The crude reaction mixture was concentrated to dryness; basified with saturated aq. NaHCO$_3$ (25 mL) solution and extracted with EtOAc (2×25 mL). The combined organic layer was dried (Na$_2$SO$_4$), filtered and concentrated to afford the title compound (1.2 g) as pale red liquid. LC-MS retention time=1.93 min; m/z=376.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-24

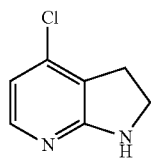

To a solution of 4-chloro-1H-pyrrolo[2,3-b]pyridine (3.5 g, 23 mmol) in MeOH (30 mL) was added Raney-Ni (9 g) and the reaction mixture was stirred under 50 psi hydrogen pressure at 70° C. for 36 h. The reaction mixture was filtered over celite pad, washed with methanol (50 mL), the combined filtrate was collected, evaporated under reduced pressure and the crude product was purified by combiflash chromatography (40 g Redisep® SiO$_2$ column, eluting with 0-15% EtOAc in hexanes) to afford the title compound (1 g) as a pale yellow solid. LC-MS retention time=2.38 min; m/z=155.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHz, DMSO-d$_6$) δ 7.63 (d, J=5.5 Hz, 1H), 6.74 (br. s., 1H), 6.45 (d, J=5.52 Hz, 1H), 3.52 (dt, J=8.53, 1.00 Hz, 2H), 3.01 (t, J=8.45 Hz, 2H).

Intermediate BB-25.1

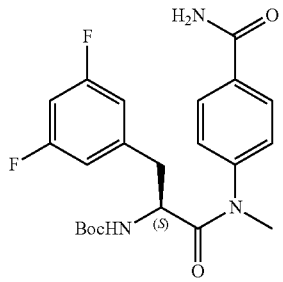

To stirred solution of (S)-2-((tert-butoxycarbonyl)amino)-3-(3,5-difluorophenyl)propanoic acid (0.250 g, 0.830 mmol) in DMF (2 mL) was added HATU (0.379 g, 0.996 mmol) and DIPEA (0.725 mL, 4.15 mmol) at 0° C. and the reaction mixture was stirred for 30 min. 4-(Methylamino)benzamide (0.125 g, 0.83 mmol) was added and the reaction mixture was stirred at room temperature for 16 h. The reaction mixture was diluted with water (20 mL) and extracted with EtOAc (3×25 mL). The combined organic layer was washed with 10% aqueous NaHCO$_3$ solution (25 mL), water (25 mL), dried (Na$_2$SO$_4$), filtered and concentrated. The crude product was purified by combiflash chromatography (12 g Redisep® SiO$_2$ column, eluting with 2.5% MeOH in CHCl$_3$) to afford the title compound (0.08 g) as a pale yellow oil. LC-MS retention time=2.19 min; m/z=434.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm UV at 220 nm.

Intermediate BB-25.2

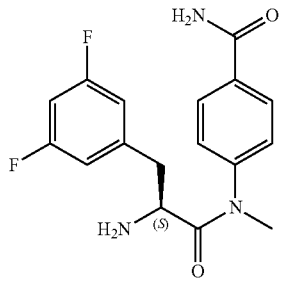

To a stirred solution of Intermediate BB-25.1 (0.080 g, 0.19 mmol) in dioxane (1 mL) at 0° C., was added 4M HCl in dioxane (1 mL, 4 mmol) and the reaction mixture was stirred at room temperature for 3 h. Then the reaction mixture was concentrated to dryness; the residue was triturated with cold diethyl ether (3×30 mL). The resulting solid was allowed to settle and the supernatant was decanted. The solid product was azeotroped with toluene (2×20 mL) to afford the title compound (0.04 g) as a yellow solid. LC-MS retention time=0.34 min; m/z=334.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/

98% ACN; 20% B to 100% B over 4 min, then hold for 0.6 min at 100% B with flow rate of 1.5 mL/min; Detection: UV at 220 nm.

Intermediate BB-26.1

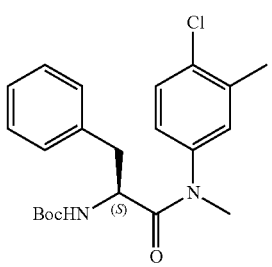

To a stirred solution of (S)-2-((tert-butoxycarbonyl)amino)-3-phenylpropanoic acid (1.39 g, 5.23 mmol) in DCM (30 mL), was added the 4-chloro-N,3-dimethylaniline (0.74 g, 4.8 mmol) and N-ethoxycarbonyl-2-ethoxy-1,2-dihydroquinoline (1.29 g, 5.23 mmol) the reaction mixture stirred at room temperature for 16 h. The reaction mixture was concentrated to dryness and the crude product was purified by combiflash chromatography (40 g Redisep® SiO$_2$ column, eluting with 30% EtOAc in n-hexanes) to afford the title compound (1.8 g) as a pale yellow oil. LC-MS retention time=3.28 min; m/z=403.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Intermediate BB-26.2

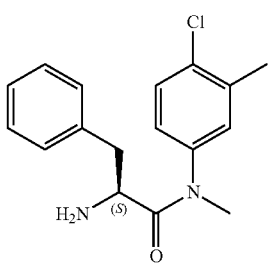

To a stirred solution of Intermediate BB-26.1 (1.8 g, 4.5 mmol) in dioxane (5 mL) was added the 4M HCl in dioxane (8 mL, 32 mmol) and the reaction mixture was stirred at room temperature for 3 h. The reaction mixture was concentrated to dryness; the residue was triturated with diethyl ether (30 mL) and the solid product was filtered, washed with hexane and dried under vacuum to afford the title product (0.74 g) as an off white solid. LC-MS retention time=2.52 min; m/z=303.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (300 MHZ, DMSO-d$_6$) δ 8.52 (br. s., 2H), 7.47-7.26 (m, 4H), 7.09-6.42 (m, 4H), 3.84 (t, J=7.0 Hz, 1H), 3.08 (s, 3H), 2.91 (d, J=7.2 Hz, 2H), 2.21 (s, 3H).

Intermediate BB-27.1

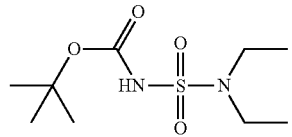 [SMILES: CCN(CC)S(=O)(=O)NC(=O)OC(C)(C)C]

To a stirred solution of 2-methylpropan-2-ol (0.671 mL, 7.07 mmol) in DCM (10 mL) was added chloro sulphonyl isocyanate (0.617 mL, 7.07 mmol) at 0° C. under nitrogen pressure followed by a mixture of diethyl amine (0.731 mL, 7.07 mmol) and triethyl amine (2.95 mL, 21.2 mmol) in DCM (5 mL) and the resulting solution was stirred at room temperature for 30 min. The reaction mixture was diluted with DCM (20 mL), washed with water (20 mL), dried (Na$_2$SO$_4$), filtered, concentrated to afford the title compound (1.7 g) as colorless liquid. $^1$H NMR (400 MHz, CDCl$_3$) δ 3.42 (q, J=7.25 Hz, 4H), 2.76-2.91 (m, 1H), 1.48 (s, 9H), 1.21 (t, J=7.13 Hz, 6H).

Intermediate BB-27.2

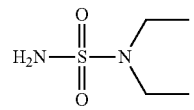

To a stirred solution of Intermediate BB-27.1 (1.7 g, 7.93 mmol) in DCM (20 mL) was added TFA (1.832 mL, 23.78 mmol) and stirred further at room temperature for 1 h. The reaction mixture was concentrated under reduced pressure to afford a TFA salt of the title compound (1.8 g) as greasy liquid. $^1$H NMR (400 MHZ, CDCl$_3$) δ 5.69 (br. s., 2H), 3.29 (q, J=7.0 Hz, 4H), 1.22 (t, J=7.1 Hz, 6H).

Intermediate BB-28.1

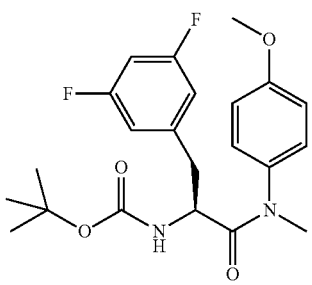 [SMILES: COc1ccc(N(C)C(=O)[C@H](Cc2cc(F)cc(F)c2)NC(=O)OC(C)(C)C)cc1]

HATU (1.39 g, 3.65 mmol) was added to a stirred solution of (S)-2-((tert-butoxycarbonyl)amino)-3-(3,5-difluorophenyl)propanoic acid (1.00 g, 3.32 mmol), 4-methoxy-N-methylaniline (0.455 g, 3.32 mmol) and N,N-diisopropylethylamine (1.16 mL, 6.64 mmol) in DMF (35 mL) and the reaction mixture was stirred at rt ON. The reaction was concentrated under high vacuum to afford the title compound (1.39 g) as a viscous oil. LC-MS retention time=3.95 min; m/z=443.11 [M+Na]$^+$; (Column: Phenomenex Luna C18 50×2.0 mm 3 μm. Solvent A=90% Water: 10% MeOH: 0.1% TFA. Solvent B=10% Water: 90% MeOH: 0.1% TFA. Flow Rate=0.8 mL/min.

Start % B=0. Final % B=100. Gradient Time=4 minutes, then a 1-minute hold at 100% B. Oven temperature=40° C. Wavelength=220 nm). $^1$H NMR (400 MHz, DMSO-d$_6$) δ 7.30 (d, J=8.8 Hz, 2H), 7.16-6.95 (m, 4H), 6.42 (d, J=6.5 Hz, 2H), 4.17-4.09 (m, 1H), 3.80 (s, 3H), 2.79-2.73 (m, 1H), 2.64 (dd, J=13.3, 10.5 Hz, 1H), 1.28 (s, 9H).

Intermediate BB-28.2

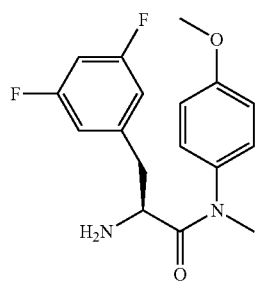 [SMILES: COc1ccc(N(C)C(=O)[C@@H](N)Cc2cc(F)cc(F)c2)cc1]

A solution of Intermediate BB-28.1 (1.39 g, 3.31 mmol) in 4M HCl in dioxane (50 mL) was stirred at ~25° C. for 1 h. The reaction mixture was then concentrated under vacuum to afford an HCl salt of the title compound (1.18 g) as grey solid. LC-MS retention time=2.98 min; m/z=321.1 [M+H]$^+$. (Column: Phenomenex Luna 50×2.0 mm 3 μm. Solvent A=90% Water: 10% MeOH: 0.1% TFA. Solvent B=10% Water: 90% MeOH: 0.1% TFA. Flow Rate=0.8 mL/min. Start % B=0. Final % B=100. Gradient Time=4 minutes, then a 1-minute hold at 100% B. Wavelength=220 nm). $^1$H NMR (400 MHZ, DMSO-d$_6$) δ ppm 8.41 (br. s., 3H), 7.21-7.05 (m, 3H), 6.98 (d, J=8.8 Hz, 2H), 6.57 (d, J=6.3 Hz, 2H), 3.90 (br. s., 1H), 3.79 (s, 3H), 3.15 (s, 3H), 3.00-2.92 (m, 1H), 2.90-2.83 (m, 1H) (HCl salt).

Intermediate BB-28.3

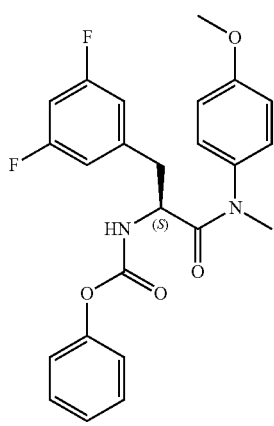

Intermediate BB-28.2 hydrochloride (250 mg, 0.701 mmol) was dissolved in DCM (10 mL), cooled to 0° C. and then pyridine (0.085 mL, 1.1 mmol) was added dropwise. The reaction mixture was then treated with phenyl chloroformate (0.11 mL, 0.84 mmol) and stirred at 0° C. for 2 h. The reaction mixture was diluted with ice H$_2$O and extracted with EtOAc (2×30 mL). The combined organic component was dried, filtered, concentrated and purified by combiflash chromatography (80 g SiO$_2$ column, eluting with 20% EtOAc in n-hexanes) to afford the title compound (230 mg) as white solid. LC-MS retention time=3.29 min; m/z=441.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example JB-1

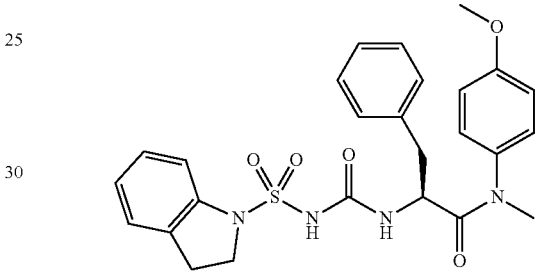

A solution of an HCl salt of Intermediate JB-2 (250 mg, 0.779 mmol) in DCM (~3 mL) was added dropwise at 0° C. to a stirred solution of sulfurisocyanatidic chloride (0.075 mL, 0.86 mmol) in DCM (1 mL) and the reaction mixture was stirred at 0° C. for 1 h. A portion of this reaction mixture (20%, ~0.8 mL) was then added via a syringe to a stirred solution of indoline (46 mg, 0.39 mmol) in TEA (0.075 mL) and DCM (1 mL) and the reaction was stirred at rt for 3 h. The reaction mixture was concentrated, partitioned between EtOAc (~2 mL) and 1M HCl (1 mL) and the organic component was washed with brine (1 mL) and concentrated. The residue was dissolved into MeOH, filtered and purified by preparative HPLC to yield the title compound (22.3 mg). LC-MS retention time=2.52 min; m/z=509.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.27-7.07 (m, 6H), 7.03-6.90 (m, 5H), 6.72 (d, J=7.0 Hz, 2H), 6.51 (d, J=8.4 Hz, 1H), 4.28 (app q, J=7.1 Hz, 1H), 4.14-3.98 (m, 2H), 3.79 (s, 3H), 3.36 (d, J=5.9 Hz, 1H), 3.07 (s, 3H), 3.01 (t, J=8.4 Hz, 2H), 2.69 (dd, J=13.4, 5.7 Hz, 1H), 2.44 (dd, J=13.4, 7.5 Hz, 1H).

Example JB-2

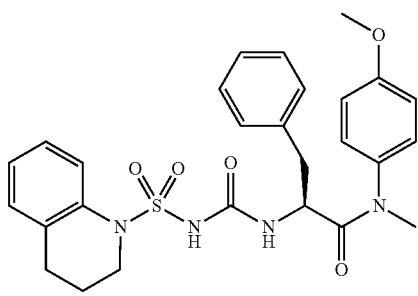 [SMILES: COc1ccc(N(C)C(=O)[C@H](Cc2ccccc2)NC(=O)NS(=O)(=O)N2CCCc3ccccc32)cc1]

Example JB-2 was synthesized using the procedure described above for Example JB-1 with 1,2,3,4-tetrahydroquinoline replacing indoline as the final amine input. LC-MS retention time=2.63 min; m/z=523.2[M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.50 (d, J=8.4 Hz, 1H), 7.21-7.08 (m, 6H), 7.05-6.98 (m, 3H), 6.94 (d, J=8.8 Hz, 2H), 6.73 (d, J=7.0 Hz, 2H), 6.50 (d, J=7.7 Hz, 1H), 4.31 (app q, J=7.0 Hz, 1H), 3.79 (s, 3H), 3.76-3.66 (m, 2H), 3.40-3.32 (m, 1H), 3.08 (s, 3H), 2.73-2.64 (m, 3H), 2.44 (dd, J=13.2, 7.3 Hz, 1H), 1.90-1.79 (m, 2H).

Example JB-3

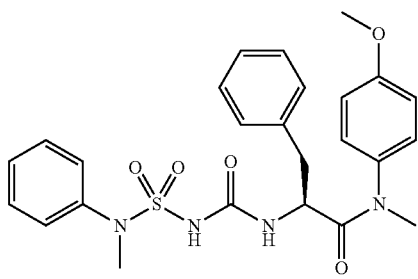 [SMILES: COc1ccc(N(C)C(=O)[C@H](Cc2ccccc2)NC(=O)NS(=O)(=O)N(C)c2ccccc2)cc1]

Example JB-3 was synthesized using the procedure described above for Example JB-1 with N-methylaniline replacing indoline as the final amine input. LC-MS retention time=2.54 min; m/z=497.2[M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.50 (d, J=8.4 Hz, 1H), 7.21-7.08 (m, 6H), 7.05-6.98 (m, 3H), 6.94 (d, J=8.8 Hz, 2H), 6.73 (d, J=7.0 Hz, 2H), 6.50 (d, J=7.7 Hz, 1H), 4.31 (app q, J=7.0 Hz, 1H), 3.79 (s, 3H), 3.76-3.66 (m, 2H), 3.40-3.32 (m, 1H), 3.08 (s, 3H), 2.73-2.64 (m, 3H), 2.44 (dd, J=13.2, 7.3 Hz, 1H), 1.90-1.79 (m, 2H).

Example JB-4

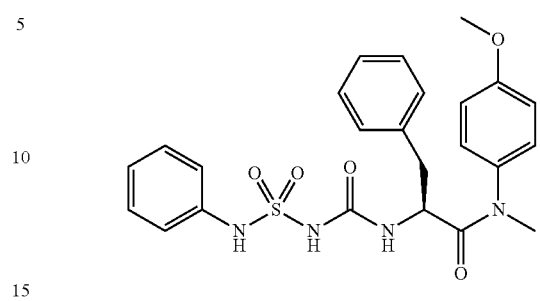

Example JB-4 was synthesized using the procedure described above for Example JB-1 with aniline replacing indoline as the final amine input. LC-MS retention time=2.39 min; m/z=483.2[M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.33-7.25 (m, 2H), 7.19-7.00 (m, 8H), 6.95 (d, J=8.8 Hz, 2H), 6.78 (d, J=6.6 Hz, 2H), 6.36 (br. s., 1H), 4.40-4.31 (m, 1H), 3.80 (s, 3H), 3.09 (s, 3H), 2.74 (dd, J=13.2, 5.1 Hz, 1H), 2.56-2.47 (m, 1H).

Example JB-5

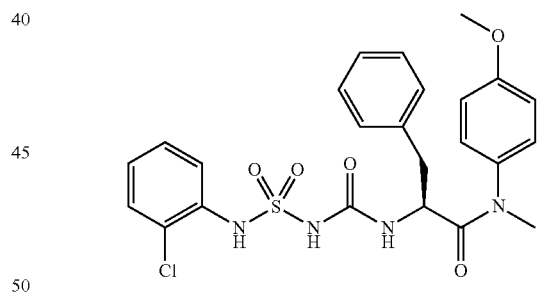

Example JB-5 was synthesized using the procedure described above for Example JB-1 with 2-chloroaniline replacing indoline as the final amine input. LC-MS retention time=2.46 min; m/z=517.7[M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.51-6.95 (m, 10H), 6.92 (d, J=8.8 Hz, 2H), 6.85 (br. s., 2H), 4.32 (br. s., 1H), 3.79 (s, 3H), 3.08 (s, 3H), 2.80-2.75 (m, 1H), 2.60-2.52 (m, 1H).

Example JB-6

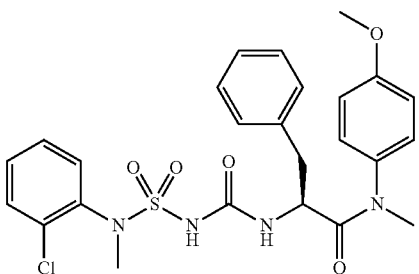 [SMILES: COc1ccc(N(C)C(=O)[C@H](Cc2ccccc2)NC(=O)NS(=O)(=O)N(C)c2ccccc2Cl)cc1]

Example JB-6 was synthesized using the procedure described above for Example JB-1 with 2-chloro-N-methylaniline replacing indoline as the final amine input. LC-MS retention time=1.82 min; m/z=531.1[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.55 (br. s., 1H), 7.47 (br. s., 1H), 7.33-6.82 (m, 11H), 6.36 (br. s., 1H), 4.46-4.39 (m, 1H), 3.80 (br. s., 3H), 3.22 (s, 3H), 2.99 (br. s., 3H), 2.84-2.75 (m, J=15.4 Hz, 1H), 2.62-2.53 (m, 1H).

Example JB-7

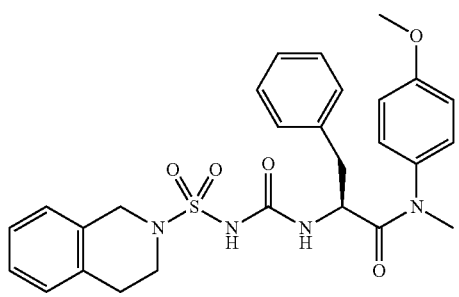 [SMILES: COc1ccc(N(C)C(=O)[C@H](Cc2ccccc2)NC(=O)NS(=O)(=O)N2CCc3ccccc3C2)cc1]

Example JB-7 was synthesized using the procedure described above for Example JB-1 with 1,2,3,4-tetrahydroisoquinoline, HCl replacing indoline as the final amine input and additional TEA (0.10 mL total) being used in the final step. LC-MS retention time=1.87 min; m/z=523.3[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.22-7.11 (m, 6H), 7.04 (d, J=6.6 Hz, 3H), 6.95 (d, J=8.8 Hz, 2H), 6.82 (d, J=7.3 Hz, 2H), 6.64 (d, J=8.4 Hz, 1H), 4.41-4.34 (m, 1H), 4.28 (app q, J=15.4 Hz, 2H), 3.78 (s, 3H), 3.36-3.28 (m, 2H), 3.10 (s, 3H), 2.85-2.77 (m, 3H), 2.54-2.47 (m, 1H).

Example JB-8

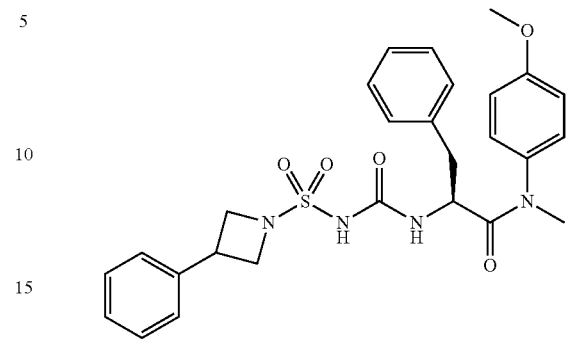

Example JB-8 was synthesized using the procedure described above for Example JB-1 with 3-phenylazetidine, HCl replacing indoline as the final amine input and additional TEA (0.10 mL total) being used in the final step. LC-MS retention time=1.91 min; m/z=523.3[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.36-7.07 (m, 10H), 6.99 (d, J=8.4 Hz, 2H), 6.87 (d, J=7.0 Hz, 2H), 6.77 (d, J=8.1 Hz, 1H), 4.50-4.42 (m, 1H), 4.20-4.09 (m, 2H), 4.03-3.90 (m, 2H), 3.80 (s, 3H), 3.73 (dd, J=16.0, 8.3 Hz, 1H), 3.13 (s, 3H), 2.89-2.83 (m, 1H), 2.60 (dd, J=13.4, 8.6 Hz, 1H).

Example JB-9

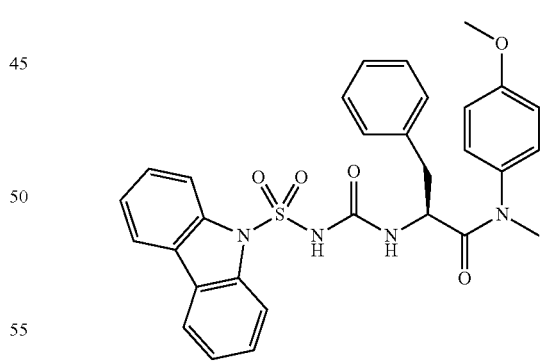

Example JB-9 was synthesized using the procedure described above for Example JB-1 with 2-chloro-N-methylaniline replacing indoline as the final amine input. LC-MS retention time=1.70 min; m/z=557.4[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-10

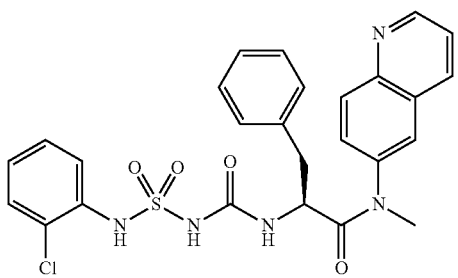 [SMILES: CN(C(=O)[C@H](Cc1ccccc1)NC(=O)NS(=O)(=O)Nc1ccccc1Cl)c1ccc2ncccc2c1]

A solution of an HCl salt of Intermediate JB-4 (210 mg, 0.555 mmol) in DCM (~2 mL) and DIPEA (0.20 mL, 1.2 mmol) was added dropwise at 0° C. to a stirred solution of sulfurisocyanatidic chloride (0.075 mL, 0.86 mmol) in DCM (2 mL) and the reaction mixture was stirred at 0° C. for 1 h and then treated with TEA (0.12 mL, 0.83 mmol) and stirred an additional 5 min. A portion of this reaction mixture (25%, ~1.0 mL) was then added via a syringe to a stirred solution of 2-chloroaniline (42.5 mg, 0.333 mmol) in TEA (0.075 mL) and DCM (1 mL) and the reaction was stirred at rt for 2 h. The reaction mixture was concentrated, partitioned between EtOAc (~2 mL) and sat. NaHCO$_3$ (~1.5 mL) and the organic component was washed with brine (1 mL) and concentrated. The residue was dissolved into MeOH, filtered and purified by preparative HPLC to yield the title compound. LC-MS retention time=1.51 min; m/z=538.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (400 MHz, CD$_3$OD) δ 8.90 (d, J=3.2 Hz, 1H), 8.25 (br. s., 1H), 7.98 (d, J=9.0 Hz, 1H), 7.66-7.55 (m, 2H), 7.47-6.96 (m, 9H), 6.94-6.85 (m, 2H), 4.56 (br. s., 1H), 3.25 (s, 3H), 2.96-2.84 (m, 1H), 2.77-2.65 (m, 1H).

Example JB-11

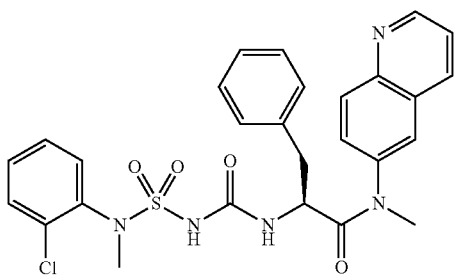 [SMILES: CN(C(=O)[C@H](Cc1ccccc1)NC(=O)NS(=O)(=O)N(C)c1ccccc1Cl)c1ccc2ncccc2c1]

Example JB-11 was synthesized using the procedure described above for Example JB-10 with 2-chloro-N-methylaniline replacing 2-chloroaniline as the final amine. LC-MS retention time=1.70 min; m/z=552.3[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-12

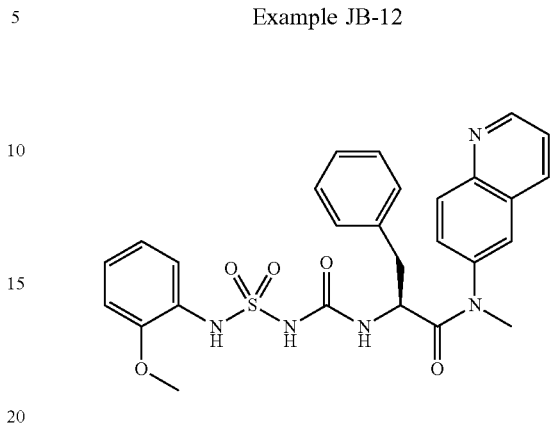

Example JB-12 was synthesized using the procedure described above for Example JB-10 with 2-methoxyaniline replacing 2-chloroaniline as the final amine. LC-MS retention time=2.28 min; m/z=534.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-13

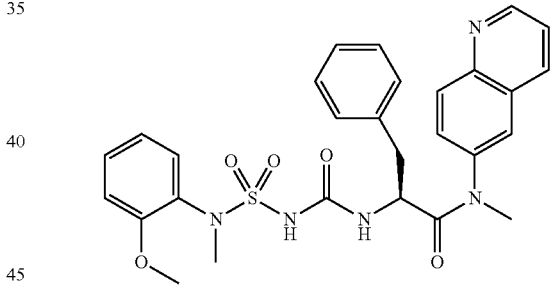

Example JB-13 was synthesized using the procedure described above for Example JB-10 with 2-methoxy-N-methylaniline replacing 2-chloroaniline as the final amine. LC-MS retention time=1.73 min; m/z=548.3[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.98 (br. s., 1H), 8.29 (d, J=7.7 Hz, 1H), 8.08 (d, J=8.8 Hz, 1H), 7.70-7.51 (m, 3H), 7.36-7.28 (m, 1H), 7.20 (d, J=7.3 Hz, 4H), 7.06 (d, J=8.1 Hz, 1H), 6.92 (t, J=7.5 Hz, 1H), 6.85 (d, J=5.9 Hz, 2H), 6.60 (d, J=8.1 Hz, 1H), 4.47 (d, J=7.0 Hz, 1H), 3.68 (s, 3H), 3.26 (s, 1H), 3.10 (s, 3H), 2.93 (br. s., 1H), 2.68-2.59 (m, 1H).

Example JB-14

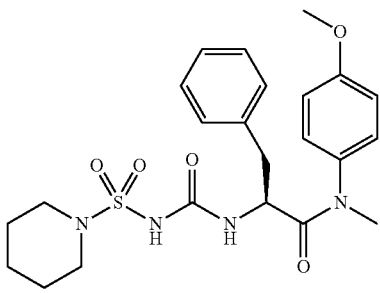 [SMILES: COc1ccc(N(C)C(=O)[C@H](Cc2ccccc2)NC(=O)NS(=O)(=O)N2CCCCC2)cc1]

Example JB-14 was synthesized using the procedure described above for Example JB-1 with piperidine replacing indoline as the final amine input. LC-MS retention time=1.85 min; m/z=475.3[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.25-7.12 (m, 5H), 7.01 (d, J=8.8 Hz, 2H), 6.85 (d, J=7.0 Hz, 2H), 6.59 (d, J=8.4 Hz, 1H), 4.46-4.37 (m, 1H), 3.81 (s, 3H), 3.12 (s, 3H), 3.00-2.90 (m, 4H), 2.85 (dd, J=13.6, 4.8 Hz, 1H), 2.58-2.52 (m, 1H), 1.52-1.35 (m, 6H).

Example JB-15

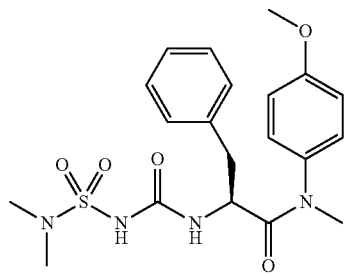 [SMILES: COc1ccc(N(C)C(=O)[C@H](Cc2ccccc2)NC(=O)NS(=O)(=O)N(C)C)cc1]

Example JB-15 was synthesized using the procedure described above for Example JB-1 with dimethylamine replacing indoline as the final amine input. LC-MS retention time=2.34 min; m/z=435.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.25-7.17 (m, 3H), 7.13 (d, J=7.7 Hz, 2H), 7.00 (d, J=8.8 Hz, 2H), 6.86 (d, J=7.0 Hz, 2H), 6.59 (d, J=7.7 Hz, 1H), 4.43-4.36 (m, 1H), 3.80 (s, 3H), 3.12 (s, 3H), 2.83 (dd, J=13.8, 5.0 Hz, 1H), 2.62 (s, 6H).

Example JB-16

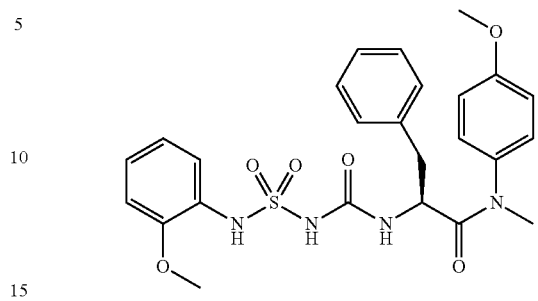

A solution of an HCl salt of (S)-2-amino-N-(4-methoxyphenyl)-N-methyl-3-phenylpropanamide (Intermediate JB-2) (700 mg, 1.86 mmol) in DCM (~2 mL) was added dropwise at 0° C. to a stirred solution of sulfurisocyanatidic chloride (0.075 mL, 0.857 mmol) in DCM (4 mL) and the reaction mixture was stirred at 0° C. for 1 h and then treated with TEA (0.827 mL, 5.93 mmol) in DCM (2.8 mL) and stirred an additional 3 min. A portion of this reaction mixture (~8.3%, ~0.8 mL) was then added via a syringe to a stirred solution of 2-methoxyaniline (45.7 mg, 0.371 mmol) in DCM (1 mL) and the reaction was stirred at rt for 2 h. The reaction mixture was concentrated, partitioned between EtOAc (~2 mL) and 1M HCl (~1 mL) (note: for reactions that followed the procedure outlined here, were there was a basic amine present in the final example, sat. aq NaHCO$_3$ was used in the work-up in place of 1 M HCl) and the organic component was washed with brine (1 mL) and concentrated. The residue was dissolved into MeOH, filtered and purified by preparative HPLC to yield the title compound. LC-MS retention time=2.57 min; m/z=513.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.25 (d, J=7.7 Hz, 1H), 7.19-7.06 (m, 6H), 6.97 (d, J=8.4 Hz, 3H), 6.89 (t, J=7.5 Hz, 1H), 6.82-6.77 (m, 2H), 6.37 (d, J=7.0 Hz, 1H), 4.40-4.31 (m, 1H), 3.66 (s, 3H), 3.38 (br. s., 2H), 3.10 (s, 3H), 2.77 (dd, J=13.2, 4.8 Hz, 1H), 2.58-2.52 (m, 1H).

Note: In subsequent reactions when Example 16 is presented as the reference procedure and the final amine input is an acid salt, sufficient additional TEA is added before, during or after the final addition to provide a freebase of said amine, unless otherwise noted.

Example JB-17

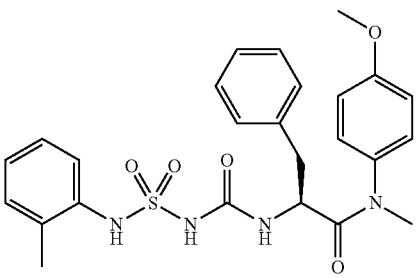 [SMILES: COc1ccc(N(C)C(=O)[C@H](Cc2ccccc2)NC(=O)NS(=O)(=O)Nc2ccccc2C)cc1]

Example JB-17 was synthesized using the procedure described above for Example JB-16 with o-toluidine replacing 2-methoxyaniline as the final amine input. LC-MS retention time=2.66 min; m/z=497.4[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-18

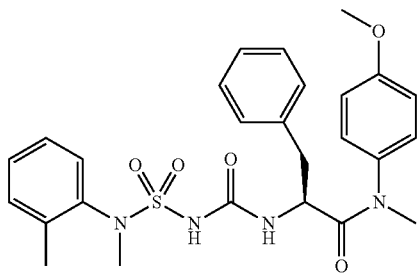 [SMILES: COc1ccc(N(C)C(=O)[C@H](Cc2ccccc2)NC(=O)NS(=O)(=O)N(C)c2ccccc2C)cc1]

Example JB-18 was synthesized using the procedure described above for Example JB-16 with 2-methyl-N-methylaniline, HCl replacing 2-methoxyaniline as the final amine input. LC-MS retention time=2.82 min; m/z=511.4[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-19

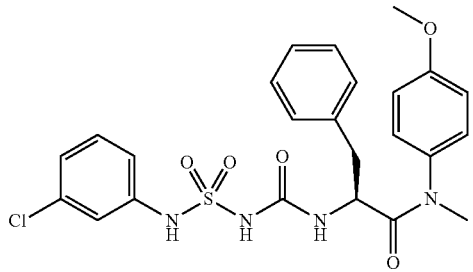 [SMILES: COc1ccc(N(C)C(=O)[C@H](Cc2ccccc2)NC(=O)NS(=O)(=O)Nc2cccc(Cl)c2)cc1]

Example JB-19 was synthesized using the procedure described above for Example JB-16 with 3-chloroaniline replacing 2-methoxyaniline as the final amine input. LC-MS retention time=2.57 min; m/z=517.2[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.36-7.30 (m, 1H), 7.22-7.01 (m, 8H), 6.95 (d, J=8.4 Hz, 2H), 6.76 (d, J=6.2 Hz, 2H), 6.46 (d, J=7.7 Hz, 1H), 4.38-4.31 (m, 1H), 3.38 (br s, 5H), 3.09 (s, 3H), 2.77-2.70 (m, 1H), 2.54-2.48 (m, 1H).

Example JB-20

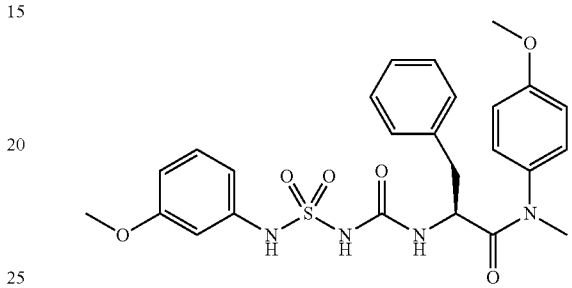

Example JB-20 was synthesized using the procedure described above for Example JB-16 with 3-methoxyaniline replacing 2-methoxyaniline as the final amine input. LC-MS retention time=2.44 min; m/z=513.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.20 (t, J=8.1 Hz, 1H), 7.17-7.10 (m, 3H), 7.03 (d, J=7.7 Hz, 2H), 6.94 (d, J=8.8 Hz, 2H), 6.77 (d, J=6.6 Hz, 2H), 6.74-6.70 (m, 2H), 6.67 (d, J=8.1 Hz, 1H), 6.45 (d, J=8.1 Hz, 1H), 4.38-4.32 (m, 1H), 3.79 (s, 3H), 3.71 (s, 3H), 3.08 (s, 3H), 2.74 (dd, J=13.6, 5.5 Hz, 1H), 2.55-2.47 (m, 1H).

Example JB-21

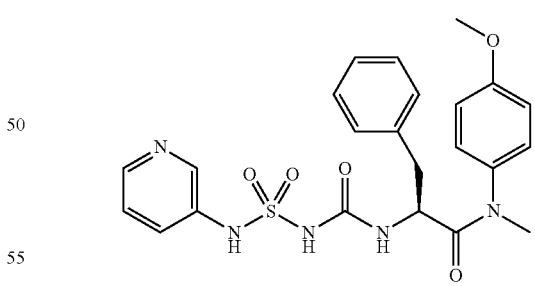

Example JB-21 was synthesized using the procedure described above for Example JB-16 with 3-aminopyridine replacing 2-methoxyaniline as the final amine input. LC-MS retention time=2.18 min; m/z=484.2 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-22

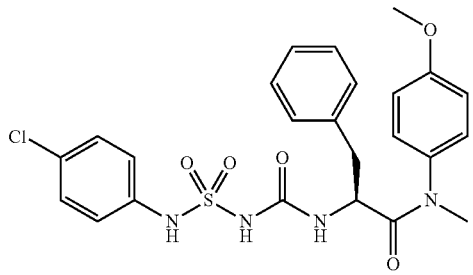 [SMILES: COc1ccc(N(C)C(=O)[C@H](Cc2ccccc2)NC(=O)NS(=O)(=O)Nc2ccc(Cl)cc2)cc1]

Example JB-22 was synthesized using the procedure described above for Example JB-16 with 4-chloroaniline replacing 2-methoxyaniline as the final amine input. LC-MS retention time=2.59 min; m/z=517.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.33 (d, J=7.3 Hz, 2H), 7.20-7.02 (m, 7H), 6.95 (d, J=7.6 Hz, 2H), 6.75 (d, J=5.8 Hz, 2H), 6.39 (d, J=6.1 Hz, 1H), 4.35 (d, J=5.5 Hz, 1H), 3.79 (br. s., 3H), 3.09 (br. s., 3H), 2.74 (br. s., 1H), 2.51 (br. s., 1H).

Example JB-24

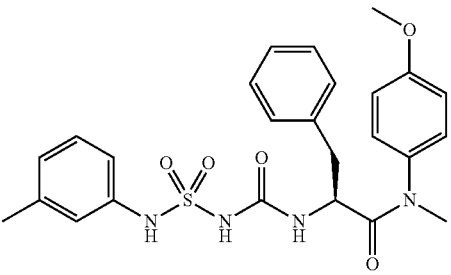

Example JB-24 was synthesized using the procedure described above for Example JB-16 with m-toluidine replacing 2-methoxyaniline as the final amine input. LC-MS retention time=2.55 min; m/z=497.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.15 (d, J=5.9 Hz, 4H), 7.03 (br. s., 2H), 6.97-6.88 (m, 4H), 6.84 (d, J=6.6 Hz, 1H), 6.81-6.77 (m, 2H), 6.26 (d, J=7.7 Hz, 1H), 4.39-4.30 (m, 1H), 3.91 (s, 3H), 3.08 (s, 3H), 2.71 (d, J=5.1 Hz, 1H), 2.56-2.52 (m, 1H), 2.24 (s, 3H).

Example JB-23

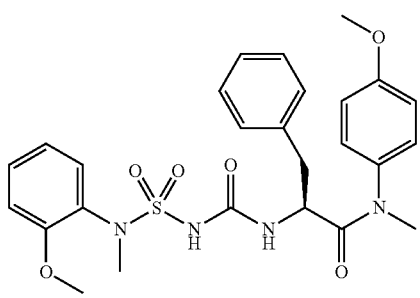 [SMILES: COc1ccc(N(C)C(=O)[C@H](Cc2ccccc2)NC(=O)NS(=O)(=O)N(C)c2ccccc2OC)cc1]

Example JB-23 was synthesized using the procedure described above for Example JB-16 with 2-methoxy-N-methylaniline replacing 2-methoxyaniline as the final amine input. LC-MS retention time=2.66 min; m/z=527.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.31 (t, J=7.9 Hz, 1H), 7.27-7.10 (m, 6H), 7.08-6.98 (m, 3H), 6.94-6.85 (m, 3H), 6.52 (d, J=8.1 Hz, 1H), 4.51-4.42 (m, 1H), 3.81 (s, 3H), 3.67 (s, 3H), 3.14 (s, 3H), 3.09 (s, 3H), 2.86 (dd, J=13.6, 5.1 Hz, 1H), 2.57 (dd, J=13.6, 8.4 Hz, 1H).

Example JB-25

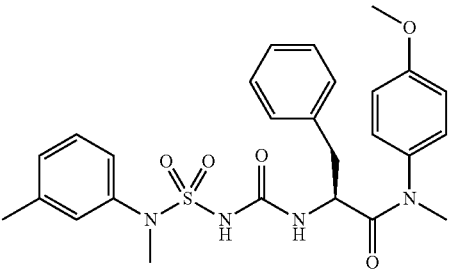 [SMILES: COc1ccc(N(C)C(=O)[C@H](Cc2ccccc2)NC(=O)NS(=O)(=O)N(C)c2cccc(C)c2)cc1]

Example JB-25 was synthesized using the procedure described above for Example JB-16 with 3-methyl-N-methylaniline replacing 2-methoxyaniline as the final amine input. LC-MS retention time=2.70 min; m/z=511.3[M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.29-7.19 (m, 4H), 7.14-7.09 (m, 4H), 7.05 (d, J=7.7 Hz, 1H), 7.01 (d, J=8.8 Hz, 2H), 6.84 (d, J=5.1 Hz, 2H), 6.46 (d, J=8.1 Hz, 1H), 4.47-4.39 (m, 1H), 3.35 (br. s., 2H), 3.91 (s, 3H), 3.13 (s, 3H), 2.81 (dd, J=13.4, 5.3 Hz, 1H), 2.58-2.52 (m, 1H), 2.30 (s, 3H).

Example JB-26

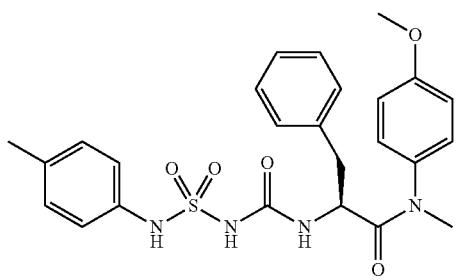 [SMILES: COc1ccc(N(C)C(=O)[C@H](Cc2ccccc2)NC(=O)NS(=O)(=O)Nc2ccc(C)cc2)cc1]

Example JB-26 was synthesized using the procedure described above for Example JB-16 with p-toluidine replacing 2-methoxyaniline as the final amine input. LC-MS retention time=1.71 min; m/z=497.3[M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-27

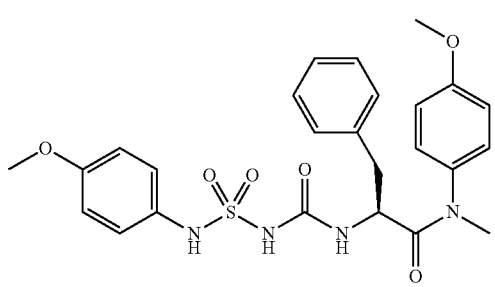 [SMILES: COc1ccc(NS(=O)(=O)NC(=O)N[C@@H](Cc2ccccc2)C(=O)N(C)c2ccc(OC)cc2)cc1]

Example JB-27 was synthesized using the procedure described above for Example JB-16 with 4-methoxyaniline replacing 2-methoxyaniline as the final amine input. LC-MS retention time=1.59 min; m/z=513.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.19 (d, J=4.0 Hz, 3H), 7.08 (d, J=7.3 Hz, 2H), 7.03-6.95 (m, 4H), 6.86-6.78 (m, 4H), 6.32 (d, J=8.4 Hz, 1H), 4.45-4.38 (m, 1H), 3.80 (s, 3H), 3.71 (s, 3H), 3.11 (s, 3H), 2.77 (dd, J=13.4, 5.0 Hz, 1H), 2.56-2.49 (m, 3H).

Example JB-28

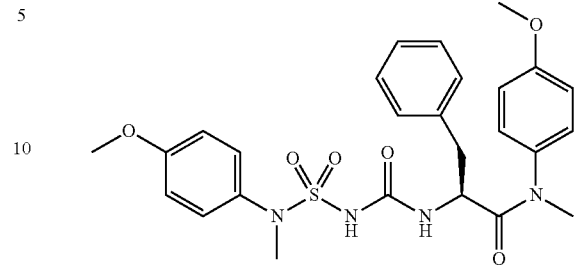

Example JB-28 was synthesized using the procedure described above for Example JB-16 with 4-methoxy-N-methylaniline replacing 2-methoxyaniline as the final amine input. LC-MS retention time=2.58 min; m/z=527.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.22 (br. s., 3H), 7.17-7.07 (m, 4H), 7.00 (d, J=8.1 Hz, 2H), 6.90-6.83 (m, 4H), 6.44 (d, J=8.1 Hz, 1H), 4.44 (d, J=5.9 Hz, 1H), 3.81 (s, 3H), 3.74 (s, 3H), 2.81 (dd, J=12.8, 4.8 Hz, 1H), 2.57-2.52 (m, 1H), 1.91 (s, 6H).

Example JB-29

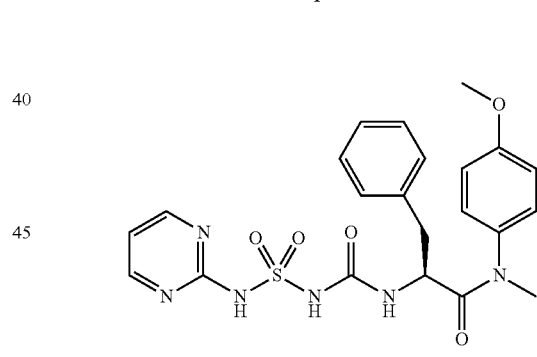

Example JB-29 was synthesized using the procedure described above for Example JB-16 with 2-aminopyrimidine replacing 2-methoxyaniline as the final amine input. LC-MS retention time=2.06 min; m/z=485.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.39 (d, J=4.4 Hz, 2H), 7.27-6.75 (m, 11H), 4.35-4.29 (m, 1H), 3.77 (s, 3H), 3.18 (s, 3H), 2.78 (dd, J=13.0, 5.7 Hz, 1H), 2.55 (dd, J=13.8, 7.9 Hz, 1H).

Example JB-30

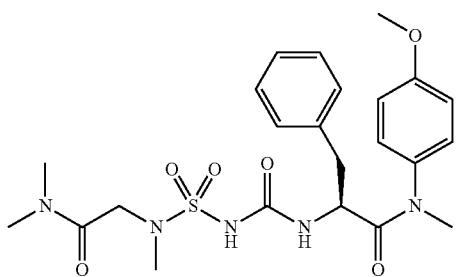 [SMILES: COc1ccc(N(C)C(=O)[C@H](Cc2ccccc2)NC(=O)NS(=O)(=O)N(C)CC(=O)N(C)C)cc1]

Example JB-30 was synthesized using the procedure described above for Example JB-16 with N,N-dimethyl-2-(methylamino)acetamide, HCl replacing 2-methoxyaniline as the final amine input. LC-MS retention time=2.23 min; m/z=506.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.26-7.05 (m, 5H), 6.97 (d, J=8.4 Hz, 2H), 6.87 (d, J=6.6 Hz, 2H), 6.63 (d, J=7.3 Hz, 1H), 4.41-4.33 (m, 1H), 3.94-3.75 (m, 2H), 3.91 (s, 3H), 3.10 (s, 3H), 2.93 (s, 3H), 2.82 (s, 3H), 2.85-2.76 (m, 1H), 2.64 (br. s., 3H), 2.58 (dd, J=13.0, 8.3 Hz, 1H).

Example JB-31

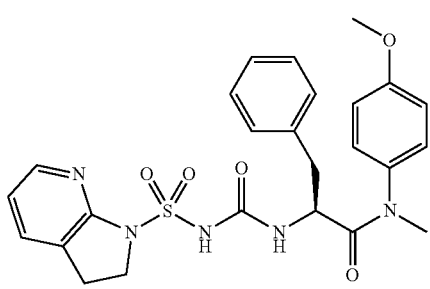 [SMILES: COc1ccc(N(C)C(=O)[C@H](Cc2ccccc2)NC(=O)NS(=O)(=O)N2CCc3cccnc32)cc1]

Example JB-31 was synthesized using the procedure described above for Example JB-16 with 2,3-dihydro-1H-pyrrolo[2,3-b]pyridine replacing 2-methoxyaniline as the final amine input. LC-MS retention time=1.49 min; m/z=510.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.96 (br. s., 1H), 7.47 (d, J=5.9 Hz, 1H), 7.13 (d, J=3.7 Hz, 3H), 6.87 (br. s., 4H), 6.78 (d, J=3.7 Hz, 3H), 6.23 (br. s., 1H), 4.24 (d, J=6.2 Hz, 1H), 3.97 (dt, J=16.5, 8.3 Hz, 2H), 3.77 (s, 3H), 3.18 (s, 3H), 2.99-2.91 (m, 2H), 2.68 (dd, J=13.2, 5.9 Hz, 1H), 2.44 (dd, J=12.7, 7.9 Hz, 1H).

Example JB-32

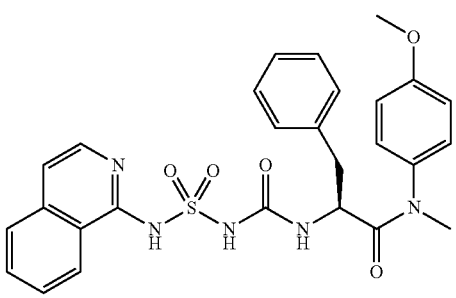 [SMILES: COc1ccc(N(C)C(=O)[C@H](Cc2ccccc2)NC(=O)NS(=O)(=O)Nc2nccc3ccccc23)cc1]

Example JB-32 was synthesized using the procedure described above for Example JB-16 with isoquinolin-1-amine replacing 2-methoxyaniline as the final amine input. LC-MS retention time=2.56 min; m/z=534.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.36 (d, J=8.1 Hz, 1H), 7.85-7.78 (m, 2H), 7.68 (d, J=7.0 Hz, 1H), 7.61 (t, J=6.4 Hz, 1H), 7.14-7.06 (m, 4H), 6.98-6.75 (m, 7H), 4.34-4.26 (m, 1H), 3.91 (s, 3H), 3.04 (s, 3H), 2.79 (dd, J=13.4, 5.7 Hz, 1H), 2.56-2.50 (m, 1H).

Example JB-33

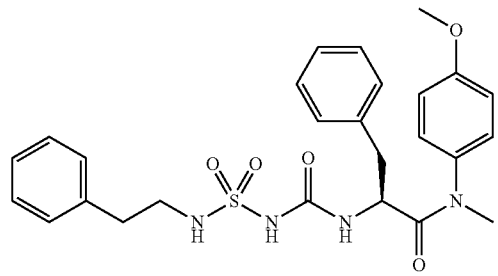 [SMILES: COc1ccc(N(C)C(=O)[C@H](Cc2ccccc2)NC(=O)NS(=O)(=O)NCCc2ccccc2)cc1]

Example JB-33 was synthesized using the procedure described above for Example JB-16 with 2-phenylethanamine replacing 2-methoxyaniline as the final amine input. LC-MS retention time=2.66 min; m/z=511.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.33-7.26 (m, 2H), 7.24-7.09 (m, 8H), 6.98 (d, J=8.8 Hz, 2H), 6.84 (d, J=6.6 Hz, 2H), 6.55 (d, J=8.1 Hz, 1H), 4.44-4.38 (m, 1H), 3.80 (s, 3H), 3.11 (s, 3H), 3.02-2.90 (m, 2H), 2.84 (dd, J=13.6, 4.8 Hz, 1H), 2.75-2.67 (m, 2H), 2.56 (dd, J=13.6, 8.8 Hz, 1H).

Example JB-34

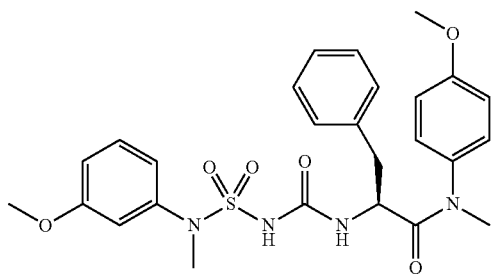 [SMILES: COc1ccc(N(C)C(=O)[C@H](Cc2ccccc2)NC(=O)NS(=O)(=O)N(C)c2cccc(OC)c2)cc1]

Example JB-34 was synthesized using the procedure described above for Example JB-16 with 3-methoxy-N-methylaniline replacing 2-methoxyaniline as the final amine input. LC-MS retention time=2.58 min; m/z=527.3 [M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (400 MHz, CD$_3$OD) δ 7.33-7.20 (m, 5H), 6.99-6.85 (m, 9H), 4.55 (t, J=7.2 Hz, 1H), 3.85 (s, 3H), 3.78 (s, 3H), 3.32 (s, 3H), 3.17 (s, 3H), 2.86 (dd, J=13.2, 7.1 Hz, 1H), 2.63 (dd, J=13.3, 7.2 Hz, 1H).

Example JB-35

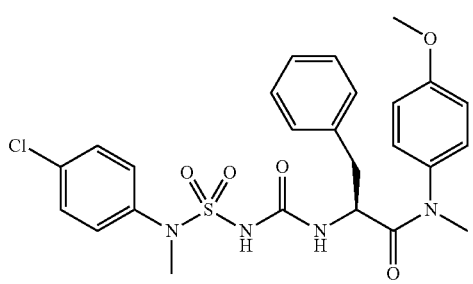 [SMILES: COc1ccc(N(C)C(=O)[C@H](Cc2ccccc2)NC(=O)NS(=O)(=O)N(C)c2ccc(Cl)cc2)cc1]

Example JB-35 was synthesized using the procedure described above for Example JB-16 with 4-chloro-N-methylaniline replacing 2-methoxyaniline as the final amine input. LC-MS retention time=2.69 min; m/z=531.3 [M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.34-7.23 (m, 4H), 7.18 (br. s., 3H), 7.05 (br. s., 2H), 6.95 (d, J=8.4 Hz, 2H), 6.82 (br. s., 2H), 6.07 (br. s., 1H), 4.33 (d, J=6.2 Hz, 1H), 3.80 (s, 3H), 3.14-3.07 (m, 6H), 2.71 (br. s., 1H), 2.54-2.46 (m, 1H).

Example JB-36

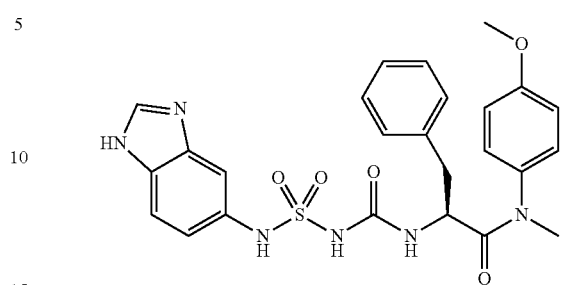

Example JB-36 was synthesized using the procedure described above for Example JB-16 with 1H-benzo[d]imidazol-6-amine replacing 2-methoxyaniline as the final amine input. LC-MS retention time=2.12 min; m/z=523.3 [M+H]+. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (400 MHz, CD$_3$OD) δ 7.60 (br. s., 1H), 7.27-7.10 (m, 5H), 7.00-6.74 (m, 7H), 4.53 (t, J=6.5 Hz, 1H), 3.83 (s, 3H), 3.13 (s, 3H), 2.81 (dd, J=13.1, 7.2 Hz, 1H), 2.61 (dd, J=13.1, 6.7 Hz, 1H).

Example JB-37

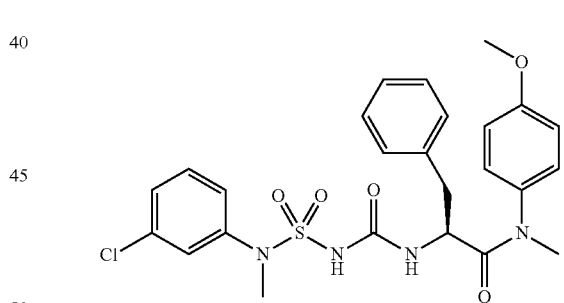

Example JB-37 was synthesized using the procedure described above for Example JB-16 with 3-chloro-N-methylaniline replacing 2-methoxyaniline as the final amine input. LC-MS retention time=1.61 min; m/z=531.3 [M+H]+. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.41-7.36 (m, 2H), 7.31 (d, J=7.7 Hz, 1H), 7.23-7.18 (m, 4H), 7.09 (d, J=7.3 Hz, 2H), 6.99 (d, J=8.4 Hz, 2H), 6.83 (d, J=5.1 Hz, 2H), 6.43 (d, J=7.3 Hz, 1H), 4.43-4.36 (m, 1H), 3.80 (s, 3H), 3.22 (s, 3H), 3.11 (s, 3H), 2.78 (dd, J=13.6, 5.5 Hz, 1H), 2.57-2.52 (m, 1H).

Example JB-38

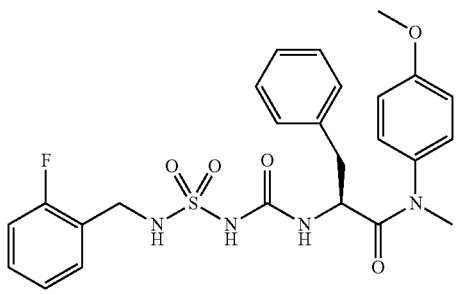

Example JB-38 was synthesized using the procedure described above for Example JB-16 with (2-fluorophenyl)methanamine replacing 2-methoxyaniline as the final amine input. LC-MS retention time=1.60 min; m/z=515.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.39 (t, J=7.5 Hz, 1H), 7.33-7.26 (m, 1H), 7.24-7.07 (m, 7H), 6.98 (d, J=8.4 Hz, 2H), 6.87 (d, J=7.0 Hz, 2H), 6.44 (d, J=7.7 Hz, 1H), 4.43-4.36 (m, 1H), 4.06-3.96 (m, 2H), 3.80 (s, 3H), 3.12 (s, 3H), 2.81 (dd, J=13.6, 4.4 Hz, 1H), 2.56 (dd, J=13.2, 8.4 Hz, 1H).

Example JB-39

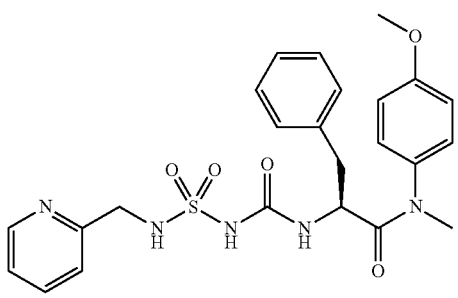

Example JB-39 was synthesized using the procedure described above for Example JB-16 with pyridin-2-ylmethanamine replacing 2-methoxyaniline as the final amine input. LC-MS retention time=2.26 min; m/z=498.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.47 (d, J=4.8 Hz, 1H), 7.77-7.70 (m, 1H), 7.40 (d, J=7.7 Hz, 1H), 7.31-7.08 (m, 6H), 6.98 (d, J=8.4 Hz, 2H), 6.86 (d, J=7.0 Hz, 2H), 6.51 (d, J=8.1 Hz, 1H), 4.43-4.34 (m, 1H), 4.18-4.00 (m, 2H), 3.80 (s, 3H), 3.12 (s, 3H), 2.82 (dd, J=13.4, 5.0 Hz, 1H), 2.55 (dd, J=13.8, 8.3 Hz, 1H).

Example JB-40

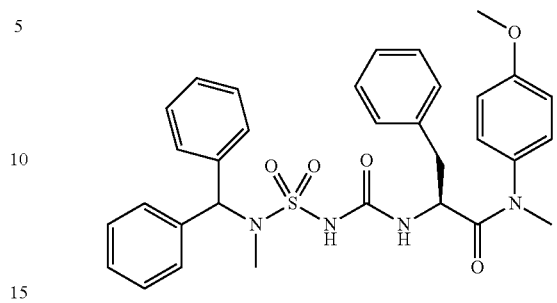

Example JB-40 was synthesized using the procedure described above for Example JB-16 with N-methyl-1,1-diphenylmethanamine replacing 2-methoxyaniline as the final amine input. LC-MS retention time=2.98 min; m/z=587.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.37-7.12 (m, 13H), 7.05-6.93 (m, 4H), 6.88-6.83 (m, 2H), 6.61 (d, J=8.1 Hz, 1H), 6.22 (s, 1H), 4.41-4.33 (m, 1H), 3.80 (s, 3H), 3.14 (s, 3H), 2.80 (dd, J=13.4, 5.7 Hz, 1H), 2.60 (s, 3H), 2.55 (dd, J=13.4, 7.9 Hz, 1H).

Example JB-41

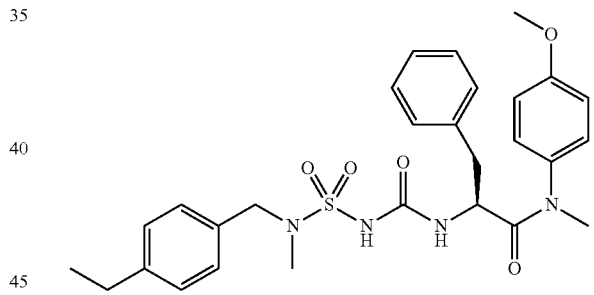

Example JB-41 was synthesized using the procedure described above for Example JB-16 with 1-(4-ethylphenyl)-N-methylmethanamine, HCl replacing 2-methoxyaniline as the final amine input. LC-MS retention time=1.99 min; m/z=539.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.26-7.12 (m, 9H), 7.01 (d, J=8.8 Hz, 2H), 6.88 (d, J=7.0 Hz, 2H), 6.63 (d, J=8.8 Hz, 1H), 4.47-4.41 (m, 1H), 4.14 (d, J=14.7 Hz, 1H), 4.04 (d, J=14.7 Hz, 1H), 3.81 (s, 3H), 3.14 (s, 3H), 2.86 (dd, J=13.6, 5.1 Hz, 1H), 2.62-2.55 (m, 3H), 2.52 (br. s., 3H), 1.17 (t, J=7.7 Hz, 3H).

Example JB-42

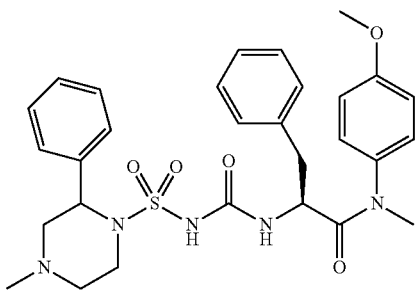 [SMILES: COc1ccc(N(C)C(=O)[C@H](Cc2ccccc2)NC(=O)NS(=O)(=O)N2CCN(C)CC2c2ccccc2)cc1]

Example JB-42 was synthesized using the procedure described above for Example JB-16 with racemic 1-methyl-3-phenylpiperazine replacing 2-methoxyaniline as the final amine input. LC-MS retention time=2.56 min; m/z=566.4 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220). $^1$H NMR spectral analysis indicates distinctive signals suggestive of a 1:1 mixture of diastereomers.

Example JB-43

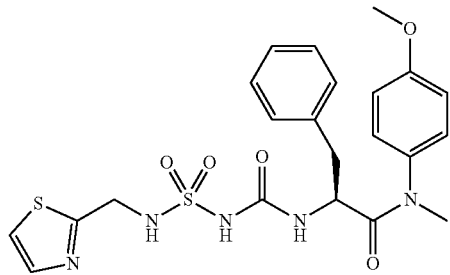 [SMILES: COc1ccc(N(C)C(=O)[C@H](Cc2ccccc2)NC(=O)NS(=O)(=O)NCc2nccs2)cc1]

Example JB-43 was synthesized using the procedure described above for Example JB-16 with thiazol-2-ylmethanamine, HCl replacing 2-methoxyaniline as the final amine input. LC-MS retention time=1.24 min; m/z=504.2 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.70 (d, J=2.9 Hz, 1H), 7.62 (d, J=2.9 Hz, 1H), 7.35-7.06 (m, 6H), 6.99 (d, J=8.8 Hz, 2H), 6.87 (d, J=7.0 Hz, 2H), 6.48 (d, J=8.1 Hz, 1H), 4.40 (d, J=5.5 Hz, 1H), 4.28 (s, 2H), 3.80 (s, 3H), 3.12 (s, 3H), 2.83 (d, J=8.8 Hz, 1H), 2.57 (dd, J=13.6, 8.4 Hz, 1H).

Example JB-44

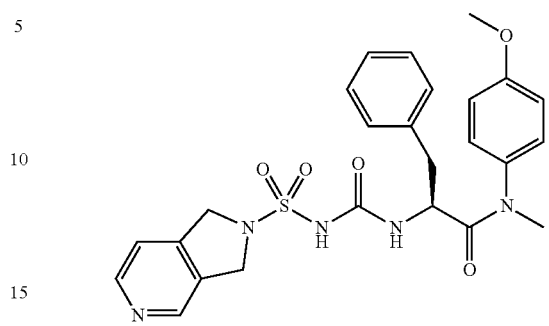

Example JB-44 was synthesized using the procedure described above for Example JB-16 with 2,3-dihydro-1H-pyrrolo[3,4-c]pyridine, HCl replacing 2-methoxyaniline as the final amine input. LC-MS retention time=2.14 min; m/z=510.4 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.53 (s, 1H), 8.47 (d, J=4.8 Hz, 1H), 7.36 (d, J=4.4 Hz, 1H), 7.16-6.95 (m, 5H), 6.88 (d, J=8.4 Hz, 2H), 6.79 (d, J=7.3 Hz, 2H), 6.48 (br. s., 1H), 4.66-4.50 (m, 4H), 4.32-4.25 (m, 1H), 3.91 (s, 3H). 3.05 (s, 3H), 2.79-2.72 (m, 1H), 2.50-2.45 (m, 1H).

Example JB-45

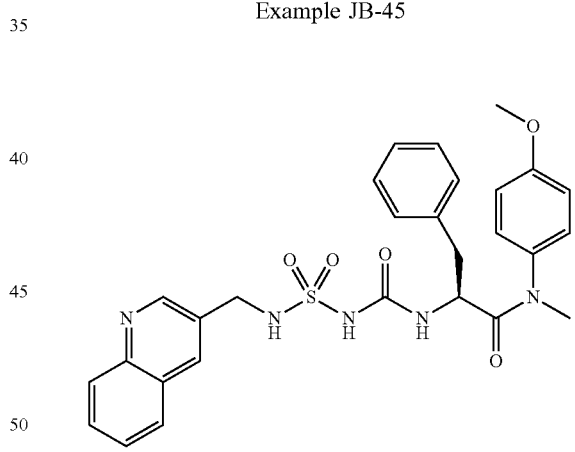

Example JB-45 was synthesized using the procedure described above for Example JB-16 with quinolin-3-ylmethanamine replacing 2-methoxyaniline as the final amine input. LC-MS retention time=2.46 min; m/z=548.3 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220). $^1$H NMR (400 MHz, CD$_3$OD) δ 8.85 (d, J=2.2 Hz, 1H), 8.31 (s, 1H), 8.03 (d, J=8.3 Hz, 1H), 7.92 (d, J=7.8 Hz, 1H), 7.76 (t, J=7.0 Hz, 1H), 7.66-7.58 (m, 1H), 7.27-7.16 (m, 4H), 6.91 (d, J=4.4 Hz, 5H), 4.51 (t, J=7.2 Hz, 1H), 4.43-4.32 (m, 2H), 3.84 (s, 3H), 3.16 (s, 3H), 2.83 (dd, J=13.4, 7.1 Hz, 1H), 2.57 (dd, J=13.3, 7.5 Hz, 1H).

Example JB-46

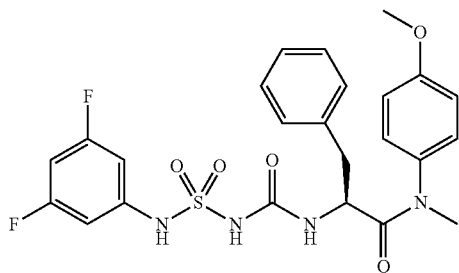 [SMILES: COc1ccc(N(C)C(=O)[C@H](Cc2ccccc2)NC(=O)NS(=O)(=O)Nc2cc(F)cc(F)c2)cc1]

Example JB-46 was synthesized using the procedure described above for Example JB-16 with 3,5-difluoroaniline replacing 2-methoxyaniline as the final amine input. LC-MS retention time=2.22 min; m/z=519.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.23-6.32 (m, 13H), 4.31 (d, J=5.9 Hz, 1H), 3.79 (s, 3H), 3.07 (s, 3H), 2.76-2.70 (m, 1H), 2.55-2.48 (m, 1H).

Example JB-47

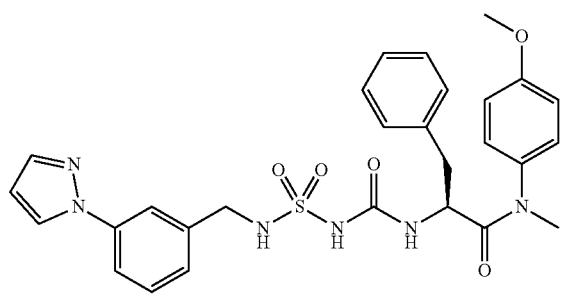 [SMILES: COc1ccc(N(C)C(=O)[C@H](Cc2ccccc2)NC(=O)NS(=O)(=O)NCc2cccc(-n3cccn3)c2)cc1]

Example JB-47 was synthesized using the procedure described above for Example JB-16 with (3-(1H-pyrazol-1-yl)phenyl)methanamine replacing 2-methoxyaniline as the final amine input. LC-MS retention time=2.49 min; m/z=563.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.42 (s, 1H), 7.80-7.66 (m, 3H), 7.41 (t, J=7.9 Hz, 1H), 7.25-7.15 (m, 4H), 7.07 (br. s., 2H), 6.97 (d, J=8.8 Hz, 2H), 6.85 (d, J=7.0 Hz, 2H), 6.55-6.45 (m, 2H), 4.45-4.36 (m, 1H), 4.09-3.98 (m, 2H), 3.80 (s, 3H), 3.11 (s, 3H), 2.80 (dd, J=13.8, 5.3 Hz, 1H), 2.58-2.52 (m, 1H).

Example JB-48

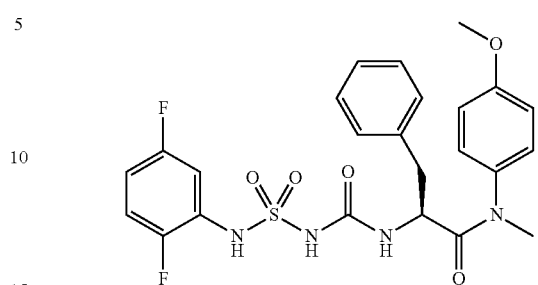

Example JB-48 was synthesized using the procedure described above for Example JB-16 with 2,5-difluoroaniline replacing 2-methoxyaniline as the final amine input. LC-MS retention time=2.39 min; m/z=519.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-49

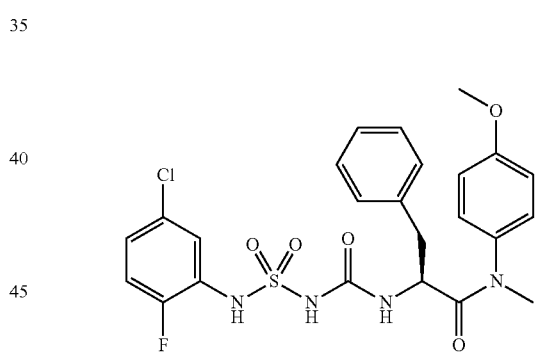

Example JB-49 was synthesized using the procedure described above for Example JB-16 with 5-chloro-2-fluoroaniline replacing 2-methoxyaniline as the final amine input. LC-MS retention time=1.48 min; m/z=535.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.45-6.39 (m, 13H), 4.34 (d, J=7.0 Hz, 1H), 3.79 (s, 3H), 3.08 (s, 3H), 2.80-2.73 (m, 1H), 2.58-2.52 (m, 1H).

Example JB-50

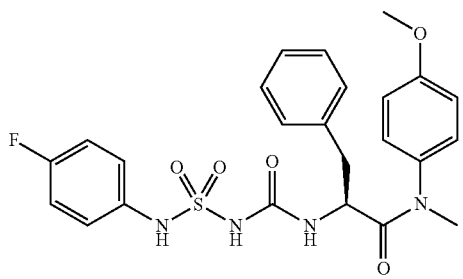 [SMILES: COc1ccc(N(C)C(=O)[C@H](Cc2ccccc2)NC(=O)NS(=O)(=O)Nc2ccc(F)cc2)cc1]

Example JB-50 was synthesized using the procedure described above for Example JB-16 with 4-fluoroaniline replacing 2-methoxyaniline as the final amine input. LC-MS retention time=2.42 min; m/z=501.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.21-7.05 (m, 9H), 6.97 (d, J=8.4 Hz, 2H), 6.77 (d, J=7.3 Hz, 2H), 6.37 (d, J=5.5 Hz, 1H), 4.43-4.33 (m, 1H), 3.80 (s, 3H), 3.10 (s, 3H), 2.78-2.72 (m, 1H), 2.55-2.47 (m, 1H).

Example JB-51

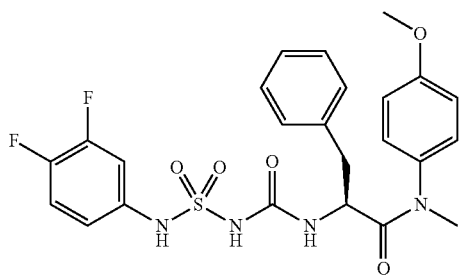 [SMILES: COc1ccc(N(C)C(=O)[C@H](Cc2ccccc2)NC(=O)NS(=O)(=O)Nc2ccc(F)c(F)c2)cc1]

Example JB-51 was synthesized using the procedure described above for Example JB-16 with 3,4-difluoroaniline replacing 2-methoxyaniline as the final amine input. LC-MS retention time=1.47 min; m/z=519.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.39-7.30 (m, 1H), 7.24-6.84 (m, 9H), 6.76 (d, J=7.3 Hz, 2H), 6.35 (br. s., 1H), 4.34 (d, J=5.9 Hz, 1H), 3.80 (s, 3H), 3.09 (s, 3H), 2.77-2.70 (m, 1H), 2.54-2.46 (m, 1H).

Example JB-52

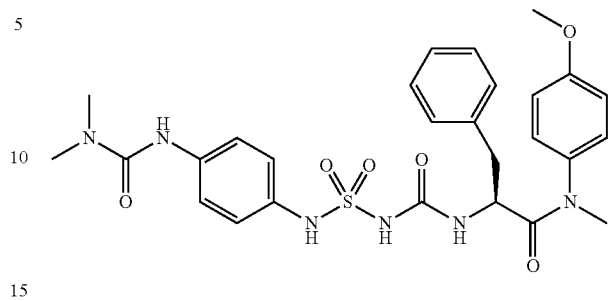

Example JB-52 was synthesized using the procedure described above for Example JB-16 with 3-(4-aminophenyl)-1,1-dimethylurea replacing 2-methoxyaniline as the final amine input. LC-MS retention time=2.19 min; m/z=569.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.25 (s, 1H), 7.38 (d, J=8.4 Hz, 2H), 7.18 (d, J=2.6 Hz, 3H), 7.03 (br. s., 2H), 6.98-6.93 (m, 4H), 6.80 (d, J=3.7 Hz, 2H), 6.38 (br. s., 1H), 4.38 (app q, J=7.2 Hz, 1H), 3.80 (s, 3H), 3.10 (s, 3H), 2.91 (s, 6H), 2.77 (dd, J=13.6, 5.5 Hz, 1H), 2.54 (d, J=7.7 Hz, 1H).

Example JB-53

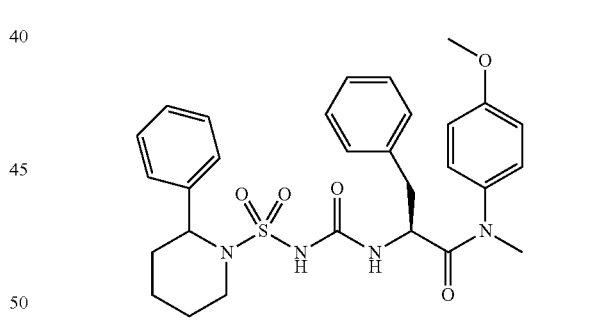

Example JB-53 was synthesized using the procedure described above for Example JB-16 with racemic 2-phenylpiperidine, HCl replacing 2-methoxyaniline as the final amine input. LC-MS retention time=2.00 min; m/z=551.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR spectral analysis indicates distinctive signals suggestive of a 1:1 mixture of diastereomers.

Example JB-54

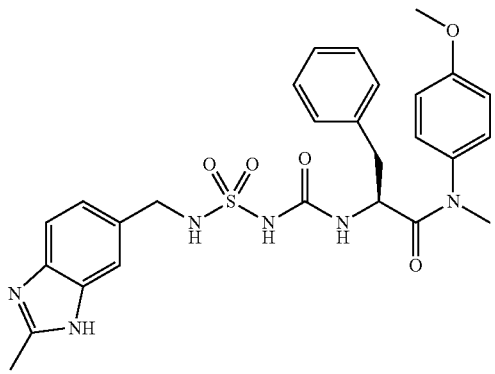 [SMILES: COc1ccc(N(C)C(=O)[C@H](Cc2ccccc2)NC(=O)NS(=O)(=O)NCc2ccc3nc(C)[nH]c3c2)cc1]

Example JB-54 was synthesized using the procedure described above for Example JB-16 with (2-methyl-1H-benzo[d]imidazol-6-yl)methanamine, 2HCl replacing 2-methoxyaniline as the final amine input. LC-MS retention time=2.24 min; m/z=551.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-55

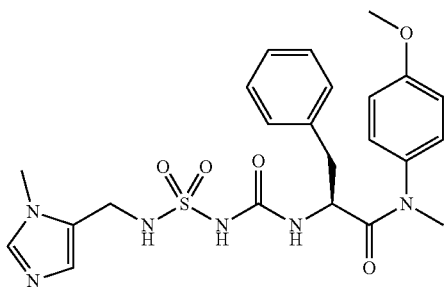 [SMILES: COc1ccc(N(C)C(=O)[C@H](Cc2ccccc2)NC(=O)NS(=O)(=O)NCc2cncn2C)cc1]

Example JB-55 was synthesized using the procedure described above for Example JB-16 with (1-methyl-1H-imidazol-5-yl)methanamine replacing 2-methoxyaniline as the final amine input. LC-MS retention time=2.08 min; m/z=501.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.52 (s, 1H), 7.25-7.08 (m, 5H), 6.98 (d, J=8.4 Hz, 2H), 6.87 (d, J=7.3 Hz, 2H), 6.75 (s, 1H), 6.46 (d, J=8.1 Hz, 1H), 4.39 (d, J=5.1 Hz, 1H), 3.98-3.88 (m, 2H), 3.80 (s, 3H), 3.53 (s, 3H), 3.12 (s, 3H), 2.85-2.79 (m, 1H), 2.56 (dd, J=13.6, 8.4 Hz, 1H).

Example JB-56

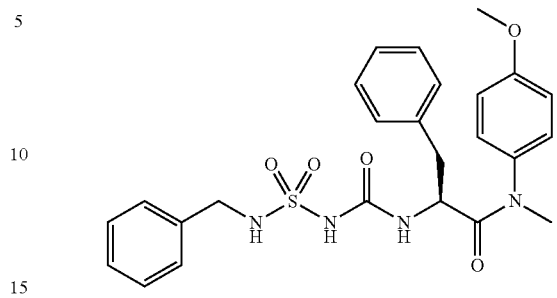

Example JB-56 was synthesized using the procedure described above for Example JB-16 with phenylmethanamine replacing 2-methoxyaniline as the final amine input. LC-MS retention time=2.55 min; m/z=497.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.35-7.07 (m, 10H), 6.98 (d, J=8.4 Hz, 2H), 6.86 (d, J=7.0 Hz, 2H), 6.49 (d, J=8.4 Hz, 1H), 4.44-4.37 (m, 1H), 4.00-3.89 (m, 2H), 3.80 (s, 3H), 3.12 (s, 3H), 2.82 (dd, J=13.0, 5.0 Hz, 1H), 2.56 (dd, J=13.2, 8.4 Hz, 1H).

Example JB-57

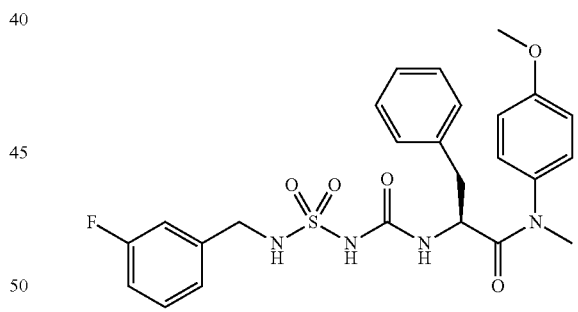

Example JB-57 was synthesized using the procedure described above for Example JB-16 with (3-fluorophenyl)methanamine replacing 2-methoxyaniline as the final amine input. LC-MS retention time=1.60 min; m/z=515.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.36-7.29 (m, 1H), 7.26-7.02 (m, 8H), 6.98 (d, J=8.4 Hz, 2H), 6.86 (d, J=7.0 Hz, 2H), 6.49 (d, J=7.7 Hz, 1H), 4.44-4.37 (m, 1H), 4.04-3.95 (m, 2H), 3.80 (s, 3H), 3.12 (s, 3H), 2.81 (dd, J=13.6, 5.1 Hz, 1H), 2.55 (dd, J=13.6, 8.1 Hz, 1H).

Example JB-58

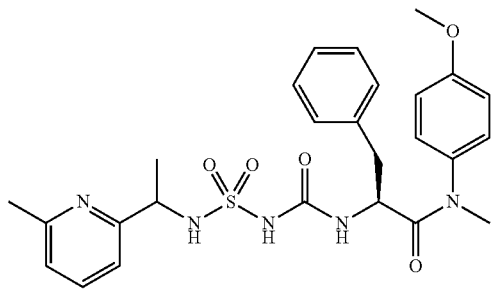 [SMILES: COc1ccc(N(C)C(=O)[C@H](Cc2ccccc2)NC(=O)NS(=O)(=O)NC(C)c2cccc(C)n2)cc1]

Example JB-58 was synthesized using the procedure described above for Example JB-16 with racemic 1-(6-methylpyridin-2-yl)ethanamine replacing 2-methoxyaniline as the final amine input. LC-MS retention time=1.65 min; m/z=526.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR spectral analysis indicates distinctive signals suggestive of a 1:1 mixture of diastereomers.

Example JB-59

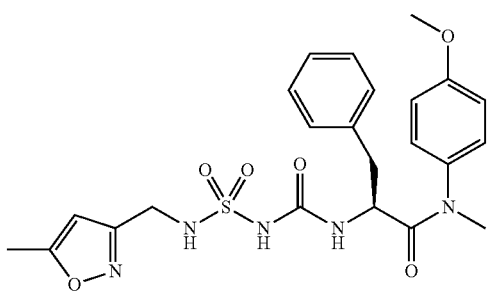 [SMILES: COc1ccc(N(C)C(=O)[C@H](Cc2ccccc2)NC(=O)NS(=O)(=O)NCc2cc(C)on2)cc1]

Example JB-59 was synthesized using the procedure described above for Example JB-16 with (5-methylisoxazol-3-yl)methanamine replacing 2-methoxyaniline as the final amine input. LC-MS retention time=1.35 min; m/z=502.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.32-7.06 (m, 5H), 6.98 (d, J=8.4 Hz, 2H), 6.86 (d, J=7.0 Hz, 2H), 6.42 (d, J=7.3 Hz, 1H), 6.14 (s, 1H), 4.38 (d, J=5.9 Hz, 1H), 3.95 (d, J=2.9 Hz, 2H), 3.80 (s, 3H), 3.11 (s, 3H), 2.81 (d, J=8.4 Hz, 1H), 2.56 (dd, J=13.8, 8.3 Hz, 1H), 2.35 (s, 3H).

Example JB-60

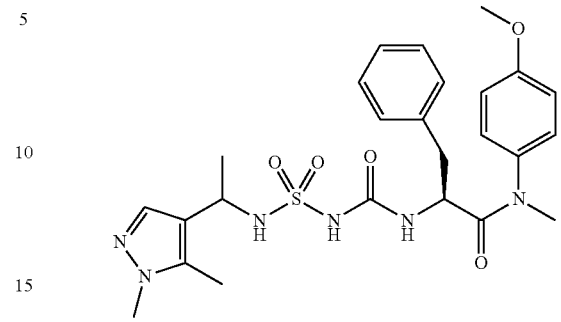

Example JB-60 was synthesized using the procedure described above for Example JB-16 with racemic1-(1,5-dimethyl-1H-pyrazol-4-yl)ethanamine replacing 2-methoxyaniline as the final amine input. LC-MS retention time=2.33 min; m/z=529.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). 1:1 mixture of diastereomers $^1$H NMR (500 MHz, DMSO-d$_6$) δ 7.30-7.08 (m, 5H), 7.01-6.82 (m, 5H), 6.45-6.35 (m, 1H), 4.46-4.31 (m, 1H), 4.29-4.16 (m, 1H), 3.80 (br. s., 1.5H), 3.80 (s, 1.5H), 3.64 (s, 1.5H), 3.61 (s, 1.5H), 3.13 (s, 1.5H), 3.08 (s, 1.5H), 2.81-2.75 (m, 1H), 2.57-2.52 (m, 1H), 2.14 (s, 1.5H), 2.10 (s, 1.5H), 1.31 (d, J=7.0 Hz, 1.5H), 1.21 (d, J=7.0 Hz, 1.5H).

Example JB-61

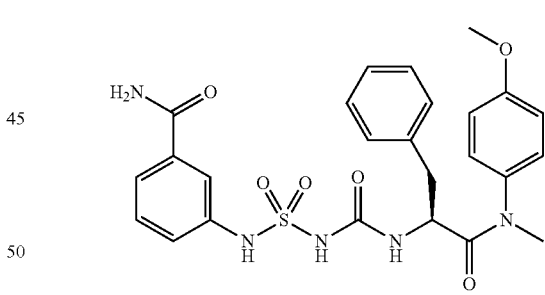

Example JB-61 was synthesized using the procedure described above for Example JB-16 with 3-aminobenzamide replacing 2-methoxyaniline as the final amine input. LC-MS retention time=2.09 min; m/z=526.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.90 (br. s., 1H), 7.61 (br. s., 1H), 7.50 (d, J=6.6 Hz, 1H), 7.38-6.88 (m, 10H), 6.78 (d, J=3.7 Hz, 2H), 6.22 (br. s., 1H), 4.32 (d, J=5.9 Hz, 1H), 3.79 (s, 3H), 3.07 (s, 3H), 2.70 (br. s., 1H), 2.53-2.48 (m, 1H).

Example JB-62

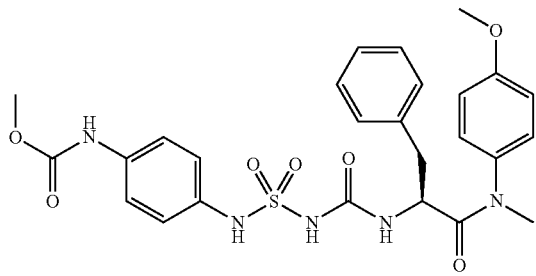 [SMILES: COC(=O)Nc1ccc(NS(=O)(=O)NC(=O)N[C@@H](Cc2ccccc2)C(=O)N(C)c2ccc(OC)cc2)cc1]

Example JB-62 was synthesized using the procedure described above for Example JB-16 with methyl (4-aminophenyl)carbamate, HCl replacing 2-methoxyaniline as the final amine input. LC-MS retention time=1.28 min; m/z=556.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 9.55 (br. s., 1H), 7.34 (d, J=7.7 Hz, 2H), 7.20-6.92 (m, 9H), 6.79 (br. s., 2H), 6.24 (br. s., 1H), 4.42-4.33 (m, J=6.2 Hz, 1H), 3.80 (s, 3H), 3.65 (s, 3H), 3.09 (s, 3H), 2.79-2.75 (m, 1H), 2.56-2.52 (m, 1H).

Example JB-63

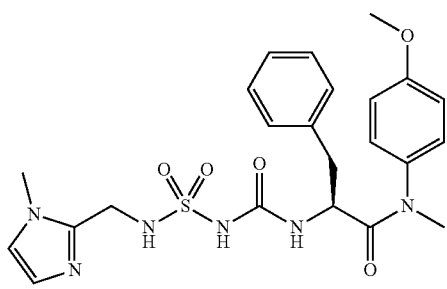 [SMILES: COc1ccc(N(C)C(=O)[C@H](Cc2ccccc2)NC(=O)NS(=O)(=O)NCc2nccn2C)cc1]

Example JB-63 was synthesized using the procedure described above for Example JB-16 with (1-methyl-1H-imidazol-2-yl)methanamine replacing 2-methoxyaniline as the final amine input. LC-MS retention time=1.60 min; m/z=501.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.25-7.08 (m, 5H), 7.04 (s, 1H), 6.98 (d, J=8.4 Hz, 2H), 6.87 (d, J=7.3 Hz, 2H), 6.75 (s, 1H), 6.42 (br. s., 1H), 4.38 (d, J=5.1 Hz, 1H), 4.02 (br. s., 2H), 3.80 (s, 4H), 3.57 (s, 4H), 2.81 (d, J=9.2 Hz, 1H), 2.57 (dd, J=13.4, 8.3 Hz, 1H).

Example JB-64

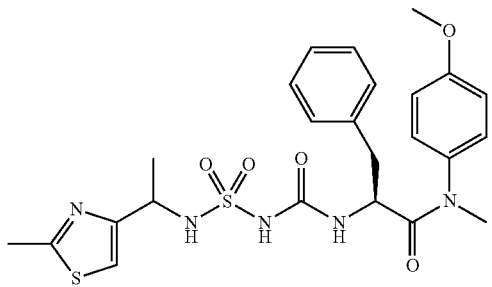 [SMILES: COc1ccc(N(C)C(=O)[C@H](Cc2ccccc2)NC(=O)NS(=O)(=O)NC(C)c2csc(C)n2)cc1]

Example JB-64 was synthesized using the procedure described above for Example JB-16 with racemic 1-(2-methylthiazol-4-yl)ethanamine replacing 2-methoxyaniline as the final amine input. LC-MS retention time=1.79 min; m/z=532.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). 1:1 mixture of diastereomers. $^1$H NMR (500 MHz, DMSO-d$_6$) δ 7.22 (t, J=7.5 Hz, 3H), 7.14 (d, J=10.3 Hz, 1H), 7.10-6.92 (m, 4H), 6.86 (d, J=7.0 Hz, 2H), 6.43 (dd, J=18.3, 8.1 Hz, 1H), 4.51-4.31 (m, 3H), 3.80 (s, 1.5H), 3.80 (s, 1.5H), 3.12 (s, 1.5H), 3.09 (s, 1.5H), 2.85-2.77 (m, 1H), 2.61 (s, 1.5H), 2.57 (s, 1.5H), 2.56-2.51 (m, 1H), 1.35 (d, J=7.0 Hz, 1.5H), 1.23 (d, J=6.6 Hz, 1.5H).

Example JB-65

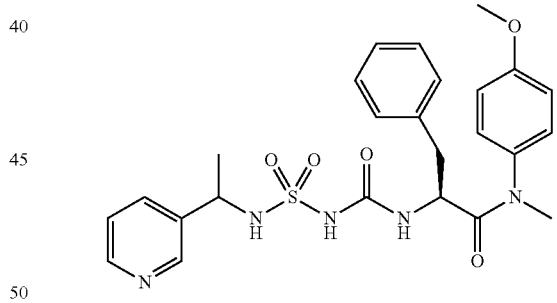

Example JB-65 was synthesized using the procedure described above for Example JB-16 with racemic 1-(pyridin-3-yl)ethanamine replacing 2-methoxyaniline as the final amine input. LC-MS retention time=2.31 min; m/z=512.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). 1:1 mixture of diastereomers. $^1$H NMR (500 MHz, DMSO-d$_6$) δ 8.52 (br. s., 1H), 8.45-8.36 (m, 1H), 7.71 (t, J=8.1 Hz, 1H), 7.34-6.92 (m, 8H), 6.86 (d, J=7.0 Hz, 2H), 6.41-6.30 (m, 1H), 4.43 (d, J=6.6 Hz, 1H), 4.33 (t, J=6.4 Hz, 1H), 3.81 (s, 1.5H), 3.80 (s, 1.5H), 3.14 (s, 1.5H), 3.08 (s, 1.5H), 2.83-2.76 (m, 1H), 2.58-2.52 (m, 1H), 1.35 (d, J=7.0 Hz, 1.5H), 1.23 (d, J=7.0 Hz, 1.5H).

Example JB-66 and JB-67

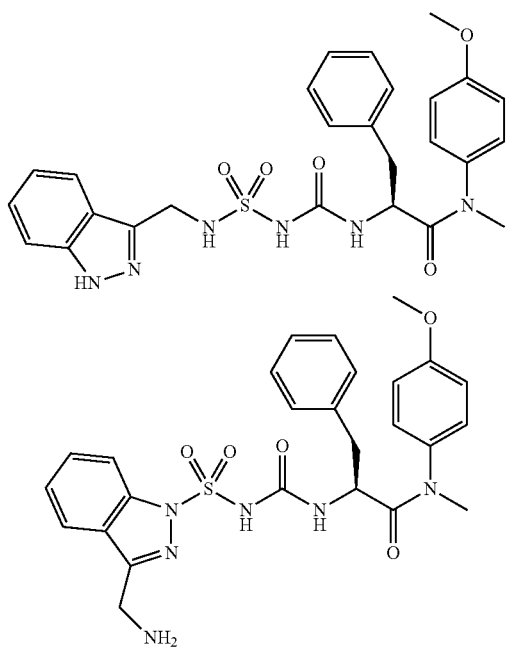

Examples JB-66 and JB-67 were synthesized using the procedure described above for Example JB-16 with (1H-indazol-3-yl)methanamine replacing 2-methoxyaniline as the final amine input. For Example 66: LC-MS retention time=1.56 min; m/z=537.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). For Example 67: LC-MS retention time=1.64 min; m/z=537.3 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (400 MHz, CD$_3$OD) δ 7.87 (d, J=8.3 Hz, 1H), 7.49 (d, J=8.3 Hz, 1H), 7.37 (ddd, J=8.4, 7.0, 1.0 Hz, 1H), 7.26-7.09 (m, 5H), 6.98-6.73 (m, 6H), 4.59-4.45 (m, 3H), 3.83 (s, 3H), 3.16 (s, 3H), 2.88 (dd, J=13.2, 7.1 Hz, 1H), 2.69-2.59 (m, 1H).

Example JB-68

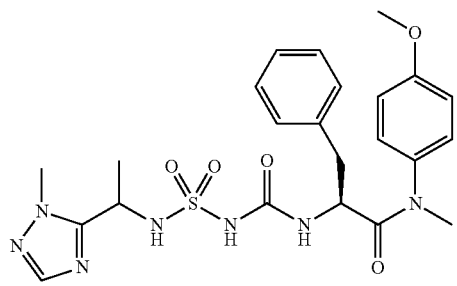 [SMILES: COc1ccc(N(C)C(=O)[C@H](Cc2ccccc2)NC(=O)NS(=O)(=O)NC(C)c2ncnn2C)cc1]

Example JB-68 was synthesized using the procedure described above for Example JB-16 with racemic 1-(1-methyl-1H-1,2,4-triazol-5-yl)ethanamine, 2HCl replacing 2-methoxyaniline as the final amine input. LC-MS retention time=2.05 min; m/z=516.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR spectral analysis indicates distinctive signals suggestive of a 1:1 mixture of diastereomers.

Example JB-69

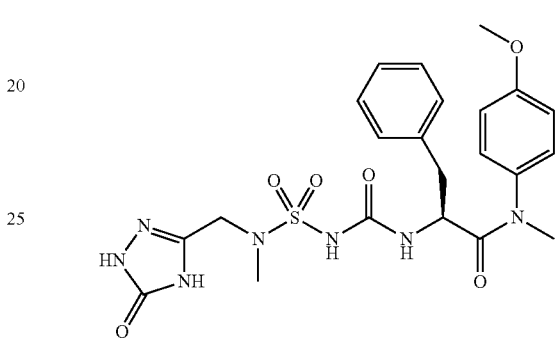

Example JB-69 was synthesized using the procedure described above for Example JB-16 with 3-((methylamino)methyl)-1H-1,2,4-triazol-5 (4H)-one replacing 2-methoxyaniline, HCl as the final amine input. LC-MS retention time=2.03 min; m/z=518.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (400 MHz, CD$_3$OD) δ 7.28-7.17 (m, 3H), 7.07-6.84 (m, 6H), 4.65-4.56 (m, 1H), 4.24-4.10 (m, 2H), 3.85 (s, 3H), 3.21 (s, 3H), 2.99-2.90 (m, 1H), 2.75-2.67 (m, 4H).

Example JB-70

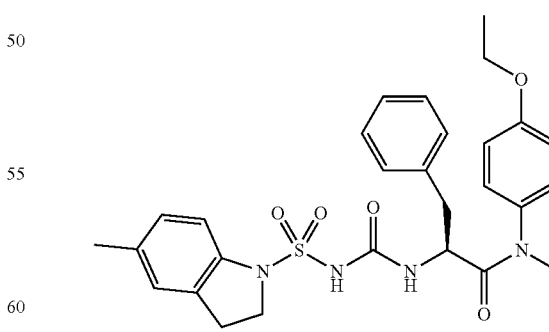

A solution of an HCl salt of Intermediate JB-6 (280 mg, 0.803 mmol) in DCM (2 mL) was added dropwise at 0° C. to a stirred solution of sulfurisocyanatidic chloride (0.010 mL, 1.1 mmol) in DCM (3 mL). The reaction mixture was stirred at 0° C. for 1 h and then TEA (0.358 mL, 2.57 mmol)

in DCM (1.1 mL) was added and reaction mixture was stirred at 0° C. for 3 min. A portion of the crude reaction mixture (~0.8 mL) was added to a stirred solution of 5-methylindoline (32.1 mg, 0.241 mmol) in DCM (1 mL) and the reaction was stirred at rt for 2 h. The reaction mixture was concentrated and partitioned between EtOAc (~2 mL) and 1M HCl (~1 mL) (note: for reactions that followed the procedure outlined here, where there was a basic amine present in the final Example, sat. aq NaHCO₃ was used in the work-up in place of 1 M HCl) and the organic component was washed with brine (1 mL) and concentrated. The residue was dissolved into MeOH, filtered and purified by preparative HPLC to yield the title compound (5.6 mg). LC-MS retention time=2.88 min; m/z=551.5 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 7.24-7.04 (m, 4H), 7.00-6.66 (m, 8H), 6.21 (br. s., 1H), 4.18 (app q, J=7.1 Hz, 1H), 4.04 (q, J=7.1 Hz, 2H), 3.94-3.82 (m, 2H), 3.58 (d, J=7.0 Hz, 1H), 3.49-3.39 (m, 1H), 2.94-2.84 (m, 2H), 2.68 (br. s., 1H), 2.47 (dd, J=13.2, 7.3 Hz, 1H), 2.21 (s, 3H), 1.35 (t, J=6.8 Hz, 3H), 0.93 (t, J=7.0 Hz, 3H).

Example JB-71

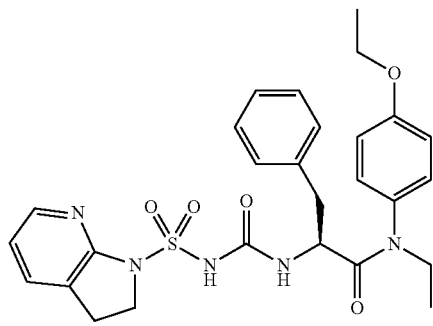 [SMILES: CCOc1ccc(N(CC)C(=O)[C@H](Cc2ccccc2)NC(=O)NS(=O)(=O)N2CCc3cccnc32)cc1]

Example JB-71 was synthesized using the procedure described above for Example JB-70 with 2,3-dihydro-1H-pyrrolo[2,3-b]pyridine replacing 5-methylindoline as the final amine input. LC-MS retention time=2.56 min; m/z=538.4 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 8.05 (d, J=4.0 Hz, 1H), 7.60 (d, J=7.3 Hz, 1H), 7.25-7.09 (m, 3H), 6.94 (br. s., 1H), 6.84 (d, J=8.8 Hz, 2H), 6.76 (d, J=7.0 Hz, 2H), 6.73-6.64 (m, 2H), 6.55 (br. s., 1H), 4.18-4.00 (m, 5H), 3.59-3.51 (m, 1H), 3.41 (dd, J=13.6, 7.0 Hz, 1H), 3.04 (t, J=8.3 Hz, 2H), 2.69 (dd, J=13.2, 6.2 Hz, 1H), 2.41 (dd, J=13.2, 7.3 Hz, 1H), 1.34 (t, J=6.8 Hz, 3H), 0.91 (t, J=7.0 Hz, 3H).

Example JB-72

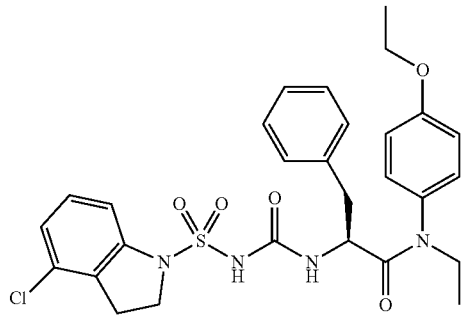 [SMILES: CCOc1ccc(N(CC)C(=O)[C@H](Cc2ccccc2)NC(=O)NS(=O)(=O)N2CCc3c(Cl)cccc32)cc1]

Example JB-72 was synthesized using the procedure described above for Example JB-70 with 4-chloroindoline replacing 5-methylindoline as the final amine input. LC-MS retention time=2.06 min; m/z=571.4 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 7.24-7.18 (m, 1H), 7.17-7.06 (m, 4H), 7.01 (d, J=7.7 Hz, 1H), 6.92-6.81 (m, 4H), 6.76 (d, J=7.3 Hz, 2H), 6.37 (br. s., 1H), 4.17 (app q, J=7.3 Hz, 1H), 4.11-4.00 (m, 4H), 3.59 (dd, J=13.6, 7.0 Hz, 1H), 3.48-3.40 (m, 1H), 3.00 (br. s., 2H), 2.71 (dd, J=13.2, 5.9 Hz, 1H), 2.45 (dd, J=13.2, 7.7 Hz, 1H), 1.35 (t, J=6.8 Hz, 3H), 0.93 (t, J=7.2 Hz, 3H).

Example JB-73

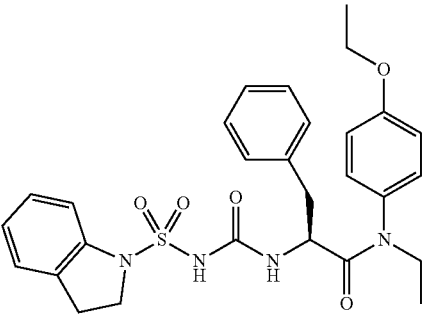 [SMILES: CCOc1ccc(N(CC)C(=O)[C@H](Cc2ccccc2)NC(=O)NS(=O)(=O)N2CCc3ccccc32)cc1]

Example JB-73 was synthesized using the procedure described above for Example JB-70 with indoline replacing 5-methylindoline as the final amine input. LC-MS retention time=2.76 min; m/z=537.4 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 7.23-7.09 (m, 6H), 6.98-6.81 (m, 5H), 6.76 (d, J=7.0 Hz, 2H), 6.38 (br. s., 1H), 4.22-4.15 (m, 1H), 4.08-3.94 (m, 4H), 3.62-3.53 (m, 1H), 3.49-3.40 (m, 1H), 2.98 (t, J=8.4 Hz, 2H), 2.69 (dd, J=12.7, 5.7 Hz, 1H), 2.45 (dd, J=13.0, 7.5 Hz, 1H), 1.35 (t, J=7.0 Hz, 3H), 0.93 (t, J=7.2 Hz, 3H).

Example JB-74

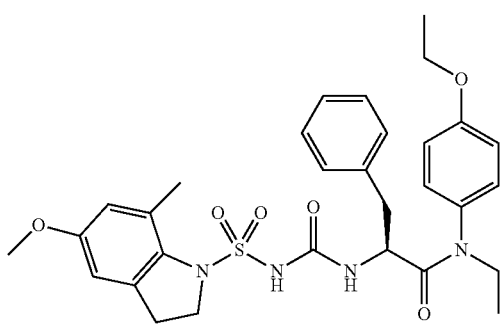 [SMILES: CCOc1ccc(N(CC)C(=O)[C@H](Cc2ccccc2)NC(=O)NS(=O)(=O)N2CCc3cc(OC)cc(C)c32)cc1]

Example JB-74 was synthesized using the procedure described above for Example JB-70 with 5-methoxy-7-methylindoline replacing 5-methylindoline as the final amine input. LC-MS retention time=2.85 min; m/z=581.5 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.20 (br. s., 3H), 6.86 (d, J=15.0 Hz, 6H), 6.65 (br. s., 1H), 6.52 (br. s., 1H), 6.40 (d, J=7.7 Hz, 1H), 4.23-4.17 (m, 1H), 4.05 (q, J=7.0 Hz, 2H), 3.91-3.78 (m, 2H), 3.68 (s, 3H), 3.62-3.52 (m, 1H), 3.51-3.42 (m, 1H), 2.81 (br. s., 2H), 2.72-2.62 (m, 1H), 2.45 (dd, J=13.4, 7.2 Hz, 1H), 2.29 (s, 3H), 1.35 (t, J=7.0 Hz, 3H), 0.95 (t, J=7.0 Hz, 3H).

Example JB-75

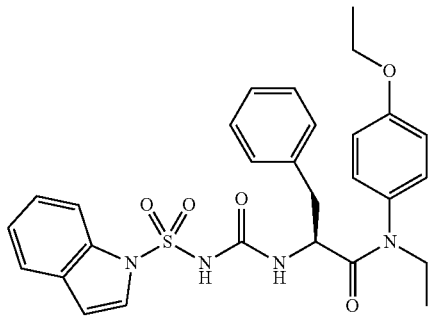 [SMILES: CCOc1ccc(N(CC)C(=O)[C@H](Cc2ccccc2)NC(=O)NS(=O)(=O)n2ccc3ccccc32)cc1]

Example JB-75 was synthesized using the procedure described above for Example JB-70 with 1H-indole replacing 5-methylindoline as the final amine input. LC-MS retention time=1.98 min; m/z=535.5 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.92 (s, 1H), 7.78 (d, J=7.7 Hz, 1H), 7.53 (d, J=8.1 Hz, 1H), 7.31-7.20 (m, 2H), 7.13-7.08 (m, 1H), 7.07-7.01 (m, 2H), 6.91-6.76 (m, 4H), 6.70 (d, J=7.0 Hz, 2H), 6.65 (d, J=8.1 Hz, 1H), 4.15 (app q, J=7.3 Hz, 1H), 4.02 (q, J=7.0 Hz, 2H), 3.61-3.52 (m, 1H), 3.50-3.42 (m, 1H), 2.73-2.69 (m, J=5.5 Hz, 1H), 2.46 (dd, J=13.2, 7.3 Hz, 1H), 1.33 (t, J=7.0 Hz, 3H), 0.92 (t, J=7.0 Hz, 3H).

Example JB-76

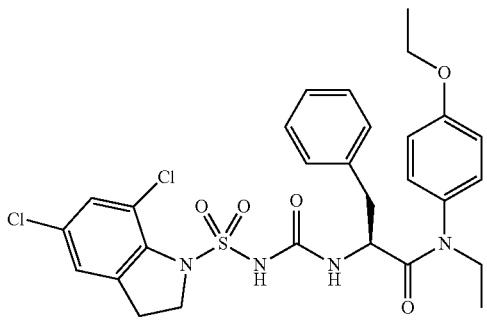 [SMILES: CCOc1ccc(N(CC)C(=O)[C@H](Cc2ccccc2)NC(=O)NS(=O)(=O)N2CCc3cc(Cl)cc(Cl)c32)cc1]

Example JB-76 was synthesized using the procedure described above for Example JB-70 with 5,7-dichloroindoline replacing 5-methylindoline as the final amine input. LC-MS retention time=2.92 min; m/z=605.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-77

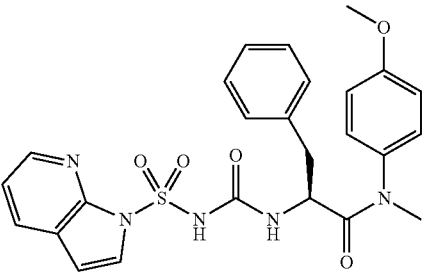 [SMILES: COc1ccc(N(C)C(=O)[C@H](Cc2ccccc2)NC(=O)NS(=O)(=O)n2ccc3cccnc32)cc1]

Example JB-77 was synthesized using the procedure described above for Example JB-16 with 1H-pyrrolo[2,3-b]pyridine replacing 2-methoxyaniline as the final amine input. LC-MS retention time=2.11 min; m/z=508.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 8.35 (br. s., 1H), 8.15 (d, J=7.0 Hz, 1H), 7.93 (br. s., 1H), 7.31-6.83 (m, 9H), 6.70 (d, J=6.6 Hz, 2H), 6.48 (br. s., 1H), 4.23 (br. s., 1H), 3.76 (s, 3H), 3.06 (s, 3H), 7.73-2.68 (m., 1H), 2.49-2.43 (m, 1H).

Example JB-78

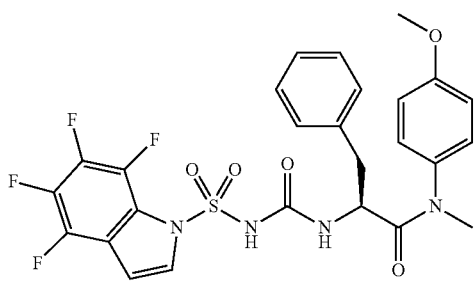 [SMILES: COc1ccc(N(C)C(=O)[C@H](Cc2ccccc2)NC(=O)NS(=O)(=O)n2ccc3c(F)c(F)c(F)c(F)c32)cc1]

Example JB-78 was synthesized using the procedure described above for Example JB-16 with 4,5,6,7-tetrafluoro-1H-indole replacing 2-methoxyaniline as the final amine input. LC-MS retention time=2.53 min; m/z=579.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-79

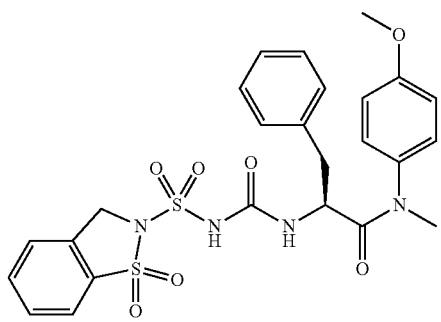 [SMILES: COc1ccc(N(C)C(=O)[C@H](Cc2ccccc2)NC(=O)NS(=O)(=O)N2Cc3ccccc3S2(=O)=O)cc1]

Example JB-79 was synthesized using the procedure described above for Example JB-16 with 2,3-dihydrobenzo[d]isothiazole 1,1-dioxide replacing 2-methoxyaniline as the final amine input. LC-MS retention time=2.19 min; m/z=559.4 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example JB-80

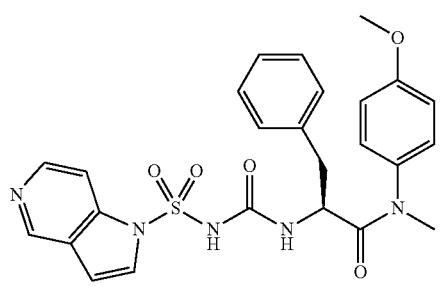 [SMILES: COc1ccc(N(C)C(=O)[C@H](Cc2ccccc2)NC(=O)NS(=O)(=O)n2ccc3cnccc32)cc1]

Example JB-80 was synthesized using the procedure described above for Example JB-16 with 1H-pyrrolo[3,2-c]pyridine replacing 2-methoxyaniline as the final amine input. LC-MS retention time=1.25 min; m/z=506.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 9.03 (s, 1H), 8.33 (d, J=6.2 Hz, 1H), 8.01 (d, J=6.2 Hz, 1H), 7.73 (d, J=3.3 Hz, 1H), 7.10 (br. s., 3H), 7.02 (d, J=8.1 Hz, 2H), 6.87 (d, J=8.4 Hz, 2H), 6.75 (br. s., 3H), 6.23 (d, J=8.1 Hz, 1H), 4.13 (d, J=4.8 Hz, 1H), 3.75 (s, 3H), 3.03 (s, 3H), 2.64 (d, J=8.1 Hz, 1H), 2.55-2.47 (m, 1H).

Example JB-81

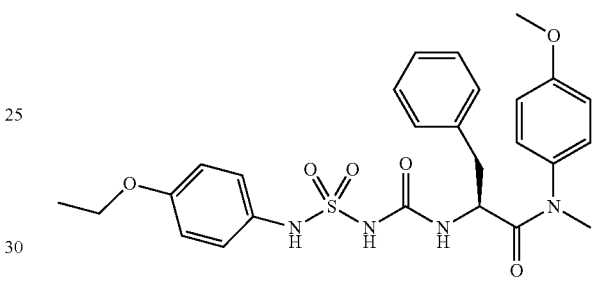

Example JB-81 was synthesized using the procedure described above for Example JB-16 with 4-ethoxy-N-methylaniline replacing 2-methoxyaniline as the final amine input. LC-MS retention time=2.58 min; m/z=527.5 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-1

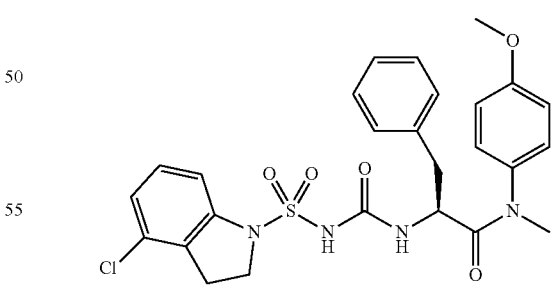

A solution of an HCl salt of Intermediate JB-2 (35 mg, 0.11 mmol) in DCE (0.50 mL) was slowly added to a stirred solution of sulfurisocyanatidic chloride (0.014 mL, 0.16 mmol) in DCE (0.25 mL) at 0° C. and the reaction mixture was allowed to stir at 0° C. for 1 h. The reaction mixture was treated with a solution of TEA (0.049 mL, 0.35 mmol) in DCE (0.25 mL), stirred at 0° C. for 5 minutes and then added to a solution of 4-chloroindoline (33.5 mg, 0.218 mmol) in DCE (0.25 mL). The reaction was sealed, shaken at rt for 2 h, concentrated and then purified by preparative HPLC to yield the title compound. LC-MS retention time=2.70 min; m/z=543.2 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 7.30-7.25 (m, 1H), 7.16-7.07 (m, 5H), 7.02-6.98 (m, 2H), 6.96-6.92 (m, 2H), 6.71 (d, J=7.3 Hz, 2H), 6.59 (d, J=8.4 Hz, 1H), 4.31-4.25 (m, 1H), 4.20-4.13 (m, 1H), 4.12-4.06 (m, 1H), 3.79 (s, 3H), 3.07 (s, 3H), 3.07-3.01 (m, 2H), 2.74-2.69 (m, 1H), 2.44 (dd, J=13.6, 7.7 Hz, 1H).

Examples CA-2 through CA-66 were synthesized using the procedure described above for Example CA-1 with the appropriate alternative precursor replacing 4-chloroindoline as the final amine input.

Example CA-2

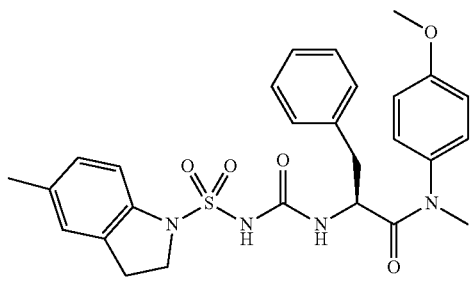 [SMILES: COc1ccc(N(C)C(=O)[C@H](Cc2ccccc2)NC(=O)NS(=O)(=O)N2CCc3cc(C)ccc32)cc1]

LC-MS retention time=2.67 min; m/z=523.1 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 7.17-7.08 (m, 3H), 7.06-6.96 (m, 5H), 6.95-6.91 (m, 2H), 6.70 (d, J=7.0 Hz, 2H), 6.54 (d, J=8.1 Hz, 1H), 4.31-4.25 (m, 1H), 4.15-4.08 (m, 1H), 4.01 (app q, J=8.9 Hz, 1H), 3.78 (s, 3H), 3.06 (s, 3H), 2.96 (t, J=8.4 Hz, 2H), 2.68 (dd, J=13.6, 5.5 Hz, 1H), 2.43 (dd, J=13.2, 7.0 Hz, 1H), 2.24 (s, 3H).

Example CA-3

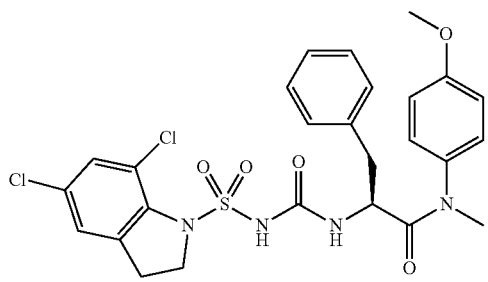 [SMILES: COc1ccc(N(C)C(=O)[C@H](Cc2ccccc2)NC(=O)NS(=O)(=O)N2CCc3cc(Cl)cc(Cl)c32)cc1]

LC-MS retention time=1.83 min; m/z=577.3 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-4

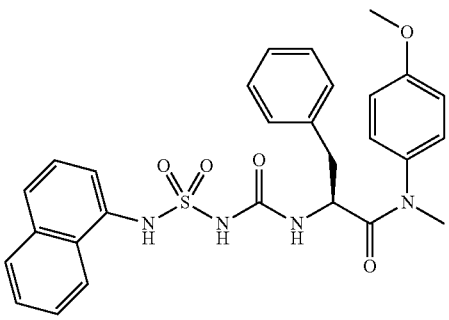 [SMILES: COc1ccc(N(C)C(=O)[C@H](Cc2ccccc2)NC(=O)NS(=O)(=O)Nc2cccc3ccccc23)cc1]

LC-MS retention time=2.74 min; m/z=533.1 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-5

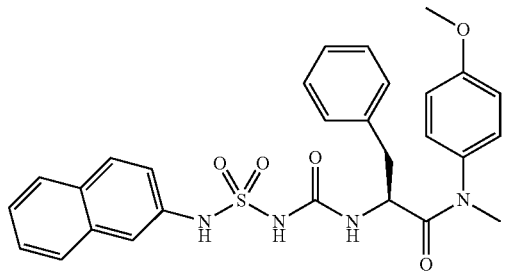 [SMILES: COc1ccc(N(C)C(=O)[C@H](Cc2ccccc2)NC(=O)NS(=O)(=O)Nc2ccc3ccccc3c2)cc1]

LC-MS retention time=2.73 min; m/z=533.1[M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 7.83 (t, J=8.6 Hz, 2H), 7.77 (d, J=8.1 Hz, 1H), 7.58 (br. s., 1H), 7.48 (t, J=7.3 Hz, 1H), 7.41 (d, J=7.0 Hz, 1H), 7.31 (d, J=8.8 Hz, 1H), 7.08-6.96 (m, 5H), 6.92 (d, J=8.1 Hz, 2H), 6.70 (d, J=7.0 Hz, 2H), 6.30 (br. s., 1H), 4.34 (d, J=6.2 Hz, 1H), 3.78 (s, 3H), 3.05 (s, 3H), 2.71-2.64 (m, 1H), 2.49-2.45 (m, 1H).

Example CA-6

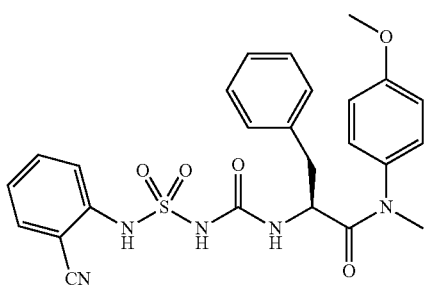 [SMILES: COc1ccc(N(C)C(=O)[C@H](Cc2ccccc2)NC(=O)NS(=O)(=O)Nc2ccccc2C#N)cc1]

LC-MS retention time=2.43 min; m/z=508.3 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-7

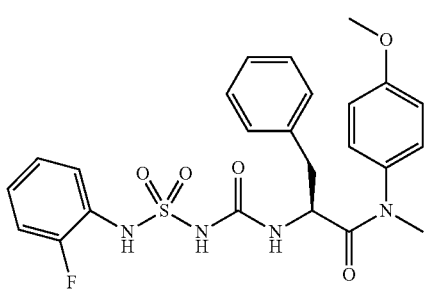 [SMILES: COc1ccc(N(C)C(=O)[C@H](Cc2ccccc2)NC(=O)NS(=O)(=O)Nc2ccccc2F)cc1]

LC-MS retention time=2.51 min; m/z=501.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-8

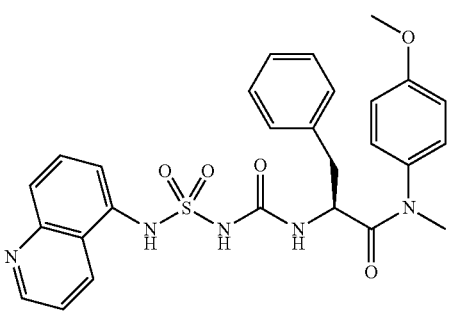 [SMILES: COc1ccc(N(C)C(=O)[C@H](Cc2ccccc2)NC(=O)NS(=O)(=O)Nc2cccc3ncccc23)cc1]

LC-MS retention time=2.34 min; m/z=534.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-9

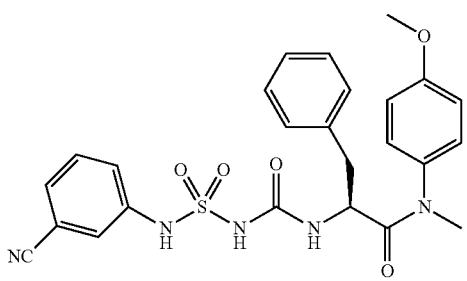 [SMILES: COc1ccc(N(C)C(=O)[C@H](Cc2ccccc2)NC(=O)NS(=O)(=O)Nc2cccc(C#N)c2)cc1]

LC-MS retention time=1.43 min; m/z=508.1 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-10

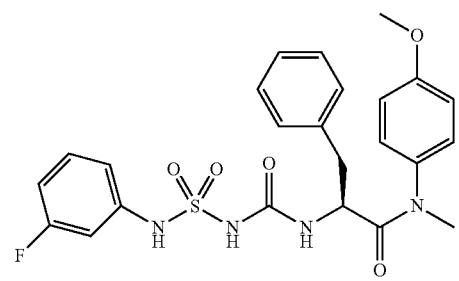 [SMILES: COc1ccc(N(C)C(=O)[C@H](Cc2ccccc2)NC(=O)NS(=O)(=O)Nc2cccc(F)c2)cc1]

LC-MS retention time=1.45 min; m/z=501.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.38-7.31 (m, 1H), 7.16-7.10 (m, 3H), 7.05 (d, J=8.1 Hz, 2H), 6.98-6.89 (m, 5H), 6.76 (d, J=7.0 Hz, 2H), 6.49 (d, J=8.1 Hz, 1H), 4.38-4.31 (m, 1H), 3.80 (s, 3H), 3.09 (s, 3H), 2.74 (dd, J=13.6, 5.5 Hz, 1H), 2.54-2.47 (m, 1H).

Example CA-11

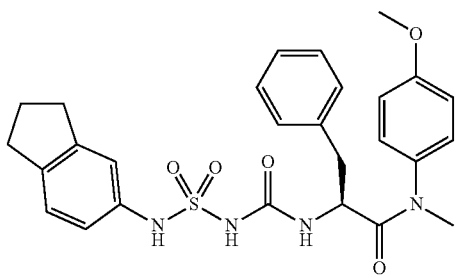 [SMILES: COc1ccc(N(C)C(=O)[C@H](Cc2ccccc2)NC(=O)NS(=O)(=O)Nc2ccc3c(c2)CCC3)cc1]

LC-MS retention time=2.80 min; m/z=523.5 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-12

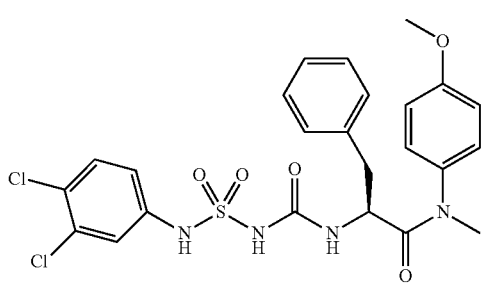 [SMILES: COc1ccc(N(C)C(=O)[C@H](Cc2ccccc2)NC(=O)NS(=O)(=O)Nc2ccc(Cl)c(Cl)c2)cc1]

LC-MS retention time=1.64 min; m/z=551.3 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-13

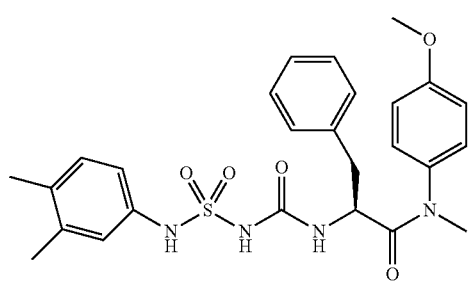 [SMILES: COc1ccc(N(C)C(=O)[C@H](Cc2ccccc2)NC(=O)NS(=O)(=O)Nc2ccc(C)c(C)c2)cc1]

LC-MS retention time=2.76 min; m/z=511.5 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-14

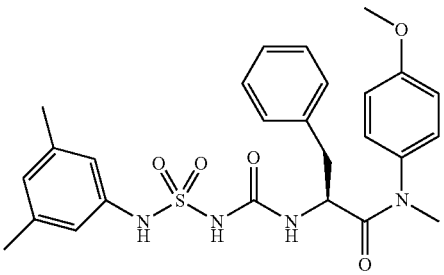 [SMILES: COc1ccc(N(C)C(=O)[C@H](Cc2ccccc2)NC(=O)NS(=O)(=O)Nc2cc(C)cc(C)c2)cc1]

LC-MS retention time=1.68 min; m/z=511.3 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-15

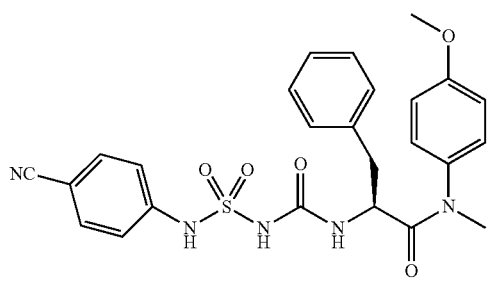 [SMILES: COc1ccc(N(C)C(=O)[C@H](Cc2ccccc2)NC(=O)NS(=O)(=O)Nc2ccc(C#N)cc2)cc1]

LC-MS retention time=1.36 min; m/z=508.2 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-16

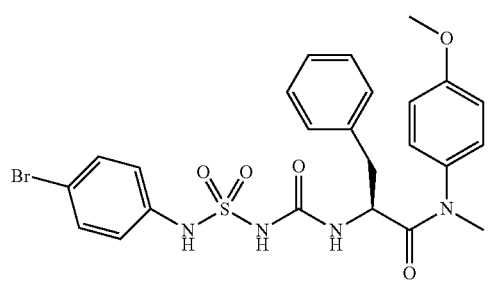 [SMILES: COc1ccc(N(C)C(=O)[C@H](Cc2ccccc2)NC(=O)NS(=O)(=O)Nc2ccc(Br)cc2)cc1]

LC-MS retention time=1.59 min; m/z=561.2 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-17

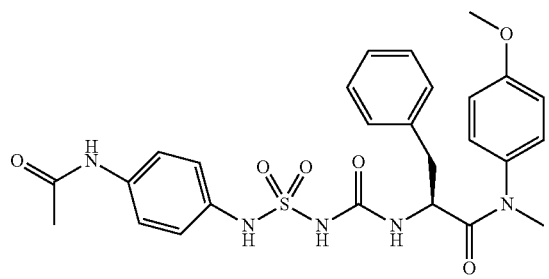 [SMILES: COc1ccc(N(C)C(=O)[C@H](Cc2ccccc2)NC(=O)NS(=O)(=O)Nc2ccc(NC(C)=O)cc2)cc1]

LC-MS retention time=2.17 min; m/z=540.1 [M+H]⁺. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-18

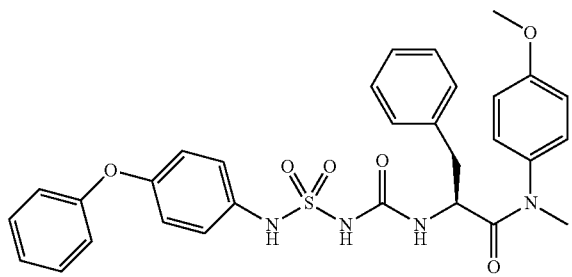

LC-MS retention time=2.88 min; m/z=575.1 [M+H]⁺. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-19

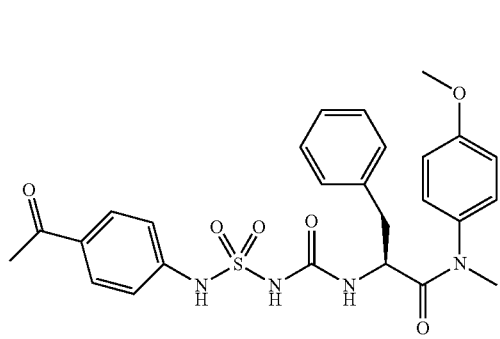 [SMILES: COc1ccc(N(C)C(=O)[C@H](Cc2ccccc2)NC(=O)NS(=O)(=O)Nc2ccc(C(C)=O)cc2)cc1]

LC-MS retention time=1.30 min; m/z=525.3 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-20

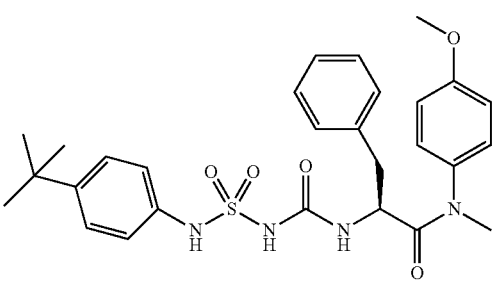 [SMILES: COc1ccc(N(C)C(=O)[C@H](Cc2ccccc2)NC(=O)NS(=O)(=O)Nc2ccc(C(C)(C)C)cc2)cc1]

LC-MS retention time=2.96 min; m/z=539.2 [M+H]⁺. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d$_6$) δ 7.29 (d, J=8.4 Hz, 2H), 7.18-7.13 (m, 3H), 7.02 (d, J=8.4 Hz, 4H), 6.96 (d, J=8.4 Hz, 2H), 6.80 (d, J=5.5 Hz, 2H), 6.36 (br. s., 1H), 4.42-4.36 (m, 1H), 3.80 (s, 3H), 3.09 (s, 3H), 2.79-2.74 (m, 1H), 2.55-2.48 (m, 1H), 1.25 (s, 9H).

Example CA-21

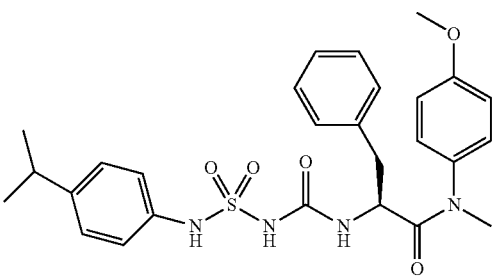 [SMILES: COc1ccc(N(C)C(=O)[C@H](Cc2ccccc2)NC(=O)NS(=O)(=O)Nc2ccc(C(C)C)cc2)cc1]

LC-MS retention time=1.83 min; m/z=525.1 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-22

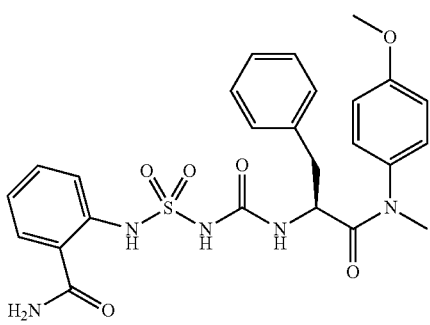 [SMILES: COc1ccc(N(C)C(=O)[C@H](Cc2ccccc2)NC(=O)NS(=O)(=O)Nc2ccccc2C(N)=O)cc1]

LC-MS retention time=1.25 min; m/z=526.4 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-23

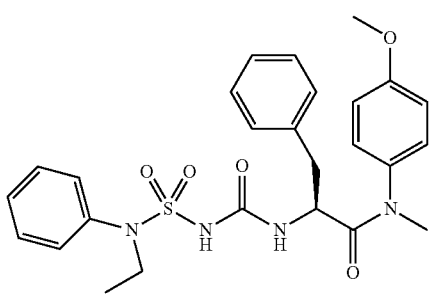 [SMILES: CCN(c1ccccc1)S(=O)(=O)NC(=O)N[C@@H](Cc1ccccc1)C(=O)N(C)c1ccc(OC)cc1]

LC-MS retention time=2.78 min; m/z=511.5 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.44-7.32 (m, 3H), 7.28-7.20 (m, 3H), 7.20-7.11 (m, 4H), 7.03 (d, J=8.4 Hz, 2H), 6.87 (d, J=7.0 Hz, 2H), 6.46 (d, J=8.4 Hz, 1H), 4.52-4.46 (m, 1H), 3.82 (s, 3H), 3.76-3.69 (m, 1H), 3.61 (dq, J=14.1, 7.3 Hz, 1H), 3.15 (s, 3H), 2.86 (dd, J=13.6, 5.1 Hz, 1H), 2.56 (dd, J=13.4, 8.3 Hz, 1H), 0.92 (t, J=7.0 Hz, 3H).

Example CA-24

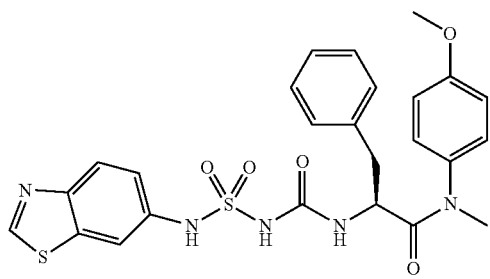 [SMILES: COc1ccc(N(C)C(=O)[C@H](Cc2ccccc2)NC(=O)NS(=O)(=O)Nc2ccc3ncsc3c2)cc1]

LC-MS retention time=1.28 min; m/z=540.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-25

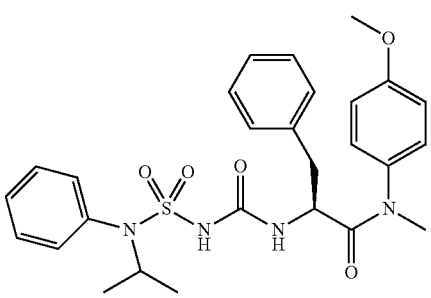 [SMILES: COc1ccc(N(C)C(=O)[C@H](Cc2ccccc2)NC(=O)NS(=O)(=O)N(c2ccccc2)C(C)C)cc1]

LC-MS retention time=2.90 min; m/z=525.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-26

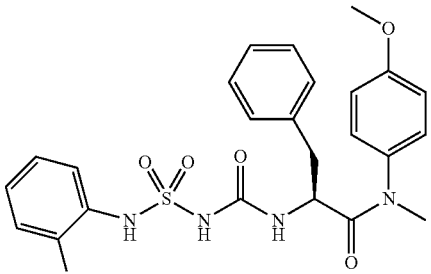

LC-MS retention time=1.62 min; m/z=567.1 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-27

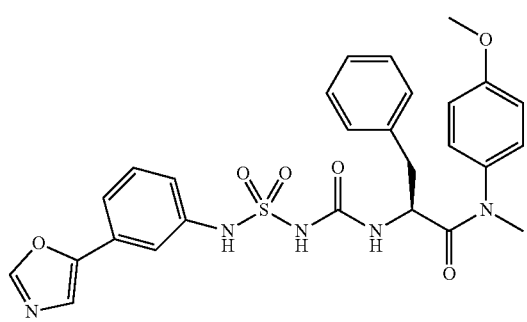 [SMILES: COc1ccc(N(C)C(=O)[C@H](Cc2ccccc2)NC(=O)NS(=O)(=O)Nc2cccc(-c3cnco3)c2)cc1]

LC-MS retention time=1.39 min; m/z=550.2 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-28

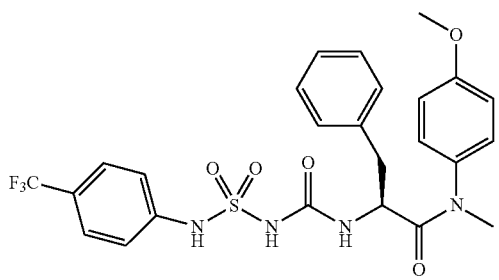 [SMILES: COc1ccc(N(C)C(=O)[C@H](Cc2ccccc2)NC(=O)NS(=O)(=O)Nc2ccc(C(F)(F)F)cc2)cc1]

LC-MS retention time=1.61 min; m/z=551.2 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-29

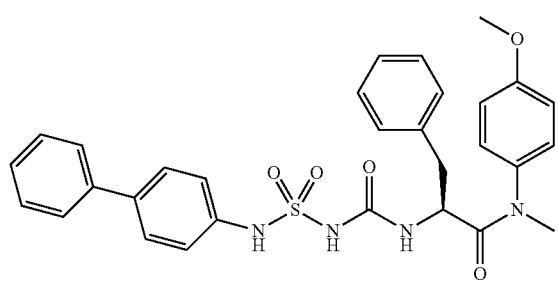 [SMILES: COc1ccc(N(C)C(=O)[C@H](Cc2ccccc2)NC(=O)NS(=O)(=O)Nc2ccc(-c3ccccc3)cc2)cc1]

LC-MS retention time=1.75 min; m/z=559.4 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-30

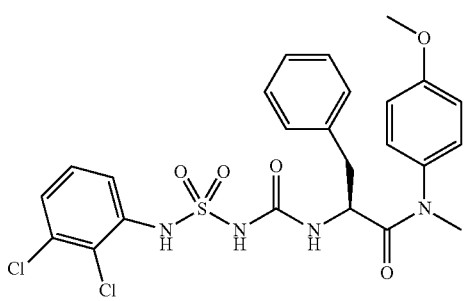 [SMILES: COc1ccc(N(C)C(=O)[C@H](Cc2ccccc2)NC(=O)NS(=O)(=O)Nc2cccc(Cl)c2Cl)cc1]

LC-MS retention time=1.61 min; m/z=551.3 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-31

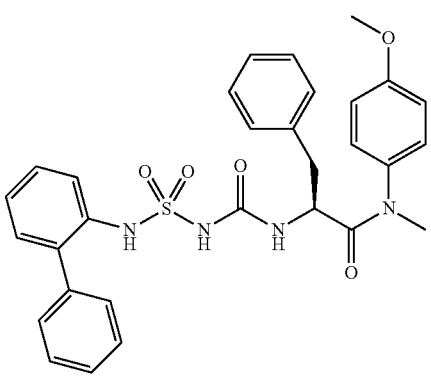 [SMILES: COc1ccc(N(C)C(=O)[C@H](Cc2ccccc2)NC(=O)NS(=O)(=O)Nc2ccccc2-c2ccccc2)cc1]

LC-MS retention time=1.76 min; m/z=559.2 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-32

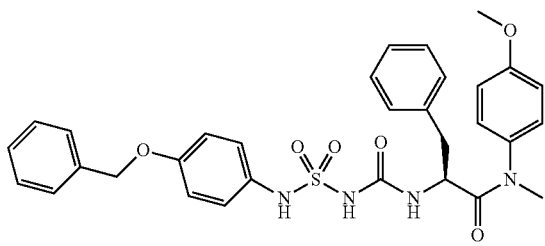 [SMILES: COc1ccc(N(C)C(=O)[C@H](Cc2ccccc2)NC(=O)NS(=O)(=O)Nc2ccc(OCc3ccccc3)cc2)cc1]

LC-MS retention time=1.84 min; m/z=589.3 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-33

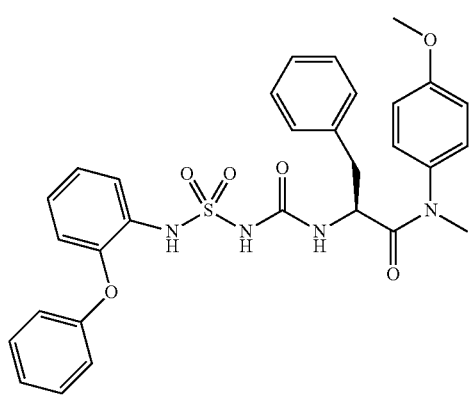 [SMILES: COc1ccc(N(C)C(=O)[C@H](Cc2ccccc2)NC(=O)NS(=O)(=O)Nc2ccccc2Oc2ccccc2)cc1]

LC-MS retention time=2.85 min; m/z=575.1 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-34

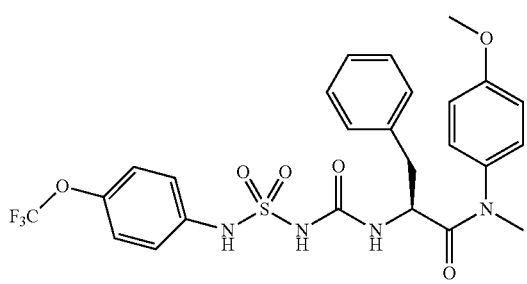 [SMILES: COc1ccc(N(C)C(=O)[C@H](Cc2ccccc2)NC(=O)NS(=O)(=O)Nc2ccc(OC(F)(F)F)cc2)cc1]

LC-MS retention time=1.65 min; m/z=567.4 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-35

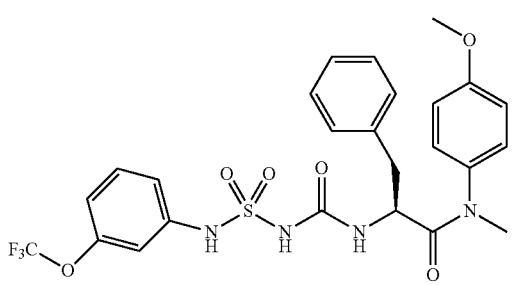 [SMILES: COc1ccc(N(C)C(=O)[C@H](Cc2ccccc2)NC(=O)NS(=O)(=O)Nc2cccc(OC(F)(F)F)c2)cc1]

LC-MS retention time=2.71 min; m/z=567.4 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-36

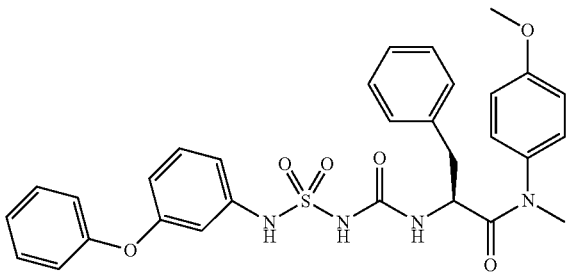 [SMILES: COc1ccc(N(C)C(=O)[C@H](Cc2ccccc2)NC(=O)NS(=O)(=O)Nc2cccc(Oc3ccccc3)c2)cc1]

LC-MS retention time=2.80 min; m/z=575.2 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-37

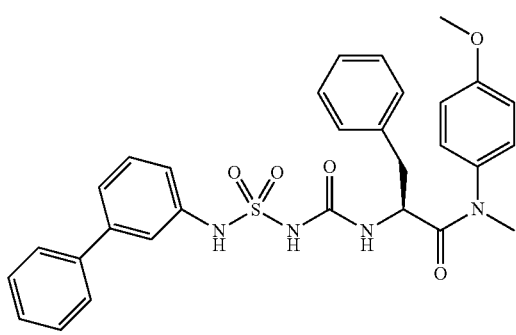 [SMILES: COc1ccc(N(C)C(=O)[C@H](Cc2ccccc2)NC(=O)NS(=O)(=O)Nc2cccc(-c3ccccc3)c2)cc1]

LC-MS retention time=2.79 min; m/z=559.5 [M+H]⁺. (Column: Waters BEH C18, 2.0×50 mm, 1.7-µm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-38

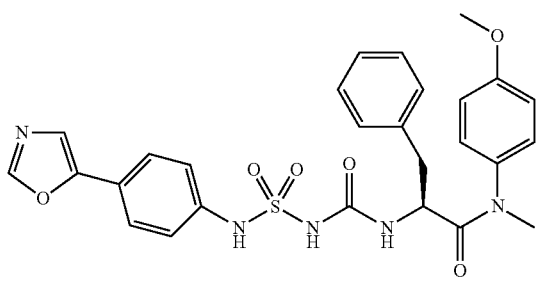 [SMILES: COc1ccc(N(C)C(=O)[C@H](Cc2ccccc2)NC(=O)NS(=O)(=O)Nc2ccc(-c3cnco3)cc2)cc1]

LC-MS retention time=1.36 min; m/z=550.2 [M+H]⁺. (Column: Waters BEH C18, 2.0×50 mm, 1.7-µm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-39

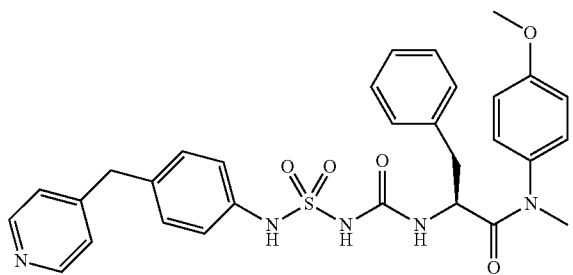 [SMILES: COc1ccc(N(C)C(=O)[C@H](Cc2ccccc2)NC(=O)NS(=O)(=O)Nc2ccc(Cc3ccncc3)cc2)cc1]

LC-MS retention time=2.49 min; m/z=574.2 [M+H]⁺. (Column: Waters BEH C18, 2.0×50 mm, 1.7-µm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-40

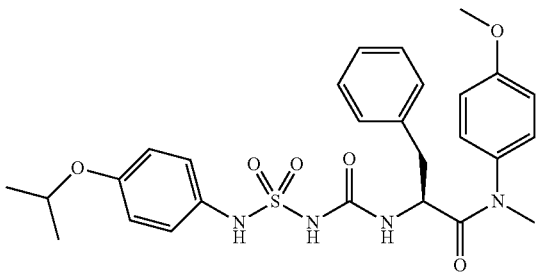 [SMILES: COc1ccc(N(C)C(=O)[C@H](Cc2ccccc2)NC(=O)NS(=O)(=O)Nc2ccc(OC(C)C)cc2)cc1]

LC-MS retention time=2.72 min; m/z=541.4 [M+H]⁺. (Column: Waters BEH C18, 2.0×50 mm, 1.7-µm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-41

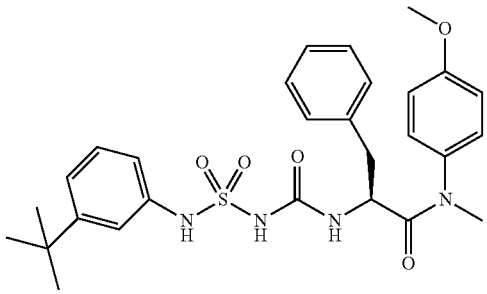 [SMILES: COc1ccc(N(C)C(=O)[C@H](Cc2ccccc2)NC(=O)NS(=O)(=O)Nc2cccc(C(C)(C)C)c2)cc1]

LC-MS retention time=2.88 min; m/z=539.5 [M+H]⁺. (Column: Waters BEH C18, 2.0×50 mm, 1.7-µm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-42

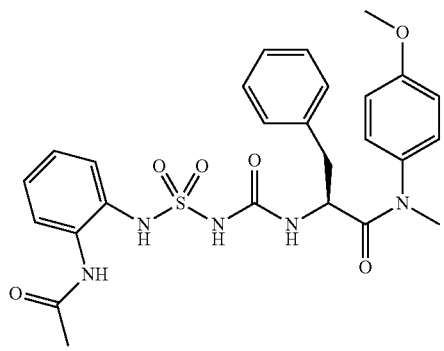 [SMILES: COc1ccc(N(C)C(=O)[C@H](Cc2ccccc2)NC(=O)NS(=O)(=O)Nc2ccccc2NC(C)=O)cc1]

LC-MS retention time=1.30 min; m/z=540.1 [M+H]+. (Column: Waters BEH C18, 2.0×50 mm, 1.7-µm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-43

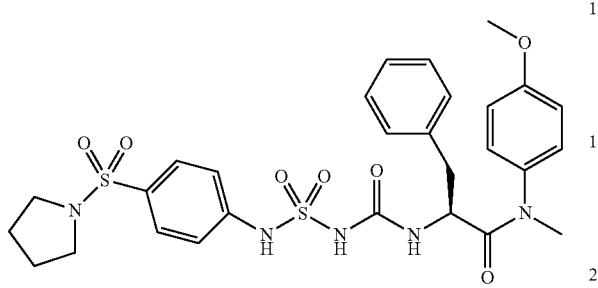

LC-MS retention time=2.41 min; m/z=616.1[M+H]+. (Column: Waters BEH C18, 2.0×50 mm, 1.7-µm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-44

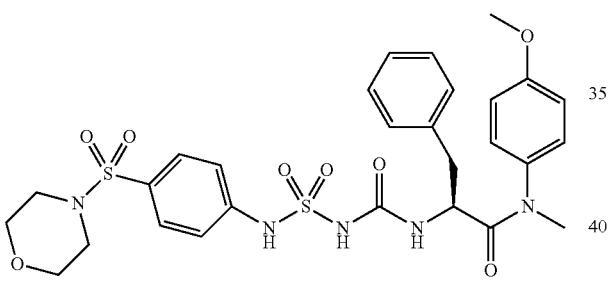

LC-MS retention time=1.34 min; m/z=632.2 [M+H]+. (Column: Waters BEH C18, 2.0×50 mm, 1.7-µm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-45

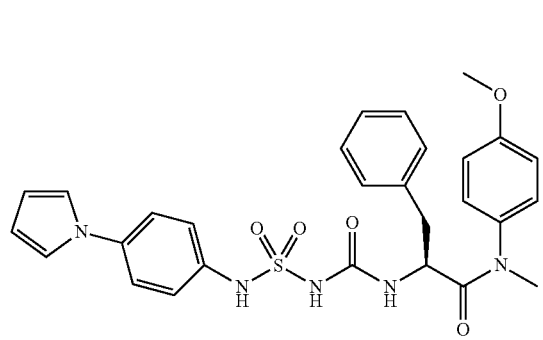 [SMILES: COc1ccc(N(C)C(=O)[C@H](Cc2ccccc2)NC(=O)NS(=O)(=O)Nc2ccc(-n3cccc3)cc2)cc1]

LC-MS retention time=2.65 min; m/z=548.2 [M+H]+. (Column: Waters BEH C18, 2.0×50 mm, 1.7-µm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-46

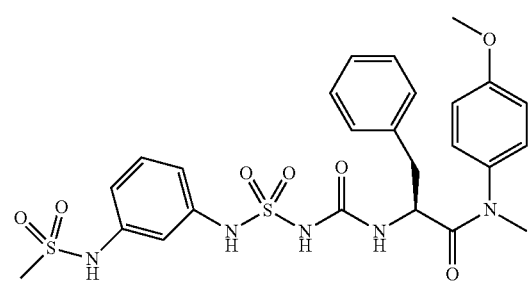 [SMILES: COc1ccc(N(C)C(=O)[C@H](Cc2ccccc2)NC(=O)NS(=O)(=O)Nc2cccc(NS(C)(=O)=O)c2)cc1]

LC-MS retention time=1.34 min; m/z=576.1 [M+H]+. (Column: Waters BEH C18, 2.0×50 mm, 1.7-µm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-47

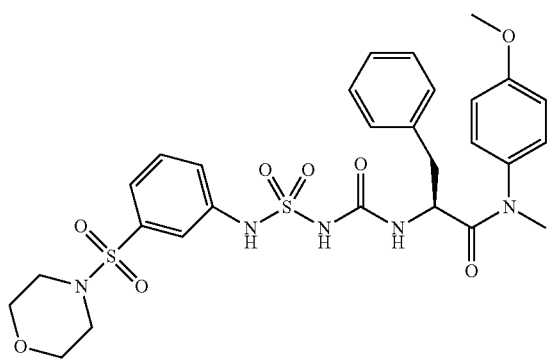 [SMILES: COc1ccc(N(C)C(=O)[C@H](Cc2ccccc2)NC(=O)NS(=O)(=O)Nc2cccc(S(=O)(=O)N3CCOCC3)c2)cc1]

LC-MS retention time=1.38 min; m/z=632.3 [M+H]+. (Column: Waters BEH C18, 2.0×50 mm, 1.7-µm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-48

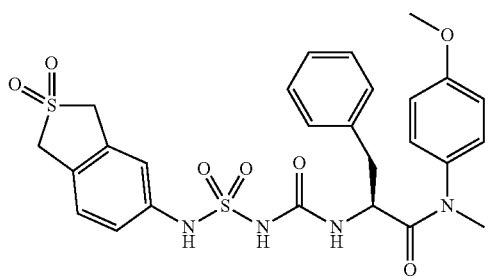 [SMILES: COc1ccc(N(C)C(=O)[C@H](Cc2ccccc2)NC(=O)NS(=O)(=O)Nc2ccc3c(c2)CS(=O)(=O)C3)cc1]

LC-MS retention time=1.25 min; m/z=573.1 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 7.27 (d, J=7.7 Hz, 1H), 7.17-7.11 (m, 4H), 7.07 (br. s., 3H), 6.95 (d, J=8.4 Hz, 2H), 6.80 (d, J=4.4 Hz, 2H), 6.30 (br. s., 1H), 4.45 (s, 2H), 4.41 (s, 2H), 4.37-4.30 (m, 1H), 3.80 (s, 3H), 3.09 (s, 3H), 2.78-2.71 (m, 1H), 2.56-2.48 (m, 1H).

Example CA-49

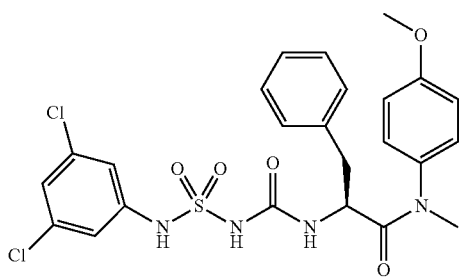 [SMILES: COc1ccc(N(C)C(=O)[C@H](Cc2ccccc2)NC(=O)NS(=O)(=O)Nc2cc(Cl)cc(Cl)c2)cc1]

LC-MS retention time=1.68 min; m/z=551.1 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-50

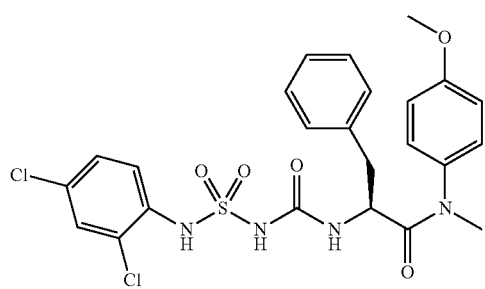 [SMILES: COc1ccc(N(C)C(=O)[C@H](Cc2ccccc2)NC(=O)NS(=O)(=O)Nc2ccc(Cl)cc2Cl)cc1]

LC-MS retention time=2.73 min; m/z=551.1 [M+H]⁺. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-51

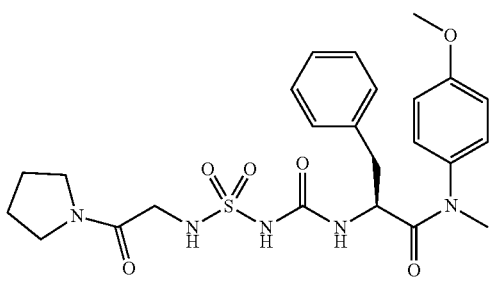 [SMILES: COc1ccc(N(C)C(=O)[C@H](Cc2ccccc2)NC(=O)NS(=O)(=O)NCC(=O)N2CCCC2)cc1]

LC-MS retention time=1.32 min; m/z=518.3 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-52

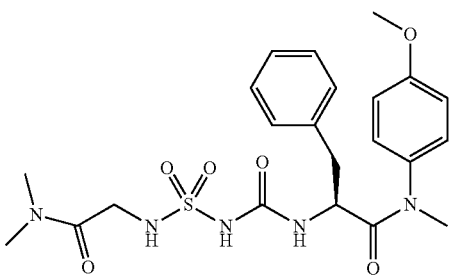 [SMILES: COc1ccc(N(C)C(=O)[C@H](Cc2ccccc2)NC(=O)NS(=O)(=O)NCC(=O)N(C)C)cc1]

LC-MS retention time=1.25 min; m/z=492.2 [M+H]⁺. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example CA-56

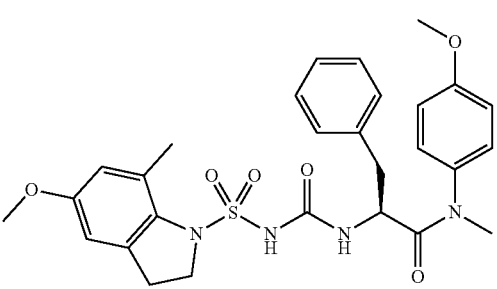 [SMILES: COc1ccc(N(C)C(=O)[C@H](Cc2ccccc2)NC(=O)NS(=O)(=O)N2CCc3cc(OC)cc(C)c32)cc1]

LC-MS retention time=2.67 min; m/z=553.5 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-58

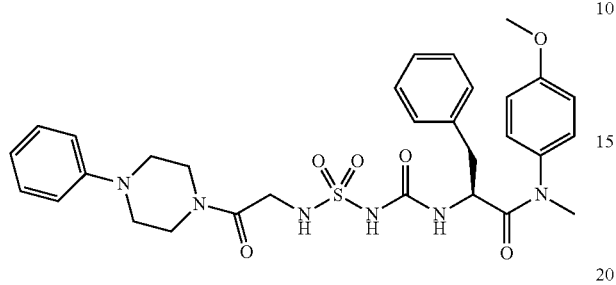

LC-MS retention time=2.64 min; m/z=609.2 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-59

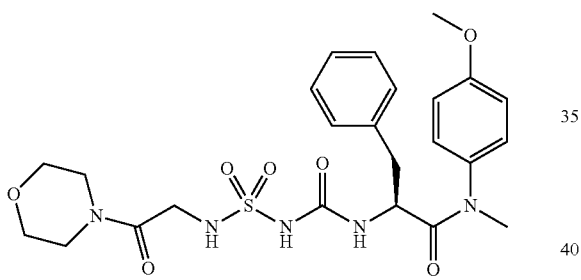

LC-MS retention time=1.19 min; m/z=534.1 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-60

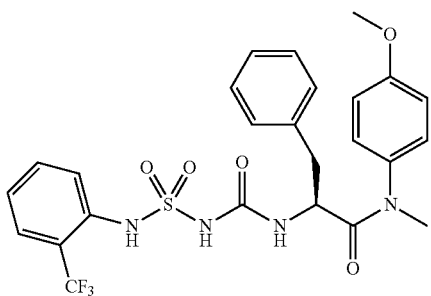 [SMILES: COc1ccc(N(C)C(=O)[C@H](Cc2ccccc2)NC(=O)NS(=O)(=O)Nc2ccccc2C(F)(F)F)cc1]

LC-MS retention time=2.61 min; m/z=551.4 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-61

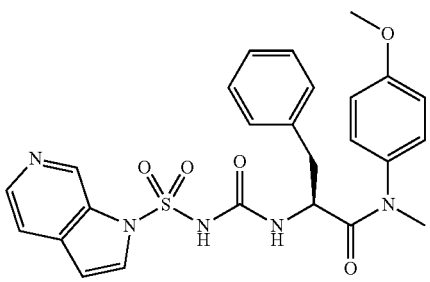 [SMILES: COc1ccc(N(C)C(=O)[C@H](Cc2ccccc2)NC(=O)NS(=O)(=O)n2ccc3ccncc32)cc1]

LC-MS retention time=1.34 min; m/z=507.9 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-62

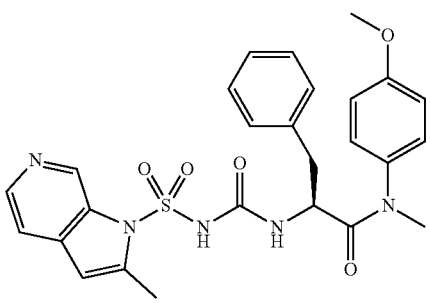 [SMILES: COc1ccc(N(C)C(=O)[C@H](Cc2ccccc2)NC(=O)NS(=O)(=O)n2c(C)cc3ccncc32)cc1]

LC-MS retention time=2.38 min; m/z=522.2 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-63

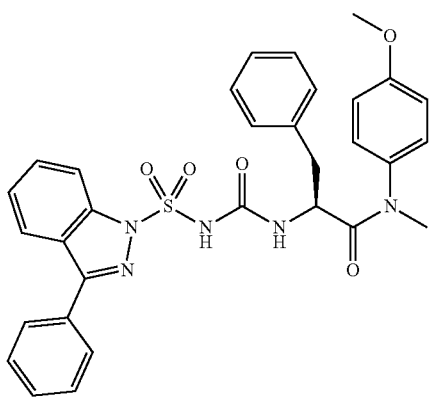 [SMILES: COc1ccc(N(C)C(=O)[C@H](Cc2ccccc2)NC(=O)NS(=O)(=O)n2nc(-c3ccccc3)c3ccccc32)cc1]

LC-MS retention time=3.09 min; m/z=584.4 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-64

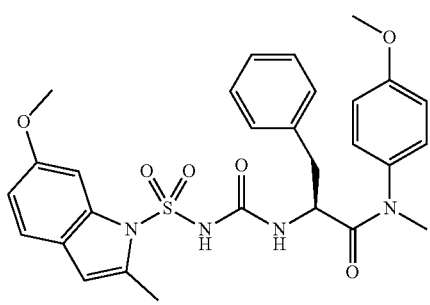 [SMILES: COc1ccc(N(C)C(=O)[C@H](Cc2ccccc2)NC(=O)NS(=O)(=O)n2c(C)cc3ccc(OC)cc32)cc1]

LC-MS retention time=1.66 min; m/z=551.2 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example CA-65

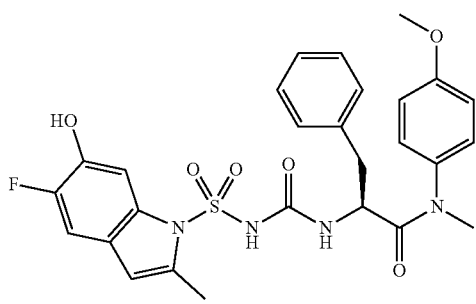 [SMILES: COc1ccc(N(C)C(=O)[C@H](Cc2ccccc2)NC(=O)NS(=O)(=O)n2c(C)cc3cc(F)c(O)cc32)cc1]

LC-MS retention time=2.53 min; m/z=555.2 [M+H]⁺. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220).

Example CA-66

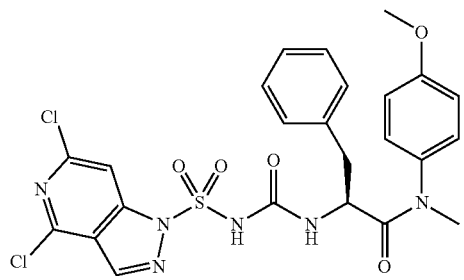 [SMILES: COc1ccc(N(C)C(=O)[C@H](Cc2ccccc2)NC(=O)NS(=O)(=O)n2ncc3c(Cl)nc(Cl)cc32)cc1]

LC-MS retention time=1.60 min; m/z=577.2 [M+H]⁺. (Column: Waters BEH C18, 2.0×50 mm, 1.7-μm particles. Solvent A=95% Water: 5% Acetonitrile: 10 mM NH₄OAc. Solvent B=5% Water: 95% Acetonitrile: 10 mM NH₄OAc. Flow Rate=0.5 mL/min. Start % B=0. Final % B=100. Gradient Time=3 minutes, then a 0.5-minute hold at 100% B. Wavelength=220).

Example ZY-1

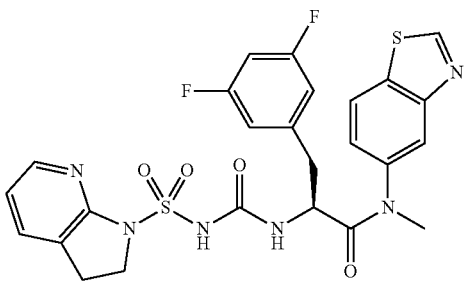 [SMILES: CN(C(=O)[C@H](Cc1cc(F)cc(F)c1)NC(=O)NS(=O)(=O)N1CCc2cccnc21)c1ccc2scnc2c1]

A solution of an HCl salt of Intermediate ZY-5 (55 mg, 0.13 mmol) in DCM (0.5 mL) and TEA (0.018 mL, 0.13 mmol) was added to a solution of sulfurisocyanatidic chloride (0.014 mL, 0.16 mmol) in DCM (0.5 mL) at 0° C. and the reaction mixture was stirred 0° C. for 20 min. Then, 2,3-dihydro-1H-pyrrolo[2,3-b]pyridine (23.6 mg, 0.196 mmol) in DCM (0.5 mL) and TEA (0.073 mL, 0.52 mmol) was added to the reaction mixture and stirring was continued at rt for 2 h. The crude reaction mixture was concentrated and the residue was dissolved into MeOH, filtered and purified by preparative HPLC to yield the title compound (24.5 mg). LC-MS retention time=2.22 min; m/z=571.1 [M–H]⁻. (Column: Waters BEH C18, 2.0×50 mm, 1.7-μm particles. Solvent A=95% Water: 5% MeOH: 10 mM NH₄OAc. Solvent B=5% Water: 95% MeOH: 10 mM NH₄OAc. Flow Rate=0.5 mL/min. Start % B=0. Final % B=100. Gradient Time=3 minutes, then a 0.5-minute hold at 100% B. Wavelength=220). ¹H NMR (500 MHz, DMSO-d₆) δ 9.49 (s, 1H), 8.19 (d, J=8.4 Hz, 1H), 7.99 (d, J=4.4 Hz, 1H), 7.82 (br. s., 1H), 7.56 (d, J=7.3 Hz, 1H), 7.19 (d, J=7.0 Hz, 1H), 7.02-6.95 (m, 1H), 6.90 (br. s., 1H), 6.66 (br. s., 1H), 6.39 (d, J=7.0 Hz, 2H), 4.28 (d, J=5.5 Hz, 1H), 4.06 (br. s., 2H), 3.17 (s, 3H), 3.07 (dd, J=18.3, 9.2 Hz, 2H), 2.80-2.74 (m, 1H), 2.57-2.52 (m, 1H).

Example ZY-2

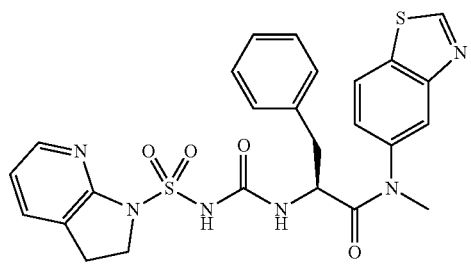 [SMILES: CN(C(=O)[C@H](Cc1ccccc1)NC(=O)NS(=O)(=O)N1CCc2cccnc21)c1ccc2scnc2c1]

A solution of an HCl salt of Intermediate ZY-3 (50 mg, 0.13 mmol) in DCM (0.5 mL) and TEA (0.036 mL, 0.26 mmol) was added to a solution of sulfurisocyanatidic chloride (0.011 mL, 0.13 mmol) in DCM (0.5 mL) at 0° C. and the reaction mixture was stirred 0° C. for 30 min. Then, 2,3-dihydro-1H-pyrrolo[2,3-b]pyridine (17.2 mg, 0.143 mmol) in DCM (0.5 mL) and TEA (0.054 mL, 0.39 mmol) was added to the reaction mixture and stirring was continued at rt for 2 h. The crude reaction mixture was concentrated and the residue was dissolved into MeOH, filtered and purified by preparative HPLC to yield the title compound (3.9 mg). LC-MS retention time=2.49 min; m/z=536.9 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3.5 minutes, then a 0.5-minute hold at 100% B. Wavelength=220).

Example ZY-8

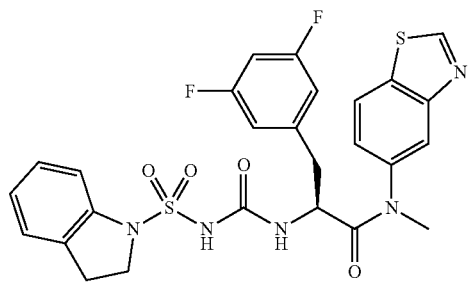 [SMILES: CN(C(=O)[C@H](Cc1cc(F)cc(F)c1)NC(=O)NS(=O)(=O)N1CCc2ccccc21)c1ccc2scnc2c1]

Example ZY-8 was synthesized using the procedure described above for Example ZY-1 with indoline replacing 2,3-dihydro-1H-pyrrolo[2,3-b]pyridine as the final amine input. LC-MS retention time=1.47 min; m/z=572.6 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-9

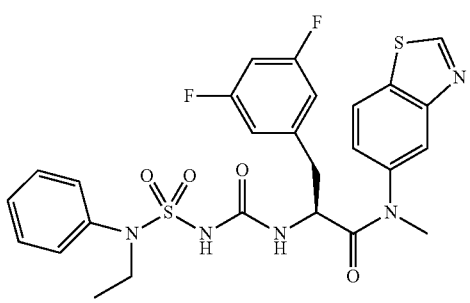 [SMILES: CCN(c1ccccc1)S(=O)(=O)NC(=O)N[C@@H](Cc1cc(F)cc(F)c1)C(=O)N(C)c1ccc2scnc2c1]

Example ZY-9 was synthesized using the procedure described above for Example ZY-1 with N-ethylaniline replacing 2,3-dihydro-1H-pyrrolo[2,3-b]pyridine as the final amine input. LC-MS retention time=1.71 min; m/z=574.6 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-10

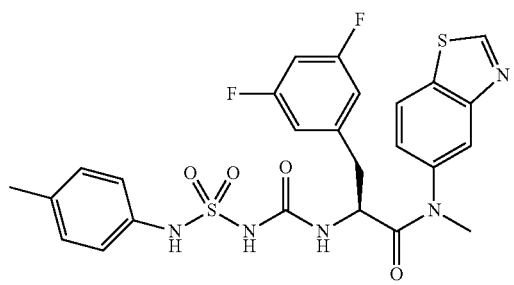 [SMILES: Cc1ccc(NS(=O)(=O)NC(=O)N[C@@H](Cc2cc(F)cc(F)c2)C(=O)N(C)c2ccc3scnc3c2)cc1]

Example ZY-10 was synthesized using the procedure described above for Example ZY-1 with p-toluidine replacing 2,3-dihydro-1H-pyrrolo[2,3-b]pyridine as the final amine input. LC-MS retention time=1.47 min; m/z=560.5 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-11

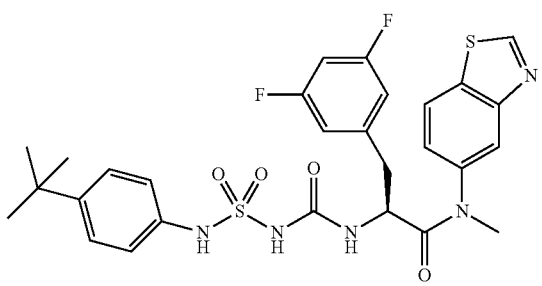 [SMILES: CN(C(=O)[C@H](Cc1cc(F)cc(F)c1)NC(=O)NS(=O)(=O)Nc1ccc(C(C)(C)C)cc1)c1ccc2scnc2c1]

Example ZY-11 was synthesized using the procedure described above for Example ZY-1 with 4-(t-butyl)aniline replacing 2,3-dihydro-1H-pyrrolo[2,3-b]pyridine as the final amine input. LC-MS retention time=1.75 min; m/z=602.7 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-12

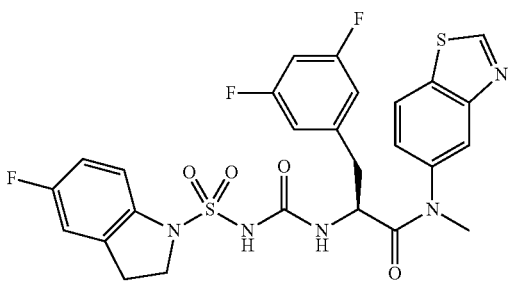 [SMILES: CN(C(=O)[C@H](Cc1cc(F)cc(F)c1)NC(=O)NS(=O)(=O)N1CCc2cc(F)ccc21)c1ccc2scnc2c1]

Example ZY-12 was synthesized using the procedure described above for Example ZY-1 with 5-fluoroindoline replacing 2,3-dihydro-1H-pyrrolo[2,3-b]pyridine as the final amine input. LC-MS retention time=1.47 min; m/z=590.2 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-15

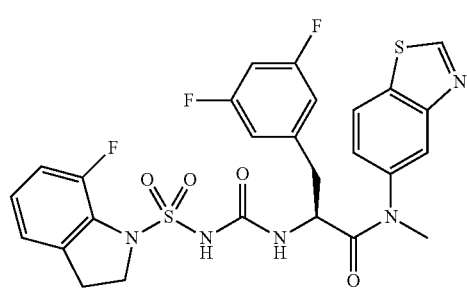 [SMILES: CN(C(=O)[C@H](Cc1cc(F)cc(F)c1)NC(=O)NS(=O)(=O)N1CCc2cccc(F)c21)c1ccc2scnc2c1]

Example ZY-15 was synthesized using the procedure described above for Example ZY-1 with 7-fluoroindoline replacing 2,3-dihydro-1H-pyrrolo[2,3-b]pyridine as the final amine input. LC-MS retention time=2.36 min; m/z=590.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

Example ZY-18

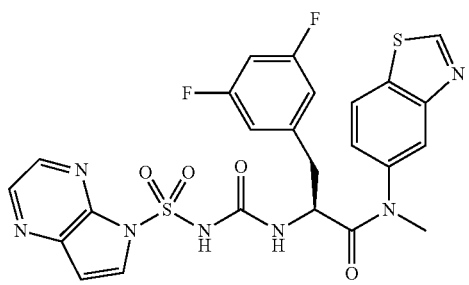 [SMILES: CN(C(=O)[C@H](Cc1cc(F)cc(F)c1)NC(=O)NS(=O)(=O)n1ccc2nccnc21)c1ccc2scnc2c1]

Example ZY-18 was synthesized using the procedure described above for Example ZY-1 with 5H-pyrrolo[2,3-b]pyrazine replacing 2,3-dihydro-1H-pyrrolo[2,3-b]pyridine as the final amine input. LC-MS retention time=2.04 min; m/z=572.1 [M+H]$^+$. (Column: Waters BEH C18, 2.0×50 mm, 1.7-μm particles. Solvent A=95% Water: 5% MeOH: 10 mM NH$_4$OAc. Solvent B=5% Water: 95% MeOH: 10 mM NH$_4$OAc. Flow Rate=0.5 mL/min. Start % B=0. Final % B=100. Gradient Time=3 minutes, then a 0.5-minute hold at 100% B. Wavelength=220).

For Examples CA-113 through CA-120, the following procedure was utilized: A solution of an HCl salt of Intermediate ZY-5 (380 mg, 1.0 mmol) and triethylamine (280 μL, 2.0 mmol) in DCM (5.0 mL) was added dropwise a solution of sulfurisocyanatidic chloride (130 μL, 1.5 mmol) in DCM (2.5 mL) at 0° C. and the reaction mixture was allowed to stir under nitrogen at 0° C. for 1 h. A solution of triethylamine (490 μL, 3.5 mmol) in DCM (2.5 mL) was then added and the reaction mixture was allowed to stir for 5 min. A portion of the crude reaction mixture (1 mL) was then added to a solution of the appropriate aniline (0.20 mmol) in DCM (0.25 mL) and the reaction mixture was allowed to shake at rt overnight. The reaction was diluted with MeOH (0.5 mL), concentrated to dryness, dissolved into DMF (1 mL), filtered and purified by preparative HPLC to yield the respective title compounds.

Example CA-113

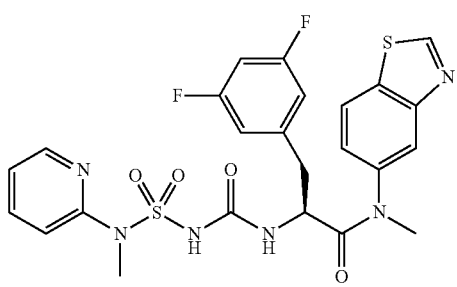 [SMILES: CN(C(=O)[C@H](Cc1cc(F)cc(F)c1)NC(=O)NS(=O)(=O)N(C)c1ccccn1)c1ccc2scnc2c1]

LC-MS retention time=1.30 min; m/z=561.1 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-114

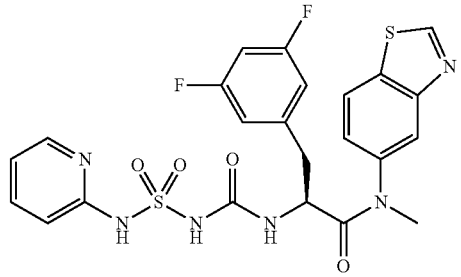 [SMILES: CN(C(=O)[C@H](Cc1cc(F)cc(F)c1)NC(=O)NS(=O)(=O)Nc1ccccn1)c1ccc2scnc2c1]

LC-MS retention time=2.14 min; m/z=547.2 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-115

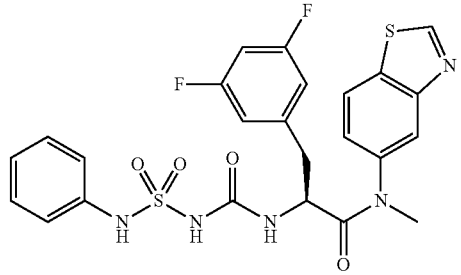 [SMILES: CN(C(=O)[C@H](Cc1cc(F)cc(F)c1)NC(=O)NS(=O)(=O)Nc1ccccc1)c1ccc2scnc2c1]

LC-MS retention time=2.75 min; m/z=545.9 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-116

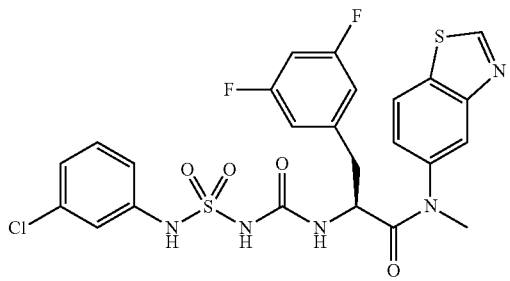 [SMILES: CN(C(=O)[C@H](Cc1cc(F)cc(F)c1)NC(=O)NS(=O)(=O)Nc1cccc(Cl)c1)c1ccc2scnc2c1]

LC-MS retention time=1.57 min; m/z=579.9 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-117

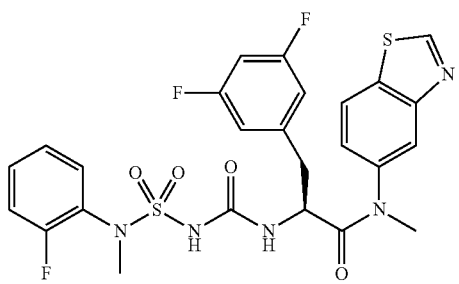 [SMILES: CN(C(=O)[C@H](Cc1cc(F)cc(F)c1)NC(=O)NS(=O)(=O)N(C)c1ccccc1F)c1ccc2scnc2c1]

LC-MS retention time=1.69 min; m/z=577.9 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-118

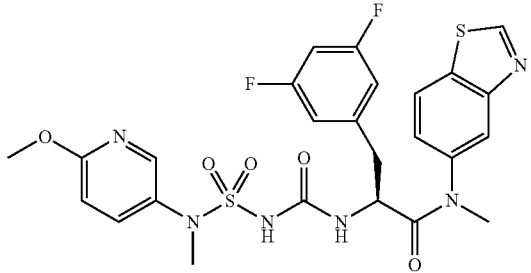 [SMILES: COc1ccc(N(C)S(=O)(=O)NC(=O)N[C@@H](Cc2cc(F)cc(F)c2)C(=O)N(C)c2ccc3scnc3c2)cn1]

LC-MS retention time=1.54 min; m/z=591.0 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-119

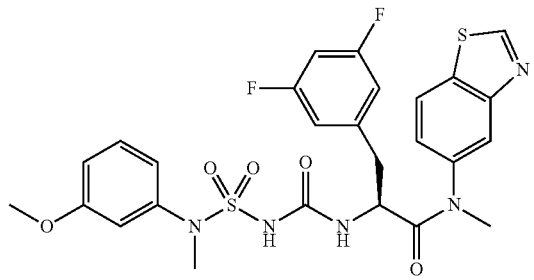 [SMILES: COc1cccc(N(C)S(=O)(=O)NC(=O)N[C@@H](Cc2cc(F)cc(F)c2)C(=O)N(C)c2ccc3scnc3c2)c1]

LC-MS retention time=2.47 min; m/z=590.3 [M+H]+. (Column: Waters BEH C18, 2.0×50 mm, 1.7-μm particles. Solvent A=95% Water: 5% MeOH: 10 mM NH4OAc. Solvent B=5% Water: 95% MeOH: 10 mM NH4OAc. Flow Rate=0.5 mL/min. Start % B=0. Final % B=100. Gradient Time=3 minutes, then a 0.5-minute hold at 100% B. Wavelength=220).

Example CA-120

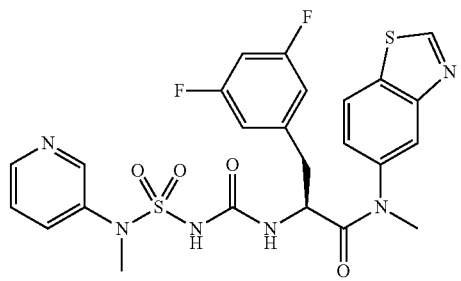 [SMILES: CN(C(=O)[C@H](Cc1cc(F)cc(F)c1)NC(=O)NS(=O)(=O)N(C)c1cccnc1)c1ccc2scnc2c1]

LC-MS retention time=1.33 min; m/z=560.9 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example CA-121

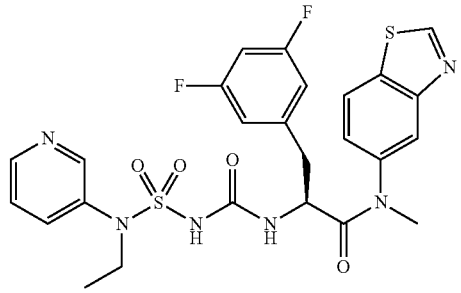 [SMILES: CCN(c1cccnc1)S(=O)(=O)NC(=O)N[C@@H](Cc1cc(F)cc(F)c1)C(=O)N(C)c1ccc2scnc2c1]

LC-MS retention time=1.41 min; m/z=575.1 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220).

Example VN-1 and VN-2

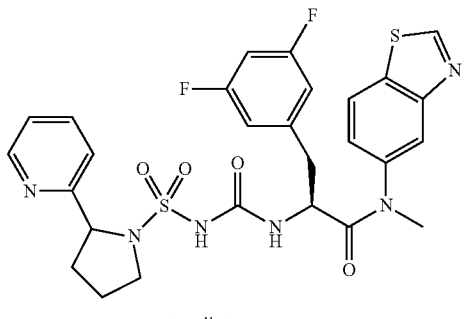

two diastereomers

Examples VN-1 and VN-2 were synthesized using the procedure described above for Example ZY-1 with 2-(pyrrolidin-2-yl)pyridine replacing 2,3-dihydro-1H-pyrrolo[2,3-b]pyridine as the final amine input. Purification by preparative HPLC (Column: XBridge C18, 19×200 mm, 5-μm particles CH3CN, water, NH4OAc) to afford Example VN-1 (39.2 mg) and Example VN-2 (21.2 mg).

Example VN-1: LC-MS retention time=1.53 min; m/z=601.1 [M+H]+. ((Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-$d_6$) δ 9.51 (s, 1H), 8.48 (s, 1H), 8.37-8.15 (m, 1H), 8.05 (s, 1H), 7.95 (s, 1H), 7.73 (app t, J=7.2 Hz, 1H), 7.51-7.30 (m, 2H), 7.30-7.14 (m, 1H), 7.14-6.92 (m, 1H), 6.79-6.58 (m, 1H), 6.57-6.45 (m, 2H), 5.08-4.85 (m, 1H), 4.50-4.31 (m, 1H), 3.25 (s, 3H), 3.19-3.14 (m, 1H), 3.00-2.84 (m, 1H), 2.72-2.58 (m, 1H), 2.19-1.98 (m, 1H), 1.96-1.82 (m, 1H), 1.82-1.62 (m, 3H).

Example VN-2: LC-MS retention time=1.58 min; m/z=601.1 [M+H]+. (Column: Waters BEH C18, 2.0×50 mm, 1.7-μm particles. Solvent A=95% Water: 5% Acetonitrile: 10 mM NH4OAc. Solvent B=5% Water: 95% Acetonitrile: 10 mM NH4OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-$d_6$) δ 9.52 (s, 1H), 8.47 (s, 1H), 8.38-8.24 (m, 1H), 8.13 (s, 1H), 7.84-7.63 (m, 1H), 7.63-7.43 (m, 1H), 7.43-7.29 (m, 2H), 7.29-7.13 (m, 1H), 7.09-6.98 (m, 1H), 6.85-6.65 (m, 1H), 6.53-6.43 (m, 2H), 5.25-5.02 (m, 1H), 4.53-4.39 (m, 1H), 3.26 (s, 3H), 3.23-3.10 (m, 2H), 3.01-2.90 (m, 1H), 2.71-2.61 (m, 1H), 1.85-1.71 (m, 1H), 1.71-1.50 (m, 3H).

Example VN-3 and VN-4

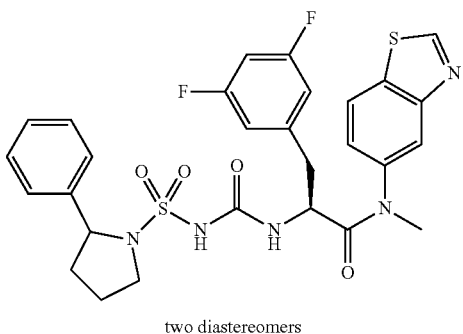 [SMILES: CN(C(=O)[C@H](Cc1cc(F)cc(F)c1)NC(=O)NS(=O)(=O)N1CCCC1c1ccccc1)c1ccc2scnc2c1]

two diastereomers

Examples VN-3 and VN-4 was synthesized using the procedure described above for Example ZY-1 with 2-phenylpyrrolidine replacing 2,3-dihydro-1H-pyrrolo[2,3-b]pyridine as the final amine input. Purification by preparative HPLC (Column: XBridge C18, 19×200 mm, 5-μm particles CH$_3$CN, water, NH$_4$OAc) to afford Example VN-3 (24.3 mg) and Example VN-4 (9.7 mg).

Example VN-3: LC-MS retention time=1.82 min; m/z=600.5 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 9.54 (s, 1H), 8.35 (app d, J=8.1 Hz, 1H), 8.16 (s, 1H), 7.51 (app d, J=9.2 Hz, 1H), 7.36-7.15 (m, 6H), 7.06 (app t, J=9.9 Hz, 1H), 6.73 (app d, J=8.1 Hz, 1H), 6.48 (app d, J=5.1 Hz, 2H), 5.05-4.98 (m, 1H), 4.50-4.42 (m, 1H), 3.48-3.38 (m, 1H), 3.28 (s, 3H), 3.23-3.10 (m, 1H), 3.06-2.87 (m, 1H), 2.74-2.55 (m, 1H), 1.99-1.77 (m, 1H), 1.72-1.55 (m, 3H).

Example VN-4: LC-MS retention time=1.85 min; m/z=600.6 [M+H]$^+$. (Column: Waters BEH C18, 2.0×50 mm, 1.7-μm particles. Solvent A=95% Water: 5% Acetonitrile: 10 mM NH$_4$OAc. Solvent B=5% Water: 95% Acetonitrile: 10 mM NH$_4$OAc. Flow Rate=0.5 mL/min. Start % B=0. Final % B=100. Gradient Time=3 minutes, then a 0.5-minute hold at 100% B. Wavelength=220). $^1$H NMR (500 MHz, DMSO-d$_6$) δ 9.54 (s, 1H), 8.35 (app d, J=8.1 Hz, 1H), 8.16 (s, 1H), 7.51 (app d, J=9.2 Hz, 1H), 7.36-7.15 (m, 6H), 7.06 (app t, J=9.9 Hz, 1H), 6.73 (app d, J=8.1 Hz, 1H), 6.48 (app d, J=5.1 Hz, 2H), 5.05-4.98 (m, 1H), 4.50-4.42 (m, 1H), 3.48-3.16 (m, 5H), 3.06-2.87 (m, 1H), 2.74-2.55 (m, 1H), 1.99-1.77 (m, 1H), 1.72-1.55 (m, 3H).

Example ZY-19

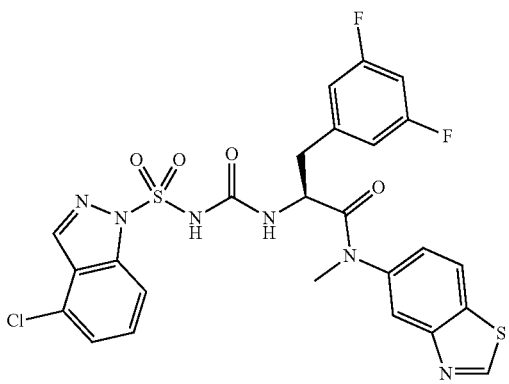 [SMILES: CN(C(=O)[C@H](Cc1cc(F)cc(F)c1)NC(=O)NS(=O)(=O)n1ncc2c(Cl)cccc21)c1ccc2scnc2c1]

To a solution of sulfurisocyanatidic chloride (0.016 mL, 0.18 mmol) in DCM (0.5 mL) was added a solution of an HCl salt of Intermediate ZY-5 (50 mg, 0.12 mmol) and TEA (0.017 mL, 0.12 mmol) in DCM (0.5 mL) and the reaction mixture was stirred at rt for 20 min. Then 4-chloro-1H-indazole (27.2 mg, 0.18 mmol) in DCM (0.5 mL) and TEA (0.066 mL, 0.47 mmol) was added and the reaction mixture was stirred at rt for 1 d. The reaction mixture was concentrated and the residue was dissolved in MeOH, filtered and purified by preparative HPLC to afford the title compound (4.7 mg). LC-MS retention time=1.48 min; m/z=605.4 [M+H]$^+$. (Column: Waters Acquity BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 0.5 mL/min; Detection: UV at 220 nm).

Example ZY-20

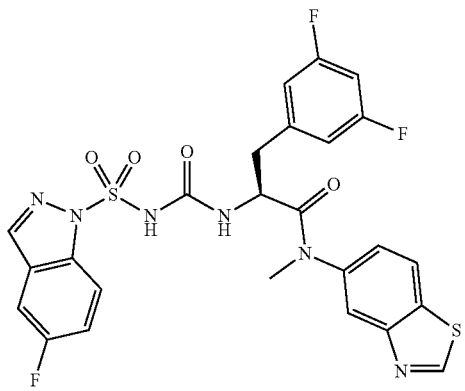 [SMILES: CN(C(=O)[C@H](Cc1cc(F)cc(F)c1)NC(=O)NS(=O)(=O)n1ncc2cc(F)ccc21)c1ccc2scnc2c1]

To a solution of sulfurisocyanatidic chloride (0.016 mL, 0.18 mmol) in DCM (0.5 mL) was added a solution of an HCl salt of Intermediate ZY-5 (50 mg, 0.12 mmol) and TEA (0.017 mL, 0.12 mmol) in DCM (0.5 mL) and the reaction mixture was stirred at rt for 1 h. Then a solution of 5-fluoro-1H-indazole (24.3 mg, 0.18 mmol) in DCM (0.5 mL) and TEA (0.066 mL, 0.47 mmol) was added and the reaction mixture was stirred at rt for 16 h. The reaction was filtered and purified by preparative HPLC to afford the title compound (10.4 mg). LC-MS retention time=1.43 min; m/z=589.5 [M+H]$^+$. (Column: Waters Acquity BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 0.5 mL/min; Detection: UV at 220 nm).

Example VN-5

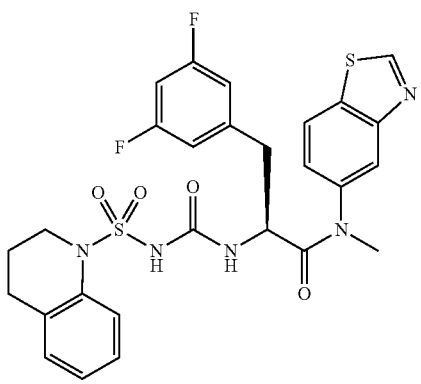 [SMILES: CN(C(=O)[C@H](Cc1cc(F)cc(F)c1)NC(=O)NS(=O)(=O)N1CCCc2ccccc21)c1ccc2scnc2c1]

To a solution of sulfurisocyanatidic chloride (0.022 g, 0.16 mmol) in CH$_2$Cl$_2$ (0.5 mL) under nitrogen at 0° C. was added a solution of an HCl salt of Intermediate ZY-5 (0.050 g, 0.130 mmol) and triethylamine (0.018 mL, 0.130 mmol) in CH$_2$Cl$_2$ (0.5 mL) dropwise over 1 min. The reaction mixture was stirred at 0° C. under nitrogen for 30 min, then a solution of 1,2,3,4-tetrahydroquinoline (0.017 g, 0.13 mmol) in CH$_2$Cl$_2$ (0.5 mL) was added dropwise, followed by the addition of triethylamine (0.091 mL, 0.65 mmol). The reaction was removed from the cold bath and stirred at ~25° C. under nitrogen for 18 h. The reaction was concentrated in vacuo. The residue was dissolved in MeOH (2 mL) and purified via preparative HPLC (AcCN/water/NH$_4$OAc) to afford the title compound (9.1 mg); LC-MS retention time=1.54 min; m/z=586.5 [M+H]$^+$. (Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example VN-6 and Example VN-7

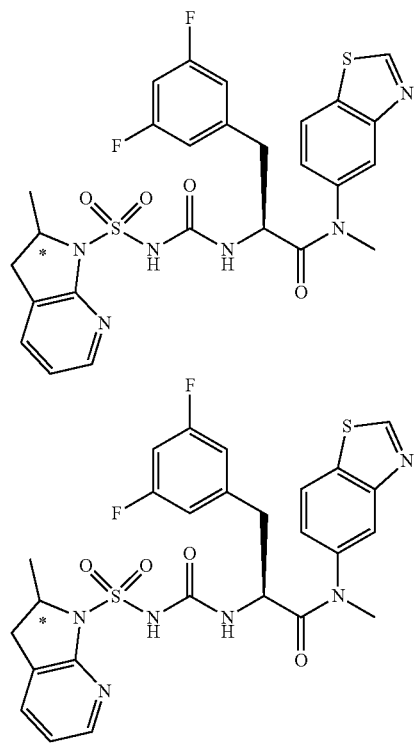

To a solution of sulfurisocyanatidic chloride (0.041 g, 0.29 mmol) in CH$_2$Cl$_2$ (1 mL) under nitrogen at 0° C. was added a solution of an HCl salt of Intermediate ZY-5 (0.10 g, 0.3 mmol) and triethylamine (0.036 mL, 0.26 mmol) in CH$_2$Cl$_2$ (1 mL). The reaction was stirred at 0° C. under nitrogen for 30 min, then a solution of an HCl salt of racemic Intermediate VN-3 (0.044 g, 0.26 mmol) in CH$_2$Cl$_2$ (1 mL) was added, followed by triethylamine (0.182 mL, 1.303 mmol). The reaction was removed from the cold bath and stirred under nitrogen at ~25° C. for 18 h. All solvents were removed in vacuo. The residue was taken up in MeOH (2 mL) and purified via preparative HPLC (AcCN/water/NH$_4$OAc), then further chiral separation by SFC (Column: Chiralpak IA preparative column, 30×250 mm, 5 µm; Mobile Phase: 35% MeOH in CO$_2$, 150 bar; Temperature: 35° C. Flow: 70 mL/min for 16 min, Detection: UV at 220 nm. Injection: 0.75 mL of ~4 mg/mL solution in MeOH (~13 mg purified by stacked injection) to afford the two title compounds:

Example VN-6 (2.2 mg); LC-MS retention time=1.476 min; m/z=587.1 [M+H]$^+$. (Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example VN-7 (6.8 mg). LC-MS retention time=1.381 min; m/z=587.1 [M+H]$^+$. (Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example VN-8

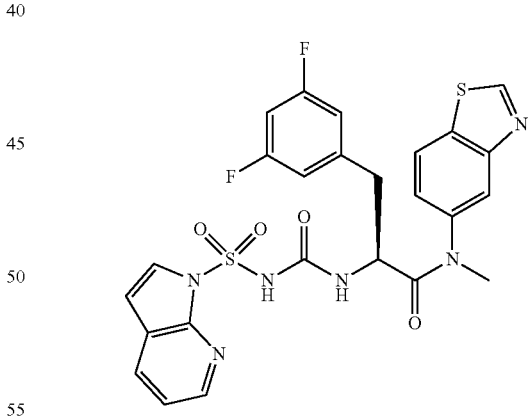

To a solution of sulfurisocyanatidic chloride (0.044 g, 0.31 mmol) in CH$_2$Cl$_2$ (1 mL) under nitrogen at 0° C. was added a solution of an HCl salt of Intermediate ZY-5 (0.10 g, 0.3 mmol) and triethylamine (0.036 mL, 0.26 mmol) in CH$_2$Cl$_2$ (1 mL) dropwise over 1 min. The reaction was stirred at 0° C. under nitrogen for 20 min. The reaction mixture was then added to a mixture of 1H-pyrrolo[2,3-b]pyridine (0.031 g, 0.26 mmol) and 60% NaH (0.031 g, 0.782 mmol) as a dispersion in mineral oil in DMF (1 mL) under nitrogen and stirred at ~25° C. for 18 h. All solvents were removed in vacuo. The residue was taken up in MeOH (1 mL) and purified via preparative HPLC (AcCN/water/NH₄OAc) to afford the title compound (4.4 mg). LC-MS retention time=1.27 min; m/z=571.5 [M+H]⁺. (Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example ZY-21

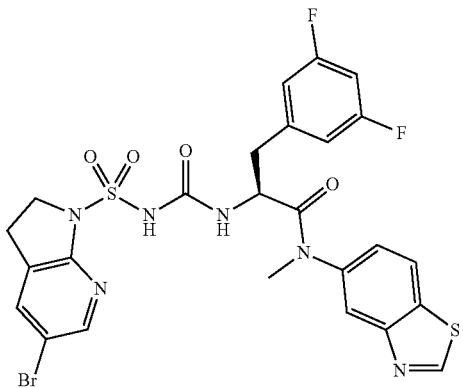 [SMILES: CN(C(=O)[C@H](Cc1cc(F)cc(F)c1)NC(=O)NS(=O)(=O)N1CCc2cc(Br)cnc21)c1ccc2scnc2c1]

To a solution of sulfurisocyanatidic chloride (0.016 mL, 0.18 mmol) in DCM (0.5 mL) was added a solution of an HCl salt of Intermediate ZY-5 (50 mg, 0.12 mmol) in DCM (0.5 mL) and TEA (0.017 mL, 0.12 mmol) and the reaction mixture was stirred at rt for 30 min. Then 5-bromo-2,3-dihydro-1H-pyrrolo[2,3-b]pyridine (35.5 mg, 0.18 mmol) in DMF and TEA (0.066 mL, 0.47 mmol) was added and the reaction mixture was stirred at rt for 16 h. The reaction mixture was concentrated and the residue was dissolved in MeOH, filtered and purified by preparative HPLC to afford the title compound (19.8 mg). LC-MS retention time=1.39 min; m/z=651.5 [M+H]⁺. (Column: Waters Acquity BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 0.5 mL/min; Detection: UV at 220 nm).

Example ZY-22

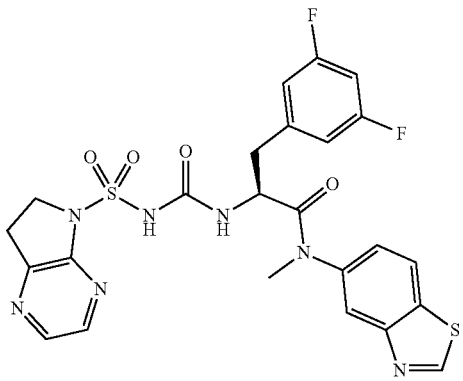 [SMILES: CN(C(=O)[C@H](Cc1cc(F)cc(F)c1)NC(=O)NS(=O)(=O)N1CCc2nccnc21)c1ccc2scnc2c1]

To a solution of sulfurisocyanatidic chloride (0.016 mL, 0.18 mmol) in DCM (0.5 mL) was added a solution of an HCl salt of Intermediate ZY-5 (50 mg, 0.12 mmol) and TEA (0.017 mL, 0.12 mmol) in DCM (1.5 mL) and the mixture was stirred at rt for 20 min. Then a solution of an HCl salt of 6,7-dihydro-5H-pyrrolo[2,3-b]pyrazine (28.1 mg, 0.18 mmol) in DCM (0.5 mL), DMF (1 mL) and TEA (0.066 mL, 0.47 mmol) was added and the reaction mixture was stirred at rt for 16 h. The reaction mixture was concentrated and the residue was dissolved in MeOH/DMF, filtered and purified by preparative HPLC to afford the title compound (12.7 mg). LC-MS retention time=1.08 min; m/z=574.5 [M+H]⁺. (Column: Waters Acquity BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 0.5 mL/min; Detection: UV at 220 nm).

Example VN-9

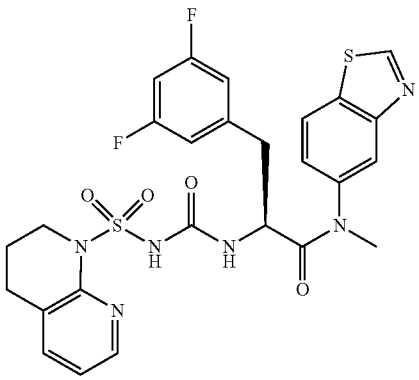 [SMILES: CN(C(=O)[C@H](Cc1cc(F)cc(F)c1)NC(=O)NS(=O)(=O)N1CCCc2cccnc21)c1ccc2scnc2c1]

To a solution of sulfurisocyanatidic chloride (0.044 g, 0.31 mmol) in CH₂Cl₂ (1 mL) under nitrogen at 0° C. was added a solution of an HCl salt of Intermediate ZY-5 (0.10 g, 0.26 mmol) and triethylamine (0.036 mL, 0.26 mmol) in CH₂Cl₂ (1 mL) dropwise over 1 min. The reaction was stirred at 0° C. under nitrogen for 25 min and then a solution of 1,2,3,4-tetrahydro-1,8-naphthyridine (0.035 g, 0.26 mmol) in CH₂Cl₂ (1 mL) was added dropwise over 1 min, followed by the addition of triethylamine (0.145 mL, 1.04 mmol). The reaction was removed from the cold bath and stirred at ~25° C. under nitrogen for 2 h. All solvents were removed in vacuo. The residue was taken up in MeOH (2 mL) and purified via preparative HPLC (MeOH/water/NH₄OAc) then repurified with (AcCN/water/NH₄OAc) to afford the title compound (18.0 mg). LC-MS retention time=3.024 min; m/z=587.05 [M+H]⁺. (Column: Waters BEH C18, 2.0×50 mm, 1.7-µm particles; Mobile Phase A: 5:95 MeOH:water with 10 mM ammonium acetate; Mobile Phase B: 95:5 MeOH:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example ZY-23

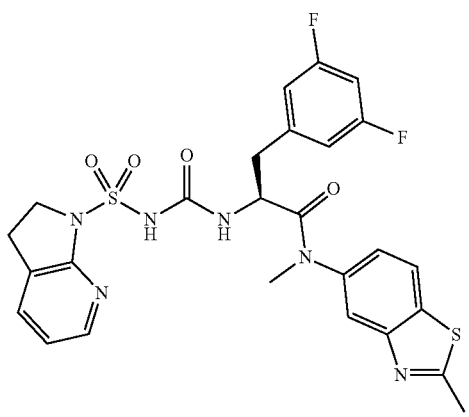 [SMILES: Cc1nc2cc(N(C)C(=O)[C@H](Cc3cc(F)cc(F)c3)NC(=O)NS(=O)(=O)N3CCc4cccnc43)ccc2s1]

To a solution of sulfurisocyanatidic chloride (0.015 mL, 0.17 mmol) in DCM (0.5 mL) was added a DCM (1 mL) solution of an HCl salt of (S)-2-amino-3-(3,5-difluorophenyl)-N-methyl-N-(2-methylbenzo[d]thiazol-5-yl)propanamide (61 mg, 0.14 mmol) and TEA (0.020 mL, 0.14 mmol) and the mixture was stirred at rt for 20 min. Then a solution of 2,3-dihydro-1H-pyrrolo[2,3-b]pyridine (25.3 mg, 0.21 mmol) in DCM (0.5 mL) and TEA (0.078 mL, 0.56 mmol) was added and the reaction mixture was stirred at rt for 4 h. The reaction mixture was concentrated and the residue was dissolved in MeOH, filtered and purified by preparative HPLC to afford the title compound (33.4 mg). LC-MS retention time=1.55 min; m/z=586.9 [M+H]$^+$. (Column: Waters Acquity BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 0.5 mL/min; Detection: UV at 220 nm).

Example VN-10 and Example VN-11

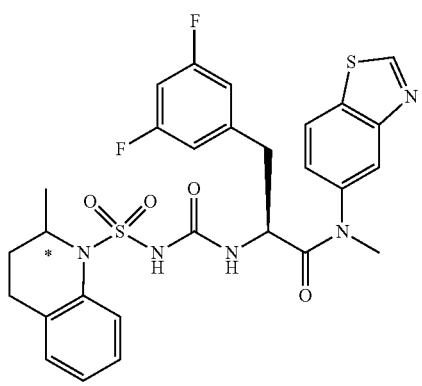

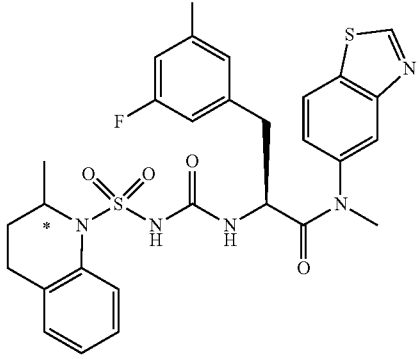

To a solution of sulfurisocyanatidic chloride (0.041 g, 0.29 mmol) in CH$_2$Cl$_2$ (1 mL) under nitrogen at 0° C. was added a solution of an HCl salt of Intermediate ZY-5 (0.1 g, 0.3 mmol) and triethylamine (0.036 mL, 0.26 mmol) in CH$_2$Cl$_2$ (1 mL) dropwise over 1 min. The reaction was stirred at 0° C. under nitrogen for 30 min. Then a solution of racemic 2-methyl-1,2,3,4-tetrahydroquinoline (0.038 g, 0.26 mmol) in CH$_2$Cl$_2$ (1 mL) was added dropwise over 1 min, followed by the addition of triethylamine (0.145 mL, 1.04 mmol). The reaction was removed from the cold bath and stirred at ~25° C. for 5.5 h. All solvents were removed in vacuo. The residue was taken up in MeOH (2 mL) and purified via preparative HPLC to afford the two title compounds:

Example VN-10 (16.1 mg): LC-MS retention time=1.81 min; m/z=600.2 [M+H]$^+$. (Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example VN-11 (13.1 mg): LC-MS retention time=1.85 min; m/z=600.2 [M+H]$^+$. (Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5 minute hold at 100% B; Flow: 1 mL/min; Detection: UV at 220 nm).

Example VN-12

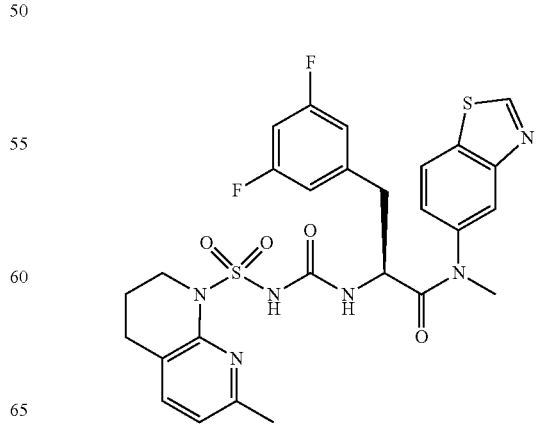

To a solution of sulfurisocyanatidic chloride (0.023 mL, 0.26 mmol) in CH$_2$Cl$_2$ (1 mL) under nitrogen at 0° C. was added a solution of an HCl salt of Intermediate ZY-5 (0.1 g, 0.3 mmol) and triethylamine (0.036 mL, 0.26 mmol) in CH$_2$Cl$_2$ (1 mL) dropwise over 1 min. The reaction was stirred under nitrogen at 0° C. for 8 min. Then a solution of a mixture of Intermediate VN-4.1 and VN 4.2 (0.039 g, 0.26 mmol) (1:0.18) in CH$_2$Cl$_2$ (1 mL) was added to the reaction mixture, followed by the addition of triethylamine (0.182 mL, 1.30 mmol) dropwise over 2 min. The reaction was removed from the cold bath and stirred at ~25° C. under nitrogen for 3.5 h. All solvents were removed in vacuo. The residue was taken up in MeOH (2 mL) and purified via preparative HPLC (AcCN/water/NH$_4$OAc) to afford the title compound (10.9 mg). LC-MS retention time=1.685 min; m/z=600.8 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example ZY-24

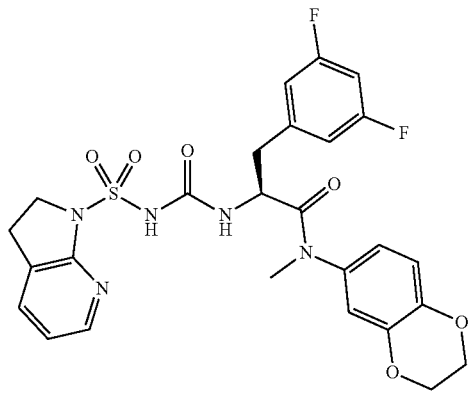 [SMILES: CN(C(=O)[C@H](Cc1cc(F)cc(F)c1)NC(=O)NS(=O)(=O)N1CCc2cccnc21)c1ccc2c(c1)OCCO2]

To a solution of sulfurisocyanatidic chloride (0.012 mL, 0.14 mmol) in DCM (0.5 mL) was added a DCM (1 mL) solution of an HCl salt of Intermediate ZY-24.2 (48 mg, 0.13 mmol) and TEA (0.017 mL, 0.13 mmol). The reaction mixture was stirred for 20 min, a solution of 2,3-dihydro-1H-pyrrolo[2,3-b]pyridine (22.5 mg, 0.19 mmol) in DCM (0.5 mL) and TEA (0.07 mL, 0.5 mmol) was added to the reaction, and stirring was continued at rt for 16 h. The reaction mixture was concentrated, dissolved in MeOH, filtered and purified by preparative HPLC to afford the title compound (7.3 mg). LC-MS retention time=1.88 min; m/z=574.0 [M+H]$^+$. (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm).

Example VN-14

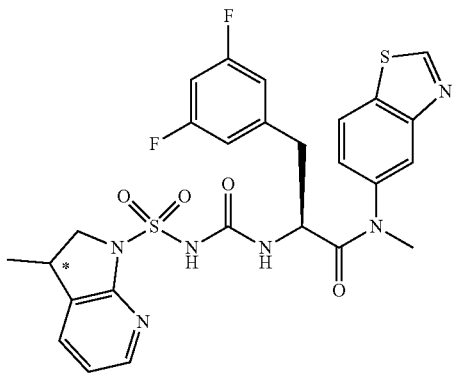 [SMILES: CC1CN(S(=O)(=O)NC(=O)N[C@@H](Cc2cc(F)cc(F)c2)C(=O)N(C)c2ccc3scnc3c2)c2ncccc21]

To a solution of sulfurisocyanatidic chloride (0.023 mL, 0.26 mmol) in CH$_2$Cl$_2$ (0.5 mL) at 0° C. under nitrogen was added a solution of an HCl salt of Intermediate ZY-5 (0.10 g, 0.26 mmol) and triethylamine (0.036 mL, 0.26 mmol) in CH$_2$Cl$_2$ (1 mL) dropwise over 1 min. The reaction was maintained at 0° C. under nitrogen for 15 min, then a solution of Intermediate VN-7 (as a single stereoisomer, absolute stereochemistry undetermined) (0.035 g, 0.26 mmol) in CH$_2$Cl$_2$ (1 mL) was added, followed by the addition of triethylamine (0.145 mL, 1.04 mmol) dropwise over 2 min under nitrogen at 0° C. The reaction was stirred at 0° C. for 25 min. All solvents were removed in vacuo. The residue was taken up in MeOH (2 mL) and purified via preparative HPLC (AcCN/water/NH$_4$OAc) to afford the title compound (49.4 mg). LC-MS retention time=1.566 min; m/z=586.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example VN-15

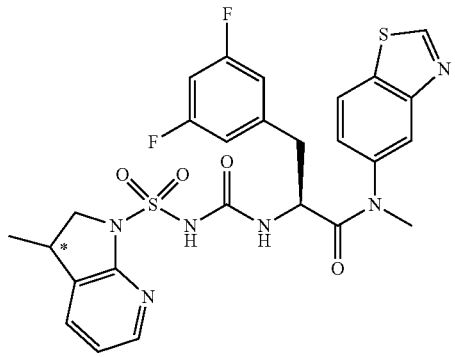 [SMILES: CC1CN(S(=O)(=O)NC(=O)N[C@@H](Cc2cc(F)cc(F)c2)C(=O)N(C)c2ccc3scnc3c2)c2ncccc21]

To a solution of sulfurisocyanatidic chloride (0.023 mL, 0.26 mmol) in CH$_2$Cl$_2$ (0.5 mL) at 0° C. under nitrogen was added a solution of an HCl salt of Intermediate ZY-5 (0.10 g, 0.26 mmol) and triethylamine (0.036 mL, 0.26 mmol) dropwise over 1 min. The reaction mixture was stirred at 0° C. under nitrogen for 20 min. Then a solution of Intermediate VN-8 (as a single stereoisomer, absolute stereochemistry undetermined) (0.035 g, 0.26 mmol) in CH$_2$Cl$_2$ (1 mL) was added, followed by the addition of triethylamine (0.145 mL, 1.04 mmol) dropwise over 2 min. The reaction mixture was stirred at 0° C. under nitrogen for 20 min. All solvents were removed in vacuo. The residue was taken up in MeOH (2 mL) and purified via preparative HPLC (AcCN/water/NH$_4$OAc) to afford the title compound (28.1 mg). LC-MS retention time=1.540 min; m/z=586.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example GW-2

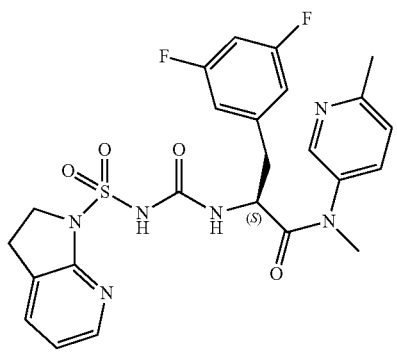

To a solution of sulfurisocyanatidic chloride (34 mg, 0.24 mmol) in DCM (1 mL) in an ice-water bath was added a solution of an HCl salt of Intermediate GW-3 (75 mg, 0.20 mmol) and TEA (0.1 mL, 0.6 mmol) in DCM (1 mL) over 2 min and the reaction mixture was stirred for 20 min. Then a solution of 2,3-dihydro-1H-pyrrolo[2,3-b]pyridine (36 mg, 0.30 mmol) in DCM (1 mL) was added, followed by TEA (0.1 mL, 0.79 mmol), the bath was removed and the reaction mixture was stirred at rt for 2 h. The reaction mixture was concentrated and the residue was redissolved in methanol and purified by preparative HPLC to afford the title compound (9.8 mg). LC-MS retention time=2.69 min; m/z=553.08 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example ZY-25

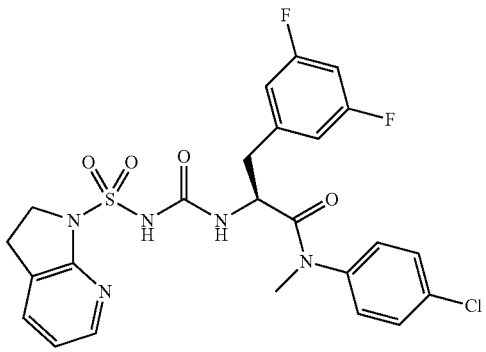 [SMILES: CN(C(=O)[C@H](Cc1cc(F)cc(F)c1)NC(=O)NS(=O)(=O)N1CCc2cccnc21)c1ccc(Cl)cc1]

To a solution of sulfurisocyanatidic chloride (0.012 mL, 0.14 mmol) in DCM (0.5 mL) was added a DCM (1 mL) solution of an HCl salt of Intermediate ZY-25.2 (46.4 mg, 0.13 mmol) and the reaction mixture was stirred for 20 min. Then solution of 2,3-dihydro-1H-pyrrolo[2,3-b]pyridine (23.1 mg, 0.19 mmol) in DCM (0.5 mL) and TEA (0.072 mL, 0.51 mmol) was added, and the reaction mixture was stirred at rt for 3 h. The reaction mixture was concentrated, dissolved in MeOH, filtered and purified by preparative HPLC to afford the title compound (27.3 mg). LC-MS retention time=1.72 min; m/z=549.9 [M+H]$^+$. (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm).

Example BB-1

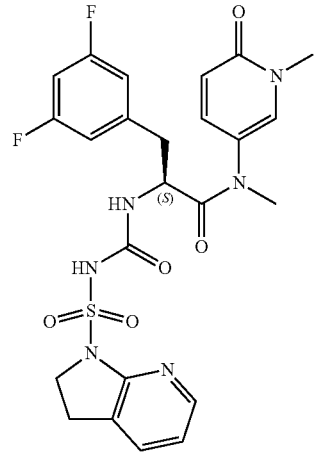

To a stirred solution of Intermediate BB-21.4 (0.05 g, 0.16 mmol) in DCM (2 mL) was added 2,3-dihydro-1H-pyrrolo[2,3-b]pyridine (0.028 g, 0.23 mmol) followed by TEA (0.022 mL, 0.16 mmol) and the reaction mixture was stirred at room temperature for 5 min to form a homogeneous solution. The reaction mixture was cooled to 0° C. and a solution of sulfurisocyanatidic chloride (0.026 g, 0.19 mmol) in DCM (2 mL) and TEA (10.84 μl, 0.078 mmol) were added and the reaction mixture stirred at room temperature for 16 h. The reaction mixture was concentrated to dryness and the crude product was purified by preparative HPLC to afford the title compound (2.8 mg) as an off white solid. LC-MS retention time=1.15 min; m/z=547.1 [M+H]$^+$. Column: Ascentis Express C18 (50×2.1) mm, 2.7 m; Flow: 1.1 mL/min; Mobile Phase A: 10 mM NH$_4$OAc in water: ACN (95:5); Mobile Phase B: 10 mM NH$_4$OAc in water: ACN (5:95); Temperature: 50° C.; 0% B to 100% B over 3 minutes; UV Detection at 220 nm.

Example BB-2

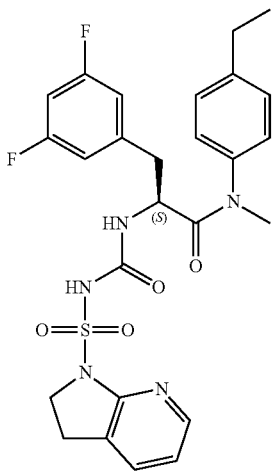

To a stirred solution of Intermediate BB-22.2 (100 mg, 0.31 mmol) and Intermediate BB-1.2 hydrochloride (57 mg, 0.47 mmol) in DCM (5 mL) was added TEA (0.04 mL, 0.3 mmol) and reaction mixture was stirred at room temperature for 5 min. The reaction mixture was cooled to 0° C., a solution chlorosulfonyl isocyanate (0.03 mL, 0.37 mmol) in DCM (1.0 mL) was added drop wise and the resulting solution was allowed to warm to room temperature and stirred for 2 h. The reaction mixture was diluted with water (15 mL) and extracted with EtOAc (2×15 mL). The combined organic layer was dried ($Na_2SO_4$), filtered, concentrated and the crude product was purified by preparative HPLC purification to afford the title compound (18 mg) as an off white solid. LC-MS retention times=1.79 min; m/z=544.2 [M+H]$^+$. Column: Ascentis Express C18 (50× 2.1) mm, 2.7 μm; Flow: 1.1 mL/min; Mobile Phase A: 10 mM $NH_4OAc$ in water: ACN (95:5); Mobile Phase B: 10 mM $NH_4OAc$ in water: ACN (5:95); Temperature: 50° C.; 0% B to 100% B over 3 minutes; UV Detection at 220 nm.

Example GW-3

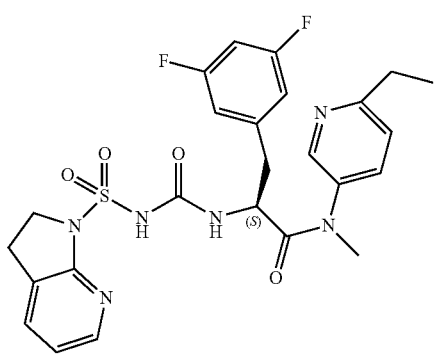

To a solution of sulfurisocyanatidic chloride (22 mg, 0.15 mmol) in DCM (1 mL) was added a solution of an HCl salt of Intermediate GW-6 (50 mg, 0.13 mmol) and TEA (0.05 mL, 0.4 mmol) in DCM (1 mL) in an ice-water bath and the reaction mixture was stirred for 20 min. Then a solution of 2,3-dihydro-1H-pyrrolo[2,3-b]pyridine (23 mg, 0.19 mmol) in DCM (1 mL) was added, followed by TEA (0.07 mL, 0.5 mmol) and the reaction mixture was stirred for 2 min, the bath was removed and stirring continued at rt for 2 h. The solvent was evaporated and the residue was redissolved in DMF and purified by preparative HPLC to afford the title compound (3.6 mg). LC-MS retention time=2.89 min; m/z=567.07 [M+Na]$^+$. (Column: Phenomenex-Luna 2.0×50 mm, 3 μm particles; Mobile Phase A: 10% MeOH-90% $H_2O$-0.1% TFA; Mobile Phase B: 90% MeOH-10% $H_2O$-0.1% TFA; Temperature: 40° C.; Gradient: 0-100% B over 4 min, then a 1-min hold at 100% B; Flow: 0.8 mL/min; Detection: UV at 220 nm).

Example AW-1

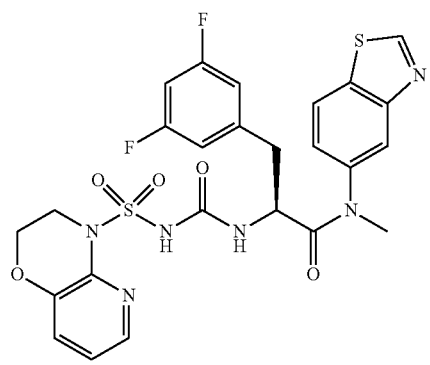 [SMILES: CN(C(=O)[C@H](Cc1cc(F)cc(F)c1)NC(=O)NS(=O)(=O)N1CCOc2cccnc21)c1ccc2scnc2c1]

To a solution of 0.1 M sulfurisocyanatidic chloride in DCM (2.88 mL, 0.288 mmol) was added a solution of Intermediate ZY-5 (100 mg, 0.288 mmol) in DCM (2 mL) at −15° C. dropwise. The reaction mixture was then stirred at −15° C. for 30 min. Then 3,4-dihydro-2H-pyrido[3,2-b][1,4]oxazine (39.2 mg, 0.288 mmol) and TEA (0.160 mL, 1.15 mmol) were added and the reaction solution was stirred at rt for 30 min. The solvent was removed in vacuo and the residue was taken up into DMF (1 mL), filtered, and purified by preparative HPLC to afford the title compound (22 mg) as a white solid. LC-MS retention time=1.07 min; m/z=589.15 [M+H]$^+$. (Start % B=0, Final % B=100, Gradient Time=2 min, Flow Rate=1.0 mL/min, Wavelength=220, Solvent Pair=Water/Acetonitrile/TFA, Solvent A=10% acetonitrile/90% Water/0.1% TFA, Solvent B=90% Acetonitrile/10% water/0.1% TFA, Column=Phenomenex Luna 30×2.0 MM 3 μm Oven Temp.=40° C.).

Example GW-4

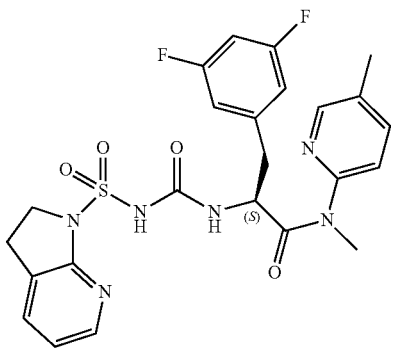

To a solution of sulfurisocyanatidic chloride (22 mg, 0.16 mmol) in DCM (1 mL) was added a mixture of an HCl salt of Intermediate GW-8 (50 mg, 0.13 mmol) and TEA (0.05 mL, 0.39 mmol) in DCM (1 mL) in an ice-water bath, and the reaction mixture was stirred for 20 min. Then a solution of 2,3-dihydro-1H-pyrrolo[2,3-b]pyridine (23.8 mg, 0.20 mmol) in DCM (1 mL) was added, followed by TEA (0.1 mL, 0.53 mmol). The reaction mixture was stirred for 3 min, the bath was removed and the stirring was continued at rt for 1.5 h. The solvent was evaporated and the residue was redissolved in DMF and purified by preparative HPLC to afford the title compound (5.5 mg). LC-MS retention time=3.41 min; m/z=553.05 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-5

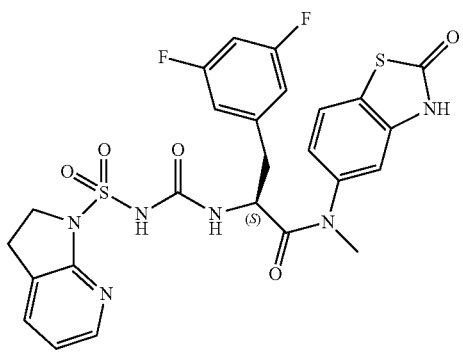

To a solution of sulfurisocyanatidic chloride (27.6 mg, 0.20 mmol) in DCM (1 mL) was added a solution of an HCl salt of Intermediate GW-4.3 (65 mg, 0.16 mmol) and TEA (0.05 mL, 0.3 mmol) in DCM (1 mL) in an ice-water bath and the reaction mixture was stirred for 20 min. Then a solution of 2,3-dihydro-1H-pyrrolo[2,3-b]pyridine (29 mg, 0.24 mmol) in DCM (1 mL) was added, followed by TEA (0.10 mL, 0.65 mmol), the bath was removed and the reaction mixture was stirred at rt for 2 h. The solvent was evaporated and the residue was redissolved in methanol and purified by preparative HPLC to afford the title compound (5.7 mg). LC-MS retention time=3.44 min; m/z=589.06 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-6

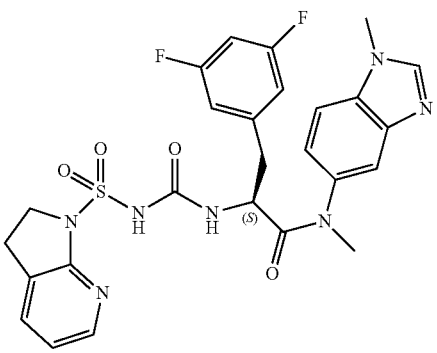

To a solution of sulfurisocyanatidic chloride (20 mg, 0.14 mmol) in DCM (1 mL) was added a mixture of an HCl salt of Intermediate GW-5.2 (50 mg, 0.12 mmol) and TEA (0.05 mL, 0.4 mmol) in DCM (1 mL) over 2 min in an ice-water bath and the reaction mixture was stirred at rt for 20 min. A solution of 2,3-dihydro-1H-pyrrolo[2,3-b]pyridine (22 mg, 0.18 mmol) in DCM (1 mL) was added, followed by TEA (0.07 mL, 0.48 mmol) and then the bath was removed and the reaction mixture was stirred at rt for 2 h. The reaction mixture was concentrated and the residue was redissolved in methanol and purified by preparative HPLC to afford the title compound (2.6 mg). LC-MS retention time=2.45 min; m/z=570.05 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-7

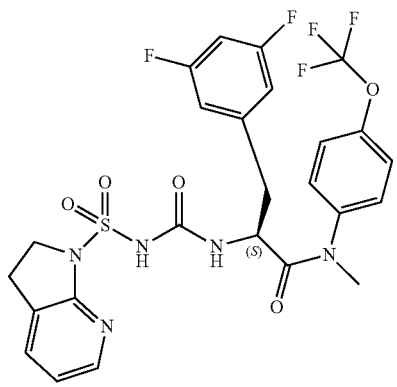

To a solution of sulfurisocyanatidic chloride (25 mg, 0.18 mmol) in DCM (1 mL) was added a mixture of an HCl salt of Intermediate GW-6.2 (60 mg, 0.15 mmol) and TEA (0.04 mL, 0.3 mmol) in DCM (1 mL) over 2 min in an ice-water bath and the reaction mixture was stirred at rt for 20 min. Then a solution of 2,3-dihydro-1H-pyrrolo[2,3-b]pyridine (26 mg, 0.22 mmol) in DCM (1 mL) was added, followed by TEA (0.08 mL, 0.6 mmol), the bath was removed and the reaction mixture was stirred at rt for 2 h. The reaction mixture was concentrated and the residue was redissolved in methanol and purified by preparative HPLC to afford the title compound (10.7 mg). LC-MS retention time=3.86 min; m/z=622.14 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-8

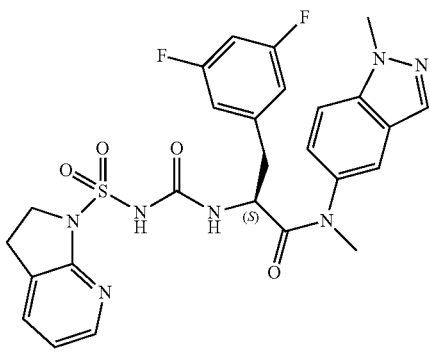

To a solution of sulfurisocyanatidic chloride (27 mg, 0.19 mmol) in DCM (1 mL) in an ice-water bath was added slowly a mixture of Intermediate GW-7.2 (65 mg, 0.16 mmol) and TEA (0.1 mL, 0.47 mmol) in DCM (1 mL) and the reaction mixture was stirred for 20 min. Then a solution of 2,3-dihydro-1H-pyrrolo[2,3-b]pyridine (28 mg, 0.23 mmol) in DCM (1 mL) was added, followed by TEA (0.10 mL, 0.62 mmol) and the reaction mixture was stirred for 5 min, the bath was removed and the stirring was continued for 2 h. The reaction mixture was concentrated and the residue was redissolved in methanol and purified by preparative HPLC to afford the title compound (1.2 mg). LC-MS retention time=3.50 min; m/z=592.21 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-3

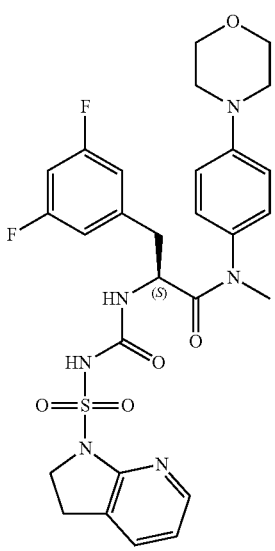

To a stirred solution of 2,3-dihydro-1H-pyrrolo[2,3-b]pyridine (96 mg, 0.80 mmol), Intermediate BB-23.3 (200 mg, 0.533 mmol) in DCM (10 mL) was added chloro sulphonyl isocyanate (0.057 mL, 0.64 mmol) and the reaction mixture was stirred at 0° C. for 30 min. The reaction mixture was diluted with DCM (20 mL), washed with water (20 mL), dried (Na$_2$SO$_4$), filtered, concentrated and the crude product was purified by preparative HPLC to afford the title product (7 mg) as a pale yellow solid. LC-MS retention time=1.54 min; m/z=601.2 [M+H]$^+$. Column: Ascentis Express C18 (50×2.1) mm, 2.7 μm; Flow: 1.1 mL/min; Mobile Phase A: 10 mM NH$_4$OAc in water: ACN (95:5); Mobile Phase B: 10 mM NH$_4$OAc in water: ACN (5:95); Temperature: 50° C.; 0% B to 100% B over 3 minutes; UV Detection at 220 nm.

Example BB-4

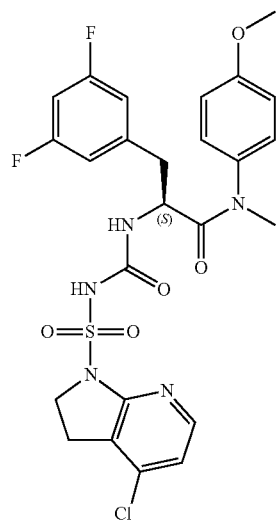

To a stirred solution of Intermediate BB-24 (145 mg, 0.937 mmol), Intermediate BB-28.2 HCl (200 mg, 0.624 mmol) in DCM (10 mL) was added sulfurisocyanatidic chloride (0.066 mL, 0.75 mmol) and stirred further at 0° C. for 30 min. The reaction mixture was diluted with DCM (20 mL), washed with water (20 mL), dried (Na$_2$SO$_4$), filtered, concentrated and the crude product was purified by preparative HPLC to afford the title product (15 mg) as off white solid. LC-MS retention time=1.64 min; m/z=580.1 [M+H]$^+$. Column: Ascentis Express C18 (50×2.1) mm, 2.7 m; Flow: 1.1 mL/min; Mobile Phase A: 10 mM NH$_4$OAc in water: ACN (95:5); Mobile Phase B: 10 mM NH$_4$OAc in water: ACN (5:95); Temperature: 50° C.; 0% B to 100% B over 3 minutes; UV Detection at 220 nm. $^1$H NMR (400 MHz, DMSO-d$_6$) δ 8.00 (d, J=5.52 Hz, 1H), 7.09 (d, J=5.52 Hz, 1H), 6.91-7.06 (m, 5H), 6.68 (d, J=8.53 Hz, 1H), 6.41 (d, J=6.4 Hz, 2H), 4.29 (dd, J=8.16, 5.27 Hz, 1H), 4.16 (t, J=8.53 Hz, 2H), 3.79 (s, 3H), 3.18 (s, 3H) 3.08-3.15 (m, 3H) 2.74 (dd, J=13.80, 5.27 Hz, 1H).

Example GW-9

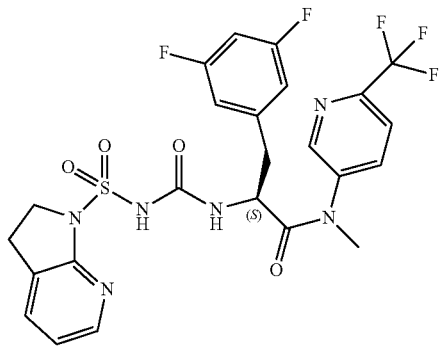

To a solution of sulfurisocyanatidic chloride (36 mg, 0.25 mmol) in DCM (2 mL) was added a solution of Intermediate GW-8.4 (90 mg, 0.25 mmol) and TEA (0.05 mL, 0.38 mmol) in DCM (2 mL) in an ice-water bath and the reaction mixture was stirred for 20 min. Then a solution of 2,3-dihydro-1H-pyrrolo[2,3-b]pyridine (45.1 mg, 0.376 mmol) in DCM (2 mL) was added, followed by TEA (0.11 mL, 0.751 mmol) and the reaction mixture was stirred for 2 min. Then the bath was removed and the stirring was continued at rt for 2 h. The reaction mixture was concentrated and the residue was redissolved in methanol and purified by preparative HPLC to afford the title compound (24.4 mg). LC-MS retention time=3.53 min; m/z=607.14 [M+Na]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-10

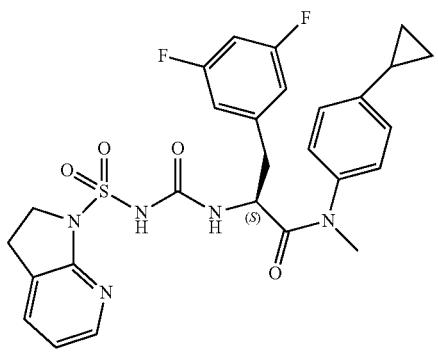

To a solution of sulfurisocyanatidic chloride (35 mg, 0.25 mmol) in DCM (2 mL) was added a solution of Intermediate GW-9.2 (100 mg, 0.25 mmol) and TEA (0.1 mL, 0.7 mmol) in DCM (2 mL) in an ice-water bath and the reaction mixture was stirred for 20 min. Then a solution of 2,3-dihydro-1H-pyrrolo[2,3-b]pyridine (45 mg, 0.37 mmol) in DCM (2 mL) was added, followed by TEA (0.14 mL, 0.99 mmol) and the reaction mixture was stirred for 2 min, the bath was removed and the stirring was continued at rt for 2 h. The reaction mixture was concentrated and the residue was redissolved in methanol and purified by preparative HPLC to afford the title compound (14.2 mg). LC-MS retention time=3.91 min; m/z=578.21 [M+Na]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-11

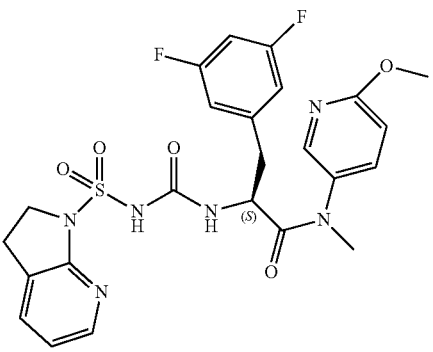

To a solution of sulfurisocyanatidic chloride (36 mg, 0.25 mmol) in DCM (2 mL) in an ice-water bath was added a solution of Intermediate GW-10.2 (100 mg, 0.25 mmol) and TEA (0.1 mL, 0.8 mmol) in DCM (2 mL), stirred for 1 min, then a solution of 2,3-dihydro-1H-pyrrolo[2,3-b]pyridine (46 mg, 0.38 mmol) in DCM (2 mL) was added, followed by TEA (0.14 mL, 1.0 mmol), stirred for 3 min, the bath was removed and the reaction mixture was stirred at rt for 4 h. The reaction mixture was concentrated, redissolved in DMF and purified by preparative HPLC (MeOH/Water/TFA) and then repurified by preparative HPLC (ACN/Water/TFA) to afford the title compound (8.0 mg). LC-MS retention time=3.43 min; m/z=569.18 [M+Na]$^+$. (Column: Phenomenex-Luna 2.0×50 mm, 3 µm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm). $^1$H NMR (400 MHZ, MeOH-d$_4$) δ 8.08 (d, J=5.5 Hz, 1H), 7.87 (d, J=8.5 Hz, 1H), 7.76 (s, 1H), 7.28 (m, 1H), 7.18 (t, J=7.3 Hz, 1H), 6.84-6.67 (m, 2H), 6.52 (d, J=6.3 Hz, 2H), 4.38 (t, J=7.1 Hz, 1H), 4.27-4.15 (m, 2H), 3.94 (s, 3H), 3.27 (t, J=8.3 Hz, 2H), 3.25 (s, 3H), 2.91 (dd, J=13.5, 7.0 Hz, 1H), 2.71 (dd, J=13.5, 7.0 Hz, 1H).

Example GW-12

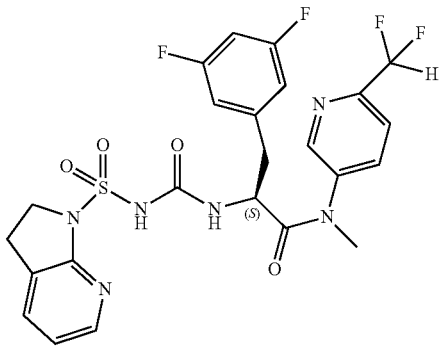

To a solution of sulfurisocyanatidic chloride (21 mg, 0.15 mmol) in DCM (1 mL) in an ice-water bath was added a solution of Intermediate GW-11.3 (50 mg, 0.15 mmol) and TEA (0.020 mL, 0.15 mmol) in DCM (1 mL) and the reaction mixture was stirred at rt for 2 min. Then a solution of 2,3-dihydro-1H-pyrrolo[2,3-b]pyridine (26 mg, 0.22 mmol) in DCM (1 mL) was added, followed by TEA (0.04 mL, 0.29 mmol), the bath was removed and the reaction mixture was stirred at rt for 2 h. The reaction mixture was concentrated, redissolved in methanol and purified by preparative HPLC to afford the title compound (2.9 mg). LC-MS retention time=2.72 min; m/z=567.00 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-5

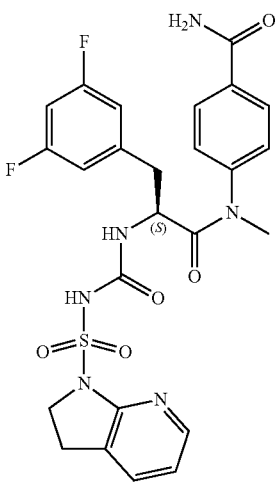

To a stirred solution of Intermediate BB-25.2 (0.120 g, 0.360 mmol) in DCM (2 mL) was added 2,3-dihydro-1H-pyrrolo[2,3-b]pyridine (0.065 g, 0.54 mmol) followed by TEA (0.050 mL, 0.36 mmol) and the reaction mixture was stirred at room temperature for 5 min to form a homogeneous solution. The reaction mixture was cooled to 0° C. and a solution of sulfurisocyanatidic chloride (0.038 mL, 0.43 mmol) in DCM (2 mL) and TEA (0.025 mL, 0.18 mmol) were added and the reaction mixture stirred at room temperature for 16 h. The reaction mixture was concentrated to dryness and the crude product was purified by preparative HPLC to afford the title product (14.5 mg) as an off white solid. LC-MS retention time=1.19 min; m/z=559.1 [M+H]$^+$. Ascentis Express C18 (50×2.1) mm, 2.7 m; Temperature 50° C.; Flow rate: 1.1 mL/min; Mobile Phase A: 10 mM NH$_4$OAc in 95% Water/5% ACN; Mobile Phase B: 10 mM NH$_4$OAc in 5% Water/95% ACN; 0% B to 100% B over 3 min; Detection: UV at 220 nm.

Example BB-6

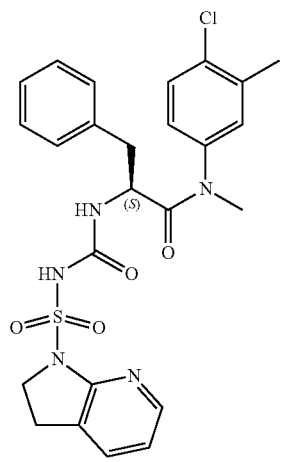

To a stirred solution of Intermediate BB-26.2 (0.20 g, 0.66 mmol) in DCM (2 mL) was added 2,3-dihydro-1H-pyrrolo[2,3-b]pyridine (0.119 g, 0.991 mmol) followed by TEA (0.092 mL, 0.66 mmol) and the reaction mixture was stirred at room temperature for 5 min to form a homogeneous solution. The reaction mixture was cooled to 0° C. and a solution of sulfurisocyanatidic chloride (0.069 mL, 0.79 mmol) in DCM (2 mL) and TEA (0.046 mL, 0.330 mmol) were added and stirred at room temperature for 16 h. The reaction mixture was concentrated to dryness and the crude product was purified by preparative HPLC to afford the title product (6 mg) as an off white solid. LC-MS retention time=1.83 min; m/z=528.1 [M+H]$^+$. Column: Ascentis Express C18 (50×2.1) mm, 2.7 m; Temperature 50° C.; Flow rate: 1.1 mL/min; Mobile Phase A: 10 mM NH$_4$OAc in 95% Water/5% ACN; Mobile Phase B: 10 mM NH$_4$OAc in 5% Water/95% ACN; 0% B to 100% B over 3 min; then hold 1 min at 100% B with flow rate of 1.1 mL/min; Detection: UV at 220 nm.

Example GW-13

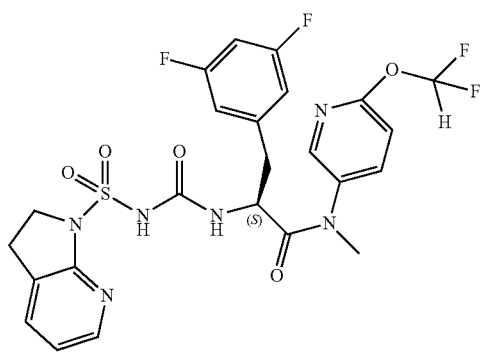

To a solution of sulfurisocyanatidic chloride (23 mg, 0.16 mmol) in DCM (2 mL) in an ice-water bath was added a solution of Intermediate GW-12.3 (70 mg, 0.16 mmol) and TEA (0.07 mL, 0.5 mmol) in DCM (2 mL) and the reaction mixture was stirred for 1 min. A solution of 2,3-dihydro-1H-pyrrolo[2,3-b]pyridine (29 mg, 0.24 mmol) in DCM (2 mL) was added, followed by TEA (0.1 mL, 0.65 mmol) and the reaction mixture was stirred for 3 min, the bath was removed and the stirring was continued at rt for 4 h. The reaction mixture was concentrated, redissolved in DMF and purified by preparative HPLC to afford the title compound (13.7 mg). LC-MS retention time=3.57 min; m/z=605.17 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-8

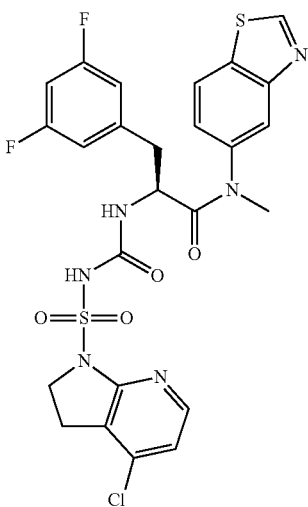 [SMILES: CN(C(=O)[C@H](Cc1cc(F)cc(F)c1)NC(=O)NS(=O)(=O)N1CCc2c(Cl)ccnc21)c1ccc2scnc2c1]

To a stirred solution of Intermediate BB-24 (66.8 mg, 0.432 mmol), Intermediate ZY-5 (100 mg, 0.288 mmol) in DCM (10 mL) added sulfurisocyanatidic chloride (0.031 mL, 0.35 mmol) and stirred further at 0° C. for 30 min. The reaction mixture was diluted with DCM (20 mL), washed with water (20 mL), dried (Na$_2$SO$_4$), filtered, concentrated and the crude product was purified by preparative HPLC to afford the title product (15 mg) as an off white solid. LC-MS retention time=2.03 min; m/z=607.1 [M+H]$^+$. Column: Ascentis Express C18 (50×2.1) mm, 2.7 μm; Temperature 50° C.; Flow rate: 1.1 mL/min; Mobile Phase A: 10 mM NH$_4$OAc in 95% Water/5% ACN; Mobile Phase B: 10 mM NH$_4$OAc in 5% Water/95% ACN; 0% B to 100% B over 3 min; then hold 1 min at 100% B with flow rate of 1.1 mL/min; Detection: UV at 220 nm. $^1$H NMR (400 MHz, DMSO-d$_6$) δ 11.73 (s., 1H), 9.51 (d, J=14.4 Hz, 1H), 8.60 (br. s., 1H), 8.36 (d, J=8.80 Hz, 1H), 8.14 (br. s., 1H), 8.02 (d, J=5.2 Hz, 1H), 7.50 (d, J=6.11 Hz, 1H), 7.12 (d, J=6.11 Hz, 1H) 6.95 (t, J=7.2 Hz, 1H), 6.26 (d, J=6.4 Hz, 2H), 4.26-4.08 (m, 1H), 3.95-3.85 (m, 2H), 3.23-3.19 (m, 2H), 3.05 (s, 3H), 2.95 (m, 1H), 2.80 (m, 1H).

Example AW-2

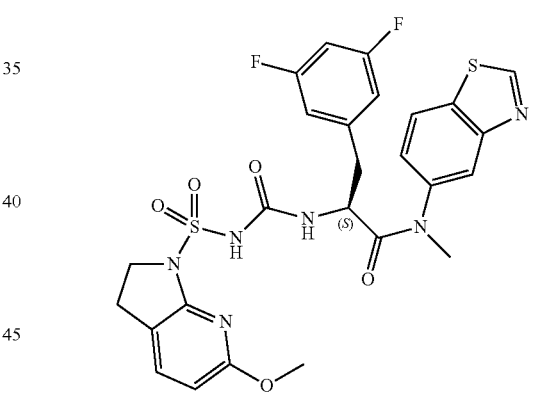

To a solution of sulfurisocyanatidic chloride (0.017 mL, 0.20 mmol) in DCM (1 mL) at 0° C. was added a pre-made solution of an HCl salt of Intermediate ZY-5 (70 mg, 0.17 mmol) and TEA (0.023 mL, 0.17 mmol) in DCM (0.5 mL) dropwise. The resulting mixture was stirred at 0° C. for 30 min. A solution of an HCl salt of Intermediate AW-2 (59.5 mg, 0.266 mmol) in DCM (0.5 mL) and TEA (0.116 mL, 0.833 mmol) was added at at 0° C., and the resulting solution was stirred at rt for 2 h. The solvent was then removed in vaco. The residue was taken up into DMF (1 mL), filtered, and purified by preparative HPLC to afford the title compound (17 mg) as a white solid. LC-MS retention time=1.18 min; m/z=603.05 [M+H]$^+$. (Start % B=0, Final % B=100, Gradient Time=2 min, Flow Rate=1.0 mL/min, Wavelength=220, Solvent Pair=Water/Acetonitrile/TFA, Solvent A=10% acetonitrile/90% Water/0.1% TFA, Solvent B=90% Acetonitrile/10% water/0.1% TFA, Column=Phenomenex Luna 30×2.0 MM 3 μm, Oven Temp.=40° C.).

Example BB-9

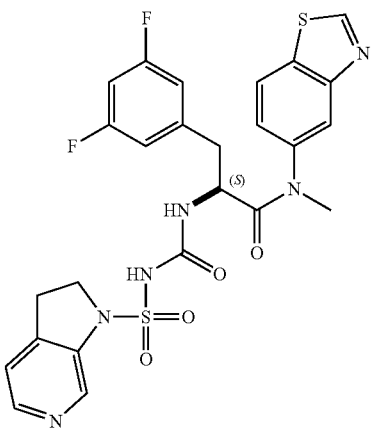

To a stirred solution of Intermediate ZY-5 (150 mg, 0.432 mmol) in DCM (10 mL) was added chlorosulfonyl isocyanate (0.030 mL, 0.35 mmol), TEA (0.181 mL, 1.30 mmol) at 0° C. and the reaction mixture was stirred for 30 min. Then added the 2,3-dihydro-1H-pyrrolo[2,3-c]pyridine (78 mg, 0.648 mmol) in DCM (10 mL) followed by TEA (0.18 mL, 1.3 mmol) and the reaction mixture was stirred at room temperature for 2 h. The reaction mixture was concentrated to dryness; the crude material was purified by preparative HPLC to afford the title product (7 mg) as an off white solid. LC-MS retention time=1.43 min; m/z=573.1 [M+H]$^+$. Column: Ascentis Express C18 (50×2.1) mm, 2.7 m; Flow: 1.1 mL/min; Mobile Phase A: 10 mM NH$_4$OAc in water: ACN (95:5); Mobile Phase B: 10 mM NH$_4$OAc in water: ACN (5:95); Temperature: 50° C.; 0% B to 100% B over 3 minutes; UV Detection at 220 nm. $^1$H NMR (400 MHZ, DMSO-d$_6$) δ 11.25-10.93 (br.s, 1H), 9.50 (s, 1H), 8.33 (s, 1H), 8.32 (s, 1H), 8.22 (d, J=8.4 Hz, 1H), 7.95 (s, 1H), 7.54 (d, J=4.4 Hz, 1H), 7.28 (d, J=8.8 Hz, 1H), 6.98 (t, J=7.2 Hz, 1H), 6.86 (d, J=8.4 Hz, 1H), 6.40 (d, J=6.8 Hz, 2H), 4.30-4.20 (m, 1H), 4.20-4.05 (m, 2H), 3.25-3.15 (m, 5H), 2.85-2.75 (m, 1H), 2.65-2.55 (m, 1H).

Example BB-10

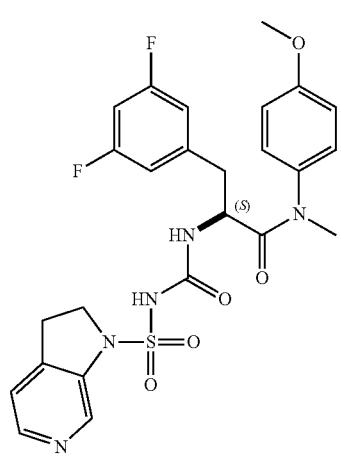

To a stirred solution of Intermediate BB-28.2 HCl (150 mg, 0.47 mmol) in DCM (10 mL) was added chlorosulfonyl isocyanate (0.033 mL, 0.38 mmol), TEA (0.20 mL, 1.4 mmol) at 0° C. and the reaction mixture was stirred for 30 min. Then added the 2,3-dihydro-1H-pyrrolo[2,3-c]pyridine (84 mg, 0.702 mmol) in DCM (10 mL) followed by TEA (0.20 mL, 1.4 mmol) and the reaction mixture stirred at room temperature for 2 h. The reaction mixture was concentrated to dryness; the crude material was purified by preparative HPLC to afford the title product (3 mg) as an off white solid. LC-MS retention time=1.53 min; m/z=546.2 [M+H]$^+$. Column: Ascentis Express C18 (50×2.1) mm, 2.7 m; Flow: 1.1 mL/min; Mobile Phase A: 10 mM NH$_4$OAc in water: ACN (95:5); Mobile Phase B: 10 mM NH$_4$OAc in water: ACN (5:95); Temperature: 50° C.; 0% B to 100% B over 3 min; UV Detection at 220 nm. $^1$H NMR (400 MHZ, DMSO-d$_6$) δ 10.82 (br.s., 1H), 8.33 (s, 1H), 8.27 (d, J=5.1 Hz, 1H), 7.43 (br. s., 1H), 7.14 (d, J=8.8 Hz, 2H), 7.02 (m, 1H), 6.96 (d, J=8.8 Hz, 2H), 6.76 (d, J=8.4 Hz, 1H), 6.40 (d, J=6.4 Hz, 2H), 4.28 (br. s., 1H), 4.10-4.00 (m, 2H), 3.79 (s, 3H), 3.16 (m, 2H), 3.08 (s, 3H), 2.80-2.50 (m, 2H).

Example VN-16

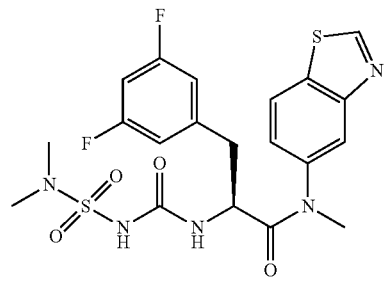 [SMILES: CN(C(=O)[C@H](Cc1cc(F)cc(F)c1)NC(=O)NS(=O)(=O)N(C)C)c1ccc2scnc2c1]

To a solution of Intermediate VN-29 (0.050 g, 0.11 mmol) and N,N-dimethylsulfamide (0.015 g, 0.12 mmol) in acetonitrile (1 mL) was added DBU (0.018 mL, 0.12 mmol). The reaction was stirred at ~25° C. under nitrogen for 45 min. All solvents were removed in vacuo. The residue was taken up in MeOH (2 mL) and purified via preparative HPLC (AcCN/water/NH$_4$OAc) to afford the title compound (33.0 mg). LC-MS retention time=1.400 min; m/z=497.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example VN-17

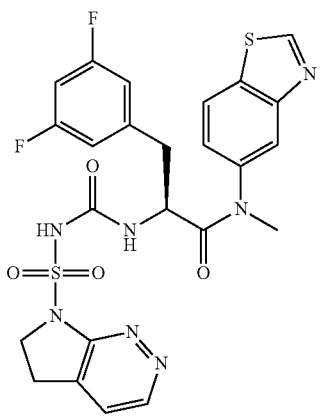 [SMILES: CN(C(=O)[C@H](Cc1cc(F)cc(F)c1)NC(=O)NS(=O)(=O)N1CCc2ccnnc21)c1ccc2scnc2c1]

To a mixture of Intermediate VN-29 (0.060 g, 0.13 mmol) and Intermediate VN-17.5 (0.028 g, 0.14 mmol) in acetonitrile (2 mL) was added DBU (0.021 mL, 0.14 mmol). The reaction was stirred at ~25° C. for 3.5 h. Another equivalent of DBU (0.021 mL, 0.14 mmol) was added and the reaction was heated at 40° C. for 3.5 h. The reaction was removed from the heat and all solvents were removed in vacuo. The residue was taken up in MeOH (2 mL) and purified via preparative HPLC (AcCN/water/NH$_4$OAc) to afford the title compound (21.3 mg); LC-MS retention time=1.348 min; m/z=573.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example GW-14

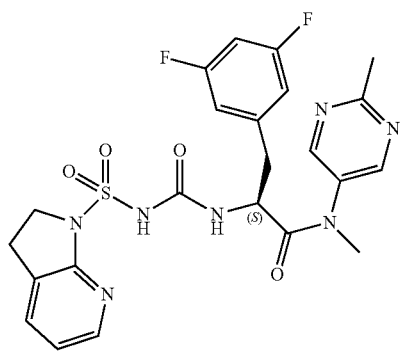

To a solution of sulfurisocyanatidic chloride (37 mg, 0.26 mmol) in DCM (2 mL) in an ice-water bath was added a solution of Intermediate GW-13.2 (100 mg, 0.26 mmol) and TEA (0.11 mL, 0.79 mmol) in DCM (2 mL) and the reaction mixture was stirred for 2 min. Then a solution of 2,3-dihydro-1H-pyrrolo[2,3-b]pyridine (48 mg, 0.39 mmol) in DCM (2 mL) was added, followed by TEA (0.15 mL, 1.1 mmol), the bath was removed and the stirring was continued at rt for 2 h. The reaction mixture was concentrated, the residue was redissolved in DMF and purified by preparative HPLC to afford the title compound (31.4 mg). LC-MS retention time=3.06 min; m/z=554.16 [M+Na]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-15

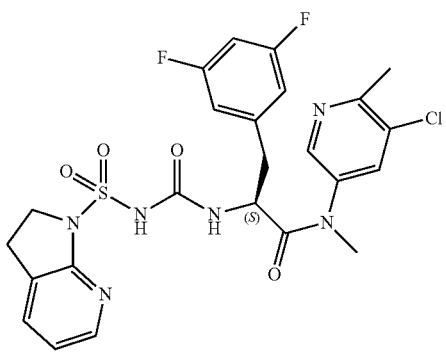

To a solution of sulfurisocyanatidic chloride (25 mg, 0.18 mmol) in DCM (2 mL) was added a solution of Intermediate GW-14.3 (60 mg, 0.18 mmol) and TEA (0.040 mL, 0.27 mmol) in DCM (2 mL) in an ice-water bath and the reaction mixture was stirred for 20 min. Then a solution of 2,3-dihydro-1H-pyrrolo[2,3-b]pyridine (32 mg, 0.27 mmol) in DCM (2 mL) was added, followed by TEA (0.07 mL, 0.5 mmol) and the reaction mixture was stirred for 2 min, the bath was removed and the stirring was continued at rt for 2 h. The reaction mixture was concentrated and the residue was redissolved in methanol and purified by preparative HPLC to afford the title compound (13.7 mg). LC-MS retention time=3.53 min; m/z=565.10 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-11

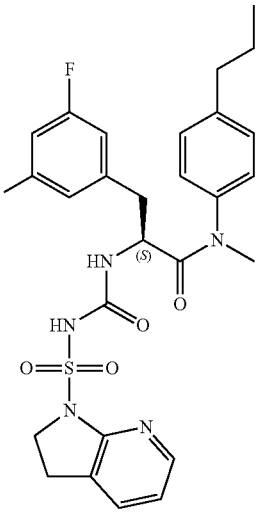

To a stirred solution of Intermediate BB-2.3 (80 mg, 0.17 mmol) and Intermediate BB-1.2 hydrochloride (35 mg, 0.17 mmol) in acetonitrile (5 mL) was added DBU (40 mg, 0.27 mmol) and reaction mixture was stirred at room temperature for 16 h. The reaction mixture was diluted with water (15 mL), extracted with EtOAc (2×15 mL) and the combined organic layer was dried (Na$_2$SO$_4$), filtered and concentrated. The crude product was purified by preparative HPLC to afford the title compound (3 mg) as an off white solid. LC-MS retention times=3.32 min; m/z=558.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example GW-16

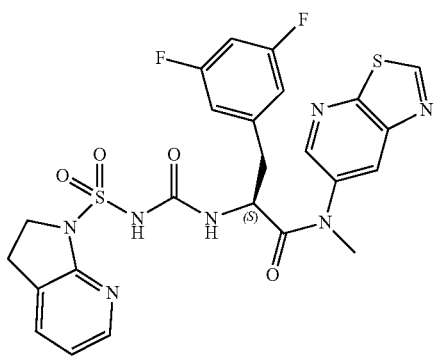

To a solution of sulfurisocyanatidic chloride (24 mg, 0.17 mmol) in DCM (2 mL) in an ice-water bath was added a solution of Intermediate GW-15.3 (70 mg, 0.17 mmol) and TEA (0.07 mL, 0.5 mmol) in DCM (2 mL) and the reaction mixture was stirred for 2 min. Then a solution of 2,3-dihydro-1H-pyrrolo[2,3-b]pyridine (30 mg, 0.25 mmol) in DCM (2 mL) was added, followed by TEA (0.050 mL, 0.33 mmol), the bath was removed and the reaction mixture was stirred at rt for 2 h. The reaction mixture was concentrated, redissolved in DMF and purified by preparative HPLC to afford the title compound (4.0 mg). LC-MS retention time=3.13 min; m/z=573.95 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-12

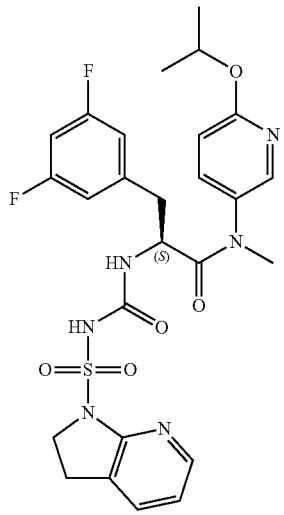

To a stirred solution of Intermediate BB-3.6 (118 mg, 0.251 mmol) in DCM (10 mL) was added Intermediate BB-1.2 hydrochloride (50 mg, 0.25 mmol), DBU (0.076 mL, 0.50 mmol) and the reaction mixture was stirred at room temperature for 16 h. The reaction mixture was diluted with water (25 mL) and extracted with EtOAc (2×25 mL). The combined organic layer was dried (Na$_2$SO$_4$), filtered, concentrated and the crude product was purified by preparative HPLC to afford the title compound (15 mg) as an off white solid. LC-MS retention time=2.64 min; m/z=575.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example BB-13

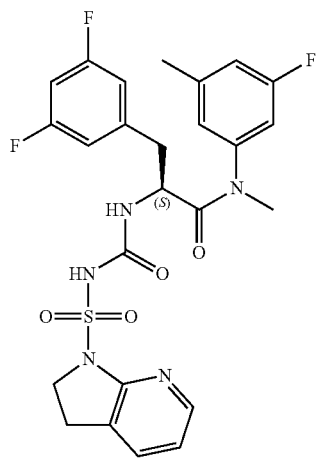

To a stirred solution of Intermediate BB-4.3 (110 mg, 0.25 mmol) and Intermediate BB-1.2 hydrochloride (50 mg, 0.25 mmol) in acetonitrile (5 mL) was added DBU (57 mg, 0.37 mmol) and reaction mixture was stirred at room temperature for 16 h. The reaction mixture was diluted with water (15 mL) and extracted with EtOAc (2×15 mL). The combined organic layer was dried (Na$_2$SO$_4$), filtered, concentrated and the crude product was purified by preparative HPLC to afford the title compound (18 mg) as an off white solid. LC-MS retention times=1.97 min; m/z=548.2 [M+H]$^+$. Column: KINETIX XB-C18, 75×3 mm, 2.6 μm; Flow rate: 1 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 8.04 (d, J=5.0 Hz, 1H), 7.59 (d, J=7.5 Hz, 1H), 7.01-6.93 (m, 2H), 6.84-6.76 (m, 1H), 6.50 (d, J=5.5 Hz, 4H), 4.48 (br. s., 1H), 4.21 (m, 2H), 3.15 (m, 5H), 2.88 (dd, J=13.3, 7.8 Hz, 1H), 2.66 (dd, J=13.6, 7.0 Hz, 1H), 2.32 (s, 3H). MeOH Example GW-17

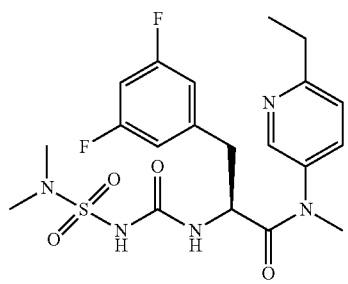 [SMILES: CCc1ccc(N(C)C(=O)[C@H](Cc2cc(F)cc(F)c2)NC(=O)NS(=O)(=O)N(C)C)cn1]

To a solution of Intermediate GW-16.1 (60 mg, 0.18 mmol) and N,N-dimethylsulfamide (19 mg, 0.15 mmol) in acetonitrile (1 mL) was added DBU (0.020 mL, 0.15 mmol) and the reaction mixture was stirred at rt for 1 h. The reaction mixture was concentrated, the residue was redissolved in DMF and purified by preparative HPLC to afford the title compound (34.7 mg). LC-MS retention time=4.73 min; m/z=470.14 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example VN-19 and Example VN-20

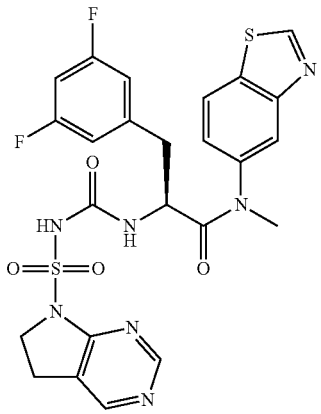

-continued

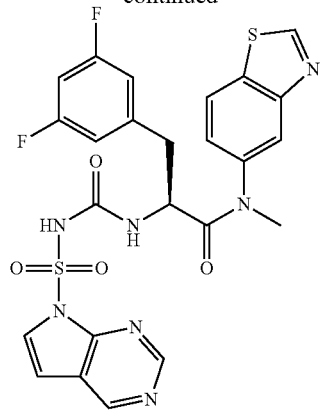

To a mixture of Intermediate VN-29 (0.060 g, 0.128 mmol) and a mixture of Intermediate VN-19.2.1/VN-19.2.2 (0.028 g) in acetonitrile (1 mL) was added DBU (0.021 mL, 0.14 mmol). The reaction was stirred at ~25° C. for 1.5 h. All solvents were removed in vacuo. The residue was taken up in MeOH (2 mL) and purified via preparative HPLC (AcCN/water/NH$_4$OAc) to afford the title compounds:

Example VN-19 (36.0 mg): LC-MS retention time=1.157 min; m/z=574.0 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm)

Example VN-20 (6 mg): LC-MS retention time=1.335 min; m/z=571.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example BB-14

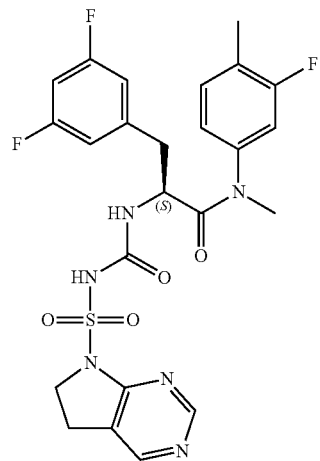

To a stirred solution of Intermediate BB-5.3 (110 mg, 0.249 mmol) and Intermediate BB-1.2 hydrochloride (50 mg, 0.25 mmol) in acetonitrile (5 mL) was added DBU (57 mg, 0.37 mmol) and reaction mixture was stirred at room temperature for 16 h. The reaction mixture was diluted with water (15 mL) and extracted with EtOAc (2×15 mL). The combined organic layer was dried (Na₂SO₄), filtered and concentrated. The crude product was purified by preparative HPLC to afford the title compound (45 mg) as an off white solid. LC-MS retention times=2.61 min; m/z=548.2 [M+H]⁺. Column: KINETIX XB-C18, 75×3 mm, 2.6 µm; Flow rate: 1 mL/min; Mobile Phase A: 5 mM HCO₂NH₄ in 98% Water/2% ACN; Mobile Phase B: 5 mM HCO₂NH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, MeOH-d₄) δ 7.92 (d, J=5.0 Hz, 1H), 7.49 (d, J=7.5 Hz, 1H), 7.12 (t, J=8.0 Hz, 1H), 6.84 (dd, J=7.0, 5.5 Hz, 1H), 6.64 (m, 1H), 6.62-6.52 (m, 2H), 6.46 (d, J=6.5 Hz, 2H), 4.49 (t, J=7.0 Hz, 1H), 4.26-4.17 (m, 2H), 3.05 (m, 1H), 3.02 (s, 3H), 2.87 (dd, J=13.3, 6.8 Hz, 1H), 2.64 (dd, J=13.6, 7.5 Hz, 1H), 2.32 (m, 1H), 2.17 (s, 3H).

Example BB-15

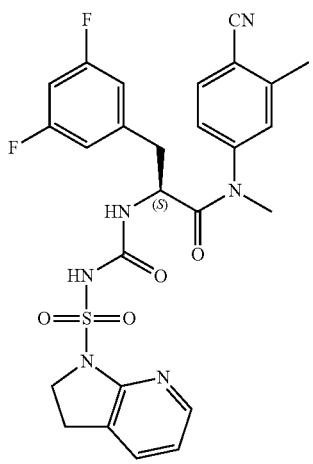

To a stirred solution of Intermediate BB-6.4 (30 mg, 0.067 mmol) and Intermediate BB-1.2 hydrochloride (18.88 mg, 0.080 mmol) in acetonitrile (4 mL) was added DBU (0.015 mL, 0.100 mmol) and reaction mixture was stirred at room temperature for 16 h. Then the reaction mixture was diluted with water (15 mL) and extracted with EtOAc (2×15 mL). The combined organic layer was dried (Na₂SO₄), filtered and concentrated. The crude product was purified by preparative HPLC to afford the title compound (2.3 mg) as an off white solid. LC-MS retention time=1.73 min; m/z=555.2 [M+H]⁺. Column: KINETIX XB-C18, 75×3 mm, 2.6 µm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection:

Example VN-21

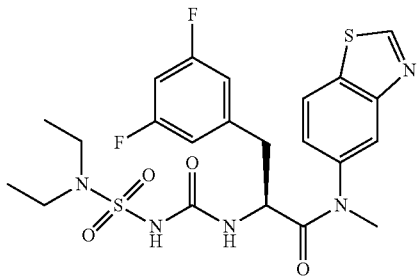 [SMILES: CCN(CC)S(=O)(=O)NC(=O)N[C@@H](Cc1cc(F)cc(F)c1)C(=O)N(C)c1ccc2scnc2c1]

To a mixture of Intermediate VN-29 (0.050 g, 0.11 mmol) and diethylsulfamide (0.018 g, 0.12 mmol) in acetonitrile (1 mL) was added DBU (0.018 mL, 0.12 mmol). The reaction mixture was stirred at ~25° C. for 2 h. All solvents were removed in vacuo. The residue was dissolved in MeOH (2 mL) and purified via preparative HPLC (AcCN/water/ NH₄OAc) to afford the title compound (47.5 mg). LC-MS retention time=1.643 min; m/z=526.0 [M+H]⁺. (Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example VN-22

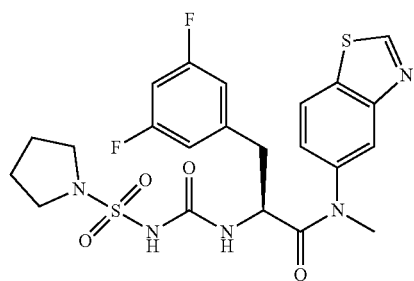 [SMILES: CN(C(=O)[C@H](Cc1cc(F)cc(F)c1)NC(=O)NS(=O)(=O)N1CCCC1)c1ccc2scnc2c1]

To a mixture of Intermediate VN-29 (0.050 g, 0.11 mmol) and pyrrolidine-1-sulfonamide (0.018 g, 0.12 mmol) in acetonitrile (1 mL) was added DBU (0.018 mL, 0.12 mmol). The reaction was stirred at ~25° C. for 2 h. All solvents were removed in vacuo. The residue was dissolved in MeOH (2 mL) and purified via preparative HPLC (AcCN/water/ NH₄OAc) to afford the title compound (45.8 mg). LC-MS retention time=1.517 min; m/z=524.0 [M+H]⁺. (Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example VN-23

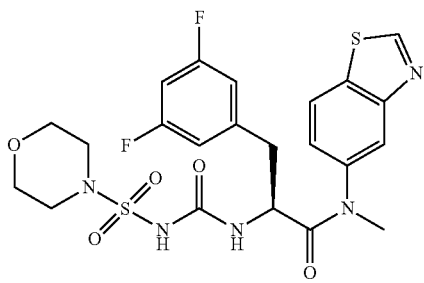 [SMILES: CN(C(=O)[C@H](Cc1cc(F)cc(F)c1)NC(=O)NS(=O)(=O)N1CCOCC1)c1ccc2scnc2c1]

To a solution of Intermediate VN-29 (0.050 g, 0.11 mmol) and morpholine-4-sulfonamide (0.020 g, 0.12 mmol) in acetonitrile (1 mL) was added DBU (0.018 mL, 0.12 mmol). The reaction was stirred at ~25° C. for 2 h. All solvents were removed in vacuo. The residue was dissolved in MeOH (2 mL) and purified via preparative HPLC (AcCN/water/NH$_4$OAc) and repurified via preparative HPLC (MeOH/water/NH$_4$OAc) to afford the title compound (44.7 mg). LC-MS retention time=1.267 min; m/z=540.0 [M+H]$^+$. (Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example VN-24

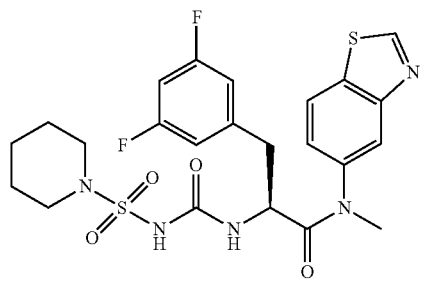 [SMILES: CN(C(=O)[C@H](Cc1cc(F)cc(F)c1)NC(=O)NS(=O)(=O)N1CCCCC1)c1ccc2scnc2c1]

To a mixture of Intermediate VN-29 (0.033 g, 0.070 mmol) and piperidine-1-sulfonamide (0.013 g, 0.077 mmol) in acetonitrile (1 mL) was added DBU (0.012 mL, 0.077 mmol). The reaction was stirred at ~25° C. for 2.5 h. All solvents were removed in vacuo. The residue was dissolved in MeOH (2 mL) and purified via preparative HPLC (AcCN/water/NH$_4$OAc) to afford the title compound (27.9 mg). LC-MS retention time=1.623 min; m/z=538.0 [M+H]$^+$. (Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example BB-16

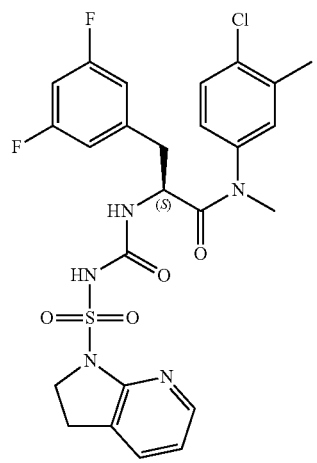

To stirred solution of Intermediate BB-7.3 (0.050 g, 0.11 mmol), Intermediate BB-1.2 hydrochloride (0.024 g, 0.12 mmol) in acetonitrile (1 mL) was added DBU (0.025 mL, 0.16 mmol) at room temperature and stirred for 16 h. The reaction mixture was diluted with water (15 mL) and extracted with EtOAc (3×10 mL). The combined organic layer was washed with water (15 mL), brine (15 mL), dried (Na$_2$SO$_4$), filtered and concentrated. The crude product was purified by combiflash chromatography (4 g Redisep® SiO$_2$ column, eluting with 2.5% MeOH in CHCl$_3$) followed by preparative HPLC to afford the title compound (4.7 mg) as an off white solid. LC-MS retention time=2.81 min; m/z=564.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example BB-17

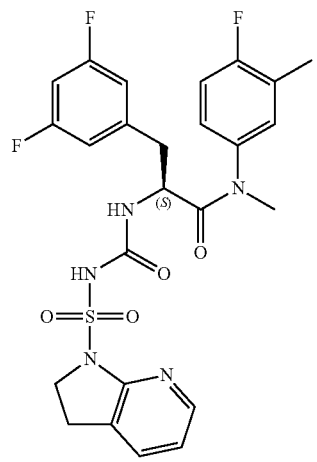

To a solution of Intermediate BB-8.4 (0.050 g, 0.11 mmol) and Intermediate BB-1.2 hydrochoride (0.025 g, 0.12 mmol) in acetonitrile (1 mL), was added DBU (0.026 mL, 0.17 mmol) and the reaction mixture was stirred at room temperature for 16 h. The reaction mixture was diluted with water (40 mL) and extracted with EtOAc (3×20 mL). The combined organic layer was washed with water (20 mL), brine (20 mL), dried (Na$_2$SO$_4$), filtered and concentrated. The crude product was purified by combiflash chromatography (4 g Redisep® SiO$_2$ column, eluting with 2.5% MeOH in CHCl$_3$) followed by preparative HPLC to afford the title compound (6 mg) as an off white solid. LC-MS retention time=1.92 min; m/z=548.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, DMSO-d$_6$) δ 7.99 (br. s., 1H), 7.58 (br. s., 1H), 7.14 (t, J=9.0 Hz, 1H), 7.03 (t, J=9.5 Hz, 1H), 6.91 (br. s., 3H), 6.69 (br. s., 1H), 6.47 (d, J=7.0 Hz, 2H), 4.24 (dd, J=13.2, 7.2 Hz, 1H), 4.10-3.98 (m, 2H), 3.05 (s, 3H), 3.10-3.00 (br., s, 2H), 2.72 (d, J=13.6, 6.0 Hz, 1H), 2.62-2.54 (m, 1H), 2.18 (s, 3H).

Example BB-18

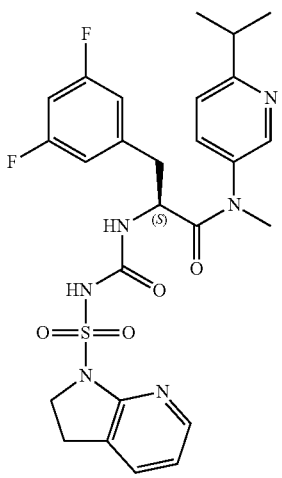

To a stirred solution of Intermediate BB-9.6 (100 mg, 0.221 mmol) and Intermediate BB-1.2 hydrochloride (43.9 mg, 0.221 mmol) in acetonitrile (4 mL) was added DBU (0.066 mL, 0.44 mmol), the reaction mixture was stirred at room temperature for 16 h. The reaction mixture was diluted with water (25 mL) and extracted with EtOAc (2×25 mL). The combined organic layer was dried (Na$_2$SO$_4$), filtered and concentrated. The crude product was purified by preparative HPLC to afford the title compound (25 mg) as an off white solid. LC-MS retention time=1.67 min; m/z=559.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR: (400 MHZ, MeOH-d$_4$) δ 8.15 (br. s., 1H), 8.03 (d, J=5.0 Hz, 1H), 7.60 (d, J=7.0 Hz, 1H), 7.40 (br, s., 1H), 7.34 (d, J=8.0 Hz, 2H), 6.96 (dd, J=7.5, 5.5 Hz, 1H), 6.78 (t, J=9.3 Hz, 1H), 6.43 (d, J=6.5 Hz, 2H), 4.39 (t, J=7.0 Hz, 1H), 4.21 (dd, J=18.8, 9.2 Hz, 2H), 3.21 (s, 3H), 3.19-3.06 (m, 3H), 2.87 (dd, J=13.6, 6.5 Hz, 1H), 2.66 (dd, J=13.6, 7.5 Hz, 1H), 1.33 (d, J=7.0 Hz, 6H).

Example BB-19

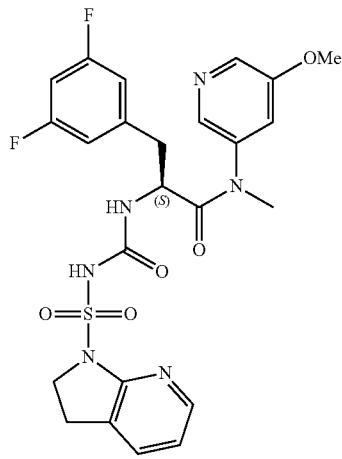

To a stirred solution of Intermediate BB-10.4 (100 mg, 0.227 mmol) and Intermediate BB-1.2 hydrochloride (45.1 mg, 0.227 mmol) in acetonitrile (4 mL) was added DBU (0.068 mL, 0.45 mmol) and the reaction mixture was stirred at room temperature for 16 h. The reaction mixture was diluted with water (25 mL) and extracted with EtOAc (2×25 mL). The combined organic layer was washed with 1.5N HCl solution (25 mL), dried (Na$_2$SO$_4$), filtered, concentrated and the crude product was purified by preparative HPLC to afford the title compound (29 mg) as an off white solid. LC-MS retention time=1.31 min; m/z=547.2 [M+H]$^+$. Column: KINETIX XB-C18, 75×3 mm, 2.6 Jam; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 8.25 (br. s., 1H), 8.03 (d, J=4.5 Hz, 1H), 7.73 (br. s., 1H), 7.61 (d, J=7.0 Hz, 1H), 7.13 (br. s., 1H), 6.97 (dd, J=7.3, 5.3 Hz, 1H), 6.80 (t, J=9.3 Hz, 1H), 6.52 (d, J=6.5 Hz, 2H), 4.42 (t, J=6.8 Hz, 1H), 4.31-4.12 (m, 2H), 3.87 (s, 3H), 3.21 (s, 3H), 3.19-3.10 (m, 2H), 2.91 (dd, J=13.2, 7.2 Hz, 1H), 2.70 (dd, J=13.2, 6.4 Hz, 1H).

Example VN-25

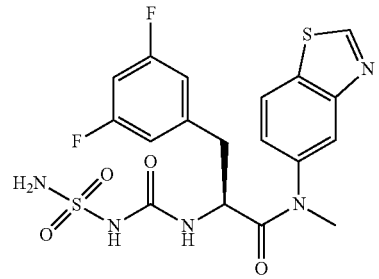 [SMILES: CN(C(=O)[C@H](Cc1cc(F)cc(F)c1)NC(=O)NS(N)(=O)=O)c1ccc2scnc2c1]

To a solution of Intermediate VN-29 (0.050 g, 0.11 mmol) and sulfuric diamide (0.011 g, 0.12 mmol) in acetonitrile (1 mL) was added DBU (0.018 mL, 0.12 mmol). The reaction was stirred at ~25° C. for 3.5 h. All solvents were removed in vacuo. The residue was dissolved in MeOH (2 mL) and purified via preparative HPLC (AcCN/water/NH$_4$OAc) to afford the title compound (47.7 mg). LC-MS retention time=1.29 min; m/z=469.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example BB-20

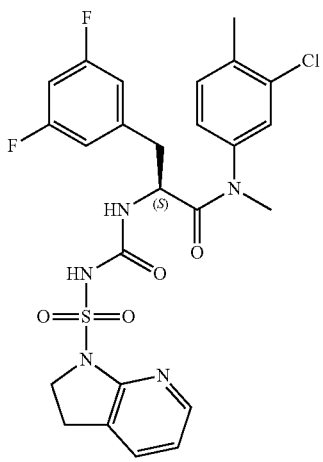

To a solution of Intermediate BB-11.3 (110 mg, 0.249 mmol) and Intermediate BB-1.2 hydrochloride (50 mg, 0.25 mmol) in acetonitrile (5 mL) was added DBU (57 mg, 0.37 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered and concentrated. The crude product was purified by preparative HPLC to afford the title compound (110 mg) as an off white solid. LC-MS retention times=2.16 min: m/z=564.2 [M+H]$^+$. Column: KINETIX XB-C18, 75×3 mm, 2.6 μm; Flow rate: 1 mL/min; Mobile Phase A: 0.1% formic acid in water; Mobile Phase B: ACN; 5% B to 40% B over 3 minutes, then hold a 0.5 min. at 100% B of flow rate 1.5 mL/min; Detection: UV at 220 nm. $^1$H NMR (400 MHz, MeOH-d$_4$) δ 8.04 (d, J=5.02 Hz, 1H), 7.61 (d, J=6.53 Hz, 1H), 7.29 (d, J=8.03 Hz, 1H), 6.97 (dd, J=7.28, 5.27 Hz, 1H), 6.90 (br. s., 1H), 6.85-6.75 (m, 2H), 6.48 (d, J=6.02 Hz, 2H), 4.44 (m, 1H), 4.29-4.14 (m, 2H), 3.20-3.10 (m, 2H), 3.15 (s, 3H), 2.87 (dd, J=13.55, 7.53 Hz, 1H), 2.65 (dd, J=13.55, 7.03 Hz, 1H), 2.39 (s, 3H).

Example GW-18

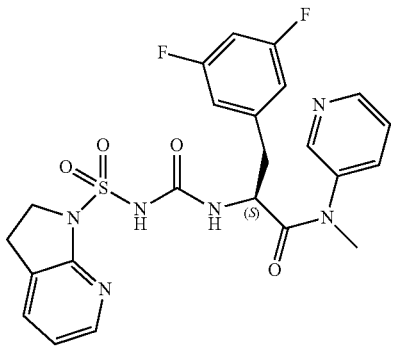

To a solution of sulfurisocyanatidic chloride (23 mg, 0.17 mmol) in DCM (1 mL) in an ice-water bath was added a solution of Intermediate GW-17.2 (60 mg, 0.17 mmol) and DIPEA (0.06 mL, 0.33 mmol) in DCM (1 mL) and the reaction mixture was stirred for 2 min. Then a solution of 2,3-dihydro-1H-pyrrolo[2,3-b]pyridine (30 mg, 0.25 mmol) in DCM (1 mL) was added, followed by DIPEA (0.1 mL, 0.66 mmol) and the reaction mixture was stirred for 2 min. The bath was removed, the reaction mixture was stirred at rt for 2 h, concentrated, the residue was redissolved in DMF and purified by preparative HPLC to afford the title compound (9.9 mg). LC-MS retention time=2.54 min; m/z=517.20 [M+H]$^+$. (Column: Phenomenex C18 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-19

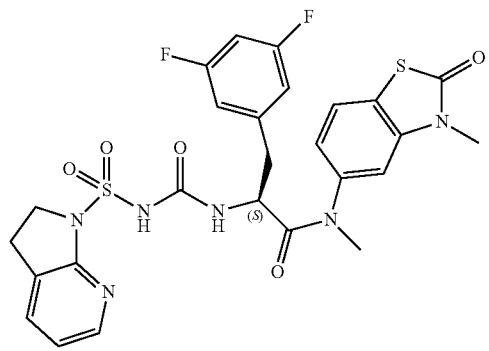

To a solution of sulfurisocyanatidic chloride (22 mg, 0.16 mmol) in DCM (2 mL) was added a solution of Intermediate GW-18.3 (70 mg, 0.15 mmol) and DIPEA (0.05 mL, 0.3 mmol) in DCM (2 mL) in an ice-water bath and the reaction mixture was stirred for 2 min. Then a solution of 2,3-dihydro-1H-pyrrolo[2,3-b]pyridine (28.0 mg, 0.233 mmol) in DCM (2 mL) was added, followed by DIPEA (0.11 mL, 0.62 mmol) and the reaction mixture was stirred for 2 min, the bath was removed and the stirring was continued at rt for 2 h. The reaction mixture was concentrated and purified by preparative HPLC to afford the title compound (19.4 mg).

LC-MS retention time=3.37 min; m/z=603.20 [M+H]+. (Column: Phenomenex C18 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Example GW-20

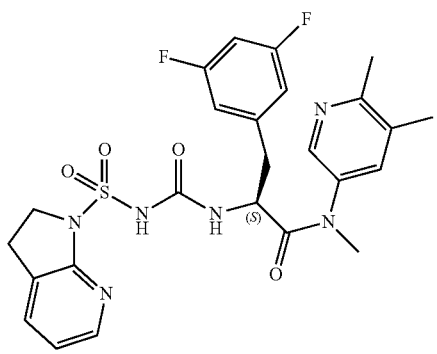

To a solution of sulfurisocyanatidic chloride (27 mg, 0.19 mmol) in DCM (2 mL) was added a solution of Intermediate GW-19.3 (75 mg, 0.19 mmol) and DIPEA (0.07 mL, 0.4 mmol) in DCM (2 mL) in an ice-water bath and the reaction mixture was stirred for 2 min. Then a solution of 2,3-dihydro-1H-pyrrolo[2,3-b]pyridine (35 mg, 0.29 mmol) in DCM (2 mL) was added, followed by DIPEA (0.13 mL, 0.77 mmol) and the reaction mixture was stirred for 2 min, the bath was removed and the stirring was continued for 1 h. The reaction mixture was concentrated, the residue was redissolved in DMF and purified by preparative HPLC to afford the title compound (19.9 mg). LC-MS retention time=2.64 min; m/z=545.20 [M+H]+. (Column: Phenomenex C18 2.0× 50 mm, 3 m particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Example AW-3

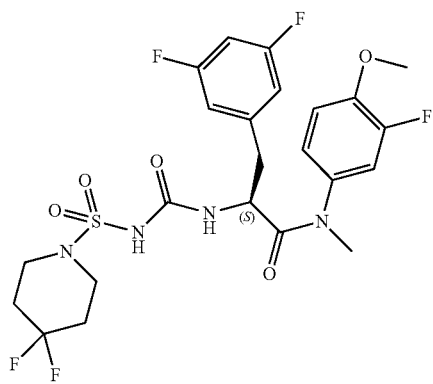

To a solution of 0.1 M sulfurisocyanatidic chloride in DCM (2.28 mL, 0.228 mmol) at 0° C. was added a pre-made solution of an HCl salt of Intermediate AW-3 (80 mg, 0.21 mmol) and TEA (0.029 mL, 0.21 mmol) in DCM (0.5 mL) dropwise. The reaction mixture was stirred at 0° C. for 30 min. Then a solution of 4,4-difluoropiperidine, HCl (49.0 mg, 0.311 mmol) and TEA (0.144 mL, 1.04 mmol) in DCM (0.5 mL) was added, the cold bath was removed and the resulting solution was stirred at rt for 1 h. The solvent was removed in vacuo, and the residue was taken up into DMF (1 mL), filtered and purified by preparative HPLC to afford the title compound (45 mg) as a white solid. LC-MS retention time=1.86 min; m/z=565.15 [M+H]+. (Start % B=0, Final % B=100, Gradient Time=2 min, Flow Rate=1.0 mL/min, Wavelength=220, Solvent Pair=Water/Acetonitrile/TFA, Solvent A=10% acetonitrile/90% Water/0.1% TFA, Solvent B=90% Acetonitrile/10% water/0.1% TFA, Column=Phenomenex Luna 30×2.0 MM 3 μm, Oven Temp.=40° C.).

Example AW-4

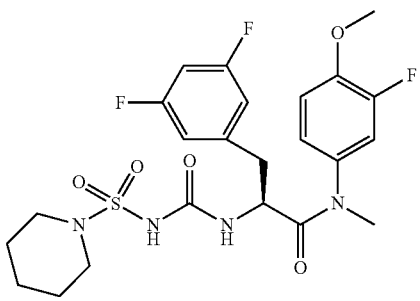 [SMILES: COc1ccc(N(C)C(=O)[C@H](Cc2cc(F)cc(F)c2)NC(=O)NS(=O)(=O)N2CCCCC2)cc1F]

To a solution of piperidine-1-sulfonamide (16 mg, 0.097 mmol) in acetonitrile (1 mL) was added DBU (0.018 mL, 0.12 mmol) and the mixture was stirred at rt for 10 min. Intermediate AW-4 (45 mg, 0.097 mmol) was then added and stirring continued at rt for 2 h. The solvent was then removed in vacuo, and the residue was dissolved into DMF (1 mL), filtered and purified by preparative HPLC to afford the title compound (26 mg) as a white solid. LC-MS retention time=1.86 min; m/z=529.20 [M+H]+. (Start % B=0, Final % B=100, Gradient Time=2 min, Flow Rate=1.0 mL/min, Wavelength=220, Solvent Pair=Water/Acetonitrile/TFA, Solvent A=10% acetonitrile/90% Water/0.1% TFA, Solvent B=90% Acetonitrile/10% water/0.1% TFA, Column=Phenomenex Luna 30×2.0 MM 3 μm, Oven Temp.=40° C.).

Example BB-21

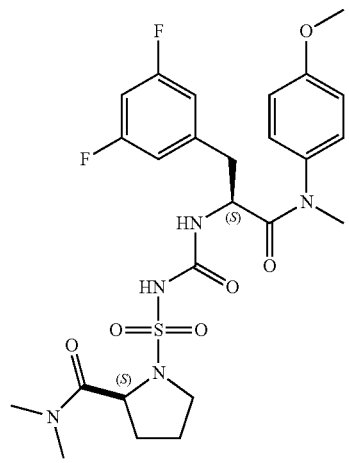

To a stirred solution of Intermediate BB-28.3 (50 mg, 0.114 mmol) and (S)—N,N-dimethyl-1-sulfamoylpyrrolidine-2-carboxamide hydrochloride (29.3 mg, 0.114 mmol) in acetonitrile (4 mL) was added DBU (0.04 mL, 0.227 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered and concentrated and the crude product was purified by preparative HPLC to afford the title compound (10 mg) as an off white solid. LC-MS retention time=2.15 min; m/z=568.2 [M+H]$^+$. Column: KINETIX XB-C18, 75×3 mm, 2.6 m; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 7.14 (d, J=8.4 Hz, 2H), 7.00 (dd, J=7.6, 1.6 Hz, 2H), 6.76 (tt, J=9.2, 2.4 Hz, 1H), 6.52 (m, 2H), 5.04 (dd, J=8.3, 4.3 Hz, 1H), 4.59 (dd, J=8.0, 6.0 Hz, 1H), 3.87 (s, 3H), 3.56-3.46 (m, 2H), 3.23 (s, 3H), 3.14 (s, 3H), 2.97 (s, 3H), 2.95 (dd, J=13.55, 7.53 Hz, 1H), 2.84 (dd, J=13.6, 5.6 Hz, 1H), 2.30-2.23 (m, 1H), 2.10-2.00 (m, 1H), 1.97-1.87 (m, 2H).

Example BB-22

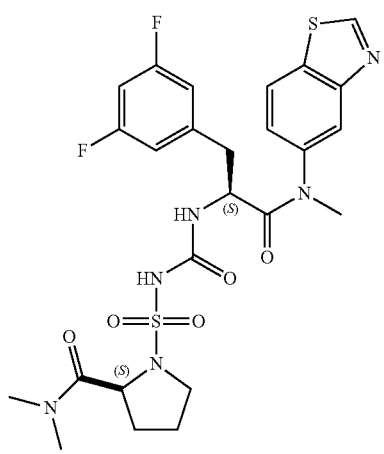

To a stirred solution of Intermediate VN-29 (50 mg, 0.107 mmol) and (S)—N,N-dimethyl-1-sulfamoylpyrrolidine-2-carboxamide hydrochloride (27.6 mg, 0.107 mmol) in acetonitrile (4 mL) was added DBU (0.032 mL, 0.214 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered, concentrated and the crude product was purified by preparative HPLC to afford the title compound (4.5 mg) as an off white solid. LC-MS retention time=1.62 min; m/z=595.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example VN-26

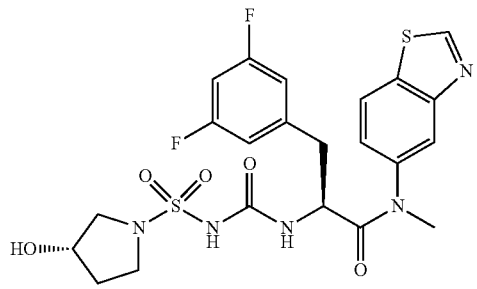 [SMILES: CN(C(=O)[C@H](Cc1cc(F)cc(F)c1)NC(=O)NS(=O)(=O)N1CC[C@H](O)C1)c1ccc2scnc2c1]

To a solution of sulfurisocyanatidic chloride (0.021 mL, 0.24 mmol) in CH$_2$Cl$_2$ (0.5 mL) at 0° C. under nitrogen was added a solution of an HCl salt of Intermediate ZY-5 (0.1 g, 0.2 mmol) and triethylamine (0.033 mL, 0.24 mmol) in CH$_2$Cl$_2$ (1 mL) dropwise over 1 min. The reaction was removed from the cold bath and stirred at ~25° C. under nitrogen for 30 min, then cooled to 0° C. and a suspension of (S)-pyrrolidin-3-ol hydrochloride (0.044 g, 0.36 mmol) and triethylamine (0.166 mL, 1.19 mmol) in CH$_2$Cl$_2$ (1 mL) was added dropwise over 1 min. The reaction was removed from the cold bath and stirred at ~25° C. for 4.5 h. All solvents were removed in vacuo. The residue was taken up in MeOH (2 mL) and purified via preparative HPLC (AcCN/water/NH$_4$OAc) and repurified (MeOH/water/NH$_4$OAc) to afford the title compound (5.6 mg). LC-MS retention time=1.682 min; m/z=539.9 [M+H]$^+$. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example BB-23

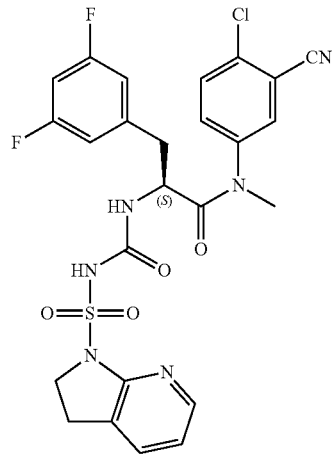

To a stirred solution of Intermediate BB-12.4 (50 mg, 0.106 mmol) and Intermediate BB-1.2 hydrochloride (21.2 mg, 0.106 mmol) in acetonitrile (4 mL) was added DBU (0.016 mL, 0.106 mmol) and reaction mixture was stirred at room temperature for 16 h. Then the reaction mixture was diluted with water (15 mL) and extracted with EtOAc (2×15 mL). The combined organic layer was dried (Na₂SO₄), filtered, concentrated and the crude product was purified by preparative HPLC to afford the title compound (5.2 mg) as an off white solid. LC-MS retention time=2.12 min; m/z=575.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm.

Example VN-27

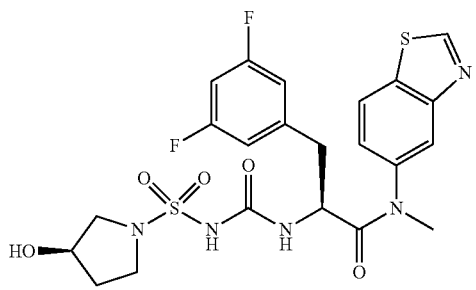 [SMILES: CN(C(=O)[C@H](Cc1cc(F)cc(F)c1)NC(=O)NS(=O)(=O)N1CC[C@@H](O)C1)c1ccc2scnc2c1]

To a solution of sulfurisocyanatidic chloride (0.025 mL, 0.29 mmol) in CH₂Cl₂ (0.5 mL) at 0° C. under nitrogen was added a solution of an HCl salt of Intermediate ZY-5 (0.10 g, 0.2 mmol) and triethylamine (0.033 mL, 0.24 mmol) in CH₂Cl₂ (1 mL) dropwise over 1 min. The reaction was removed from the cold bath and stirred at ~25° C. under nitrogen for 35 min, then cooled to 0° C. and treated dropwise with a solution of (R)-pyrrolidin-3-ol (0.031 g, 0.357 mmol) and triethylamine (0.166 mL, 1.190 mmol) in CH₂Cl₂ (1 mL) over 1 min. The reaction was then removed from the cold bath and stirred at ~25° C. under nitrogen for 1.5 h. All solvents were removed in vacuo. The residue was taken up in MeOH (2 mL) and purified via preparative HPLC (ACN/water/NH₄OAc) to afford the tittle compound (13.6 mg). LC-MS retention time=1.275 min; m/z=540.0 [M+H]⁺. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example VN-28

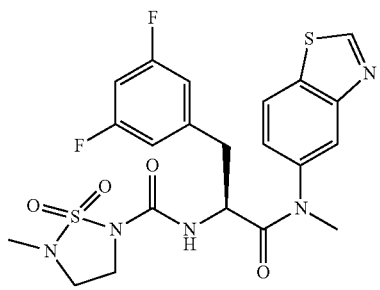 [SMILES: CN(C(=O)[C@H](Cc1cc(F)cc(F)c1)NC(=O)N1CCN(C)S1(=O)=O)c1ccc2scnc2c1]

To a mixture of Intermediate VN-29 (0.050 g, 0.11 mmol) and Intermediate VN-28.1 (0.016 g, 0.118 mmol) in acetonitrile (1 mL) was added DBU (0.018 mL, 0.12 mmol). The reaction mixture was stirred at ~25° C. for 3 h. The reaction was diluted with acetonitrile (1 mL) and purified via preparative HPLC (AcCN/water/NH₄OAc) to afford the tittle compound (9.3 mg). LC-MS retention time=1.579 min; m/z=510.0 [M+H]⁺. (Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm).

Example BB-24

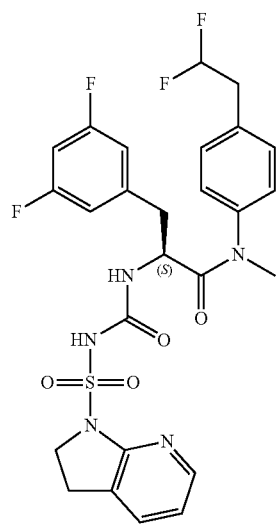

To a stirred solution of Intermediate BB-14.6 (100 mg, 0.211 mmol) in acetonitrile (5 mL) was added Intermediate BB-1.2 hydrochloride (42.0 mg, 0.211 mmol) and DBU (0.048 mL, 0.32 mmol) and the reaction mixture was stirred at room temperature for 3 h. The reaction mixture was diluted with water (25 mL) and extracted with EtOAc (2×25 mL). The combined organic layer was dried (Na₂SO₄), filtered, concentrated and the crude product was purified by preparative HPLC to afford the title compound (25 mg) as an off white solid. LC-MS retention time=1.83 min; m/z=580.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, CDCl₃) δ 8.09 (d, J=4.8 Hz, 1H), 7.49 (d, J=7.5 Hz, 1H), 7.23 (d, J=8.0 Hz, 2H), 6.95-6.85 (m, 4H), 6.61-6.54 (m, 1H), 6.33 (d, J=6.0 Hz, 2H), 5.94 (tt, J=56.4, 4.8 Hz, 1H), 4.65 (dd, J=15.6, 6.9 Hz, 1H), 4.36-4.21 (m, 2H), 3.23 (s, 3H), 3.17-3.09 (m, 4H), 2.76 (dd, J=13.3, 6.8 Hz, 1H), 2.58 (dd, J=13.6, 7.0 Hz, 1H).

Example BB-25

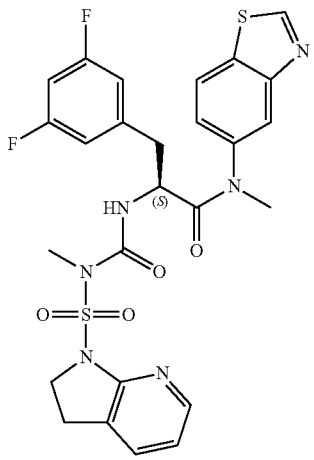

To a solution of Example ZY-1 (80 mg, 0.14 mmol) in acetonitrile (10 mL) was added Na$_2$CO$_3$ (14.81 mg, 0.14 mmol) followed by methyl iodide (0.04 mL, 0.7 mmol) and the resulting reaction was allowed to stir at room temperature for 16 h. The reaction mixture was quenched with water, extracted with DCM (2×25 mL), the combined organic layer was dried (Na$_2$SO$_4$), evaporated and the crude product was purified HPLC to afford title compound (10 mg) as an off white solid. LC-MS retention time=3.27 min; m/z=587.2 [M+H]$^+$. Column: KINETIX XB-C18, 75×3 mm, 2.6 μm; Flow rate: 0.7 mL/min; Mobile Phase A: 5 mM NH$_4$OAc in 98% Water/2% ACN; Mobile Phase B: 5 mM NH$_4$OAc in 2% Water/98% ACN; 20% B to 100% B over 4 min, then hold for 0.6 min at 100% B with flow rate of 1.5 mL/min; Detection: UV at 220 nm.

Example BB-26

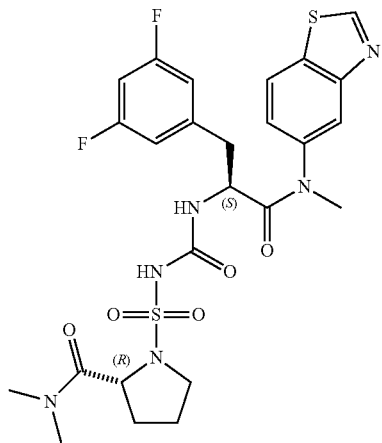

To a stirred solution of Intermediate VN-29 (75 mg, 0.160 mmol) and (R)—N,N-dimethyl-1-sulfamoylpyrrolidine-2-carboxamide hydrochloride (41.3 mg, 0.160 mmol) in acetonitrile (4 mL) was added DBU (0.048 mL, 0.32 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered and concentrated. The crude product was purified by preparative HPLC to afford the title compound (4.5 mg) as an off white solid. LC-MS retention time=1.70 min; m/z=595.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 9.38 (s, 1H), 8.21 (d, J=8.5 Hz, 1H), 7.98 (br. s., 1H), 7.36 (d, J=7.2 Hz, 1H), 6.77 (t, J=9.2 Hz, 1H), 6.49 (d, J=6.5 Hz, 2H), 5.06 (dd, J=8.0, 4.0 Hz, 1H), 4.62 (dd, J=8.0, 5.6 Hz, 1H), 3.42 (br. s., 1H), 3.36 (s, 3H), 3.25 (m, 1H), 3.13 (s, 3H), 3.06-2.99 (dd, J=13.6, 9.0 Hz, 1H), 2.97 (s, 3H), 2.82 (dd, J=13.6, 9.0 Hz, 1H), 2.10-1.90 (m, 2H), 1.80 (br. s., 2H).

Example BB-27

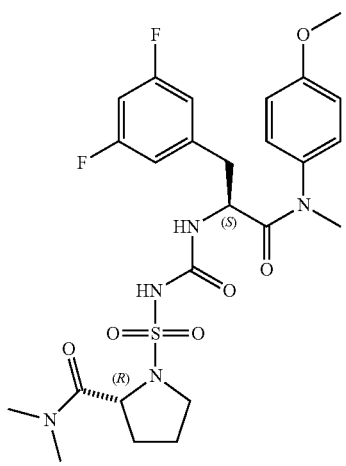

To a stirred solution of Intermediate BB-28.3 (75 mg, 0.17 mmol) and (R)—N,N-dimethyl-1-sulfamoylpyrrolidine-2-carboxamide hydrochloride (43.9 mg, 0.170 mmol) in acetonitrile (4 mL) was added DBU (0.034 mL, 0.34 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered, concentrated and the crude product was purified by preparative HPLC to afford the title compound (4.5 mg) as an off white solid. LC-MS retention time=1.94 min; m/z=568.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 7.20 (d, J=8.0 Hz, 2H), 7.05 (d, J=9.0 Hz, 2H), 6.81 (t, J=9.3 Hz, 1H), 6.51 (d, J=6.5 Hz, 2H), 5.07 (dd, J=7.6, 3.2 Hz, 1H), 4.65 (dd, J=8.8, 4.8 Hz, 1H), 3.88 (s, 3H), 3.51-3.40 (m, 1H), 3.25 (s, 3H), 3.25-3.13 (m, 1H), 3.13 (s, 3H), 2.97 (s, 3H), 3.02-2.95 (m, 1H), 2.75 (dd, J=13.6, 9.0 Hz, 1H), 2.15-1.95 (m, 2H), 1.80 (m, 2H).

Examples CA-122 to CA-158

Generic Experimental Procedure

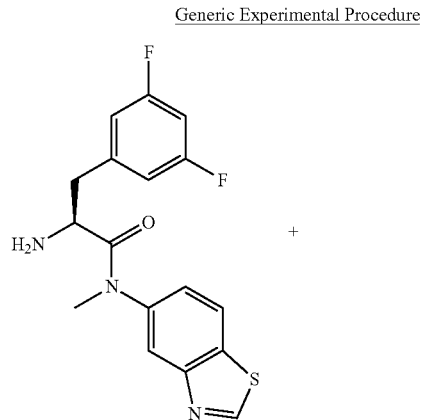

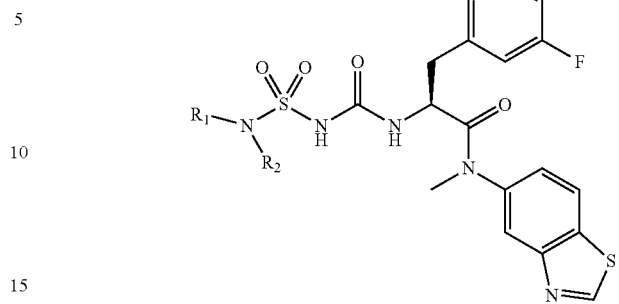

To a solution of sulfurisocyanatidic chloride (750 μL, 8.5 mmol) in DCM (8.5 mL) at 0° C. was added dropwise a solution of an HCl salt of Intermediate ZY-5 (1.4 g, 3.4 mmol) and TEA (950 μL, 6.8 mmol) in DCM (17 mL). The reaction mixture was allowed to stir under nitrogen at 0° C. for 5 minutes before adding a solution of triethylamine (2.1 mL, 15 mmol) in DCM (8.5 mL). A portion (1.0 mL, 0.10 mmol) of the above reaction mixture was then added to a solution of an amine input (0.20 mmol) in DCM (0.25 mL) and the reaction vessel was sealed and allowed to shake at rt for 1 h. The reaction mixture was then diluted with MeOH (0.5 mL), concentrated to dryness, dissolved into DMF (1 mL), filtered and purified by preparative HPLC to afford the examples (CA-122 through CA-158) in the table below.

| Ex # | Amine input | Example Structure | Mass (mg) | RT (min) | Obs'd Mass [M + 1] | LC-MS Cond.* |
|---|---|---|---|---|---|---|
| CA-122 | 1-methylpiperazine | structure | 13.0 TFA | 1.19 | 553.0 | QC-ACN-AA-XB |
| CA-123 | 3-aminopyridine | structure | 2.0 | 1.22 | 547.0 | QC-ACN-TFA-XB |

-continued

| Ex # | Amine input | Example Structure | Mass (mg) | RT (min) | Obs'd Mass [M + 1] | LC-MS Cond.* |
|---|---|---|---|---|---|---|
| CA-124 | ethylamine | | 3.4 | 2.00 | 498.0 | QC-ACN-AA-XB |
| CA-125 | 2-(methylamino)ethanol | | 19.5 | 1.40 | 528.0 | QC-ACN-TFA-XB |
| CA-126 | benzylamine | | 5.7 | 1.63 | 560.0 | QC-ACN-AA-XB |
| CA-127 | cyclopropylmethanamine | | 11.2 | 1.71 | 524.0 | QC-ACN-TFA-XB |

-continued

| Ex # | Amine input | Example Structure | Mass (mg) | RT (min) | Obs'd Mass [M + 1] | LC-MS Cond.* |
|---|---|---|---|---|---|---|
| CA-128 | | | 8.3 TFA | 1.41 | 540.0 | QC-ACN-AA-XB |
| CA-129 | | | 5.2 TFA | 1.34 | 540.0 | QC-ACN-AA-XB |
| CA-130 | | | 11.1 | 1.76 | 545.9 | QC-ACN-TFA-XB |
| CA-131 | | | 8.7 | 1.44 | 554.0 | QC-ACN-AA-XB |

-continued

| Ex # | Amine input | Example Structure | Mass (mg) | RT (min) | Obs'd Mass [M + 1] | LC-MS Cond.* |
|---|---|---|---|---|---|---|
| CA-132 | cyclobutylmethanamine | | 14.4 | 1.58 | 524.0 | QC-ACN-AA-XB |
| CA-133 | 4-benzylpiperidine | | 15.9 | 2.10 | 628.0 | QC-ACN-AA-XB |
| CA-134 | pyridin-2-ylmethanamine | | 13.3 | 1.31 | 561.0 | QC-ACN-TFA-XB |

-continued

| Ex # | Amine input | Example Structure | Mass (mg) | RT (min) | Obs'd Mass [M + 1] | LC-MS Cond.* |
|---|---|---|---|---|---|---|
| CA-135 | 3-(aminomethyl)pyridine | (structure) | 18.5 | 1.28 | 561.0 | QC-ACN-TFA-XB |
| CA-136 | isopropylamine | (structure) | 9.5 | 1.57 | 512.0 | QC-ACN-AA-XB |
| CA-137 | N-acetylethylenediamine | (structure) | 14.4 | 1.26 | 555.0 | QC-ACN-AA-XB |
| CA-138 | 2-aminoethanol | (structure) | 8.0 | 1.38 | 513.9 | QC-ACN-TFA-XB |

-continued
| Ex # | Amine input | Example Structure | Mass (mg) | RT (min) | Obs'd Mass [M + 1] | LC-MS Cond.* |
|---|---|---|---|---|---|---|
| CA-139 | 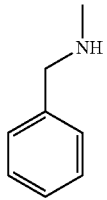 | 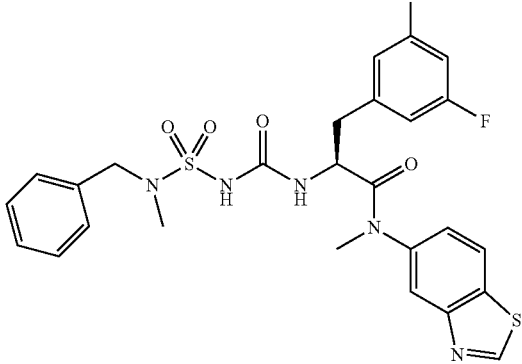 | 12.3 | 1.85 | 574.0 | QC-ACN-AA-XB |
| CA-140 | 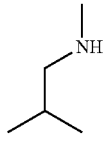 | 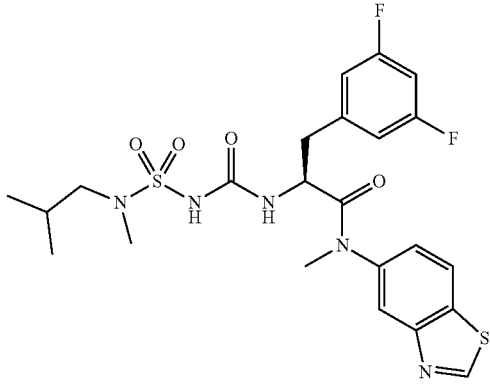 [SMILES: CC(C)CN(C)S(=O)(=O)NC(=O)N[C@@H](Cc1cc(F)cc(F)c1)C(=O)N(C)c1ccc2scnc2c1] | 12.3 | 1.82 | 540.1 | QC-ACN-AA-XB |
| CA-141 | 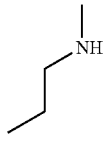 | 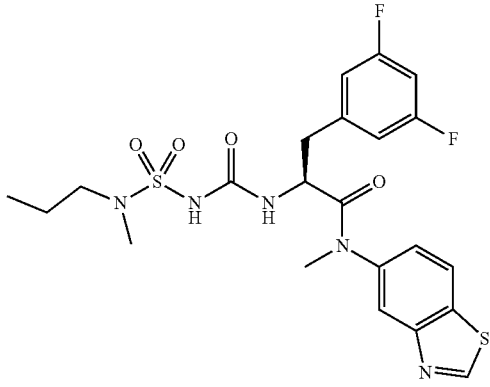 [SMILES: CCCN(C)S(=O)(=O)NC(=O)N[C@@H](Cc1cc(F)cc(F)c1)C(=O)N(C)c1ccc2scnc2c1] | 5.7 | 1.79 | 526.0 | QC-ACN-TFA-XB |
| CA-142 |  | 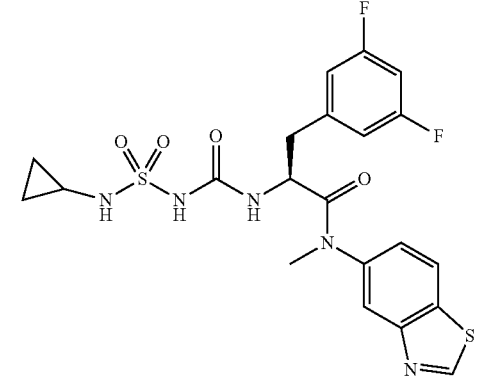 [SMILES: CN(C(=O)[C@H](Cc1cc(F)cc(F)c1)NC(=O)NS(=O)(=O)NC1CC1)c1ccc2scnc2c1] | 3.2 | 1.58 | 509.9 | QC-ACN-TFA-XB |

-continued
| Ex # | Amine input | Example Structure | Mass (mg) | RT (min) | Obs'd Mass [M + 1] | LC-MS Cond.* |
|---|---|---|---|---|---|---|
| CA-143 | 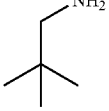 | 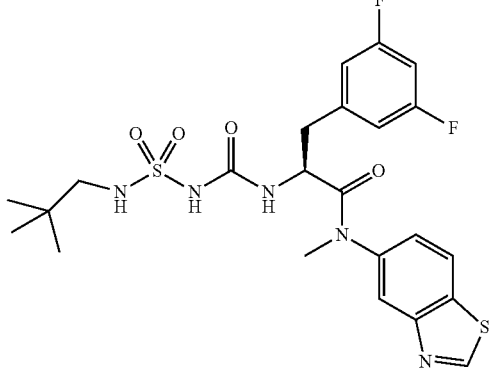 | 3.6 | 1.80 | 540.0 | QC-ACN-AA-XB |
| CA-144 | 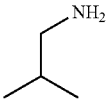 | 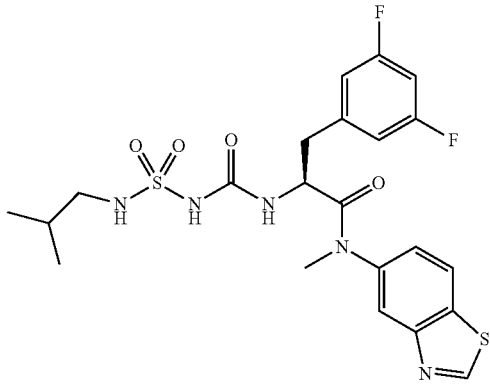 [SMILES: CC(C)CNS(=O)(=O)NC(=O)N[C@@H](Cc1cc(F)cc(F)c1)C(=O)N(C)c1ccc2scnc2c1] | 6.0 | 1.70 | 526.0 | QC-ACN-AA-XB |
| CA-145 | 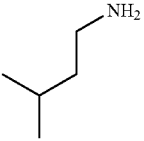 | 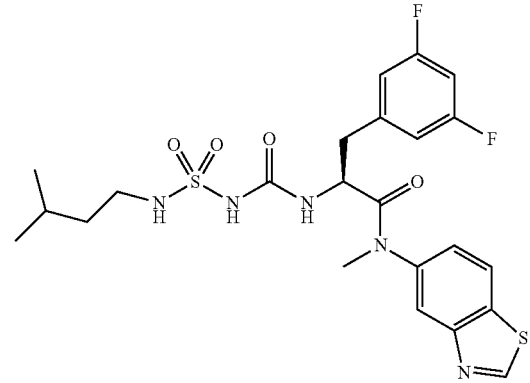 [SMILES: CC(C)CCNS(=O)(=O)NC(=O)N[C@@H](Cc1cc(F)cc(F)c1)C(=O)N(C)c1ccc2scnc2c1] | 7.6 | 1.88 | 540.0 | QC-ACN-TFA-XB |
| CA-146 | 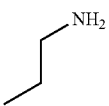 | 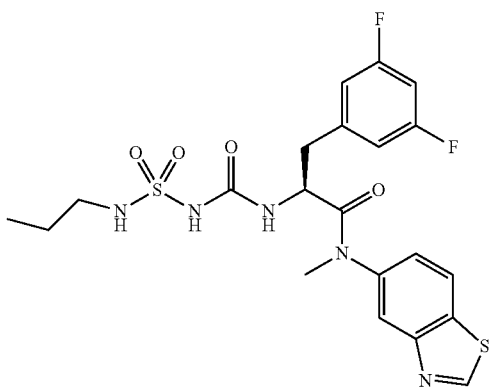 [SMILES: CCCNS(=O)(=O)NC(=O)N[C@@H](Cc1cc(F)cc(F)c1)C(=O)N(C)c1ccc2scnc2c1] | 10.0 | 1.58 | 512.0 | QC-ACN-AA-XB |

-continued
| Ex # | Amine input | Example Structure | Mass (mg) | RT (min) | Obs'd Mass [M + 1] | LC-MS Cond.* |
|---|---|---|---|---|---|---|
| CA-147 | 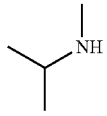 | 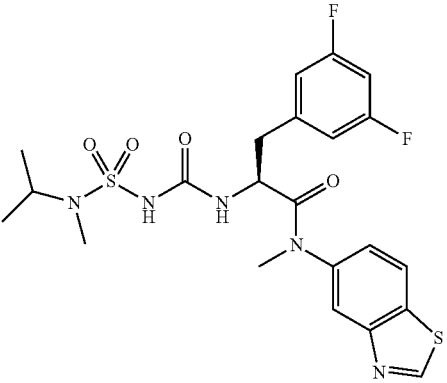 [SMILES: CC(C)N(C)S(=O)(=O)NC(=O)N[C@@H](Cc1cc(F)cc(F)c1)C(=O)N(C)c1ccc2scnc2c1] | 11.5 | 1.76 | 526.0 | QC-ACN-TFA-XB |
| CA-148 | 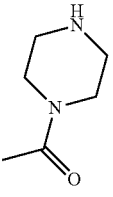 | 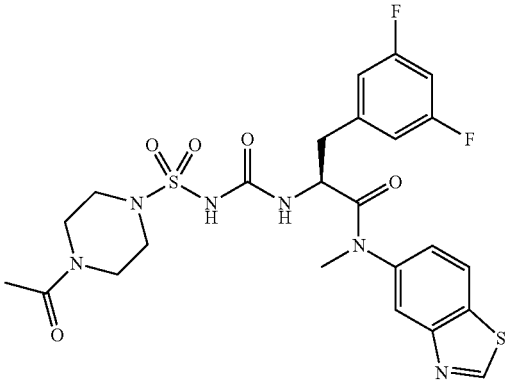 [SMILES: CC(=O)N1CCN(S(=O)(=O)NC(=O)N[C@@H](Cc2cc(F)cc(F)c2)C(=O)N(C)c2ccc3scnc3c2)CC1] | 45.6 | 1.27 | 581.0 | QC-ACN-AA-XB |
| CA-149 | 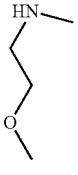 | 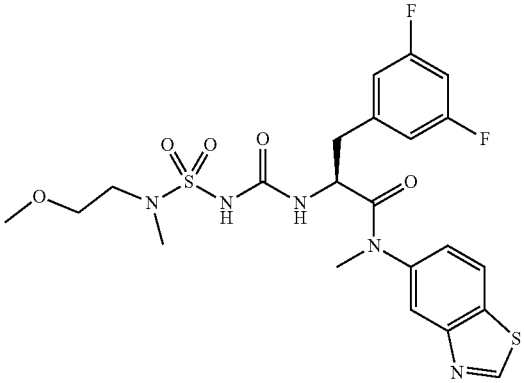 [SMILES: COCCN(C)S(=O)(=O)NC(=O)N[C@@H](Cc1cc(F)cc(F)c1)C(=O)N(C)c1ccc2scnc2c1] | 15.6 | 1.54 | 542.0 | QC-ACN-AA-XB |
| CA-150 | 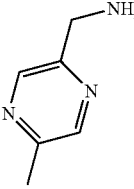 | 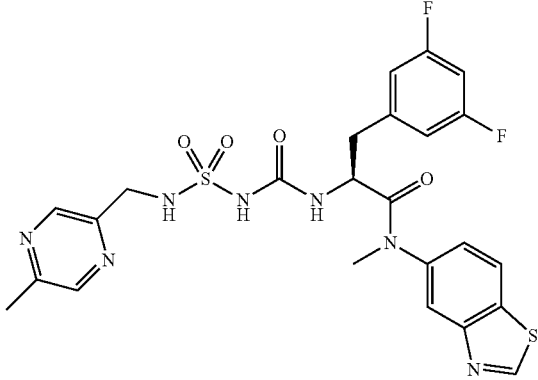 [SMILES: Cc1cnc(CNS(=O)(=O)NC(=O)N[C@@H](Cc2cc(F)cc(F)c2)C(=O)N(C)c2ccc3scnc3c2)cn1] | 18.4 | 1.39 | 576.0 | QC-ACN-AA-XB |

-continued

| Ex # | Amine input | Example Structure | Mass (mg) | RT (min) | Obs'd Mass [M + 1] | LC-MS Cond.* |
|---|---|---|---|---|---|---|
| CA-151 | | | 22.0 | 1.36 | 553.0 | QC-ACN-TFA-XB |
| CA-152 | | | 10.0 | 2.01 | 600.1 | QC-ACN-AA-XB |
| | | (Diastereomeric mix) | | | | |
| CA-153 | | | 1.1 | 1.52 | 528.0 | QC-ACN-TFA-XB |

-continued

| Ex # | Amine input | Example Structure | Mass (mg) | RT (min) | Obs'd Mass [M + 1] | LC-MS Cond.* |
|---|---|---|---|---|---|---|
| CA-154 | ethyl(methyl)amine | (structure) | 1.2 TFA | 1.68 | 512.0 | QC-ACN-TFA-XB |
| CA-155 | 4-hydroxypiperidine | (structure) | 5.1 | 1.27 | 554.0 | QC-ACN-AA-XB |
| CA-156 | 4-phenylpiperidine | (structure) | 7.3 TFA | 1.94 | 614.1 | QC-ACN-AA-XB |
| CA-157 | 1,2,3,4-tetrahydroisoquinoline | (structure) | 2.9 TFA | 1.74 | 586.0 | QC-ACN-AA-XB |

| Ex # | Amine input | Example Structure | Mass (mg) | RT (min) | Obs'd Mass [M + 1] | LC-MS Cond.* |
|---|---|---|---|---|---|---|
| CA-158 | 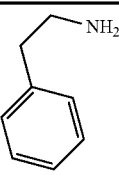 | 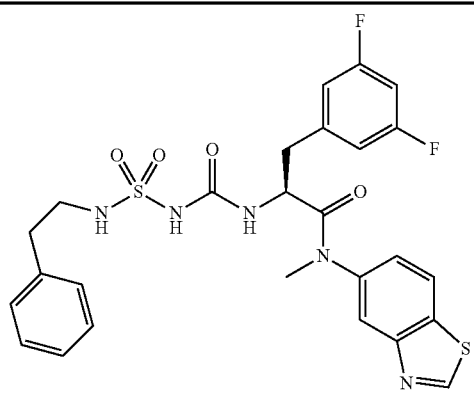 | 8.6 TFA | 1.78 | 574.0 | QC-ACN-AA-XB |

*QC-ACN-TFA-XB-Column: Waters Acquity UPLC BEH C18, 2.1 × 50 mm, 1.7-μm particles;
Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.
*QC-ACN-AA-XB-Column: Waters Acquity UPLC BEH C18, 2.1 × 50 mm, 1.7-μm particles;
Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm
Note:
If "TFA" is present directly under the mass quantity in the table above, then the preparative HPLC purification utilized TFA buffered eluents but the exact TFA composition of the final product was not determined.

Example GW-21

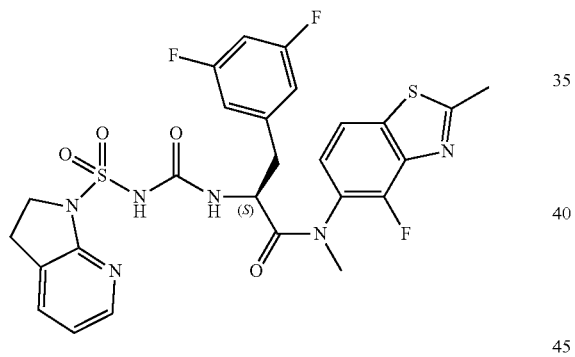

To a solution of sulfurisocyanatidic chloride (15 mg, 0.11 mmol) in DCM (1 mL) in an ice-water bath was added a solution of Intermediate GW-20.5 (40 mg, 0.11 mmol) and TEA (0.018 mL, 0.11 mmol) in DCM (1 mL). The reaction mixture was stirred for 1 min and then a solution of 2,3-dihydro-1H-pyrrolo[2,3-b]pyridine (19 mg, 0.16 mmol) in DCM (1 mL) was added, followed by TEA (0.04 mL, 0.21 mmol) and the reaction mixture was stirred for 2 min. Then the bath was removed and the stirring was continued at rt for 2 h. The reaction mixture was concentrated and the residue was redissolved in DMF and purified by preparative HPLC to afford the title compound (17.3 mg). LC-MS retention time=3.03 min; m/z=605.20 [M+H]$^+$. (Column: Phenomenex C18 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-28 & Example BB-29

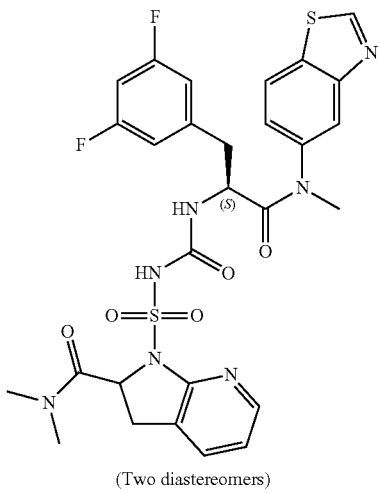

(Two diastereomers)

To a stirred solution of Intermediate VN-29 (100 mg, 0.21 mmol), Intermediate BB-16.5 (57.8 mg, 0.21 mmol) in acetonitrile (5 mL) was added DBU (49 mg, 0.32 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered, concentrated and the crude product was purified by preparative HPLC to afford the two diastereomers of the title compound Example BB-28 (22 mg, off white solid and Example BB-29 (4 mg) as an off white solid.

Example BB-28: LC-MS retention times=1.25 min m/z=644.2 [M+H]$^+$. Column: KINETIX XB-C18, 75×3 mm, 2.6 μm; Flow rate: 1 mL/min; Mobile Phase A: 10 mM HCO$_2$NH$_4$ in 98% Water/2% ACN; Mobile Phase B: 10 mM HCO₂NH₄ in 2% Water/98% ACN; 20% B to 100% B over 4 min, then hold for 0.6 min at 100% B with flow rate of 1.5 mL/min; Detection: UV at 220 nm. ¹H NMR (400 MHz, CDCl₃) δ 9.10 (s, 1H), 8.23 (br. s., 1H), 7.94 (d, J=8.5 Hz, 1H), 7.64 (br. s., 1H), 7.41 (d, J=7.0 Hz, 1H), 7.09 (br. s., 1H), 6.89 (br. s., 1H), 6.65 (t, J=8.9 Hz, 1H), 6.47 (m, 2H), 5.46 (d, J=9.5 Hz, 1H), 4.75 (dd, J=14.0, 6.8 Hz, 1H), 3.56 (dd, J=15.8, 11.0 Hz, 1H), 3.32 (s, 3H), 3.15 (s, 3H), 3.10-2.90 (m, 2H), 3.03 (s, 3H), 2.90-2.75 (br. s., 2H)

Example BB-29: LC-MS retention times=1.26 min m/z=644.2 [M+H]⁺. Column: KINETIX XB-C18, 75×3 mm, 2.6 μm; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 20% B to 100% B over 4 min, then hold for 0.6 min at 100% B with flow rate of 1.5 mL/min; Detection: UV at 220 nm. ¹H NMR (400 MHz, CDCl₃) δ 9.10 (s, 1H), 8.23 (br. s., 1H), 7.94 (d, J=8.5 Hz, 1H), 7.64 (br. s., 1H), 7.41 (d, J=7.0 Hz, 1H), 7.09 (br. s., 1H), 6.89 (br. s., 1H), 6.65 (t, J=8.9 Hz, 1H), 6.47 (m, 2H), 5.46 (d, J=9.5 Hz, 1H), 4.75 (dd, J=14.0, 6.8 Hz, 1H), 3.56 (dd, J=15.8, 11.0 Hz, 1H), 3.32 (s, 3H), 3.15 (s, 3H), 3.10-2.90 (m, 2H), 3.03 (s, 3H), 2.90-2.75 (br. s., 2H)

Example GW-22

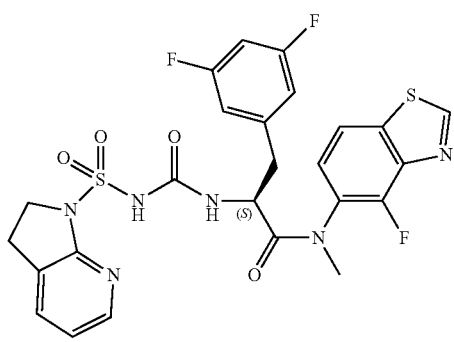

To a solution of sulfurisocyanatidic chloride (17 mg, 0.12 mmol) in DCM (1 mL) in an ice-water bath was added a solution of Intermediate GW-21.3 (45 mg, 0.12 mmol) and TEA (0.02 mL, 0.1 mmol) in DCM (1 mL) and the reaction mixture was stirred for 2 min. Then a solution of 2,3-dihydro-1H-pyrrolo[2,3-b]pyridine (22 mg, 0.18 mmol) in DCM (1 mL) was added, followed by TEA (0.040 mL, 0.25 mmol), the bath was removed and the stirring was continued at rt for 18 h. The reaction mixture was concentrated, the residue was redissolved in DMF and purified by preparative HPLC to afford the title compound (4.8 mg). LC-MS retention time=2.37 min; m/z=591.25 [M+H]⁺. (Column: Phenomenex C18 2.0×50 mm, 3 μm particles; Mobile Phase A: 10% MeOH-90% H₂O-0.1% TFA; Mobile Phase B: 90% MeOH-10% H₂O-0.1% TFA; Temperature: 40° C.; Gradient: 0-100% B over 4 min, then a 1-min hold at 100% B; Flow: 0.8 mL/min; Detection: UV at 220 nm).

Example BB-30

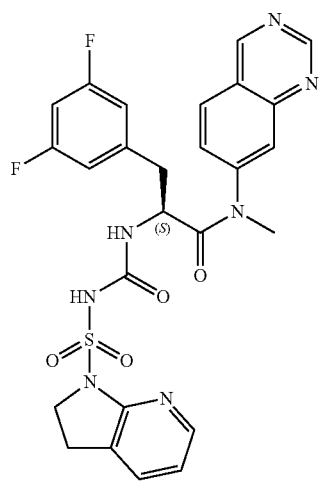

To a stirred solution Intermediate BB-17.4 and Intermediate BB-1.2 hydrochloride (0.019 g, 0.095 mmol) in acetonitrile (1 mL) was added DBU (0.020 mL, 0.13 mmol) and the reaction mixture was stirred at room temperature for 16 h. The reaction mixture was diluted with water (20 mL), extracted with EtOAc (3×20 mL) and the combined organic layer was washed with brine (40 mL), dried (Na₂SO₄), filtered and concentrated. The crude product was purified by preparative HPLC to afford the title compound (5.76 mg) as an off white solid. LC-MS retention time=1.02 min; m/z=568.2 [M+H]⁺. Column: KINETIX XB-C18, 75×3 mm, 2.6 μm; Flow rate: 1 mL/min; Mobile Phase A: 10 mM HCOONH₄ in 98% Water/2% ACN; Mobile Phase B: 10 mM HCOONH₄ in 2% Water/98% ACN; 20% B to 100% B over 4 min, then hold for 0.6 min at 100% B with flow rate of 1.5 mL/min; Detection: UV at 220 nm. ¹H NMR (400 MHZ, MeOH-d₄) δ 9.42 (br. s., 1H), 9.28 (s, 1H), 8.03 (d, J=8.8 Hz, 2H), 7.68 (br. s, 1H), 7.56 (d, J=6.0 Hz, 2H), 6.93 (br. s., 1H), 6.81 (t, J=9.3 Hz, 1H), 6.48 (br. s., 2H), 4.51 (br. s., 1H), 4.25-4.08 (m, 2H), 3.30 (s., 3H), 3.29 (m, 2H), 2.92 (d, J=10.0 Hz, 1H), 2.72 (br. s., 1H).

Example GW-23

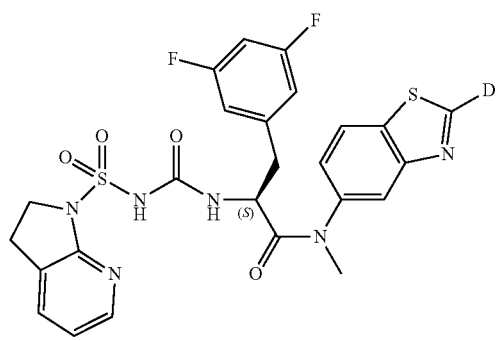

To a solution of sulfurisocyanatidic chloride (20.2 mg, 0.142 mmol) in DCM (1 mL) in an ice-water bath was added a solution of an HCl salt of Intermediate GW-22.4 (60 mg, 0.14 mmol) and TEA (0.050 mL, 0.29 mmol) in DCM (1 mL) and the reaction mixture was stirred for 1 min. Then a solution of 2,3-dihydro-1H-pyrrolo[2,3-b]pyridine (26 mg, 0.21 mmol) in DCM (1 mL) was added, followed by TEA (0.08 mL, 0.43 mmol), the bath was removed and stirring was continued at rt for 3 h. The reaction mixture was concentrated and the residue was redissolved in DMF and purified by preparative HPLC to afford the title compound (1.5 mg). LC-MS retention time=3.46 min; m/z=574.22 [M+H]$^+$. (Column: Phenomenex-Luna 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example GW-24

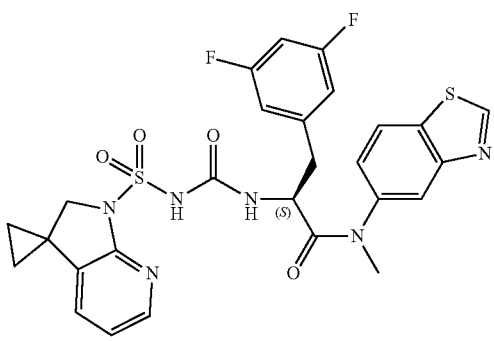

A solution of Intermediate ZY-5 (39 mg, 0.09 mmol) and TEA (0.030 mL, 0.18 mmol) in DCM (1 mL) was added to a solution of sulfurisocyanatidic chloride (0.09 M in DCM, 1 mL, 0.09 mmol) and the reaction mixture was sealed and stirred for 1 min. Then a solution of Intermediate GW-23.5 (20 mg, 0.14 mmol) in DCM (1 mL) was added, followed by TEA (0.050 mL, 0.28 mmol), the bath was removed and stirring was continued at rt for 2 h. The reaction mixture was concentrated, the residue was redissolved in DMF and purified by preparative HPLC to afford the title compound (1.4 mg). LC-MS retention time=3.10 min; m/z=599.10 [M+H]$^+$. (Column: Phenomenex C18 2.0×50 mm, 3 μm particles; Mobile Phase A: 10% MeOH-90% H$_2$O-0.1% TFA; Mobile Phase B: 90% MeOH-10% H$_2$O-0.1% TFA; Temperature: 40° C.; Gradient: 0-100% B over 4 min, then a 1-min hold at 100% B; Flow: 0.8 mL/min; Detection: UV at 220 nm).

Example BB-31

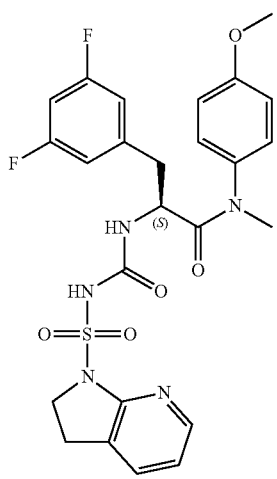

To a stirred solution of Intermediate BB-28.3 (80 mg, 0.18 mmol) and Intermediate BB-1.2 hydrochloride (39.8 mg, 0.200 mmol) in acetonitrile (2 mL) was added DBU (0.041 mL, 0.27 mmol), the reaction mixture was stirred at room temperature for 16 h. The reaction mixture was diluted with water (25 mL), extracted with EtOAc (2×25 mL), the combined organic layer was dried (Na$_2$SO$_4$), filtered and concentrated. The crude product was purified by preparative HPLC to afford the title compound (13.6 mg) as an off white solid. LC-MS retention time=1.49 min; m/z=546.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHz, CDCl$_3$) δ 8.12 (d, J=4 Hz, 1H), 7.48 (d, J=6.02 Hz, 1H), 7.00 (s, 1H), 6.92 (dd, J=7.2, 5.2 Hz, 1H), 6.85 (br. s., 4H), 6.59 (tt, J=8.97, 2.32 Hz, 1H), 6.40 (d, J=6.02 Hz, 2H), 4.63 (dd, J=15.2, 7.2 Hz, 1H), 4.26 (dd, J=17.6, 8.4 Hz, 1H), 4.21 (dd, J=18.8, 7.6 Hz, 1H), 3.82 (s, 3H), 3.20 (s, 3H), 3.13 (t, J=8.53 Hz, 2H), 2.81 (dd, J=13.6, 7.0 Hz, 1H), 2.61 (dd, J=13.4, 6.8 Hz, 1H).

Example BB-32

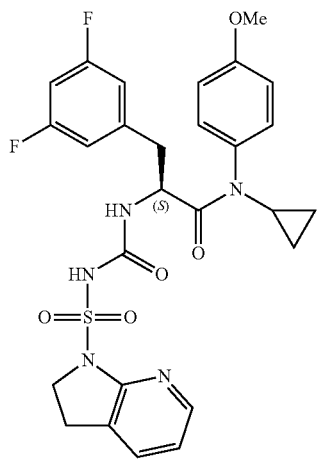

315

To a stirred solution of Intermediate BB-18.4 (120 mg, 0.25 mmol) and Intermediate BB-1.2 hydrochloride (62 mg, 0.31 mmol) in acetonitrile (10 mL) was added DBU (0.08 mL, 0.5 mmol) and reaction mixture was stirred at room temperature for 16 h. Then the reaction mixture was diluted with water (15 mL) and extracted with EtOAc (2×15 mL). The combined organic layer was dried (Na$_2$SO$_4$), filtered, concentrated and the crude product was purified by preparative HPLC to afford the title compound (2.26 mg) as an off white solid. LC-MS retention time=1.81 min; m/z=572.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example BB-33

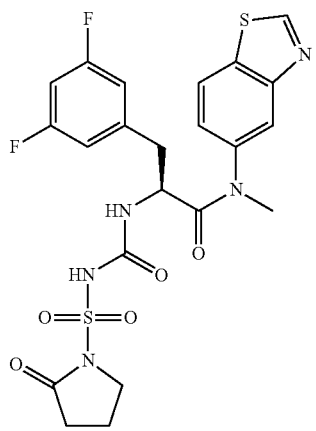 [SMILES: CN(C(=O)[C@H](Cc1cc(F)cc(F)c1)NC(=O)NS(=O)(=O)N1CCCC1=O)c1ccc2scnc2c1]

To a solution of pyrrolidin-2-one (50 mg, 0.59 mmol) in THF (10 mL) added N-methyl-N-(trimethylsilyl)trifluoroacetamide (0.33 mL, 1.8 mmol) and the reaction mixture was stirred at room temperature for 1 h and evaporated under reduced pressure slowly for over a period of 30 min to afford a residue. Intermediate ZY-5 (204 mg, 0.588 mmol) in DCM (1 mL) was cooled to 0° C. and then added sulfurisocyanatidic chloride (0.052 mL, 0.588 mmol) followed by a THF (5 mL) solution of the above residue and stirred for 16 h. The reaction mixture was diluted with water and extracted with 10% MeOH in DCM (2×50 mL). The combined organic layer was dried (Na$_2$SO$_4$), filtered, concentrated, the crude product was purified by preparative HPLC to afford the title compound (55 mg) as an off white solid. LC-MS retention time=1.11 min; m/z=538.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHz, DMSO-d$_6$) δ 9.50 (s, 1H), 8.24 (d, J=6.0 Hz, 1H), 8.03 (s, 1H), 7.40 (br. s., 1H), 7.06-6.99 (m, 4H), 6.48 (br. s., 2H), 4.34 (br. s., 2H), 3.69 (br. s., 2H), 3.22 (s, 3H), 2.81 (br. s., 1H), 2.51 (m, 1H), 2.25 (br. s., 2H), 1.84 (br. s., 2H).

316

Example BB-34

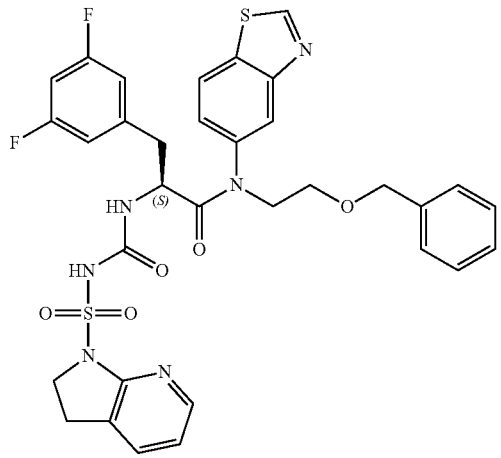

To a stirred solution of Intermediate BB-19.4 (85 mg, 0.15 mmol) and Intermediate BB-1.2 hydrochloride (34.6 mg, 0.174 mmol) in acetonitrile (3 mL) was added DBU (0.033 mL, 0.22 mmol) and the reaction mixture was stirred at room temperature for 16 h. The reaction mixture was diluted with water (25 mL), extracted with EtOAc (2×25 mL), the combined organic layer was dried (Na$_2$SO$_4$), filtered and concentrated. The crude product was purified by preparative HPLC to afford the title compound (12.17 mg) as an off white solid. LC-MS retention time=2.08 min; m/z=693.2 [M+H]$^+$. Column: KINETIX XB-C18, 75×3 mm, 2.6 μm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm.

Example BB-35

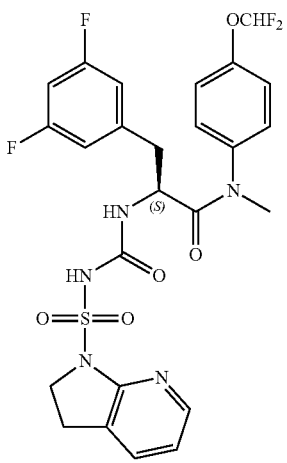

To a stirred solution of Intermediate BB-20.3 (100 mg, 0.210 mmol) and Intermediate BB-1.2 hydrochloride (41.8 mg, 0.210 mmol) in acetonitrile (4 mL) was added DBU (0.063 mL, 0.42 mmol) and the reaction mixture was stirred at room temperature for 16 h. The reaction mixture was diluted with water (25 mL) and extracted with EtOAc (2×25 mL). The combined organic layer was washed with 1.5N HCl solution (25 mL), dried (Na$_2$SO$_4$), filtered and concentrated. The crude product was purified by preparative HPLC to afford the title compound (28 mg) as an off white solid. LC-MS retention time=1.73 min; m/z=582.2 [M+]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 8.02 (d, J=4.4 Hz., 1H), 7.58 (d, J=6.5 Hz, 1H), 7.13 (d, J=8.3 Hz, 2H), 7.06-6.62 (m, 4H), 6.84 (t, J=73.6 Hz, 1H), 6.73 (t, J=9.2 Hz, 1H), 6.45 (d, J=7.3 Hz, 2H), 4.46 (t, J=7.2 Hz, 1H), 4.18 (dd, J=16.0, 6.8 Hz, 2H), 3.23 (s, 3H), 3.16-3.10 (m, 2H), 2.86 (dd, J=12.9, 6.6 Hz, 1H), 2.63 (dd, J=12.6, 7.4 Hz, 1H).

Example BB-36

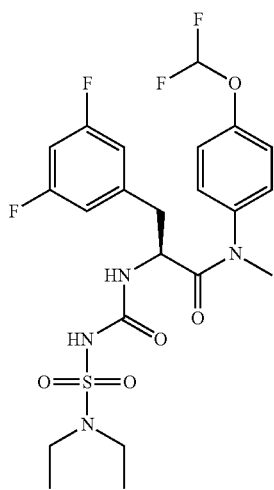 [SMILES: CCN(CC)S(=O)(=O)NC(=O)N[C@@H](Cc1cc(F)cc(F)c1)C(=O)N(C)c1ccc(OC(F)F)cc1]

To a stirred solution of Intermediate BB-20.3 (100 mg, 0.210 mmol) in acetonitrile (5 mL) was added a TFA salt of Intermediate BB-27.2 (55.9 mg, 0.210 mmol) and DBU (0.095 mL, 0.630 mmol) and reaction mixture was stirred at room temperature for 16 h. The reaction mixture was diluted with DCM (20 mL), washed with water (20 mL), dried (Na$_2$SO$_4$), filtered, concentrated and the crude material was purified by preparative HPLC to afford the title product (35 mg) as off white solid. LC-MS retention time=2.68 min; m/z=535.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHz, CDCl$_3$) δ 7.17 (d, J=9.0 Hz, 2H), 7.02-6.95 (br.s., 2H), 6.93 (d, J=8.3 Hz, 1H), 6.70 (tt, J=8.9, 2.3 Hz, 1H), 6.57 (t, J=72.0 Hz, 1H), 6.47 (dd, J=7.9, 2.1 Hz, 2H), 4.71 (dd, J=8.16, 5.27 Hz, 1H), 3.34 (m, 4H), 3.26 (s, 3H), 2.87 (dd, J=13.6, 7.2 Hz, 1H), 2.75 (dd, J=13.2, 6.8 Hz, 1H), 1.19 (t, J=7.1 Hz, 6H).

Example BB-37

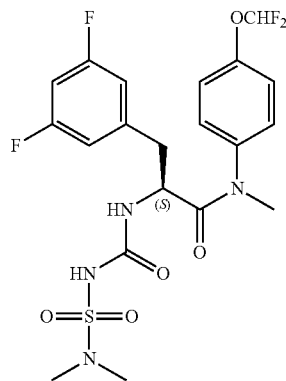

To a stirred solution of Intermediate BB-20.3 (50 mg, 0.11 mmol) and DBU (0.016 mL, 0.11 mmol) in acetonitrile (2 mL) was added dimethylsulfamoyl amine (0.020 g, 0.16 mmol) and reaction mixture was stirred at room temperature for 16 h. The reaction mixture was diluted with water (25 mL) and extracted with EtOAc (2×25 mL). The combined organic layer was washed with 1.5N HCl solution (25 mL), dried (Na$_2$SO$_4$), filtered and concentrated. The crude product was purified by preparative HPLC to afford the title compound (17 mg) as an off white solid. LC-MS retention time=2.07 min; m/z=507.2 [M+H]$^+$. Column: KINETIX XB-C18, 75×3 mm, 2.6 µm; Flow rate: 1 mL/min; Mobile Phase A: 10 mM HCOONH$_4$ in 98% Water/2% ACN; Mobile Phase B: 10 mM HCOONH$_4$ in 2% Water/98% ACN; 20% B to 100% B over 4 min, then hold for 0.6 min at 100% B with flow rate of 1.5 mL/min; Detection: UV at 220 nm. $^1$H NMR (400 MHZ, MeOH-d$_4$) δ 7.27 (s, 4H), 6.91 (t, J=73.6 Hz, 1H), 6.82 (t, J=7.2 Hz, 1H), 6.54 (d, J=6.0 Hz, 2H), 4.60 (m, 1H), 3.26 (s, 3H), 2.96 (dd, J=13.3, 5.8 Hz, 1H), 2.80 (s, 6H), 2.75 (dd, J=13.3, 5.8 Hz, 1H).

Biological Methods

HIV cell culture assay—MT-2 cells, 293T cells and the proviral DNA clone of NL$_{4-3}$ virus were obtained from the NIH AIDS Research and Reference Reagent Program. MT-2 cells were propagated in RPMI 1640 media supplemented with 10% heat inactivated fetal bovine serum (FBS), 100 jag/ml penicillin G and up to 100 units/mL streptomycin. The 293T cells were propagated in DMEM media supplemented with 10% heat inactivated FBS, 100 µg/mL penicillin G and 100 µg/mL streptomycin. A recombinant NL$_{4-3}$ proviral clone, in which a section of the nef gene was replaced with the *Renilla* luciferase gene, was used to make the reference virus used in these studies. The recombinant virus was prepared through transfection of the recombinant NL$_{4-3}$ proviral clone into 293T cells using Transit-293 Transfection Reagent from Mirus Bio LLC (Madison, Wis.). Supernatant was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration (EC$_{50}$) was calculated by using the exponential form of the median effect equation where (Fa)=1/[1+(ED$_{50}$/drug conc.)$^m$] (Johnson V A, Byington R T. Infectivity Assay. In Techniques in HIV Research. ed. Aldovini A, Walker B D. 71-76. New York: Stockton Press. 1990).

Compound cytotoxicity and the corresponding CC$_{50}$ values were determined using the same protocol as described in the antiviral assay except that uninfected cells were used. Cytotoxicity was assessed on day 4 in uninfected MT2 cells by using a XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

Compounds demonstrate antiviral activity as depicted in Table 1 below. Activity equal to A refers to a compound having an EC$_{50}$≤100 nM, while B and C denote compounds having an EC$_{50}$ between 100 nM and 1 μM (B) or >1 μM (C).

TABLE 1

| Example # | EC50 (uM) | CC50 (uM) |
|---|---|---|
| JB-2 | 0.11 | >33.3 |
| JB-3 | 0.13 | >100.0 |
| JB-4 | 0.14 | >100.0 |
| JB-5 | 0.10 | >100.0 |
| JB-6 | 0.66 | >100.0 |
| JB-7 | 0.20 | >100.0 |
| JB-8 | 2.69 | >100.0 |
| JB-1 | 0.11 | >100.0 |
| JB-9 | 0.44 | 74.2 |
| JB-11 | 0.04 | >100.0 |
| JB-12 | 0.17 | 57.7 |
| JB-13 | 0.26 | >33.3 |
| JB-14 | 0.69 | >100.0 |
| JB-15 | 1.92 | >100.0 |
| JB-10 | 0.05 | >100.0 |
| JB-17 | 0.08 | >100.0 |
| JB-18 | 0.56 | >100.0 |
| JB-16 | 0.17 | >100.0 |
| JB-19 | 0.05 | >100.0 |
| JB-20 | 0.10 | >100.0 |
| JB-21 | 1.78 | >100.0 |
| JB-22 | 0.07 | >100.0 |
| JB-23 | 0.87 | >100.0 |
| JB-24 | 0.10 | >100.0 |
| JB-25 | 0.08 | >100.0 |
| JB-26 | 0.04 | >100.0 |
| JB-27 | 0.15 | >100.0 |
| JB-28 | 0.21 | >100.0 |
| JB-29 | 1.60 | >100.0 |
| JB-30 | 1.95 | >100.0 |
| JB-31 | 0.14 | >100.0 |
| JB-32 | 1.45 | >100.0 |
| JB-33 | 0.68 | >100.0 |
| JB-34 | 0.08 | >100.0 |
| JB-35 | 0.08 | >100.0 |
| JB-36 | 2.26 | >100.0 |
| JB-37 | 0.06 | >100.0 |
| JB-38 | 1.60 | >100.0 |
| JB-39 | 1.38 | >100.0 |
| JB-40 | 2.88 | 66.5 |
| JB-41 | 5.06 | >33.3 |
| JB-42 | 0.45 | >100.0 |
| JB-43 | 0.76 | >100.0 |
| JB-44 | 1.75 | >100.0 |
| JB-45 | 9.45 | >50.0 |
| JB-46 | 0.08 | >100.0 |
| JB-47 | 3.41 | >100.0 |
| JB-48 | 0.17 | >100.0 |
| JB-49 | 0.20 | >100.0 |
| JB-50 | 0.10 | >100.0 |
| JB-51 | 0.11 | >100.0 |
| JB-52 | 5.94 | >100.0 |
| JB-53 | 1.10 | 85.5 |
| JB-54 | 11.98 | >100.0 |

TABLE 1-continued

| Example # | EC50 (uM) | CC50 (uM) |
|---|---|---|
| JB-55 | 14.78 | >100.0 |
| JB-56 | 1.87 | >100.0 |
| JB-57 | 6.43 | >100.0 |
| JB-58 | 0.69 | >100.0 |
| JB-59 | 1.86 | >100.0 |
| JB-60 | 0.27 | >100.0 |
| JB-61 | 4.91 | >100.0 |
| JB-62 | 0.29 | >100.0 |
| JB-63 | 6.50 | >100.0 |
| JB-64 | 0.68 | >100.0 |
| JB-65 | 0.62 | >100.0 |
| JB-66 | 1.18 | >100.0 |
| JB-67 | 0.18 | >100.0 |
| JB-68 | 2.37 | >100.0 |
| JB-69 | 3.69 | >100.0 |
| JB-70 | 0.10 | >33.3 |
| JB-71 | 0.13 | >33.3 |
| JB-72 | 0.18 | >33.3 |
| JB-73 | 0.05 | >33.3 |
| JB-74 | 1.12 | >100.0 |
| JB-75 | 0.07 | >33.3 |
| CA-1 | 0.25 | 21.4 |
| CA-2 | 0.14 | >33.3 |
| CA-3 | 5.72 | >100.0 |
| JB-76 | 8.75 | >33.3 |
| CA-4 | 0.41 | 89.4 |
| CA-5 | 0.18 | >33.3 |
| CA-6 | 0.38 | >100.0 |
| CA-7 | 0.14 | >100.0 |
| CA-8 | 0.59 | >100.0 |
| CA-9 | 0.26 | >100.0 |
| CA-10 | 0.07 | >100.0 |
| CA-11 | 0.07 | >100.0 |
| CA-12 | 0.09 | >33.3 |
| CA-13 | 0.06 | >100.0 |
| CA-14 | 0.12 | >33.3 |
| CA-15 | 0.07 | >100.0 |
| CA-16 | 0.09 | >100.0 |
| CA-17 | 1.94 | >100.0 |
| CA-18 | 0.35 | >33.3 |
| CA-19 | 0.12 | >100.0 |
| CA-20 | 0.04 | >100.0 |
| CA-21 | 0.08 | >100.0 |
| CA-22 | 2.51 | >100.0 |
| CA-23 | 0.06 | >100.0 |
| CA-24 | 0.06 | >100.0 |
| CA-25 | 1.01 | >33.3 |
| CA-26 | 0.27 | >100.0 |
| CA-27 | 0.31 | >100.0 |
| CA-28 | 0.05 | >100.0 |
| CA-29 | 3.26 | >33.3 |
| CA-30 | 0.08 | >100.0 |
| CA-31 | 1.17 | >33.3 |
| CA-32 | 0.98 | >33.3 |
| CA-33 | 2.04 | >33.3 |
| CA-34 | 0.18 | >33.3 |
| CA-35 | 0.38 | 30.3 |
| CA-36 | 0.20 | >33.3 |
| CA-37 | 1.20 | >33.3 |
| CA-38 | 0.25 | >100.0 |
| CA-39 | 0.33 | >100.0 |
| CA-40 | 0.22 | >100.0 |
| CA-41 | 0.26 | >33.3 |
| CA-42 | 4.12 | >100.0 |
| CA-43 | 0.30 | >100.0 |
| CA-44 | 0.62 | >100.0 |
| CA-45 | 0.52 | >33.3 |
| CA-46 | 11.55 | >100.0 |
| CA-47 | 2.14 | >100.0 |
| CA-48 | 0.26 | >100.0 |
| CA-49 | 0.18 | >33.3 |
| CA-50 | 0.11 | >100.0 |
| CA-51 | 4.59 | >100.0 |
| CA-52 | 0.91 | >100.0 |
| CA-56 | 1.31 | >100.0 |
| CA-58 | 7.45 | >100.0 |
| CA-59 | 6.14 | >100.0 |
| CA-60 | 0.87 | >100.0 |

TABLE 1-continued

| Example # | EC50 (uM) | CC50 (uM) |
|---|---|---|
| JB-77 | 0.45 | >100.0 |
| JB-78 | 0.37 | >33.3 |
| JB-79 | 8.61 | >100.0 |
| JB-80 | 0.36 | >100.0 |
| JB-81 | 0.26 | >100.0 |
| CA-61 | 0.40 | >100.0 |
| CA-62 | 3.69 | >100.0 |
| CA-63 | 30.24 | 73.7 |
| CA-64 | 0.44 | 62.4 |
| CA-65 | 4.04 | >100.0 |
| CA-66 | 14.56 | >100.0 |
| ZY-1 | 0.01 | >100.0 |
| ZY-2 | 0.05 | >53.0 |
| ZY-8 | 0.02 | 88.0 |
| ZY-9 | 0.18 | >100.0 |
| ZY-10 | 0.05 | >100.0 |
| ZY-11 | 0.08 | 66.9 |
| ZY-12 | 0.11 | >100.0 |
| ZY-15 | 0.03 | >33.3 |
| ZY-18 | 0.15 | >100.0 |
| CA-113 | 0.14 | >100.0 |
| CA-114 | 0.10 | >100.0 |
| CA-115 | 0.06 | >100.0 |
| CA-116 | 0.06 | 73.2 |
| CA-117 | 0.12 | >100.0 |
| CA-118 | 0.16 | >100.0 |
| CA-119 | 0.06 | >33.3 |
| CA-120 | 0.27 | >100.0 |
| VN-1 | 2.48 | >100.0 |
| VN-2 | 0.61 | >100.0 |
| CA-121 | 0.99 | 7.3 |
| VN-3 | 0.85 | 52.4 |
| VN-4 | 0.19 | 57.5 |
| ZY-19 | 0.36 | >33.3 |
| ZY-20 | 4.19 | >100.0 |
| VN-5 | 0.04 | 95.9 |
| VN-6 | 0.02 | >1.0 |
| VN-7 | 0.05 | >1.0 |
| VN-8 | 0.05 | >100.0 |
| ZY-21 | 0.49 | >100.0 |
| ZY-22 | 0.52 | >100.0 |
| VN-9 | 0.01 | >100.0 |
| ZY-23 | 0.08 | >100.0 |
| VN-10 | 0.10 | >33.3 |
| VN-11 | 0.09 | 93.5 |
| VN-12 | 0.01 | >50.0 |
| ZY-24 | 0.06 | 53.4 |
| VN-14 | 0.00 | >100.0 |
| VN-15 | 0.03 | >100.0 |
| GW-2 | 0.07 | >100.0 |
| ZY-25 | 0.03 | 97.1 |
| BB-1 | 11.04 | >100.0 |
| BB-2 | 0.02 | 96.0 |
| GW-3 | 0.02 | >100.0 |
| AW-1 | 0.11 | >100.0 |
| GW-4 | 0.22 | >100.0 |
| GW-5 | 0.32 | >100.0 |
| GW-6 | 0.63 | >25.0 |
| GW-7 | 0.03 | 16.8 |
| GW-8 | 0.10 | >25.0 |
| BB-3 | 0.34 | 68.1 |
| BB-4 | 0.42 | 61.9 |
| GW-9 | 0.18 | 35.1 |
| GW-10 | 0.03 | 91.0 |
| GW-11 | 0.09 | >100.0 |
| GW-12 | 0.12 | >100.0 |
| BB-5 | 4.91 | >100.0 |
| BB-6 | 0.34 | >33.3 |
| GW-13 | 0.06 | >100.0 |
| BB-8 | 0.44 | 82.4 |
| AW-2 | 0.01 | >100.0 |
| BB-9 | 0.41 | >100.0 |
| BB-10 | 1.08 | >100.0 |
| VN-16 | 0.03 | >100.0 |
| VN-17 | 0.07 | >100.0 |
| GW-14 | 1.61 | >100.0 |
| GW-15 | 0.97 | 5.1 |
| BB-11 | 0.01 | 66.3 |
| GW-16 | 0.28 | >100.0 |
| BB-12 | 0.02 | 94.9 |
| BB-13 | 0.27 | 89.5 |
| GW-17 | 0.10 | >100.0 |
| VN-19 | 0.68 | 70.5 |
| VN-20 | 0.94 | >100.0 |
| BB-14 | 0.02 | 93.1 |
| BB-15 | 0.46 | >100.0 |
| VN-21 | 0.02 | >33.3 |
| VN-22 | 0.05 | >100.0 |
| VN-23 | 0.17 | >100.0 |
| VN-24 | 0.09 | >100.0 |
| BB-16 | 0.03 | 56.3 |
| BB-17 | 0.07 | 91.2 |
| BB-18 | 0.01 | >100.0 |
| BB-19 | 3.27 | >100.0 |
| VN-25 | 0.15 | 79.6 |
| BB-20 | 0.06 | 60.7 |
| GW-18 | 0.18 | >100.0 |
| GW-19 | 0.06 | >100.0 |
| GW-20 | 0.23 | >100.0 |
| AW-3 | 0.98 | >100.0 |
| AW-4 | 0.48 | >100.0 |
| BB-21 | 0.75 | >100.0 |
| BB-22 | 0.38 | >100.0 |
| VN-26 | 0.11 | 20.0 |
| BB-23 | 0.28 | >100.0 |
| VN-27 | 0.09 | >100.0 |
| VN-28 | 0.25 | >100.0 |
| BB-24 | 0.01 | >33.3 |
| BB-25 | 0.53 | >33.3 |
| BB-26 | 0.31 | >100.0 |
| BB-27 | 0.97 | >100.0 |
| CA-122 | 0.28 | >33.3 |
| CA-123 | 0.16 | >100.0 |
| CA-124 | 0.11 | >100.0 |
| CA-125 | 0.16 | >100.0 |
| CA-126 | 0.52 | >100.0 |
| CA-127 | 0.06 | >100.0 |
| CA-128 | 0.10 | >100.0 |
| CA-129 | 0.14 | >100.0 |
| CA-130 | 0.45 | >100.0 |
| GW-21 | 0.08 | >100.0 |
| CA-131 | 0.21 | >100.0 |
| CA-132 | 0.05 | >100.0 |
| CA-133 | 0.72 | 86.4 |
| CA-134 | 0.43 | >100.0 |
| CA-135 | 1.53 | >100.0 |
| CA-136 | 0.06 | >100.0 |
| CA-137 | 1.22 | >100.0 |
| CA-138 | 0.27 | >100.0 |
| CA-139 | 0.22 | >100.0 |
| CA-140 | 0.04 | >100.0 |
| CA-141 | 0.04 | >100.0 |
| CA-142 | 0.04 | >100.0 |
| CA-143 | 0.05 | >100.0 |
| CA-144 | 0.04 | >100.0 |
| CA-145 | 0.12 | >100.0 |
| CA-146 | 0.05 | >100.0 |
| CA-147 | 0.08 | >100.0 |
| CA-148 | 10.26 | >100.0 |
| CA-149 | 0.08 | >100.0 |
| CA-150 | 0.46 | >100.0 |
| CA-151 | 1.07 | >100.0 |
| CA-152 | 0.55 | >100.0 |
| CA-153 | 0.15 | 9.0 |
| CA-154 | 0.03 | >50.0 |
| CA-155 | 0.20 | >100.0 |
| CA-156 | 8.32 | 99.2 |
| CA-157 | 0.88 | 99.7 |
| CA-158 | 0.34 | >100.0 |
| BB-28 | 6.05 | >100.0 |
| BB-29 | 2.43 | >100.0 |
| GW-22 | 0.01 | >100.0 |
| BB-30 | 0.26 | >100.0 |
| GW-23 | 0.02 | >10.0 |
| GW-24 | | |
| BB-31 | 0.01 | >33.3 |

TABLE 1-continued

| Example # | EC50 (uM) | CC50 (uM) |
|---|---|---|
| BB-32 | 0.05 | 62.6 |
| BB-33 | 0.45 | >100.0 |
| BB-34 | 0.04 | 70.6 |
| BB-35 | 0.01 | 97.2 |
| BB-36 | 0.16 | >100.0 |
| BB-37 | 0.10 | >100.0 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:

1. A compound of Formula I, or a pharmaceutically acceptable salt thereof:

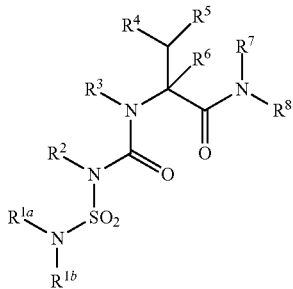

I wherein:

$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO($R^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —CH$_2$NH$_2$, -alkyl-heteroaryl, —CO-alkyl, CO($R^x$), —CON($R^y$)$_2$, —NHCON($R^y$)$_2$, —NHCO-alkyl, —NHCO$_2$alkyl, —NHSO$_2$-alkyl, —OCH$_2$-aryl, —SO$_2$-alkyl, —SO$_2$—N($R^y$)$_2$, and —SO$_2$-heterocyclyl; or $R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —CH$_2$NH$_2$, -alkyl-heteroaryl, —CO-alkyl, —CO($R^x$), —CON($R^y$)$_2$, —N($R^y$)CON($R^y$)$_2$, —N($R^y$)CO-alkyl, —N($R^y$)CO$_2$alkyl, —N($R^y$)SO$_2$-alkyl, —OCH$_2$-aryl, —SO$_2$-alkyl, —SO$_2$—N($R^y$)$_2$, and —SO$_2$-heterocyclyl;

$R^2$ is —H, $C_1$-$C_4$ alkyl or $C_3$-$C_4$ cycloalkyl;

$R^3$ is —H, $C_1$-$C_4$ alkyl or $C_3$-$C_4$ cycloalkyl;

$R^4$ is —H, alkyl, aryl, $C_5$-$C_{10}$ bicycloalkyl, $C_3$-$C_7$ cycloalkyl or heteroaryl with 0-4 groups independently selected from alkenoxy, alkenyl, alkoxy, alkoxycarbonyl, alkyl, benzyloxy, carboamide, cyano, halo, haloalkyl, haloalkyloxy, —NHCO(alkyl), —SO$_2$($R^x$), —OH, and —CH$_2$OH;

$R^5$ and $R^6$ are independently H or alkyl, or $R^5$ and $R^6$ together with the atoms to which they are attached form a $C_3$-$C_4$ cycloalkyl;

$R^7$ is —H, alkyl, aryl, heterocyclyl, or $C_3$-$C_7$ cycloalkyl, wherein said aryl or heterocyclyl is substituted with 0-3 groups selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl;

$R^8$ is —H, alkyl, cycloalkyl, haloalkyl, halocycloalkyl alkenyl, or aryloxyalkyl;

or $R^7$ and $R^8$ together with the nitrogen atom to which they are attached form a heterocycle that is substituted with 0-4 groups independently selected from —OH, —NHCOalkyl, —NHCON(alkyl)$_2$, —NHCO$_2$-alkyl, —CONH$_2$, —CN, —SO$_2$N(alkyl)$_2$, alkoxy, alkyl, halo, haloalkoxy, and haloalkyl;

$R^x$ is dialkylamino or a nitrogen-containing heterocycle which is attached to the parent fragment through a nitrogen atom; and each $R^y$ is independently hydrogen, alkyl, haloalkyl or aryl.

2. The compound or salt of claim 1, wherein $R^{1a}$ and $R^{1b}$ are each independently selected from hydrogen, alkyl, aryl, heteroaryl, arylalkyl, heteroarylalkyl, and -alkylCO($R^x$), wherein the heteroaryl is attached to the parent structure through a carbon atom.

3. The compound or salt of claim 2, wherein $R^{1a}$ and $R^{1b}$ are each independently selected from hydrogen, alkyl, phenyl, biphenyl, naphthalene, dihydroindene, pyridine, pyrimidine, quinoline, isoquinoline, benzothiazole, benzimidazole, 1,3-dihydrobenzo[c]thiophene 2,2-dioxide, —CH$_2$CO($R^x$) and an alkyl moiety attached to any one of the following groups: phenyl, biphenyl, pyridiyl, quinoline, benzimidazole, imidazole, isothiazole, pyrrazole, thiazole, indazole, triazole, and triazolone.

4. The compound or salt of claim 2, wherein $R^{1a}$ and $R^{1b}$ are each independently substituted by at least one member selected from alkyl, haloalkyl, alkoxy, haloalkoxy, halide, phenyl, thiazole, pyrrazole, phenoxy, oxazole, pyrrole, benzyloxy, pyridiylalkyl, methylcarbamate, cyano, acetamide, morpholin-4-ylsulfonyl, pyrrolidin-1-ylsulfonyl, piperidin-1-yl sulfonyl, —NHSO$_2$Me, —CONH$_2$, —NHCONMe$_2$, and —COCH$_3$.

5. The compound or salt of claim 3, wherein $R^{1a}$ and $R^{1b}$ are each independently substituted by at least one member selected from alkyl, haloalkyl, alkoxy, haloalkoxy, halide, phenyl, thiazole, pyrrazole, phenoxy, oxazole, pyrrole, benzyloxy, pyridiylalkyl, methylcarbamate, cyano, acetamide, morpholin-4-ylsulfonyl, pyrrolidin-1-ylsulfonyl, piperidin-1-yl sulfonyl, —NHSO$_2$Me, —CONH$_2$, —NHCONMe$_2$, and —COCH$_3$.

6. The compound or salt of claim 1, wherein $R^{1a}$ and $R^{1b}$ taken together form a heterocycle together with the nitrogen to which they are attached, and wherein said heterocycle has 1-3 rings with a total of 4-14 carbon atoms and at least one internal nitrogen atom, and optionally at least one atom selected from oxygen and sulfur.

7. The compound or salt of claim 6, wherein the formed heterocycle will be selected from tetrahydroquinoline, azatetrahydroquinoline, diazatetrahydroquinoline, tetrahydroisoquinoline, indoline, azaindoline, diazaindoline, indole, azaindole, diazaindole, indazole, carbazole, azetidine, pyrrolidine, piperidine, piperizine, morpholine, 2,3- dihydro-1H-pyrrolo[3,4-c]pyridine, 2,3-dihydrobenzo[d]isothiazole 1,1-dioxide, 1H-pyrazolo[4,3-c]pyridine, 3,4-dihydro-2H-pyrido[3,2-b][1,4]oxazine, and spiro[cyclopropane-1,3'-indoline].

8. The compound or salt of claim 6, wherein the formed heterocycle is substituted with at least one member selected from phenyl, aminoalkyl, alkyl, alkoxy, haloalkyl, haloalkoxy, halide, hydroxyl, pyridine, sulfonylalkyl, —CO₂NMe₂, and cyano.

9. The compound or salt of claim 7, wherein the formed heterocycle is substituted with at least one member selected from phenyl, aminoalkyl, alkyl, alkoxy, haloalkyl, haloalkoxy, halide, hydroxyl, pyridine, sulfonylalkyl, —CO₂NMe₂, and cyano.

10. The compound or salt of claim 2, wherein at least one of said $R^{1a}$ and $R^{1b}$ is phenyl.

11. The compound or salt of claim 10, wherein said phenyl is substituted with at least one member selected from alkyl, haloalkyl, alkoxy, haloalkoxy, halide, phenyl, thiazole, pyrrazole, phenoxy, oxazole, pyrrole, benzyloxy, pyridiylalkyl, methylcarbamate, cyano, acetamide, morpholin-4-ylsulfonyl, pyrrolidin-1-ylsulfonyl, piperidin-1-ylsulfonyl, —NHSO₂Me, —CONH₂, —NHCONMe₂, and —COCH₃.

12. A composition comprising a compound or salt of claim 1 and a pharmaceutically acceptable carrier, excipient and/or diluent.

13. A method of treating HIV infection comprising administering a composition according to claim 12 to a patient in need thereof.

14. A compound of Formula II, or a pharmaceutically acceptable salt thereof:

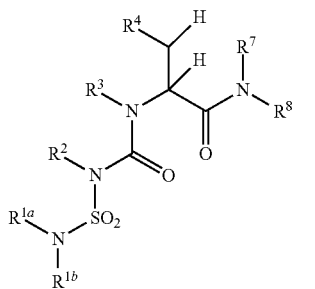

II wherein:
$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO(R$^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —CH₂NH₂, -alkyl-heteroaryl, —CO-alkyl, CO(R$^x$), —CON(R$^y$)₂, —NHCON(R$^y$)₂, —NHCO-alkyl, —NHCO₂alkyl, —NHSO₂-alkyl, —OCH₂-aryl, —SO₂-alkyl, —SO₂—N(R$^y$)₂, and —SO₂-heterocyclyl; or
$R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —CH₂NH₂, -alkyl-heteroaryl, —CO-alkyl, —CO(R$^x$), —CON(R$^y$)₂, —N(R$^y$)CON(R$^y$)₂, —N(R$^y$)CO-alkyl, —N(R$^y$)CO₂alkyl, —N(R$^y$)SO₂-alkyl, —OCH₂-aryl, —SO₂-alkyl, —SO₂—N(R$^y$)₂, and —SO₂-heterocyclyl;

$R^2$ is —H, $C_1$-$C_2$ alkyl or $C_3$-$C_4$ cycloalkyl;
$R^3$ is —H, or $C_1$-$C_4$ alkyl;
$R^4$ aryl, $C_5$-$C_{10}$ bicycloalkyl, $C_3$-$C_7$ cycloalkyl or heteroaryl with 0-4 groups independently selected from alkoxy, alkyl, cyano, halo, haloalkyl, and haloalkyloxy;
$R^7$ is aryl, heterocyclyl, or $C_3$-$C_7$ cycloalkyl, wherein said aryl or heterocyclyl is substituted with 0-3 groups selected from —OH, —NHCOalkyl, —NHCON(alkyl)₂, —NHCO₂-alkyl, —CONH₂, —CN, —SO₂N(alkyl)₂, alkoxy, alkyl, halo, haloalkoxy, and haloalkyl;
$R^8$ is alkyl, cycloalkyl, haloalkyl, halocycloalkyl alkenyl, or aryloxyalkyl;
$R^x$ is dialkylamine or a nitrogen-containing heterocycle which is attached to the parent fragment through a nitrogen atom; and
each $R^y$ is independently hydrogen, alkyl, haloalkyl or aryl.

15. The compound or salt of claim 14, wherein $R^2$ and $R^3$ are each H.

16. The compound or salt of claim 14, wherein $R^4$ is aryl.

17. A compound of Formula III, or a pharmaceutically acceptable salt thereof:

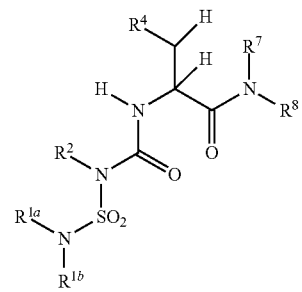

III wherein:
$R^{1a}$ and $R^{1b}$ are each independently selected from hydrogen, alkyl, aryl, arylalkyl, aryloxyaryl, cycloalkyl, heterocyclyl, heterocyclylalkyl, and -alkylCO(R$^x$); wherein said heterocyclyl is linked to the parent molecule through a carbon atom, and further wherein said $R^{1a}$ and $R^{1b}$ groups are substituted with 0-4 groups independently selected from alkenyl, alkoxy, alkoxycarbonyl, alkyl, alkylthioxy, benzyloxy, alkynyl, aryl, arylalkyl, aryloxy, carboxylic acid, cyano, cycloalkyl, halo, haloalkyl, haloalkoxy, heterocyclyl, heterocylyl alkyl, hydroxy, hydroxyalkyl, thioxy, —CH₂NH₂, -alkyl-heteroaryl, —CO-alkyl, CO(R$^x$), —CON(R$^y$)₂, —NHCON(R$^y$)₂, —NHCO-alkyl, —NHCO₂alkyl, —NHSO₂-alkyl, —OCH₂-aryl, —SO₂-alkyl, —SO₂—N(R$^y$)₂, and —SO₂-heterocyclyl; or
$R^{1a}$ and $R^{1b}$ together with the nitrogen atom to which they are attached form a heterocycle that is substituted with 0-4 groups independently selected from alkenyl, alkoxy, alkoxycarbonyl, alkyl, alkylthioxy, benzyloxy, alkynyl, aryl, carboxylic acid, cyano, halo, haloalkyl, haloalkoxy, hydroxy, hydroxyalkyl, thioxy, —CH₂NH₂, -alkyl-heteroaryl, —CO-alkyl, —CO(R$^x$), —CON(R$^y$)₂, —N(R$^y$)CON(R$^y$)₂, —N(R$^y$)CO-alkyl, —N(R$^y$)CO$_2$alkyl, —N(R$^y$)SO$_2$-alkyl, —OCH$_2$-aryl, —SO$_2$-alkyl, —SO$_2$—N(R$^y$)$_2$, and —SO$_2$-heterocyclyl;

R$^2$ is —H, or C$_1$-C$_2$ alkyl;

R$^4$ aryl, or heteroaryl with 0-3 groups independently selected from alkoxy, alkyl, cyano, or halo;

R$^7$ is aryl, heterocyclyl, wherein said aryl or heterocyclyl is substituted with 0-3 groups selected from —OH, —NHCOalkyl, —NHCON(alkyl)$_2$, —NHCO$_2$-alkyl, —CONH$_2$, —CN, alkoxy, alkyl, halo, haloalkoxy, and haloalkyl;

R$^8$ is alkyl, cycloalkyl, haloalkyl, halocycloalkyl alkenyl, or benzyloxyalkyl;

R$^x$ is dialkylamine or a nitrogen-containing heterocycle which is attached to the parent fragment through a nitrogen atom; and each R$^y$ is independently hydrogen, alkyl, haloalkyl or aryl.

18. The compound or salt of claim 17, wherein R$^2$ is —H.

19. The compound or salt of claim 17, wherein said aryl is phenyl.

20. The compound or salt of claim 17, wherein R$^8$ is alkyl.

* * * * *